United States Patent
Kearney et al.

(10) Patent No.: US 11,467,167 B2
(45) Date of Patent: Oct. 11, 2022

(54) SRM METHODS IN ALZHEIMER'S DISEASE AND NEUROLOGICAL DISEASE ASSAYS

(71) Applicant: Biodesix, Inc., Boulder, CO (US)

(72) Inventors: Paul E. Kearney, Seattle, WA (US); Xiao-Jun Li, Bellevue, WA (US); Clive Hayward, Seattle, WA (US)

(73) Assignee: Biodesix, Inc., Boulder, CO (US)

( * ) Notice: Subject to any disclaimer, the term of this patent is extended or adjusted under 35 U.S.C. 154(b) by 0 days.

(21) Appl. No.: 16/703,027

(22) Filed: Dec. 4, 2019

(65) Prior Publication Data

US 2020/0348310 A1    Nov. 5, 2020

Related U.S. Application Data

(63) Continuation of application No. 16/002,123, filed on Jun. 7, 2018, now abandoned, which is a continuation of application No. 15/355,213, filed on Nov. 18, 2016, now abandoned, which is a continuation of application No. 14/390,447, filed as application No. PCT/US2013/031520 on Mar. 14, 2013, now abandoned.

(60) Provisional application No. 61/620,770, filed on Apr. 5, 2012.

(51) Int. Cl.
*G01N 33/68* (2006.01)

(52) U.S. Cl.
CPC . *G01N 33/6848* (2013.01); *G01N 2800/2821* (2013.01)

(58) Field of Classification Search
CPC ........ A61K 31/519; A61P 19/02; A61P 37/06; C07D 487/04; G01N 33/6848; G01N 2800/2821
See application file for complete search history.

(56) References Cited

U.S. PATENT DOCUMENTS

| | | | | |
|---|---|---|---|---|
| 8,574,860 B2* | 11/2013 | Diamandis | ............... | C12Q 1/37 435/7.4 |
| 9,091,651 B2* | 7/2015 | Kearney | ................... | C07K 7/08 |
| 9,201,044 B2* | 12/2015 | Kearney | ................ | G01N 27/62 |
| 9,304,137 B2* | 4/2016 | Kearney | ............ | G01N 33/6893 |
| 9,733,214 B2 | 8/2017 | Hunter et al. | | |
| 2009/0326828 A1* | 12/2009 | Prakash | ............. | G01N 33/6848 702/19 |
| 2012/0009174 A1 | 1/2012 | Van Eyk et al. | | |
| 2012/0071337 A1* | 3/2012 | Lovestone | ......... | G01N 33/6896 435/23 |
| 2012/0238476 A1* | 9/2012 | Li | ...................... | G01N 33/6896 506/18 |
| 2015/0168421 A1* | 6/2015 | Kearney | ............ | G01N 33/6848 506/12 |
| 2017/0299604 A1* | 10/2017 | Kearney | ............ | G01N 33/6848 |
| 2017/0299605 A1* | 10/2017 | Kearney | ............ | G01N 33/6848 |
| 2018/0284128 A1* | 10/2018 | Kearney | ............ | G01N 33/6848 |

FOREIGN PATENT DOCUMENTS

WO    WO-2013/096862 A2    6/2013

OTHER PUBLICATIONS

Gallien et al. Selected reaction monitoring applied to proteomics. J Mass Spectrom 2011, vol. 46, pp. 298-312. (Year: 2011).*
Lange et al. Selected reaction monitoring for quantitative proteomics: a tutorial. Molecular Systems Biology, 2008. vol. 4, No. 222, pp. 1-14. (Year: 2008).*
Cilento et al. Mass Spectrometry: A platform for biomarker discovery and validation for Alzheimer's adn Parkinson's diseases. Journal of Neurochemistry, 2019, vol. 151, pp. 397-416. (Year: 2018).*
Chen et al. Mass spectrometry quantification of clusterin in the human brain. Mol Neurodegener. Aug. 2012; vol. 7: No. 41, pp. 1-6. (Year: 2012).*
Cho et al., "Verification of a biomarker discovery approach for detection of Down syndrome in amniotic fluid via multiplex selected reaction monitoring (SRM) assay," J Proteomics, 74(10):2052-2059 (2011).
Dillen et al., "A screening UHPLC-MS/MS method for the analysis of amyloid peptides in cerebrospinal fluid of preclinical species," Biosciences Information Service, 3(1):45-55 (2011).
International Search Report issued for application No. PCT/US2013/031520, dated Aug. 9, 2013.
Kiyonami et al., "Increased Selectivity, Analytical Precision, and Throughput in Targeted Proteomics," Mol Cell Proteomics, 10(2):1-11 (2011).

* cited by examiner

*Primary Examiner* — Marcela M Cordero Garcia
(74) *Attorney, Agent, or Firm* — Foley Hoag LLP; Hathaway P. Russell

(57) ABSTRACT

Provided herein are methods for developing selected reaction monitoring mass spectrometry (LC-SRM-MS) assays.

16 Claims, No Drawings
Specification includes a Sequence Listing.

SRM METHODS IN ALZHEIMER'S DISEASE AND NEUROLOGICAL DISEASE ASSAYS

RELATED APPLICATIONS

This application is a continuation of U.S. Ser. No. 16/002,123, filed Jun. 7, 2018, which is a continuation of U.S. Ser. No. 15/355,213, filed Nov. 18, 2016, which is a continuation of U.S. application Ser. No. 14/390,447, filed Oct. 3, 2014, which is a national stage application, filed under 35 U.S.C. § 371, of International Application No. PCT/US2013/031520, filed on Mar. 14, 2013, which claims priority and benefit of U.S. Provisional Application No. 61/620,770, filed Apr. 5, 2012, the contents of each of which are incorporated by reference in their entirety.

SEQUENCE LISTING

The instant application contains a Sequence Listing which has been submitted electronically in ASCII format and is hereby incorporated by reference in its entirety. Said ASCII copy, created on Nov. 30, 2020, is named BDR-00605_SL.txt and is 259,366 bytes in size, is incorporated herein by reference in its entirety.

BACKGROUND

Liquid Chromatography Selected Reaction Monitoring Mass Spectrometry (LC-SRM-MS) has emerged as an alternative technology to immunoassays for quantification of target proteins in biological samples. LC-SRM-MS methods are highly desirable because LC-SRM-MS methods provide both absolute structural specificity for the target protein and relative or absolute measurement of the target protein concentration when suitable internal standards are utilized. In contrast to immunoassays, LC-SRM-MS does not involve the manufacturing of biologics. LC-SRM-MS protein assays can be rapidly and inexpensively developed in contrast to the development of immunoassays. LC-SRM-MS are highly multiplexed, with simultaneous assays for hundreds of proteins performed in a single sample analysis. Using LC-SRM-MS in contrast to other proteomic technologies allows for complex assays for the identification diagnostic proteins in complex diseases such as cancer, autoimmune, and metabolic disease. In particular, the development of a highly multiplexed LC-SRM-MS assay that reproducibly identifies a specific set of proteins relevant to a clinical disease presents diagnostic advantages and efficiencies. To date, proteomic techniques have not enabled such assays to exist where hundreds of proteins can be accurately quantified within a single sample. The present disclosure provides accurate measurement of hundreds of Alzheimer's disease associated proteins within a single sample using multiplexed techniques.

SUMMARY

The present disclosure provides a LC-SRM-MS assay for the measurement of at least 357 Alzheimer's disease associated proteins in a single sample and in a single LC-SRM-MS assay. The assay was optimized for protein quantification and minimal interference among proteins in the assay. This LC-SRM-MS assay is novel because measurement of a large number of proteins in a single sample specifically associated with Alzheimer's disease has not been accomplished. Simultaneous measurement of such a large number of proteins without interference among the proteins requires specific techniques to distinguish among the proteins. The current disclosure provides clinical utility as this assay was used for development of Alzheimer's disease diagnostic tests for the early detection of Alzheimer's disease, managing disease treatment, as well as testing for disease recurrence.

The object of the present disclosure is to provide improved methods for the use of LC-SRM-MS in the development of assays. Accordingly, provided herein is a method for developing peptides and transitions for a plurality of at least 200 proteins for a single sample selected reaction monitoring mass spectrometry (LC-SRM-MS) assay, including the steps of providing a set of 200 or more proteins; generating transitions for each protein; determining the Mascot score for SRM-triggered tandem mass spectrometry (MS/MS) spectra; performing collision energy optimization on the transitions; selecting peptides with transitions showing the greatest peak areas of their transitions; selecting a set of transitions for each peptide, wherein the transitions for each peptide have one of the four most intense b or y transition ions; the transitions for each peptide have m/z values of at least 30 m/z above or below those of the precursor ion; the transitions for each peptide do not interfere with transitions from other peptides; and the transitions represent transitions due to breakage of peptide bond at different sites of the protein.

In one embodiment of the method, each selected peptide in the set of peptides has a monoisotopic mass of 700-5000 Da; and does not contain a cysteine or a methionine or does not contain cysteine or methionine. In other embodiments, each selected peptide contains cysteine or methionine. In another embodiment, the transitions for each peptide have one of the four most intense b or y transition ions; have m/z values of at least 30 m/z above or below those of a precursor ion; do not interfere with transitions from other peptides; and represent transitions due to breakage of peptide bond at different sites of the protein.

In another embodiment of the method, the peptides do not include any peptide that is bounded by KK, KR, RK or RR (either upstream or downstream) in the corresponding protein sequence. Specifically, the amino acid is charged at pH 7.0. In another embodiment, each peptide of said set of peptides is unique to the corresponding protein. In yet another embodiment, the peptides do not include peptides which were observed in post-translational modified forms. In still another embodiment, each set of peptides is prioritized according to one or more of the following ordered set of criteria: unique peptides first, then non-unique; peptides with no observed post-translational modifications first, then those observed with post-translational modifications; peptides within the mass range 800-3500 Da first, then those outside of 800-3500 Da; and sorted by decreasing number of variant residues. In certain embodiments, the peptides are unique in that they only appear once among the peptides run in a single assay.

In one embodiment, each set of peptides is prioritized according to all of the ordered set of criteria. In another embodiment, each prioritized set of peptides contains 1-5 peptides.

In certain embodiments of the preceding methods, the two best peptides per protein and the two best transitions per peptide are selected based on experimental data resulting from LC-SRM-MS analysis of one or more of the following experimental samples: a biological disease sample, a biological control sample, and a mixture of synthetic peptides of interest. In a particular embodiment, the biological disease and biological control samples are processed using an immunodepletion method prior to LC-SRM-MS analysis. In another embodiment, the experimental samples contain internal standard peptides. In yet another embodiment, the LC-SRM-MS analysis method specifies a maximum of 7000 transitions, including transitions of the internal standard peptides and transitions. In other embodiments the method specifies a maximum of between 1000-7000, 2000-6000, 3000-5000 and about 3500 transitions.

In one embodiment of the method, the top two transitions per peptide are selected according to one or more of the following criteria the transitions exhibit the largest peak areas measured in either of the two biological experimental samples; the transitions are not interfered with by other ions; the transitions do not exhibit an elution profile that visually differs from those of other transitions of the same peptide; or the transitions are not beyond the detection limit of both of the two biological experimental samples.

In another embodiment of the method, the top two peptides per protein are selected according to one or more of the following criteria: one or more peptides exhibit two transitions and represent the largest combined peak areas of the two transitions; or one or more peptides exhibit one transition and represent the largest combined peak areas of the two transitions.

In another aspect, provided herein is an assay developed according to the foregoing method, and embodiments thereof.

In yet another aspect provided herein is the use of an assay developed according to the foregoing method, and embodiments thereof, to detect a plurality of at least 200 proteins in a single biological sample.

In another aspect, provided herein is an assay developed according to the foregoing method, and embodiments thereof.

The disclosure provides a use of a composition, as described above, for the development of an assay to detect a disease, disorder or condition in a mammal.

The disclosure provides a method comprising analyzing a composition, as described above, using mass spectrometry. The method can use selected reaction monitoring mass spectrometry.

DETAILED DESCRIPTION

The present disclosure relates to methods for developing peptides and transitions for a single sample selected reaction monitoring mass spectrometry (LC-SRM-MS) assay, generally comprising the steps of providing a set of proteins; identifying representative proteolytic peptides for each protein according to a set of criteria; identifying representative transitions for each peptide according to another set of criteria; and selecting the optimum peptides per protein and the optimum transitions per peptide.

Selected reaction monitoring mass spectrometry is capable of highly sensitive and accurate protein quantification based on the quantification of proteolytic peptides. In terms of clinical utility, mass spectrometry-based assays are often compared to immunoassays (e.g., Enzyme-Linked Immunosorbent Assay, or ELISA), which have the ability to quantify specific analytes in large sample sets (e.g., 96 or 384 samples in parallel microtitre plate-based format). Until recently, mass spectrometry-based protein assays were not able to match these sample sizes or quantitative accuracy. Considerable time and expense is required to generate and characterize antibodies required for immunoassays. Increasingly efficient LC-SRM-MS assays, therefore, may surpass immunoassays such as ELISA in the rapid development of clinically useful, multiplexed protein assays.

LC-SRM-MS is a highly selective method of tandem mass spectrometry which has the potential to effectively filter out all molecules and contaminants except the desired analyte(s). This is particularly beneficial if the analysis sample is a complex mixture which may comprise several isobaric species within a defined analytical window. LC-SRM-MS methods may utilize a triple quadrupole mass spectrometer which, as is known in the art, includes three quadrupole rod sets. A first stage of mass selection is performed in the first quadrupole rod set, and the selectively transmitted ions are fragmented in the second quadrupole rod set. The resultant transition (product) ions are conveyed to the third quadrupole rod set, which performs a second stage of mass selection. The product ions transmitted through the third quadrupole rod set are measured by a detector, which generates a signal representative of the numbers of selectively transmitted product ions. The RF and DC potentials applied to the first and third quadrupoles are tuned to select (respectively) precursor and product ions that have m/z values lying within narrow specified ranges. By specifying the appropriate transitions (m/z values of precursor and product ions), a peptide corresponding to a targeted protein may be measured with high degrees of sensitivity and selectivity. Signal-to-noise ratio in LC_SRM_MS is often superior to conventional tandem mass spectrometry (MS/MS) experiments, that do not selectively target (filter) particular analytes but rather aim to survey all analytes in the sample.

Accordingly, provided herein is a method for developing peptides and transitions for a plurality of proteins for use in selected reaction monitoring mass spectrometry (LC-SRM-MS) assay. In a preferred embodiment, the assay involves the analysis of a single sample containing all analytes of interest (e.g., a proteolytic digest of plasma proteins). As to the selection of the protease(s) used, trypsin, which cleaves exclusively C-terminal to arginine and lysine residues, is a preferred choice to generate peptides because the masses of generated peptides are compatible with the detection ability of most mass spectrometers (up to 2000 m/z), the number and average length of generated peptides, and also the availability of efficient algorithms for the generation of databases of theoretical trypsin-generated peptides. High cleavage specificity, availability, and cost are other advantages of trypsin. Other suitable proteases will be known to those of skill in the art. Miscleavage is a factor for failure or ambiguous protein identification. A miscleavage can be defined as partial enzymatic protein cleavages generating peptides with internal missed cleavage sites reflecting the allowed number of sites (targeted amino acids) per peptide that were not cut. The presence of post-translational modifications (PTMs) is also a potential contributor to the problem of miscleavages.

LC-SRM-MS mass spectrometry involves the fragmentation of gas phase ions and occurs between the different stages of mass analysis. There are many methods used to fragment the ions and these can result in different types of fragmentation and thus different information about the structure and composition of the molecule. The transition ions observed in an LC-SRM-MS spectrum result from several different factors, which include, but are not limited to, the primary sequence, the amount of internal energy, the means of introducing the energy, and charge state. Transitions must carry at least one charge to be detected. An ion is categorized as either a, b or c if the charge is on a transition comprising the original N terminus of the peptide, whereas the ion is categorized as either x, y or z if the charge is on a transition comprising the original C terminus of the peptide. A subscript indicates the number of residues in the transition (e.g., one peptide residue in $x_1$, two peptide residues in $y_2$, and three peptide residues in $z_3$, etc.).

In a generic peptide repeat unit represented —N—C(O)—C—, an x ion and an a ion resulting from cleavage of the carbonyl-carbon bond (i.e., C(O)—C). The x ion is an acylium ion, and the a ion is an iminium ion. A y ion and a b ion result from cleavage of the carbonyl-nitrogen bond (i.e., C(O)—N, also known as the amide bond). In this case, the y ion is an ammonium ion and the b ion is an acylium ion. Finally, a z ion and a c ion result from cleavage of the nitrogen-carbon (i.e., C—N) bond. The z ion is a carbocation and the c ion is an ammonium ion.

Superscripts are sometimes used to indicate neutral losses in addition to the backbone fragmentation, for example, * for loss of ammonia and ° for loss of water. In addition to protons, c ions and y ions may abstract an additional proton from the precursor peptide. In electrospray ionization, tryptic peptides may carry more than one charge.

Internal transitions arise from double backbone cleavage. These may be formed by a combination of b-type and y-type cleavage (i.e., cleavage producing b and y ions). Internal cleavage ions may also be formed by a combination of a-type and y-type cleavage. An internal transition with a single side chain formed by a combination of a-type and y-type cleavage is called an iminium ion (sometimes also referred to as an imonium or immonium ion). These ions are labeled with the one letter code for the corresponding amino acid.

Low energy CID (i.e., collision induced dissociation in a triple quadrupole or an ion trap) involves the fragmentation of a peptide carrying a positive charge, primarily along its backbone, to generate primarily a, b and y ions.

In one aspect, provided herein is a method for developing peptides and transitions for a plurality of proteins for a single sample selected reaction monitoring mass spectrometry (LC-SRM-MS) assay: (a) providing a panel or plurality of proteins; (b) identifying a set of peptides for each protein, wherein (i) each peptide in the set of peptides corresponds to a transition of said protein; (ii) the peptides have a monoisotopic mass of 700-5000 Da; and (iii) the peptides do not contain cysteine or does not contain cysteine or methionine. In other embodiments, each selected peptide contains cysteine or methionine; and; (c) identifying a set of transitions for each peptide, wherein (i) the transitions for each peptide have one of the four most intense b or y transition ions; (ii) the transitions for each peptide have m/z values of at least 30 m/z above or below those of the precursor ion; (iii) the transitions for each peptide do not interfere with transitions from other peptides; and (iv) the transitions represent transitions due to breakage of peptide bond at different sites of the protein; and (d) selecting the peptides for each protein that best fit the criteria of step (b) and the transitions per peptide that best fit the criteria of step (c); thereby developing peptides and transitions for a LC-SRM-MS assay.

By plurality of proteins it is meant that at least 2, 3, 4, 5, 6, 7, 8, 9, 10, 15, 20, 25, 50, 100, 150, 200, 250, 300, 400, 450, 500 or more proteins. In certain embodiments, the plurality of proteins can encompass between 2 and 10, 10 and 20, 20 and 50, 50 and 100, 100 and 200 or 200 and 500 proteins. In other embodiments, the plurality of proteins can encompass between 250 and 450; or 300 and 400 proteins.

Trypsin-like proteases cleave peptide bonds following a positively charged amino acid (e.g., lysine (K) or arginine (R)). This specificity is driven by the residue which lies at the base of the enzyme's S1 pocket (generally a negatively charged aspartic acid or glutamic acid). Accordingly, in one embodiment of the method, the peptides do not include any peptide that is bounded by KK, KR, RK or RR, either upstream of downstream in the corresponding protein sequence. In another embodiment, each peptide of said set of peptides is unique to the corresponding protein.

Post-translational modification (PTM) is the chemical modification of a protein after its translation. It can include any modification following translation, including cleavage. It is one of the later steps in protein biosynthesis, and thus gene expression, for many proteins. It is desirable to avoid such peptides for the purpose of protein identification. Thus, in another embodiment, the peptides do not include peptides which were observed in post-translational modified forms.

In still another embodiment, each set of peptides is prioritized according to one or more of the following ordered set of criteria: (a) unique peptides first, then non-unique; (b) peptides with no observed post-translational modifications first, then those observed with post-translational modifications; (c) peptides within the mass range 800-3500 Da first, then those outside of 800-3500 Da; and (d) sorted by decreasing number of variant residues. In one embodiment, each set of peptides is prioritized according to all of the ordered set of criteria. In another embodiment, each prioritized set of peptides contains 1-5 peptides.

In certain embodiments, one or more liquid chromatography (LC) purification steps are performed prior to a subsequent LC-SRM-MS analysis step. Traditional LC analysis relies on the chemical interactions between sample components and column packing materials, where laminar flow of the sample through the column is the basis for separation of the analyte of interest from the test sample. The skilled artisan will understand that separation in such columns is a diffusional process. A variety of column packing materials are available for chromatographic separation of samples, and selection of an appropriate separation protocol is an empirical process that depends on the sample characteristics, the analyte of interest, the interfering substances present and their characteristics, etc. Various packing chemistries can be used depending on the needs (e.g., structure, polarity, and solubility of compounds being purified). In various embodiments the columns are polar, ion exchange (both cation and anion), hydrophobic interaction, phenyl, C-2, C-8, C-18 columns, polar coating on porous polymer, or others that are commercially available. During chromatography, the separation of materials is effected by variables such as choice of eluant (also known as a "mobile phase"), choice of gradient elution and the gradient conditions, temperature, etc. In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. As discussed above, such procedures may enrich the amount of one or more analytes of interest relative to one or more other components of the sample.

The following parameters are used to specify an LC-SRM-MS assay of a protein under a particular LC-SRM-MS system: (1) a tryptic peptide of the protein; (2) the retention time (RT) of the peptide; (3) the m/z value of the peptide precursor ion; (4) the declustering potential used to ionize the precursor ion; (5) m/z value of a fragment ion generated from the peptide precursor ion; and (6) the collision energy (CE) used to fragment the peptide precursor ion that is optimized for the particular peptide.

In certain embodiments of the preceding methods, the two best peptides per protein and the two best transitions per peptide are selected based on experimental data resulting from LC-SRM-MS analysis of one or more of the following experimental samples: a biological disease sample, a biological control sample, and a mixture of synthetic peptides of interest. Biological samples include body fluids, tissue samples and cell samples. Body fluid samples can include blood, serum, sputum, genital secretions, cerebrospinal fluid, sweat or excreta such as urine. Body tissue samples can include lung, skin, brain, spine, bone, muscle, epithelial, liver, kidney, pancreas, gastrointestinal tract, cardiovascular tissue, heart or nervous tissue. Biological disease samples can include cancer, benign tumors, infected tissue and tissue subject to trauma. In a particular embodiment, the biological disease and biological control samples are processed using an immunodepletion method prior to LC-SRM-MS analysis. Immunodepletion involves removal of one or more proteins through the use of antibodies. Numerous immunodepletion techniques are known to those of skill in the art. In another embodiment, the biological disease and biological control samples are processed using an immunocapture method prior to LC-SRM-MS analysis. Immunocapture involves selection of one or more proteins through the use of antibodies. Numerous immunocapture techniques are known to those of skill in the art.

To facilitate accurate quantification of the peptide transitions by the methods disclosed herein, a set of isotopically-labeled synthetic versions of the peptides of interest may be added in known amounts to the sample for use as internal standards. Since the isotopically-labeled peptides have physical and chemical properties identical to the corresponding surrogate peptide, they co-elute from the chromatographic column and are easily identifiable on the resultant mass spectrum. The addition of the labeled standards may occur before or after proteolytic digestion. Methods of synthesizing isotopically-labeled peptides will be known to those of skill in the art. Thus, in another embodiment, the experimental samples contain internal standard peptides. Other embodiments may utilize external standards or other expedients for peptide quantification.

In yet another embodiment, the LC-SRM-MS analysis method specifies a maximum of 7000 transitions, including transitions of the internal standard peptides and transitions. As used herein, the term "transition" refers to the specific pair of m/z (mass-to-charge) values associated with the precursor and transition ions corresponding to a specific peptide and, therefore, to a specific protein.

In one embodiment of the method, the top two transitions per peptide are selected according to one or more of the following criteria (A): (1) the transitions exhibit the largest peak areas measured in either of the two biological experimental samples; (2) the transitions are not interfered with by other ions; (3) the transitions do not exhibit an elution profile that visually differs from those of other transitions of the same peptide; (4) the transitions are not beyond the detection limit of both of the two biological experimental samples; (5) the transitions do not exhibit interferences.

For the mass spectrometric analysis of a particular peptide, the quantities of the peptide transitions in the sample may be determined by integration of the relevant mass spectral peak areas, as known in the prior art. When isotopically-labeled internal standards are used, as described above, the quantities of the peptide transitions of interest are established via an empirically-derived or predicted relationship between peptide transition quantity (which may be expressed as concentration) and the area ratio of the peptide transition and internal standard peaks at specified transitions.

In another embodiment of the method, the top two peptides per protein are selected according to one or more of the following criteria (B): (1) one or more peptides exhibit two transitions according to criteria (A) and represent the largest combined peak areas of the two transitions according to criteria (A); and (2) one or more peptides exhibit one transition according to criteria (A) and represent the largest combined peak areas of the two transitions according to criteria (A).

Assays

The methods of the present disclosure allow the quantification of high abundance and low abundance plasma proteins that serve as detectable markers for various health states (including diseases and disorders), thus forming the basis for assays that can be used to determine the differences between normal levels of detectable markers and changes of such detectable markers that are indicative of changes in health status. In one aspect of the disclosure, provided herein is an assay developed according to the foregoing method, and embodiments thereof. In another aspect, provided herein is the use of an assay developed according to the foregoing method, and embodiments thereof, to detect a plurality of at least 200, 300 or more proteins in a single sample.

Definitions

As used herein, "transition" refers to a pair of m/z values associated with a peptide. Normally, labeled synthetic peptides are used as quality controls in SRM assays. However, for very large SRM assays, labeled peptides are not feasible. However, correlation techniques (Keary, Butler et al. 2008) were used to confirm the identity of protein transitions with high confidence. The correlation between a pair of transitions is obtained from their expression profile over all samples in the training set study detailed below. As expected, transitions from the same peptide are highly correlated. Similarly, transitions from different peptide fragments of the same protein are also highly correlated. In contrast, transitions form different proteins are not highly correlated. This methodology enables a statistical analysis of the quality of the protein's SRM assay. For example, if the correlation of the transitions from the two peptides from the same protein is above 0.5 then there is less than a 5% probability that the assay is false As used herein, a "tryptic peptide" refers to the peptide that is formed by the treatment of a protein with trypsin.

As used herein, "RT" refers to "retention time", the elapsed time between injection and elution of an analyte.

As used herein, "m/z" indicates the mass-to-charge ratio of an ion.

As used herein "DP" refers to the "declustering potential", a voltage potential to dissolvate and dissociate ion clusters. It is also known as "fragmentor voltage" or "ion transfer capillary offset voltage" depending upon the manufacturer.

As used herein, "CE" refers to "collision energy", the amount of energy precursor ions receive as they are accelerated into the collision cell.

As used herein, "LC-SRM-MS" is an acronym for "selected reaction monitoring" and may be used interchangeably with "LC-MRM-MS".

As used herein, "MS/MS" represents tandem mass spectrometry, which is a type of mass spectrometry involving multiple stages of mass analysis with some form of fragmentation occurring in between the stages.

As used herein, "ISP" refers to "internal standard peptides".

As used herein, "HGS" refers to "human gold standard", which is comprised of a pool of plasma from healthy individuals.

As used herein, "MGF" refers to "Mascot generic file". Mascot is a search engine that uses mass spectrometry data to identify proteins from primary sequence databases. A Mascot generic file is a plain text (ASCII) file containing peak list information and, optionally, search parameters.

Mascot is a tool for assessing mass spectrometry data against protein sequences. This data can be acquired from any mass spectrometry technique including MALDI-TOF and electrospray ionization MS (including LC-SRM-MS) data. Mascot uses a 'probability-based MOWSE' algorithm to estimate the significance of a match (i.e., that the observed transitions correspond to a particular protein). The total score is the absolute probability that the observed match is a random event. They are reported as −10×LOG 10(P), where P is the absolute probability. Lower probabilities, therefore, are reported as higher scores. For example, if the absolute probability that an observed match is random is $1 \times 10^{-12}$, Mascot reports it as 120.

The disclosure also provides compositions. These compositions can include any of the transition ions described in Table II. These transition ions exist while peptides derived from the proteins in Table II are undergoing analysis with LC-SRM-MS. In one embodiment, the composition includes any of the transition ions described in Table II. In another embodiment, the composition includes any two transition ions described in Table II. In other embodiments, the composition includes, any 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300 or 331 transition ions described in Table II.

In another embodiment, each of the transition ions in the composition corresponds and/or is derived from a different protein. In another embodiment, 90% of the transition ions in the composition correspond with and/or are derived from a protein that no other transition ion in the composition corresponds. In other embodiments, 80, 70, 60, 50, 40, 30, 20, 10 or 0% of the transition ions in the composition correspond and/or are derived from a protein that no other transition ion in the composition corresponds.

The compositions described herein included synthetic peptides. Synthetic peptides can be used as controls for the abundance of proteins they are derived from and/or correspond. In certain embodiments, the abundance of the synthetic peptides is defined and the results are compared to LC-SRM-MS results from a peptide found in a sample to the LC-SRM-MS results in the corresponding synthetic peptide. This allows for the calculation of the abundance of the peptide in the sample. In certain embodiments, by knowing the abundance of a peptide in a sample, the abundance of the protein it corresponded to is determined.

Synthetic peptides can be generated using any method known in the art. These methods can include recombinant expression techniques such as expression in bacteria or in vitro expression in eukaryotic cell lysate. These methods can also include solid phase synthesis.

In one embodiment, the composition includes synthetic peptides selected from any of the peptides described in Table II. In another embodiment, the composition included any two peptides described in Table II. In other embodiments, the composition included, any 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 331 or more peptides described in Table II.

In another embodiment, each of the peptides in the composition each corresponds with a different protein. In another embodiment, 90% of the peptides in the composition correspond with a protein that no other peptide in the composition corresponds with. In other embodiments, 80, 70, 60, 50, 40, 30, 20, 10 or 0% of the peptides in the composition correspond with from a protein that no other peptide in the composition corresponds with.

The peptides can be isotopically labeled. The isotopes with which they can be labeled include $^{13}C$, $^{2}H$, $^{15}N$ and $^{18}O$. The peptides can also include a polar solvent. Polar solvents can include water and mixtures of ethanol and water.

In certain embodiments, the samples described herein are taken from mammals. These mammals include rats, mice, rabbits, dogs, non-human primates and humans. Samples can be isolated from any tissue or organ or from any bodily fluid. Organs from which samples can be taken include skin, heart, lung, brain, kidney, liver, pancreas, spleen, testes, ovaries, gall bladder, thymus, thyroid, eye, ear, nose, mouth, tongue, penis, vagina, bladder or larynx. Tissues include nervous tissue, vascular tissue, muscle, bone, gastrointestinal tract, epithelial tissue, fibroblastic tissue, mucous membranes, hair, skin, reproductive tissue and connective tissue. Body fluids and excretions include, blood, serum, saliva, urine, semen, vaginal secretions, excrement, bile, tears, lymph, ear wax, mucous, shed skin, finger nails, toe nails, skin oils, sweat and dandruff.

The relative abundance of one or more of the proteins represented by the transition ions and synthetic peptides described above can be used to diagnose, determine likelihood of the presence of, develop prognoses for and/or stage various diseases and pathologies. Often the organ, tissue or bodily fluid or excretion from which the sample is taken is distinct from the organ, tissue or bodily fluid or excretion involved with the disease or pathology. For example, the presence of Alzheimer's disease can be determined from a sample taken from blood. Any type of body fluid may be used in the assays.

Diseases and pathologies that status, diagnosis, presence or prognosis can be found using the transition ions and/or synthetic peptides described herein include cancer, metabolic diseases, neurological disorders, infectious diseases and cardiovascular disorders.

EXAMPLES

I. Exemplary Standard Operating Procedure

Protein Selection

Proteins known to be over-expressed or under-expressed in Alzheimer's disease patients were obtained (through literature searching, experimental data or proprietary databases) as shown in Table I. The set of proteins was reduced to a set of 357 proteins (see Table II) by prioritizing those proteins that have been previously detected my LC-MS/MS in blood (serum or plasma).

Selected proteins were then identified by their UniProt protein name and accession, their Entrez gene symbol and gene name, the isoform accession and their amino acid sequence. The canonical isoform in UniProt was selected if a protein has more than one isoform.

Peptide Selection for Synthesis

The five best peptides per protein for LC-SRM-MS assay were selected for as follows. Fully tryptic peptides having a monoisotopic mass of 800-3500 mass units, without miscleavages, not containing a cysteine (C) or a methionine (M), without having high miscleavage probability were selected. Further, any peptide that was bounded by KK, KR, RK or RR (either upstream or downstream) in the corresponding protein sequence was not selected.

Peptides were selected that were unique to the protein of interest. Peptides were only selected that match only one protein or protein family including analogues of the one protein, when searched in protein databases. Further, peptides which were observed in post-translational modified forms were not selected. Databases were assessed that showed expression of the proteins from which the peptides were isolated in human blood. Also databases of good quality MS peptides were searched. Peptides that appeared in human blood and were good quality MS peptides were favored. If these methods did not result in a sufficient number of peptides, rules were relaxed in a step wise manner to allow a greater number of peptides until a sufficient number was reached. The purity of the synthesized peptides was >75% and the amount of material was ≥25 µg. Peptides did not need to be desalted.

The four best transitions per peptide are then selected and optimized based on experimental results from a mixture of synthetic peptides. LC-SRM-MS-triggered MS/MS spectra was acquired for each synthetic peptide, using a QTRAP 5500 instrument. One spectrum or the doubly—and one for the triply—charged precursor ion was collected for each of the identified peptides (Mascot score ≥15), retention time was recorded for the four most intense b or y transition ions. The selected transition ions possessed m/z values were at least 30 m/z above or below those of the precursor ions; they did not interfere with other synthetic peptides; and they were transition ions due to breakage of peptide bond at different sites.

If an insufficient percentage of the synthetic peptides were acquired, the steps were repeated. In some cases, the second transition with first with theoretical y+ ions with m/z values at least 30 m/z above those of the doubly charged precursor ion was selected if an insufficient percentage was acquired. Peptides that failed to trigger the acquisition of MS/MS spectrum were discarded.

II. Exemplary Protein List

The abundance of the following proteins can be assessed substantially simultaneously using the MS-LC-SRM-MS system described herein. Transitions from these proteins can be used to diagnose diseases including Alzheimer's disease when their abundance is measured in a biological specimen from a subject to be diagnosed for Alzheimer's disease. In one embodiment, the abundances of these proteins are measure in the blood serum of the subject.

Lengthy table referenced here

US11467167-20221011-T00001

Please refer to the end of the specification for access instructions.

Lengthy table referenced here

US11467167-20221011-T00002

Please refer to the end of the specification for access instructions.

Lengthy table referenced here

US11467167-20221011-T00003

Please refer to the end of the specification for access instructions.

VI. Exemplary Assayed Protein

The expression of the following 357 proteins were assessed substantially simultaneously using the MS-LC-SRM-MS system described herein.

41_HUMAN
5HT2C_HUMAN
A1AG1_HUMAN
A1AG2_HUMAN
A1BG_HUMAN
A2MG_HUMAN
A4_HUMAN
AACT_HUMAN
ABCA1_HUMAN
ACBD7_HUMAN
ACE2_HUMAN
ACHA2_HUMAN
ACHA4_HUMAN
ACHA5_HUMAN
ACHB_HUMAN
ACHB2_HUMAN
ADA12_HUMAN
ADA23_HUMAN
AFAM_HUMAN
AGAL_HUMAN
AGAP2_HUMAN
ALBU_HUMAN
ALS_HUMAN
AMFR2_HUMAN
AMNLS_HUMAN
AMPB_HUMAN
ANGP1_HUMAN
ANGT_HUMAN
ANO3_HUMAN
ANT3_HUMAN
AP1B1_HUMAN
APC2_HUMAN
APLP1_HUMAN
APOA1_HUMAN
APOA2_HUMAN
APOA4_HUMAN
APOB_HUMAN
APOC2_HUMAN
APOD_HUMAN

APOE_HUMAN
APOL4_HUMAN
APOOL_HUMAN
ARHG7_HUMAN
ARP21_HUMAN
ARSA_HUMAN
ARSE_HUMAN
ARTN_HUMAN
ASGR1_HUMAN
AT12A_HUMAN
AT2A2_HUMAN
AT2B3_HUMAN
ATS1_HUMAN
BAX_HUMAN
BCAS1_HUMAN
BDNF_HUMAN
BEST1_HUMAN
BTNL8_HUMAN
C1QL2_HUMAN
C1QT4_HUMAN
CACB2_HUMAN
CAD11_HUMAN
CAD19_HUMAN
CAD22_HUMAN
CADH3_HUMAN
CADH5_HUMAN
CADH7_HUMAN
CALL3_HUMAN
CAMKV_HUMAN
CAR14_HUMAN
CATD_HUMAN
CB080_HUMAN
CB085_HUMAN
CBPN_HUMAN
CD3D_HUMAN
CD72_HUMAN
CEL3A_HUMAN
CEL3B_HUMAN
CERU_HUMAN
CETP_HUMAN
CF072_HUMAN
CFAB_HUMAN
CFAH_HUMAN
CHAD_HUMAN
CK041_HUMAN
CLC4M_HUMAN
CLUS_HUMAN
CNTN1_HUMAN
CNTN2_HUMAN
CO1A2_HUMAN
CO2_HUMAN
CO3_HUMAN
CO4A_HUMAN
CO4A4_HUMAN
CO4B_HUMAN
CO6_HUMAN
CO8A_HUMAN
CO9A2_HUMAN
COIA1_HUMAN
CORT_HUMAN
CP46A_HUMAN
CPLX2_HUMAN
CRLF1_HUMAN
CRUM1_HUMAN
CSF1_HUMAN
CSF1R_HUMAN
DBC1_HUMAN
DCBD1_HUMAN
DCBD2_HUMAN
DDR2_HUMAN
DIRA2_HUMAN
E41L3_HUMAN
EAA2_HUMAN
EDNRB_HUMAN
ELAV3_HUMAN
EMIL2_HUMAN
EMIL3_HUMAN
EPHA8_HUMAN
ERLN1_HUMAN
ERMIN_HUMAN
ERO1B_HUMAN
F123A_HUMAN
F13A_HUMAN
FA20A_HUMAN
FCGRN_HUMAN
FETUA_HUMAN
FEZ1_HUMAN
FGFR2_HUMAN
FGFR3_HUMAN
FGL1_HUMAN
FIBA_HUMAN
FIBB_HUMAN
FIBG_HUMAN
FINC_HUMAN
FRS2_HUMAN
GABR2_HUMAN
GALR3_HUMAN
GAS6_HUMAN
GBRA2_HUMAN
GBRB2_HUMAN
GELS_HUMAN
GFRA2_HUMAN
GNAQ_HUMAN
GOLM1_HUMAN
GOPC_HUMAN
GP113_HUMAN
GP125_HUMAN
GP158_HUMAN
GP2_HUMAN
GPC5_HUMAN
GPC5D_HUMAN
GPC6_HUMAN
GPR88_HUMAN
GRIA2_HUMAN
GRM5_HUMAN
GRN_HUMAN
GT253_HUMAN
HAS1_HUMAN
HCN1_HUMAN
HCN2_HUMAN
HEMO_HUMAN
HEP2_HUMAN
HPCA_HUMAN
HPT_HUMAN
HRG_HUMAN
HS3S5_HUMAN
I12R1_HUMAN
IC1_HUMAN
ICAM3_HUMAN
IGF1R_HUMAN
IL12B_HUMAN
IL1AP_HUMAN
IL1R2_HUMAN
INADL_HUMAN

INHBA_HUMAN
IPSP_HUMAN
ITA3_HUMAN
ITAM_HUMAN
ITB2_HUMAN
ITB5_HUMAN
ITIH1_HUMAN
ITIH2_HUMAN
ITIH3_HUMAN
ITIH4_HUMAN
JPH3_HUMAN
KAIN_HUMAN
KALRN_HUMAN
KCC1G_HUMAN
KCC2A_HUMAN
KCNA1_HUMAN
KCNA2_HUMAN
KCNA3_HUMAN
KCNA5_HUMAN
KCNQ1_HUMAN
KCNV2_HUMAN
KCTD4_HUMAN
KIF5A_HUMAN
KIRR2_HUMAN
KLK3_HUMAN
KLKB1_HUMAN
KNG1_HUMAN
KSYK_HUMAN
LAMB2_HUMAN
LAT2_HUMAN
LAT3_HUMAN
LCK_HUMAN
LCN8_HUMAN
LGI1_HUMAN
LGMN_HUMAN
LIPE_HUMAN
LRMP_HUMAN
LRP8_HUMAN
LRTM2_HUMAN
LSHR_HUMAN
LTBP1_HUMAN
LYG2_HUMAN
MAMC2_HUMAN
MAP4_HUMAN
MICA_HUMAN
MMP1_HUMAN
MMP16_HUMAN
MMP17_HUMAN
MMP20_HUMAN
MMP24_HUMAN
MMP9_HUMAN
MOT2_HUMAN
MPDZ_HUMAN
MTOR_HUMAN
MYP2_HUMAN
NCAN_HUMAN
NCKX2_HUMAN
NDF6_HUMAN
NECP2_HUMAN
NETO1_HUMAN
NETR_HUMAN
NEUG_HUMAN
NEUM_HUMAN
NFL_HUMAN
NKX62_HUMAN
NMDE1_HUMAN
NMDE3_HUMAN
NMDZ1_HUMAN
NMS_HUMAN
NOE3_HUMAN
NPT4_HUMAN
NPTX1_HUMAN
NRG3_HUMAN
NTRK2_HUMAN
ODP2_HUMAN
OLFL3_HUMAN
OLIG1_HUMAN
OPCM_HUMAN
OTOAN_HUMAN
P2RX1_HUMAN
P4K2A_HUMAN
PACN1_HUMAN
PAK3_HUMAN
PAQR6_HUMAN
PAR6B_HUMAN
PARD3_HUMAN
PARK7_HUMAN
PCD18_HUMAN
PCDA5_HUMAN
PCDAA_HUMAN
PCDB6_HUMAN
PCDB7_HUMAN
PCDBC_HUMAN
PCDBF_HUMAN
PCDGE_HUMAN
PCDGF_HUMAN
PCSK1_HUMAN
PDIA2_HUMAN
PDYN_HUMAN
PEDF_HUMAN
PERL_HUMAN
PGCB_HUMAN
PGCP_HUMAN
PICAL_HUMAN
PIN1_HUMAN
PKDRE_HUMAN
PLCB1_HUMAN
PON1_HUMAN
PRIO_HUMAN
PSMG1_HUMAN
PTN5_HUMAN
PTPRB_HUMAN
PTPRO_HUMAN
PTPRT_HUMAN
PVRL1_HUMAN
PZP_HUMAN
RCN1_HUMAN
RELN_HUMAN
RES18_HUMAN
RGS11_HUMAN
RGS20_HUMAN
RGS4_HUMAN
RRAGC_HUMAN
RUN3A_HUMAN
S12A5_HUMAN
S12A6_HUMAN
S15A2_HUMAN
S39A4_HUMAN
SAA4_HUMAN
SCG1_HUMAN
SCG3_HUMAN
SCN2A_HUMAN
SCNNA_HUMAN
SCRT1_HUMAN

| | |
|---|---|
| SEM4A_HUMAN | TAU_HUMAN |
| SEMG1_HUMAN | TBB2B_HUMAN |
| SEPP1_HUMAN | TERA_HUMAN |
| SEPT3_HUMAN | TFR2_HUMAN |
| SGCZ_HUMAN | TLR7_HUMAN |
| SHSA7_HUMAN | TM9S1_HUMAN |
| SIA8C_HUMAN | TMPS2_HUMAN |
| SIG12_HUMAN | TNF6B_HUMAN |
| SIX3_HUMAN | TNR19_HUMAN |
| SLIK1_HUMAN | TR11B_HUMAN |
| SLIT1_HUMAN | TRFR_HUMAN |
| SNP25_HUMAN | TRIM9_HUMAN |
| SNTB1_HUMAN | TRPV5_HUMAN |
| SO1A2_HUMAN | TYRO_HUMAN |
| SO1B3_HUMAN | UGGG2_HUMAN |
| SPB5_HUMAN | UNC5C_HUMAN |
| SREC_HUMAN | VGFR3_HUMAN |
| STH_HUMAN | VTDB_HUMAN |
| SYN2_HUMAN | VTNC_HUMAN |
| SYNPR_HUMAN | WNK4_HUMAN |
| SYTL4_HUMAN | WNT8B_HUMAN |
| SYUA_HUMAN | XLRS1_HUMAN |
| SYUB_HUMAN | YQ051_HUMAN |
| T151A_HUMAN | ZIC1_HUMAN |
| TADBP_HUMAN | ZIC2_HUMAN |

LENGTHY TABLES

The patent contains a lengthy table section. A copy of the table is available in electronic form from the USPTO web site (https://seqdata.uspto.gov/?pageRequest=docDetail&DocID=US11467167B2). An electronic copy of the table will also be available from the USPTO upon request and payment of the fee set forth in 37 CFR 1.19(b)(3).

The invention claimed is:

1. A multiplexed LC-SRM-MS assay for the measurement of a plurality of Alzheimer's disease associated proteins in a single sample comprising:
   a) generating a set of optimal peptides and corresponding transitions for each protein monitored;
   b) optimizing the collision energy for each transition such that interference among the transitions monitored is avoided;
   c) selecting a set of transitions that have the greatest peak areas are monitored for each of the proteins, and wherein the selected transitions do not interfere with the ions in the sample;
   d) monitoring the detected set of transitions for each protein in the sample, there by measuring a plurality of proteins in the sample.

2. The assay of claim 1, wherein each monitored peptide
   (i) has a monoisotopic mass of 700-5000 Da; and
   (ii) does not contain a cysteine or a methionine.

3. The assay of claim 1, wherein the transitions for each peptide
   (i) have one of the four most intense b or y transition ions;
   (ii) has m/z values of at least 30 m/z above or below those of a precursor ion;
   (iii) do not interfere with transitions from other peptides; and
   (iv) represent transitions due to breakage of peptide bond at different sites of the protein.

4. The assay according to claim 1, wherein the peptides do not include any peptide that is bounded by KK, KR, RK or RR, either upstream or downstream in the corresponding protein sequence.

5. The assay according to claim 1, wherein each peptide of said set of peptides is unique to the corresponding protein.

6. The assay according to claim 1, wherein the peptides do not include peptides which were observed in post-translational modified forms.

7. The assay according to claim 1, wherein each set of peptides is prioritized according to one or more of the following ordered set of criteria:

(a) unique peptides first, then non-unique;
(b) peptides with no observed post-translational modifications first, then those observed with post-translational modifications;
(c) peptides within the mass range 800-3500 Da first, then those outside of 800-3500 Da; and
(d) sorted by decreasing number of variant residues.

8. The assay according to claim 7, wherein each set of peptides is prioritized according to all of the ordered set of criteria.

9. The assay according to claim 1, wherein each prioritized set of peptides contains 1-5 peptides.

10. The assay according to claim 1, wherein the two best peptides per protein and the two best transitions per peptide are selected based on experimental data resulting from LC-SRM-MS analysis of one or more of the following experimental samples: a biological disease sample, a biological control sample, and a mixture of synthetic peptides of interest.

11. The assay according to claim 10, wherein the biological disease and biological control samples are processed using an immunodepletion method prior to LC-SRM-MS analysis.

12. The assay according to claim 11, wherein the experimental samples contain internal standard peptides.

13. The assay according to claim 11, wherein the LC-SRM-MS analysis method specifies a maximum of 7000 transitions, including transitions of the internal standard peptides and transitions.

14. The assay according to claim 1, wherein the top two transitions per peptide are selected according to one or more of the following criteria:
   (1) the transitions exhibit the largest peak areas measured in either of the two biological experimental samples;
   (2) the transitions are not interfered with by other ions;
   (3) the transitions do not exhibit an elution profile that visually differs from those of other transitions of the same peptide;
   (4) the transitions are not beyond the detection limit of both of the two biological experimental samples; and
   (5) the transitions do not exhibit interferences.

15. The assay according to claim 1, wherein the top two peptides per protein are selected according to one or more of the following criteria:
   (1) one or more peptides exhibit two transitions according to claim 12 and represent the largest combined peak areas of the two transitions according to claim 12; and
   (2) one or more peptides exhibit one transition according to claim 12 and represent the largest combined peak areas of the two transitions according to claim 12.

16. A diagnostic assay developed according to the method of claim 1.

* * * * *

```
                       SEQUENCE LISTING

<160> NUMBER OF SEQ ID NOS: 1460

<210> SEQ ID NO 1
<211> LENGTH: 19
<212> TYPE: PRT
<213> ORGANISM: Homo sapiens

<400> SEQUENCE: 1

Gly Ser Leu Val Gln Ala Ser Glu Ala Asn Leu Gln Ala Ala Gln Asp
1               5                   10                  15

Phe Val Arg

<210> SEQ ID NO 2
<211> LENGTH: 12
<212> TYPE: PRT
<213> ORGANISM: Homo sapiens

<400> SEQUENCE: 2

Thr Ser Leu Glu Asp Phe Tyr Leu Asp Glu Glu Arg
1               5                   10

<210> SEQ ID NO 3
<211> LENGTH: 15
<212> TYPE: PRT
<213> ORGANISM: Homo sapiens

<400> SEQUENCE: 3
```

```
Leu Ile Ala Leu Thr Leu Leu Gly Met Gly Leu Ala Leu Phe Arg
1               5                   10                  15
```

<210> SEQ ID NO 4
<211> LENGTH: 15
<212> TYPE: PRT
<213> ORGANISM: Homo sapiens

<400> SEQUENCE: 4

```
Glu Val Gln Gly Phe Glu Ser Ala Thr Phe Leu Gly Tyr Phe Lys
1               5                   10                  15
```

<210> SEQ ID NO 5
<211> LENGTH: 15
<212> TYPE: PRT
<213> ORGANISM: Homo sapiens

<400> SEQUENCE: 5

```
Leu Tyr Leu Val Gln Gly Thr Gln Val Tyr Val Phe Leu Thr Lys
1               5                   10                  15
```

<210> SEQ ID NO 6
<211> LENGTH: 12
<212> TYPE: PRT
<213> ORGANISM: Homo sapiens

<400> SEQUENCE: 6

```
Leu Gln Ser Leu Phe Asp Ser Pro Asp Phe Ser Lys
1               5                   10
```

<210> SEQ ID NO 7
<211> LENGTH: 14
<212> TYPE: PRT
<213> ORGANISM: Homo sapiens

<400> SEQUENCE: 7

```
Gln Ser Leu Phe Phe Tyr Pro Ser Tyr Pro Asp Glu Val Arg
1               5                   10
```

<210> SEQ ID NO 8
<211> LENGTH: 14
<212> TYPE: PRT
<213> ORGANISM: Homo sapiens

<400> SEQUENCE: 8

```
Ile Tyr Ile Ser Gly Met Ala Pro Arg Pro Ser Leu Ala Lys
1               5                   10
```

<210> SEQ ID NO 9
<211> LENGTH: 11
<212> TYPE: PRT
<213> ORGANISM: Homo sapiens

<400> SEQUENCE: 9

```
Leu Ile Ala Ser Met Ser Ser Asp Ser Leu Arg
1               5                   10
```

<210> SEQ ID NO 10
<211> LENGTH: 11
<212> TYPE: PRT
<213> ORGANISM: Homo sapiens

<400> SEQUENCE: 10

```
Leu Ile His Gln Leu Leu Thr Asp Ile Gly Arg
1               5                   10
```

```
<210> SEQ ID NO 11
<211> LENGTH: 15
<212> TYPE: PRT
<213> ORGANISM: Homo sapiens

<400> SEQUENCE: 11

Glu Ala Leu Ile Gln Phe Leu Glu Gln Val His Gln Gly Ile Lys
1               5                   10                  15

<210> SEQ ID NO 12
<211> LENGTH: 11
<212> TYPE: PRT
<213> ORGANISM: Homo sapiens

<400> SEQUENCE: 12

Glu Leu Asp Glu Ser Leu Gln Val Ala Glu Arg
1               5                   10

<210> SEQ ID NO 13
<211> LENGTH: 10
<212> TYPE: PRT
<213> ORGANISM: Homo sapiens

<400> SEQUENCE: 13

Ala Leu Val Gln Gln Met Glu Gln Leu Arg
1               5                   10

<210> SEQ ID NO 14
<211> LENGTH: 11
<212> TYPE: PRT
<213> ORGANISM: Homo sapiens

<400> SEQUENCE: 14

Phe Tyr Asn Gln Val Ser Thr Pro Leu Leu Arg
1               5                   10

<210> SEQ ID NO 15
<211> LENGTH: 12
<212> TYPE: PRT
<213> ORGANISM: Homo sapiens

<400> SEQUENCE: 15

Phe Thr Tyr Asp Leu Tyr Leu Val Thr Asn Gly Lys
1               5                   10

<210> SEQ ID NO 16
<211> LENGTH: 12
<212> TYPE: PRT
<213> ORGANISM: Homo sapiens

<400> SEQUENCE: 16

Asp Ile Tyr Pro Ser Val Ser Leu Gln Ile Gln Lys
1               5                   10

<210> SEQ ID NO 17
<211> LENGTH: 13
<212> TYPE: PRT
<213> ORGANISM: Homo sapiens

<400> SEQUENCE: 17

Ala Tyr Pro Phe Tyr Trp Ala Trp Leu Pro Gln Ala Lys
1               5                   10
```

-continued

```
<210> SEQ ID NO 18
<211> LENGTH: 23
<212> TYPE: PRT
<213> ORGANISM: Homo sapiens

<400> SEQUENCE: 18

Glu Ser Asp His Phe Ser Thr Glu Leu Asp Asp Ile Thr Val Thr Asp
1               5                   10                  15

Thr Tyr Leu Ser Ala Thr Lys
            20

<210> SEQ ID NO 19
<211> LENGTH: 22
<212> TYPE: PRT
<213> ORGANISM: Homo sapiens

<400> SEQUENCE: 19

Thr Pro Gly Ala Ala Ala Asn Leu Glu Leu Ile Phe Val Gly Pro Gln
1               5                   10                  15

His Ala Gly Asn Tyr Arg
            20

<210> SEQ ID NO 20
<211> LENGTH: 15
<212> TYPE: PRT
<213> ORGANISM: Homo sapiens

<400> SEQUENCE: 20

Ala Glu Ala Leu Pro Pro Glu Ala Ala Asp Glu Gly Gly Pro Arg
1               5                   10                  15

<210> SEQ ID NO 21
<211> LENGTH: 17
<212> TYPE: PRT
<213> ORGANISM: Homo sapiens

<400> SEQUENCE: 21

Val Ile Pro Gly Pro Pro Ala Leu Thr Leu Val Pro Ala Glu Leu Val
1               5                   10                  15

Arg

<210> SEQ ID NO 22
<211> LENGTH: 16
<212> TYPE: PRT
<213> ORGANISM: Homo sapiens

<400> SEQUENCE: 22

Leu Leu Gln Ala Leu Glu Ala Pro Glu Gly Trp Gly Pro Thr Pro Arg
1               5                   10                  15

<210> SEQ ID NO 23
<211> LENGTH: 10
<212> TYPE: PRT
<213> ORGANISM: Homo sapiens

<400> SEQUENCE: 23

Leu Glu Thr Pro Asp Phe Gln Leu Phe Lys
1               5                   10

<210> SEQ ID NO 24
<211> LENGTH: 18
<212> TYPE: PRT
<213> ORGANISM: Homo sapiens
```

```
<400> SEQUENCE: 24

Phe Gly Gly Asn Pro Gly Gly Phe Gly Asn Gln Gly Gly Phe Gly Asn
1               5                   10                  15

Ser Arg

<210> SEQ ID NO 25
<211> LENGTH: 14
<212> TYPE: PRT
<213> ORGANISM: Homo sapiens

<400> SEQUENCE: 25

Val Glu Phe Leu Arg Pro Ser Phe Thr Asp Gly Thr Ile Arg
1               5                   10

<210> SEQ ID NO 26
<211> LENGTH: 11
<212> TYPE: PRT
<213> ORGANISM: Homo sapiens

<400> SEQUENCE: 26

Ile Val Gly Ser Glu Ile Asp Ser Thr Gly Lys
1               5                   10

<210> SEQ ID NO 27
<211> LENGTH: 12
<212> TYPE: PRT
<213> ORGANISM: Homo sapiens

<400> SEQUENCE: 27

Asp Ile Asp Pro Gly Ala Phe Gln Asp Leu Asn Lys
1               5                   10

<210> SEQ ID NO 28
<211> LENGTH: 11
<212> TYPE: PRT
<213> ORGANISM: Homo sapiens

<400> SEQUENCE: 28

Asn Tyr Ile Trp Ala Leu Ser Glu Ile Leu Arg
1               5                   10

<210> SEQ ID NO 29
<211> LENGTH: 24
<212> TYPE: PRT
<213> ORGANISM: Homo sapiens

<400> SEQUENCE: 29

Ala Asp Ser Gln Ala Gln Leu Leu Leu Ser Thr Val Val Gly Val Phe
1               5                   10                  15

Thr Ala Pro Gly Leu His Leu Lys
            20

<210> SEQ ID NO 30
<211> LENGTH: 13
<212> TYPE: PRT
<213> ORGANISM: Homo sapiens

<400> SEQUENCE: 30

Phe Asp Pro Asp Ala Thr Gln Phe Ile Glu Phe Ala Lys
1               5                   10

<210> SEQ ID NO 31
<211> LENGTH: 13
```

-continued

```
<212> TYPE: PRT
<213> ORGANISM: Homo sapiens

<400> SEQUENCE: 31

Thr Pro Glu Ile Tyr Ser Val Glu Leu Ser Gly Thr Lys
1               5                   10

<210> SEQ ID NO 32
<211> LENGTH: 12
<212> TYPE: PRT
<213> ORGANISM: Homo sapiens

<400> SEQUENCE: 32

Glu Ser Tyr Ile Pro Thr Val Glu Asp Thr Tyr Arg
1               5                   10

<210> SEQ ID NO 33
<211> LENGTH: 14
<212> TYPE: PRT
<213> ORGANISM: Homo sapiens

<400> SEQUENCE: 33

Ser Tyr Thr Ile Thr Gly Leu Gln Pro Gly Thr Asp Tyr Lys
1               5                   10

<210> SEQ ID NO 34
<211> LENGTH: 18
<212> TYPE: PRT
<213> ORGANISM: Homo sapiens

<400> SEQUENCE: 34

Val Leu Asp Gly Glu Leu Glu Val Ala Pro Gly Tyr Pro Gln Ser Thr
1               5                   10                  15

Ala Arg

<210> SEQ ID NO 35
<211> LENGTH: 13
<212> TYPE: PRT
<213> ORGANISM: Homo sapiens

<400> SEQUENCE: 35

Val Ala Leu Ser Ser Glu Thr Glu Val Ala Leu Ala Arg
1               5                   10

<210> SEQ ID NO 36
<211> LENGTH: 19
<212> TYPE: PRT
<213> ORGANISM: Homo sapiens

<400> SEQUENCE: 36

Tyr Glu Gln Leu Leu Phe Leu Ala Pro Leu Ser Thr Ser Glu Glu Pro
1               5                   10                  15

Leu Gly Arg

<210> SEQ ID NO 37
<211> LENGTH: 12
<212> TYPE: PRT
<213> ORGANISM: Homo sapiens

<400> SEQUENCE: 37

Asn Asn Phe Pro Val Leu Ala Ala Asn Ser Phe Arg
1               5                   10
```

<210> SEQ ID NO 38
<211> LENGTH: 19
<212> TYPE: PRT
<213> ORGANISM: Homo sapiens

<400> SEQUENCE: 38

Ala Gln Ser Leu Thr Thr Gly Gln Glu Gly Phe Ile Pro Phe Asn Phe
1               5                   10                  15

Val Ala Lys

<210> SEQ ID NO 39
<211> LENGTH: 14
<212> TYPE: PRT
<213> ORGANISM: Homo sapiens

<400> SEQUENCE: 39

Thr Ser Glu Ser Thr Gly Ser Leu Pro Ser Pro Phe Leu Arg
1               5                   10

<210> SEQ ID NO 40
<211> LENGTH: 25
<212> TYPE: PRT
<213> ORGANISM: Homo sapiens

<400> SEQUENCE: 40

Leu Pro Glu Gly Ser Val Ser Leu Ile Ile Leu Leu Thr Asp Gly Asp
1               5                   10                  15

Pro Thr Val Gly Glu Thr Asn Pro Arg
            20                  25

<210> SEQ ID NO 41
<211> LENGTH: 21
<212> TYPE: PRT
<213> ORGANISM: Homo sapiens

<400> SEQUENCE: 41

Gly Ala Phe Tyr Leu Leu Gly Glu Ala Tyr Phe Ile Gln Pro Leu Pro
1               5                   10                  15

Ala Ala Ser Glu Arg
            20

<210> SEQ ID NO 42
<211> LENGTH: 17
<212> TYPE: PRT
<213> ORGANISM: Homo sapiens

<400> SEQUENCE: 42

Val Val Tyr Ser Ile Leu Gln Gly Gln Pro Tyr Phe Ser Val Glu Pro
1               5                   10                  15

Lys

<210> SEQ ID NO 43
<211> LENGTH: 18
<212> TYPE: PRT
<213> ORGANISM: Homo sapiens

<400> SEQUENCE: 43

Gly Tyr His Tyr Ile Ile Ala Asn Leu Gly Phe Thr Asp Gly Asp Leu
1               5                   10                  15

Leu Lys

<210> SEQ ID NO 44

```
<211> LENGTH: 11
<212> TYPE: PRT
<213> ORGANISM: Homo sapiens

<400> SEQUENCE: 44

Leu Leu Glu Pro Glu Ser Glu Phe Ile Ile Lys
1               5                   10

<210> SEQ ID NO 45
<211> LENGTH: 10
<212> TYPE: PRT
<213> ORGANISM: Homo sapiens

<400> SEQUENCE: 45

Ala Glu Gln Val Asn Thr Glu Glu Asn Lys
1               5                   10

<210> SEQ ID NO 46
<211> LENGTH: 12
<212> TYPE: PRT
<213> ORGANISM: Homo sapiens

<400> SEQUENCE: 46

Ile Ala Val Ala Gly Asp Leu Phe Gln Pro Glu Arg
1               5                   10

<210> SEQ ID NO 47
<211> LENGTH: 15
<212> TYPE: PRT
<213> ORGANISM: Homo sapiens

<400> SEQUENCE: 47

Ala Val Gly Ser Leu Asp Pro Ser Ala Asp Leu Ser Ser Gln Arg
1               5                   10                  15

<210> SEQ ID NO 48
<211> LENGTH: 11
<212> TYPE: PRT
<213> ORGANISM: Homo sapiens

<400> SEQUENCE: 48

Phe Leu Glu Leu Glu Ser Pro Gly Leu Ser Lys
1               5                   10

<210> SEQ ID NO 49
<211> LENGTH: 11
<212> TYPE: PRT
<213> ORGANISM: Homo sapiens

<400> SEQUENCE: 49

Asn Phe Pro Ser Pro Val Asp Ala Ala Phe Arg
1               5                   10

<210> SEQ ID NO 50
<211> LENGTH: 14
<212> TYPE: PRT
<213> ORGANISM: Homo sapiens

<400> SEQUENCE: 50

Gly Ser Leu Ala Leu Pro Phe Pro Ala Asp Val Gln Gly Lys
1               5                   10

<210> SEQ ID NO 51
<211> LENGTH: 26
<212> TYPE: PRT
```

<213> ORGANISM: Homo sapiens

<400> SEQUENCE: 51

Val Thr Ala Ser Asp Pro Leu Asp Thr Leu Gly Ser Glu Gly Ala Leu
1               5                   10                  15
Ser Pro Gly Gly Val Ala Ser Leu Leu Arg
            20                  25

<210> SEQ ID NO 52
<211> LENGTH: 14
<212> TYPE: PRT
<213> ORGANISM: Homo sapiens

<400> SEQUENCE: 52

Leu Ile Thr Glu Pro Leu Pro Glu Leu Gln Leu Val Glu Lys
1               5                   10

<210> SEQ ID NO 53
<211> LENGTH: 11
<212> TYPE: PRT
<213> ORGANISM: Homo sapiens

<400> SEQUENCE: 53

Ser Leu Gly Pro Ala Leu Leu Leu Leu Gln Lys
1               5                   10

<210> SEQ ID NO 54
<211> LENGTH: 10
<212> TYPE: PRT
<213> ORGANISM: Homo sapiens

<400> SEQUENCE: 54

Leu Phe Thr Ala Leu Phe Pro Phe Glu Lys
1               5                   10

<210> SEQ ID NO 55
<211> LENGTH: 9
<212> TYPE: PRT
<213> ORGANISM: Homo sapiens

<400> SEQUENCE: 55

Phe Tyr Phe Glu Asn Leu Trp Ser Arg
1               5

<210> SEQ ID NO 56
<211> LENGTH: 10
<212> TYPE: PRT
<213> ORGANISM: Homo sapiens

<400> SEQUENCE: 56

Asn Phe Ala Asp Ile Asp Asp Ser Trp Lys
1               5                   10

<210> SEQ ID NO 57
<211> LENGTH: 11
<212> TYPE: PRT
<213> ORGANISM: Homo sapiens

<400> SEQUENCE: 57

Ala Val Glu Pro Glu Ser Glu Phe Val Ile Lys
1               5                   10

<210> SEQ ID NO 58
<211> LENGTH: 22

```
<212> TYPE: PRT
<213> ORGANISM: Homo sapiens

<400> SEQUENCE: 58

Leu Val Tyr His Leu Gly Leu Pro Phe Ser Phe Leu Thr Phe Pro Tyr
1               5                   10                  15

Val Glu Glu Ala Ile Lys
            20

<210> SEQ ID NO 59
<211> LENGTH: 12
<212> TYPE: PRT
<213> ORGANISM: Homo sapiens

<400> SEQUENCE: 59

Leu Asn Ala Ser Asp Ala Asp Glu Gly Ile Asn Lys
1               5                   10

<210> SEQ ID NO 60
<211> LENGTH: 13
<212> TYPE: PRT
<213> ORGANISM: Homo sapiens

<400> SEQUENCE: 60

Phe Gly Phe Gly Gly Ser Thr Asp Ser Gly Pro Ile Arg
1               5                   10

<210> SEQ ID NO 61
<211> LENGTH: 14
<212> TYPE: PRT
<213> ORGANISM: Homo sapiens

<400> SEQUENCE: 61

Tyr Leu Glu Thr Leu Trp Leu Asp Asn Thr Asn Leu Glu Lys
1               5                   10

<210> SEQ ID NO 62
<211> LENGTH: 18
<212> TYPE: PRT
<213> ORGANISM: Homo sapiens

<400> SEQUENCE: 62

Ala Asp Phe Pro Val Asp Glu Glu Leu Gly Leu Asp Leu Gly Asp Leu
1               5                   10                  15

Ser Arg

<210> SEQ ID NO 63
<211> LENGTH: 10
<212> TYPE: PRT
<213> ORGANISM: Homo sapiens

<400> SEQUENCE: 63

Asn Phe Met Glu Ser Val Pro Glu Pro Arg
1               5                   10

<210> SEQ ID NO 64
<211> LENGTH: 10
<212> TYPE: PRT
<213> ORGANISM: Homo sapiens

<400> SEQUENCE: 64

Ile Gln Asn Ile Leu Thr Glu Glu Pro Lys
1               5                   10
```

```
<210> SEQ ID NO 65
<211> LENGTH: 12
<212> TYPE: PRT
<213> ORGANISM: Homo sapiens

<400> SEQUENCE: 65

Leu Ser Glu Pro Ala Glu Leu Thr Asp Ala Val Lys
1               5                   10

<210> SEQ ID NO 66
<211> LENGTH: 11
<212> TYPE: PRT
<213> ORGANISM: Homo sapiens

<400> SEQUENCE: 66

Ser Leu Ala Asp Val Asp Ala Ile Leu Ala Arg
1               5                   10

<210> SEQ ID NO 67
<211> LENGTH: 10
<212> TYPE: PRT
<213> ORGANISM: Homo sapiens

<400> SEQUENCE: 67

Val Leu Glu Ala Glu Leu Leu Val Leu Arg
1               5                   10

<210> SEQ ID NO 68
<211> LENGTH: 12
<212> TYPE: PRT
<213> ORGANISM: Homo sapiens

<400> SEQUENCE: 68

Ala Ala Ala Ala Thr Gly Thr Ile Phe Thr Phe Arg
1               5                   10

<210> SEQ ID NO 69
<211> LENGTH: 20
<212> TYPE: PRT
<213> ORGANISM: Homo sapiens

<400> SEQUENCE: 69

Ala Pro Ala Ala Pro Asp Pro Ala Ser Val Asp Pro Ser Asp Pro
1               5                   10                  15

Ser Ala Asp Arg
            20

<210> SEQ ID NO 70
<211> LENGTH: 17
<212> TYPE: PRT
<213> ORGANISM: Homo sapiens

<400> SEQUENCE: 70

Phe Leu Trp Ala Ala Val Gly Pro Ala Gly Ala Ala Ala Glu Ala
1               5                   10                  15

Arg

<210> SEQ ID NO 71
<211> LENGTH: 11
<212> TYPE: PRT
<213> ORGANISM: Homo sapiens

<400> SEQUENCE: 71
```

```
Asn Ile Pro Val Ala Thr Asn Asn Pro Ala Arg
1               5                   10

<210> SEQ ID NO 72
<211> LENGTH: 11
<212> TYPE: PRT
<213> ORGANISM: Homo sapiens

<400> SEQUENCE: 72

Ser Gly Leu Pro Ala Pro Trp Ile Ser Leu Arg
1               5                   10

<210> SEQ ID NO 73
<211> LENGTH: 11
<212> TYPE: PRT
<213> ORGANISM: Homo sapiens

<400> SEQUENCE: 73

Asp Ile Phe Gly Gly Leu Ala Gly Phe Leu Arg
1               5                   10

<210> SEQ ID NO 74
<211> LENGTH: 15
<212> TYPE: PRT
<213> ORGANISM: Homo sapiens

<400> SEQUENCE: 74

Ala Phe Ala Leu Trp Ser Ala Val Thr Pro Leu Thr Phe Thr Arg
1               5                   10                  15

<210> SEQ ID NO 75
<211> LENGTH: 11
<212> TYPE: PRT
<213> ORGANISM: Homo sapiens

<400> SEQUENCE: 75

Asn Leu Thr Pro Tyr Val Ala Ile Glu Asp Lys
1               5                   10

<210> SEQ ID NO 76
<211> LENGTH: 16
<212> TYPE: PRT
<213> ORGANISM: Homo sapiens

<400> SEQUENCE: 76

Ser Gly Ala Gln Ala Thr Trp Thr Glu Leu Pro Trp Pro His Glu Lys
1               5                   10                  15

<210> SEQ ID NO 77
<211> LENGTH: 12
<212> TYPE: PRT
<213> ORGANISM: Homo sapiens

<400> SEQUENCE: 77

Thr Asp Tyr Ile Pro Leu Leu Asp Val Asp Glu Lys
1               5                   10

<210> SEQ ID NO 78
<211> LENGTH: 12
<212> TYPE: PRT
<213> ORGANISM: Homo sapiens

<400> SEQUENCE: 78

Ser Thr Val Leu Thr Ile Pro Glu Ile Ile Ile Lys
1               5                   10
```

<210> SEQ ID NO 79
<211> LENGTH: 28
<212> TYPE: PRT
<213> ORGANISM: Homo sapiens

<400> SEQUENCE: 79

Asp Asp Phe Ser Leu Gly Asn Val His Leu Ile Gly Tyr Ser Leu Gly
1               5                   10                  15

Ala His Val Ala Gly Tyr Ala Gly Asn Phe Val Lys
            20                  25

<210> SEQ ID NO 80
<211> LENGTH: 15
<212> TYPE: PRT
<213> ORGANISM: Homo sapiens

<400> SEQUENCE: 80

Gly Ala Gln Ala Ala Val Ser Gly Ala Pro Gly Gly Leu Leu Arg
1               5                   10                  15

<210> SEQ ID NO 81
<211> LENGTH: 12
<212> TYPE: PRT
<213> ORGANISM: Homo sapiens

<400> SEQUENCE: 81

Leu Leu Ala Gly Gly Gly Gln Gly Pro Glu Pro Arg
1               5                   10

<210> SEQ ID NO 82
<211> LENGTH: 10
<212> TYPE: PRT
<213> ORGANISM: Homo sapiens

<400> SEQUENCE: 82

Ser Ser Ala Leu Asp Met Glu Asn Phe Arg
1               5                   10

<210> SEQ ID NO 83
<211> LENGTH: 12
<212> TYPE: PRT
<213> ORGANISM: Homo sapiens

<400> SEQUENCE: 83

Ala Ser Ser Ile Ile Asp Glu Leu Phe Gln Asp Arg
1               5                   10

<210> SEQ ID NO 84
<211> LENGTH: 15
<212> TYPE: PRT
<213> ORGANISM: Homo sapiens

<400> SEQUENCE: 84

Leu Thr Gly Asp Glu Asn Phe Thr Ile Pro Tyr Trp Asp Trp Arg
1               5                   10                  15

<210> SEQ ID NO 85
<211> LENGTH: 11
<212> TYPE: PRT
<213> ORGANISM: Homo sapiens

<400> SEQUENCE: 85

Ile Thr Asn Ile Ser Ser Asp Asp Ser Gly Lys

-continued

```
1               5                   10

<210> SEQ ID NO 86
<211> LENGTH: 10
<212> TYPE: PRT
<213> ORGANISM: Homo sapiens

<400> SEQUENCE: 86

Val Thr Ser Val Ser Asp Gln Asn Asp Arg
1               5                   10

<210> SEQ ID NO 87
<211> LENGTH: 14
<212> TYPE: PRT
<213> ORGANISM: Homo sapiens

<400> SEQUENCE: 87

Thr Ala Ser Asp Gln Glu Ser Gly Asp Glu Glu Leu Asn Arg
1               5                   10

<210> SEQ ID NO 88
<211> LENGTH: 14
<212> TYPE: PRT
<213> ORGANISM: Homo sapiens

<400> SEQUENCE: 88

Leu Ser Glu Gly Asp Leu Leu Ala Glu Ile Glu Thr Asp Lys
1               5                   10

<210> SEQ ID NO 89
<211> LENGTH: 14
<212> TYPE: PRT
<213> ORGANISM: Homo sapiens

<400> SEQUENCE: 89

Leu Phe Gly Leu Leu Ser Ser Pro Leu Ser Ser Leu Ala Arg
1               5                   10

<210> SEQ ID NO 90
<211> LENGTH: 9
<212> TYPE: PRT
<213> ORGANISM: Homo sapiens

<400> SEQUENCE: 90

Ser Leu Asp Leu Asp Asp Trp Pro Arg
1               5

<210> SEQ ID NO 91
<211> LENGTH: 11
<212> TYPE: PRT
<213> ORGANISM: Homo sapiens

<400> SEQUENCE: 91

Ile Ile Ser Val Glu Leu Pro Gly Asp Ala Lys
1               5                   10

<210> SEQ ID NO 92
<211> LENGTH: 13
<212> TYPE: PRT
<213> ORGANISM: Homo sapiens

<400> SEQUENCE: 92

Thr Ser Thr Asp Leu Asp Val Asp Val Asp Gln Pro Lys
1               5                   10
```

```
<210> SEQ ID NO 93
<211> LENGTH: 11
<212> TYPE: PRT
<213> ORGANISM: Homo sapiens

<400> SEQUENCE: 93

Tyr Glu Ile Pro Glu Ser Leu Leu Ala Gln Arg
1               5                   10

<210> SEQ ID NO 94
<211> LENGTH: 12
<212> TYPE: PRT
<213> ORGANISM: Homo sapiens

<400> SEQUENCE: 94

Ser Leu Val Gly Ser Asp Ala Gly Pro Gly Pro Arg
1               5                   10

<210> SEQ ID NO 95
<211> LENGTH: 10
<212> TYPE: PRT
<213> ORGANISM: Homo sapiens

<400> SEQUENCE: 95

Phe Gln Pro Thr Leu Leu Thr Leu Pro Arg
1               5                   10

<210> SEQ ID NO 96
<211> LENGTH: 15
<212> TYPE: PRT
<213> ORGANISM: Homo sapiens

<400> SEQUENCE: 96

Gly Thr Ser Ser Ser Pro Leu Ala Val Ala Ser Gly Pro Ala Lys
1               5                   10                  15

<210> SEQ ID NO 97
<211> LENGTH: 9
<212> TYPE: PRT
<213> ORGANISM: Homo sapiens

<400> SEQUENCE: 97

Ala Met Asp Tyr Asp Leu Leu Leu Arg
1               5

<210> SEQ ID NO 98
<211> LENGTH: 13
<212> TYPE: PRT
<213> ORGANISM: Homo sapiens

<400> SEQUENCE: 98

Leu Ile Val Pro Glu Pro Asp Val Asp Phe Asp Ala Lys
1               5                   10

<210> SEQ ID NO 99
<211> LENGTH: 13
<212> TYPE: PRT
<213> ORGANISM: Homo sapiens

<400> SEQUENCE: 99

Glu Val Val Ser Ala Gln Pro Ala Thr Phe Leu Ala Arg
1               5                   10

<210> SEQ ID NO 100
```

```
<211> LENGTH: 24
<212> TYPE: PRT
<213> ORGANISM: Homo sapiens

<400> SEQUENCE: 100

Asp Pro Gly Glu Asn Tyr Asn Leu Leu Gly Val Ala Gly Ala Thr
1               5                   10                  15

Pro Glu Val Leu Gln Ala Leu Lys
            20

<210> SEQ ID NO 101
<211> LENGTH: 10
<212> TYPE: PRT
<213> ORGANISM: Homo sapiens

<400> SEQUENCE: 101

Asp Tyr Ile Phe Gly Asn Tyr Ile Glu Arg
1               5                   10

<210> SEQ ID NO 102
<211> LENGTH: 20
<212> TYPE: PRT
<213> ORGANISM: Homo sapiens

<400> SEQUENCE: 102

Val Glu Ala His Gly Glu Ala Thr Ala Thr Ala Pro Pro Ser Pro Ala
1               5                   10                  15

Ala Glu Thr Lys
            20

<210> SEQ ID NO 103
<211> LENGTH: 11
<212> TYPE: PRT
<213> ORGANISM: Homo sapiens

<400> SEQUENCE: 103

Glu Glu Glu Pro Glu Ala Asp Gln Glu His Ala
1               5                   10

<210> SEQ ID NO 104
<211> LENGTH: 9
<212> TYPE: PRT
<213> ORGANISM: Homo sapiens

<400> SEQUENCE: 104

Phe Thr Glu Tyr Glu Thr Gln Val Lys
1               5

<210> SEQ ID NO 105
<211> LENGTH: 21
<212> TYPE: PRT
<213> ORGANISM: Homo sapiens

<400> SEQUENCE: 105

His Glu Tyr Ala Leu Pro Leu Ala Pro Pro Glu Pro Glu Tyr Ala Thr
1               5                   10                  15

Pro Ile Val Glu Arg
            20

<210> SEQ ID NO 106
<211> LENGTH: 9
<212> TYPE: PRT
<213> ORGANISM: Homo sapiens
```

```
<400> SEQUENCE: 106

Ile Leu Leu Thr Phe Ser Thr Gly Arg
1               5

<210> SEQ ID NO 107
<211> LENGTH: 8
<212> TYPE: PRT
<213> ORGANISM: Homo sapiens

<400> SEQUENCE: 107

Leu Ser Leu Glu Glu Phe Ile Arg
1               5

<210> SEQ ID NO 108
<211> LENGTH: 12
<212> TYPE: PRT
<213> ORGANISM: Homo sapiens

<400> SEQUENCE: 108

Ile Ala Tyr Leu Leu Thr Asn Leu Glu Tyr Pro Arg
1               5                   10

<210> SEQ ID NO 109
<211> LENGTH: 11
<212> TYPE: PRT
<213> ORGANISM: Homo sapiens

<400> SEQUENCE: 109

Ser Gly Val Asp Leu Ala Asp Ser Asn Gln Lys
1               5                   10

<210> SEQ ID NO 110
<211> LENGTH: 12
<212> TYPE: PRT
<213> ORGANISM: Homo sapiens

<400> SEQUENCE: 110

Gly Ile Leu Leu Tyr Gly Pro Pro Gly Thr Gly Lys
1               5                   10

<210> SEQ ID NO 111
<211> LENGTH: 15
<212> TYPE: PRT
<213> ORGANISM: Homo sapiens

<400> SEQUENCE: 111

Gly Val Pro Pro Ala Pro Pro Pro Ala Ala Ala Leu Pro Arg
1               5                   10                  15

<210> SEQ ID NO 112
<211> LENGTH: 11
<212> TYPE: PRT
<213> ORGANISM: Homo sapiens

<400> SEQUENCE: 112

Ile Thr Leu Leu Ser Ala Leu Val Glu Thr Arg
1               5                   10

<210> SEQ ID NO 113
<211> LENGTH: 10
<212> TYPE: PRT
<213> ORGANISM: Homo sapiens

<400> SEQUENCE: 113
```

Leu Pro Thr Asp Ser Glu Leu Ala Pro Arg
1               5                   10

<210> SEQ ID NO 114
<211> LENGTH: 23
<212> TYPE: PRT
<213> ORGANISM: Homo sapiens

<400> SEQUENCE: 114

Ile Ser Ser Leu Arg Pro Gln Gly Leu Ser Asn Pro Ser Thr Leu Ser
1               5                   10                  15

Ala Gln Pro Gln Leu Ser Arg
            20

<210> SEQ ID NO 115
<211> LENGTH: 14
<212> TYPE: PRT
<213> ORGANISM: Homo sapiens

<400> SEQUENCE: 115

Asp Gly Ile Val Pro Phe Leu Gln Val Phe Gly His Gly Lys
1               5                   10

<210> SEQ ID NO 116
<211> LENGTH: 14
<212> TYPE: PRT
<213> ORGANISM: Homo sapiens

<400> SEQUENCE: 116

Asp Val Ser Gln Ser Ser Ile Tyr Ser Gln Thr Glu Glu Lys
1               5                   10

<210> SEQ ID NO 117
<211> LENGTH: 25
<212> TYPE: PRT
<213> ORGANISM: Homo sapiens

<400> SEQUENCE: 117

Glu Thr Phe Ala Ser Thr Ala Ser Gln Leu His Ser Asn Val Val Asn
1               5                   10                  15

Tyr Val Gln Gln Ile Val Ala Pro Lys
            20                  25

<210> SEQ ID NO 118
<211> LENGTH: 12
<212> TYPE: PRT
<213> ORGANISM: Homo sapiens

<400> SEQUENCE: 118

Ser Ile Leu Asp Trp Thr Ser Phe Asn Gln Glu Arg
1               5                   10

<210> SEQ ID NO 119
<211> LENGTH: 9
<212> TYPE: PRT
<213> ORGANISM: Homo sapiens

<400> SEQUENCE: 119

Ala Leu Thr Phe Glu Leu Thr Leu Arg
1               5

<210> SEQ ID NO 120
<211> LENGTH: 20
<212> TYPE: PRT

```
<213> ORGANISM: Homo sapiens

<400> SEQUENCE: 120

Phe Pro His Leu Val Pro Ala Ser Leu Gly Leu Ala Ala Val Gln Ala
1               5                   10                  15

Gln Phe Ser Lys
            20

<210> SEQ ID NO 121
<211> LENGTH: 11
<212> TYPE: PRT
<213> ORGANISM: Homo sapiens

<400> SEQUENCE: 121

Asp Val Glu Asp Glu Ser Thr Gly Leu Glu Lys
1               5                   10

<210> SEQ ID NO 122
<211> LENGTH: 12
<212> TYPE: PRT
<213> ORGANISM: Homo sapiens

<400> SEQUENCE: 122

Leu Asn Ala Ser Asp Ser Asp Glu Gly Ile Asn Lys
1               5                   10

<210> SEQ ID NO 123
<211> LENGTH: 12
<212> TYPE: PRT
<213> ORGANISM: Homo sapiens

<400> SEQUENCE: 123

Asn Thr Leu Ser Leu Val Asn Asp Phe Ile Ile Arg
1               5                   10

<210> SEQ ID NO 124
<211> LENGTH: 10
<212> TYPE: PRT
<213> ORGANISM: Homo sapiens

<400> SEQUENCE: 124

Ser Val Glu Asp Ala Leu Thr Ser Leu Lys
1               5                   10

<210> SEQ ID NO 125
<211> LENGTH: 12
<212> TYPE: PRT
<213> ORGANISM: Homo sapiens

<400> SEQUENCE: 125

Val Leu Gly Leu Leu Gly Ala Leu Asp Pro Tyr Lys
1               5                   10

<210> SEQ ID NO 126
<211> LENGTH: 11
<212> TYPE: PRT
<213> ORGANISM: Homo sapiens

<400> SEQUENCE: 126

Glu Tyr Val Pro Thr Asp Leu Val Asp Ser Lys
1               5                   10

<210> SEQ ID NO 127
<211> LENGTH: 10
```

```
<212> TYPE: PRT
<213> ORGANISM: Homo sapiens

<400> SEQUENCE: 127

Gly Val Glu Asp Ala Leu Val Ser Leu Lys
1               5                   10

<210> SEQ ID NO 128
<211> LENGTH: 10
<212> TYPE: PRT
<213> ORGANISM: Homo sapiens

<400> SEQUENCE: 128

Trp Thr Ala Pro Glu Ala Ile Ala Phe Arg
1               5                   10

<210> SEQ ID NO 129
<211> LENGTH: 12
<212> TYPE: PRT
<213> ORGANISM: Homo sapiens

<400> SEQUENCE: 129

Ile Tyr Gln Gly Ser Ser Gly Ser Tyr Phe Val Lys
1               5                   10

<210> SEQ ID NO 130
<211> LENGTH: 11
<212> TYPE: PRT
<213> ORGANISM: Homo sapiens

<400> SEQUENCE: 130

Ala Ala Val Gly Glu Leu Pro Asp Gln Ser Lys
1               5                   10

<210> SEQ ID NO 131
<211> LENGTH: 16
<212> TYPE: PRT
<213> ORGANISM: Homo sapiens

<400> SEQUENCE: 131

Ala Asp Leu Phe Tyr Asp Val Glu Ala Leu Asp Leu Glu Ser Pro Lys
1               5                   10                  15

<210> SEQ ID NO 132
<211> LENGTH: 16
<212> TYPE: PRT
<213> ORGANISM: Homo sapiens

<400> SEQUENCE: 132

Leu Val Ser Gln Glu His Leu Leu Ser Ser Pro Glu Ala Leu Arg
1               5                   10                  15

<210> SEQ ID NO 133
<211> LENGTH: 10
<212> TYPE: PRT
<213> ORGANISM: Homo sapiens

<400> SEQUENCE: 133

Val Leu Asp Val Asn Asp Asn Ala Pro Lys
1               5                   10

<210> SEQ ID NO 134
<211> LENGTH: 10
<212> TYPE: PRT
<213> ORGANISM: Homo sapiens
```

```
<400> SEQUENCE: 134

Ala Val Ser Thr Ala Asn Pro Leu Leu Arg
1               5                   10

<210> SEQ ID NO 135
<211> LENGTH: 19
<212> TYPE: PRT
<213> ORGANISM: Homo sapiens

<400> SEQUENCE: 135

Ala Gly Leu Trp Ala Ser His Ala Asp His Leu Leu Ala Leu Leu Glu
1               5                   10                  15

Ser Pro Lys

<210> SEQ ID NO 136
<211> LENGTH: 13
<212> TYPE: PRT
<213> ORGANISM: Homo sapiens

<400> SEQUENCE: 136

Gly Ala Tyr Pro Leu Ser Ile Glu Pro Ile Gly Val Arg
1               5                   10

<210> SEQ ID NO 137
<211> LENGTH: 19
<212> TYPE: PRT
<213> ORGANISM: Homo sapiens

<400> SEQUENCE: 137

Ser Tyr Tyr Asn Val Val Leu Gln Asn Ile Leu Glu Thr Glu Asn Glu
1               5                   10                  15

Tyr Ser Lys

<210> SEQ ID NO 138
<211> LENGTH: 17
<212> TYPE: PRT
<213> ORGANISM: Homo sapiens

<400> SEQUENCE: 138

Leu Ile Gly Leu Asp Ile Pro His Phe Ala Ala Asp Leu Pro Leu Asn
1               5                   10                  15

Arg

<210> SEQ ID NO 139
<211> LENGTH: 9
<212> TYPE: PRT
<213> ORGANISM: Homo sapiens

<400> SEQUENCE: 139

Val Phe Phe Pro Val Ser Glu Tyr Lys
1               5

<210> SEQ ID NO 140
<211> LENGTH: 11
<212> TYPE: PRT
<213> ORGANISM: Homo sapiens

<400> SEQUENCE: 140

Val Pro Thr Leu Leu Thr Asp Tyr Ile Leu Lys
1               5                   10
```

<210> SEQ ID NO 141
<211> LENGTH: 10
<212> TYPE: PRT
<213> ORGANISM: Homo sapiens

<400> SEQUENCE: 141

Leu Asp Leu Ser Asn Asn Phe Leu Asp Arg
1               5                   10

<210> SEQ ID NO 142
<211> LENGTH: 9
<212> TYPE: PRT
<213> ORGANISM: Homo sapiens

<400> SEQUENCE: 142

Leu Ser Pro Glu Asp Tyr Thr Leu Lys
1               5

<210> SEQ ID NO 143
<211> LENGTH: 9
<212> TYPE: PRT
<213> ORGANISM: Homo sapiens

<400> SEQUENCE: 143

Thr Ala Ala Gln Asn Leu Tyr Glu Lys
1               5

<210> SEQ ID NO 144
<211> LENGTH: 9
<212> TYPE: PRT
<213> ORGANISM: Homo sapiens

<400> SEQUENCE: 144

His Ala Phe Ile Leu Gln Asp Thr Lys
1               5

<210> SEQ ID NO 145
<211> LENGTH: 15
<212> TYPE: PRT
<213> ORGANISM: Homo sapiens

<400> SEQUENCE: 145

Asp Val Pro Phe Gly Phe Gln Thr Val Thr Ser Asp Val Asn Lys
1               5                   10                  15

<210> SEQ ID NO 146
<211> LENGTH: 9
<212> TYPE: PRT
<213> ORGANISM: Homo sapiens

<400> SEQUENCE: 146

Asp Leu Ser Glu Asn Asn Asp Gln Arg
1               5

<210> SEQ ID NO 147
<211> LENGTH: 9
<212> TYPE: PRT
<213> ORGANISM: Homo sapiens

<400> SEQUENCE: 147

Ile Ser Ala Ser Ala Glu Glu Leu Arg
1               5

<210> SEQ ID NO 148
<211> LENGTH: 12

```
<212> TYPE: PRT
<213> ORGANISM: Homo sapiens

<400> SEQUENCE: 148

Ser Asn Glu Ile Pro Ser Thr Asp Val Thr Asp Lys
1               5                   10

<210> SEQ ID NO 149
<211> LENGTH: 10
<212> TYPE: PRT
<213> ORGANISM: Homo sapiens

<400> SEQUENCE: 149

Glu Val Ala Phe Asp Leu Glu Ile Pro Lys
1               5                   10

<210> SEQ ID NO 150
<211> LENGTH: 12
<212> TYPE: PRT
<213> ORGANISM: Homo sapiens

<400> SEQUENCE: 150

Glu Leu Glu Ala Pro Ser Glu Asp Asn Ser Gly Arg
1               5                   10

<210> SEQ ID NO 151
<211> LENGTH: 18
<212> TYPE: PRT
<213> ORGANISM: Homo sapiens

<400> SEQUENCE: 151

Leu Leu Ile Tyr Ala Val Leu Pro Thr Gly Asp Val Ile Gly Asp Ser
1               5                   10                  15

Ala Lys

<210> SEQ ID NO 152
<211> LENGTH: 12
<212> TYPE: PRT
<213> ORGANISM: Homo sapiens

<400> SEQUENCE: 152

Ala Ser Leu Ala Leu Pro Thr Ser Ser Leu Ser Arg
1               5                   10

<210> SEQ ID NO 153
<211> LENGTH: 9
<212> TYPE: PRT
<213> ORGANISM: Homo sapiens

<400> SEQUENCE: 153

Val Ser Ala Phe Val Pro Trp Ile Lys
1               5

<210> SEQ ID NO 154
<211> LENGTH: 23
<212> TYPE: PRT
<213> ORGANISM: Homo sapiens

<400> SEQUENCE: 154

Gly Pro Glu Glu Glu His Leu Gly Ile Leu Gly Pro Val Ile Trp Ala
1               5                   10                  15

Glu Val Gly Asp Thr Ile Arg
            20
```

<210> SEQ ID NO 155
<211> LENGTH: 12
<212> TYPE: PRT
<213> ORGANISM: Homo sapiens

<400> SEQUENCE: 155

Ser Leu Ser Leu Gly Glu Val Leu Asp Gly Asp Arg
1               5                   10

<210> SEQ ID NO 156
<211> LENGTH: 13
<212> TYPE: PRT
<213> ORGANISM: Homo sapiens

<400> SEQUENCE: 156

Trp Asp Phe Asp Leu Leu Asn Gly Gln Gly Gly Trp Lys
1               5                   10

<210> SEQ ID NO 157
<211> LENGTH: 12
<212> TYPE: PRT
<213> ORGANISM: Homo sapiens

<400> SEQUENCE: 157

Leu Ala Ala Gln Glu Gly Pro Leu Ser Leu Ser Arg
1               5                   10

<210> SEQ ID NO 158
<211> LENGTH: 14
<212> TYPE: PRT
<213> ORGANISM: Homo sapiens

<400> SEQUENCE: 158

Gly Ser Ser Gly Ser Phe Leu Gln Pro Asp Ile Thr Glu Arg
1               5                   10

<210> SEQ ID NO 159
<211> LENGTH: 10
<212> TYPE: PRT
<213> ORGANISM: Homo sapiens

<400> SEQUENCE: 159

Leu Ala Gly Gly Glu Val Pro Gln Asp Arg
1               5                   10

<210> SEQ ID NO 160
<211> LENGTH: 11
<212> TYPE: PRT
<213> ORGANISM: Homo sapiens

<400> SEQUENCE: 160

Leu Thr Leu Tyr Asn Gln Asn Asp Pro Asn Arg
1               5                   10

<210> SEQ ID NO 161
<211> LENGTH: 10
<212> TYPE: PRT
<213> ORGANISM: Homo sapiens

<400> SEQUENCE: 161

Val Leu Gln Ala Glu Glu Leu His Glu Lys
1               5                   10

<210> SEQ ID NO 162

```
<211> LENGTH: 21
<212> TYPE: PRT
<213> ORGANISM: Homo sapiens

<400> SEQUENCE: 162

His Glu Leu Thr Asp Glu Glu Leu Gln Ser Leu Phe Thr Asn Phe Ala
1               5                   10                  15

Asn Val Val Asp Lys
            20

<210> SEQ ID NO 163
<211> LENGTH: 9
<212> TYPE: PRT
<213> ORGANISM: Homo sapiens

<400> SEQUENCE: 163

Asp Phe Phe Leu Ala Glu Leu Glu Lys
1               5

<210> SEQ ID NO 164
<211> LENGTH: 12
<212> TYPE: PRT
<213> ORGANISM: Homo sapiens

<400> SEQUENCE: 164

Asp Gly Pro Phe Gly Phe Ser Pro Ile Ile Gly Arg
1               5                   10

<210> SEQ ID NO 165
<211> LENGTH: 13
<212> TYPE: PRT
<213> ORGANISM: Homo sapiens

<400> SEQUENCE: 165

Gly Pro Glu Val Thr Ser Asn Ala Ala Leu Thr Leu Arg
1               5                   10

<210> SEQ ID NO 166
<211> LENGTH: 15
<212> TYPE: PRT
<213> ORGANISM: Homo sapiens

<400> SEQUENCE: 166

Ile Glu Gly Asn Leu Ile Phe Asp Pro Asn Asn Tyr Leu Pro Lys
1               5                   10                  15

<210> SEQ ID NO 167
<211> LENGTH: 9
<212> TYPE: PRT
<213> ORGANISM: Homo sapiens

<400> SEQUENCE: 167

Thr Leu Asp Gln Ser Pro Glu Leu Arg
1               5

<210> SEQ ID NO 168
<211> LENGTH: 10
<212> TYPE: PRT
<213> ORGANISM: Homo sapiens

<400> SEQUENCE: 168

Thr Val Glu Asp Val Gly Ser Pro Leu Lys
1               5                   10
```

```
<210> SEQ ID NO 169
<211> LENGTH: 18
<212> TYPE: PRT
<213> ORGANISM: Homo sapiens

<400> SEQUENCE: 169

Val Gln Ile Gly Asp Thr Phe Phe Glu Pro Ile Ser Trp His Leu Ala
1               5                   10                  15

Thr Lys

<210> SEQ ID NO 170
<211> LENGTH: 12
<212> TYPE: PRT
<213> ORGANISM: Homo sapiens

<400> SEQUENCE: 170

Ile Ser Asp Val Gln Val Phe Gly Tyr Ser Leu Arg
1               5                   10

<210> SEQ ID NO 171
<211> LENGTH: 11
<212> TYPE: PRT
<213> ORGANISM: Homo sapiens

<400> SEQUENCE: 171

Tyr Ser Pro Gly Gly Thr Pro Thr Ala Ile Lys
1               5                   10

<210> SEQ ID NO 172
<211> LENGTH: 22
<212> TYPE: PRT
<213> ORGANISM: Homo sapiens

<400> SEQUENCE: 172

Val Pro Thr Ala Asp Leu Glu Asp Val Leu Pro Leu Ala Glu Asp Ile
1               5                   10                  15

Thr Asn Ile Leu Ser Lys
            20

<210> SEQ ID NO 173
<211> LENGTH: 9
<212> TYPE: PRT
<213> ORGANISM: Homo sapiens

<400> SEQUENCE: 173

Asn His Pro Glu Val Leu Asn Ile Arg
1               5

<210> SEQ ID NO 174
<211> LENGTH: 14
<212> TYPE: PRT
<213> ORGANISM: Homo sapiens

<400> SEQUENCE: 174

Ser Tyr Gly Leu Asn Leu Ala Ile Gln Asn Gly Pro Ile Lys
1               5                   10

<210> SEQ ID NO 175
<211> LENGTH: 15
<212> TYPE: PRT
<213> ORGANISM: Homo sapiens

<400> SEQUENCE: 175

Leu Trp Ala Ala Gly Thr Pro Ser Pro Ser Ala Pro Gly Ala Arg
```

```
<210> SEQ ID NO 176
<211> LENGTH: 14
<212> TYPE: PRT
<213> ORGANISM: Homo sapiens

<400> SEQUENCE: 176

Ser Gln Asn Pro Val Gln Pro Ile Gly Pro Gln Thr Pro Lys
1               5                   10

<210> SEQ ID NO 177
<211> LENGTH: 13
<212> TYPE: PRT
<213> ORGANISM: Homo sapiens

<400> SEQUENCE: 177

Ile Ser Ala Glu Ser Pro Thr Gly Leu Pro Ser His Lys
1               5                   10

<210> SEQ ID NO 178
<211> LENGTH: 15
<212> TYPE: PRT
<213> ORGANISM: Homo sapiens

<400> SEQUENCE: 178

Tyr Val Gly Gly Gln Glu His Phe Ala His Leu Leu Ile Leu Arg
1               5                   10                  15

<210> SEQ ID NO 179
<211> LENGTH: 15
<212> TYPE: PRT
<213> ORGANISM: Homo sapiens

<400> SEQUENCE: 179

Ile Thr Ala Ala Gln His Ser Val Thr Gly Ser Ala Val Ser Lys
1               5                   10                  15

<210> SEQ ID NO 180
<211> LENGTH: 9
<212> TYPE: PRT
<213> ORGANISM: Homo sapiens

<400> SEQUENCE: 180

His Thr Phe Thr Leu Ser Leu Pro Arg
1               5

<210> SEQ ID NO 181
<211> LENGTH: 10
<212> TYPE: PRT
<213> ORGANISM: Homo sapiens

<400> SEQUENCE: 181

Asn Leu Thr Ile Val Asp Ser Gly Leu Lys
1               5                   10

<210> SEQ ID NO 182
<211> LENGTH: 12
<212> TYPE: PRT
<213> ORGANISM: Homo sapiens

<400> SEQUENCE: 182

Phe Val Ser Pro Leu Ser Trp Asp Leu Val Gly Arg
1               5                   10
```

<210> SEQ ID NO 183
<211> LENGTH: 10
<212> TYPE: PRT
<213> ORGANISM: Homo sapiens

<400> SEQUENCE: 183

Val Ile Ser Gly Ile Leu Thr Gln Gly Arg
1               5                   10

<210> SEQ ID NO 184
<211> LENGTH: 14
<212> TYPE: PRT
<213> ORGANISM: Homo sapiens

<400> SEQUENCE: 184

Asp Ser Leu Ile Ser Ser Glu Glu Glu Gly Leu Val Arg
1               5                   10

<210> SEQ ID NO 185
<211> LENGTH: 9
<212> TYPE: PRT
<213> ORGANISM: Homo sapiens

<400> SEQUENCE: 185

Ser Gly Gly Asp Tyr Ser Tyr Val Lys
1               5

<210> SEQ ID NO 186
<211> LENGTH: 17
<212> TYPE: PRT
<213> ORGANISM: Homo sapiens

<400> SEQUENCE: 186

Asn Arg Pro Ser Phe Asp Gly Ile Leu Tyr Tyr Gln Ser Gly Gly
1               5                   10                  15

Arg

<210> SEQ ID NO 187
<211> LENGTH: 13
<212> TYPE: PRT
<213> ORGANISM: Homo sapiens

<400> SEQUENCE: 187

Tyr Pro Asp Thr Phe Leu Glu Gly Ile Val Asn Gly Lys
1               5                   10

<210> SEQ ID NO 188
<211> LENGTH: 14
<212> TYPE: PRT
<213> ORGANISM: Homo sapiens

<400> SEQUENCE: 188

Glu Glu Gln Gly Thr Gln Ser Gln Gly Pro Gly Leu Asp Arg
1               5                   10

<210> SEQ ID NO 189
<211> LENGTH: 13
<212> TYPE: PRT
<213> ORGANISM: Homo sapiens

<400> SEQUENCE: 189

Leu Ala Gly Pro Ala Pro Ala Gly Gly Val Leu Asp Lys
1               5                   10

```
<210> SEQ ID NO 190
<211> LENGTH: 9
<212> TYPE: PRT
<213> ORGANISM: Homo sapiens

<400> SEQUENCE: 190

Trp Phe Tyr Ile Ala Ser Ala Phe Arg
1               5

<210> SEQ ID NO 191
<211> LENGTH: 10
<212> TYPE: PRT
<213> ORGANISM: Homo sapiens

<400> SEQUENCE: 191

Asp Ala Asp Pro Asp Thr Phe Phe Ala Lys
1               5                   10

<210> SEQ ID NO 192
<211> LENGTH: 16
<212> TYPE: PRT
<213> ORGANISM: Homo sapiens

<400> SEQUENCE: 192

Glu Ser Val Ser Thr Ala Ser Asp Gln Pro Ser His Ser Leu Glu Arg
1               5                   10                  15

<210> SEQ ID NO 193
<211> LENGTH: 9
<212> TYPE: PRT
<213> ORGANISM: Homo sapiens

<400> SEQUENCE: 193

Leu Ser Tyr Glu Gly Glu Val Thr Lys
1               5

<210> SEQ ID NO 194
<211> LENGTH: 9
<212> TYPE: PRT
<213> ORGANISM: Homo sapiens

<400> SEQUENCE: 194

Leu Val Asp Leu Thr Gly Glu Tyr Lys
1               5

<210> SEQ ID NO 195
<211> LENGTH: 22
<212> TYPE: PRT
<213> ORGANISM: Homo sapiens

<400> SEQUENCE: 195

Glu Ser Val Ser Pro Thr Ala Gln Pro Glu Glu Pro Pro Leu Leu Pro
1               5                   10                  15

Glu Pro Pro Asp Asn Arg
            20

<210> SEQ ID NO 196
<211> LENGTH: 9
<212> TYPE: PRT
<213> ORGANISM: Homo sapiens

<400> SEQUENCE: 196

Ile Pro Thr Thr Phe Glu Asn Gly Arg
1               5
```

<210> SEQ ID NO 197
<211> LENGTH: 14
<212> TYPE: PRT
<213> ORGANISM: Homo sapiens

<400> SEQUENCE: 197

Val Leu Leu Val Val Asp Glu Pro His Ala Asp Trp Ala Lys
1               5                   10

<210> SEQ ID NO 198
<211> LENGTH: 11
<212> TYPE: PRT
<213> ORGANISM: Homo sapiens

<400> SEQUENCE: 198

Glu Glu Pro Val Glu Ala Leu Thr Phe Ser Arg
1               5                   10

<210> SEQ ID NO 199
<211> LENGTH: 22
<212> TYPE: PRT
<213> ORGANISM: Homo sapiens

<400> SEQUENCE: 199

Glu Gly Pro Glu Gln Val Ile Pro Ile Asn Ser Glu Glu Leu Phe Val
1               5                   10                  15

His Pro Leu Trp Asn Arg
            20

<210> SEQ ID NO 200
<211> LENGTH: 9
<212> TYPE: PRT
<213> ORGANISM: Homo sapiens

<400> SEQUENCE: 200

Glu Ile Gly Glu Leu Tyr Leu Pro Lys
1               5

<210> SEQ ID NO 201
<211> LENGTH: 13
<212> TYPE: PRT
<213> ORGANISM: Homo sapiens

<400> SEQUENCE: 201

Val Gly Pro Asp Gly Thr Pro Tyr Val Thr Val Leu Lys
1               5                   10

<210> SEQ ID NO 202
<211> LENGTH: 10
<212> TYPE: PRT
<213> ORGANISM: Homo sapiens

<400> SEQUENCE: 202

Asp Val Ala Gln Asp Gly Ser Thr Ile Lys
1               5                   10

<210> SEQ ID NO 203
<211> LENGTH: 12
<212> TYPE: PRT
<213> ORGANISM: Homo sapiens

<400> SEQUENCE: 203

Leu Val Phe Phe Ala Glu Asp Val Gly Ser Asn Lys

```
<210> SEQ ID NO 204
<211> LENGTH: 9
<212> TYPE: PRT
<213> ORGANISM: Homo sapiens

<400> SEQUENCE: 204

Ala Leu Asp Glu Thr Asp Ser Pro Arg
1               5

<210> SEQ ID NO 205
<211> LENGTH: 10
<212> TYPE: PRT
<213> ORGANISM: Homo sapiens

<400> SEQUENCE: 205

Gly Leu Ser Glu Pro Ser Ser Ile Ala Lys
1               5                   10

<210> SEQ ID NO 206
<211> LENGTH: 11
<212> TYPE: PRT
<213> ORGANISM: Homo sapiens

<400> SEQUENCE: 206

Leu Tyr Leu Val Asp Leu Ala Gly Ser Glu Lys
1               5                   10

<210> SEQ ID NO 207
<211> LENGTH: 17
<212> TYPE: PRT
<213> ORGANISM: Homo sapiens

<400> SEQUENCE: 207

Leu Ser Ala Leu Pro Ser Trp Ala Phe Ala Asn Leu Ser Ser Leu Gln
1               5                   10                  15

Arg

<210> SEQ ID NO 208
<211> LENGTH: 12
<212> TYPE: PRT
<213> ORGANISM: Homo sapiens

<400> SEQUENCE: 208

Ala Glu Ala Gln Glu Ala Glu Asp Gln Gln Ala Arg
1               5                   10

<210> SEQ ID NO 209
<211> LENGTH: 12
<212> TYPE: PRT
<213> ORGANISM: Homo sapiens

<400> SEQUENCE: 209

Leu Ser Gly Ala Ala Asp Thr Gln Ala Leu Leu Arg
1               5                   10

<210> SEQ ID NO 210
<211> LENGTH: 12
<212> TYPE: PRT
<213> ORGANISM: Homo sapiens

<400> SEQUENCE: 210

Thr Ala Ser Phe Gly Gly Ile Thr Val Leu Thr Arg
```

```
1               5                   10
```

<210> SEQ ID NO 211
<211> LENGTH: 10
<212> TYPE: PRT
<213> ORGANISM: Homo sapiens

<400> SEQUENCE: 211

```
His Val Leu Glu Asp Ser Pro Ala Gly Lys
1               5                   10
```

<210> SEQ ID NO 212
<211> LENGTH: 13
<212> TYPE: PRT
<213> ORGANISM: Homo sapiens

<400> SEQUENCE: 212

```
Phe Asn Ser Val Pro Leu Thr Asp Thr Gly His Glu Arg
1               5                   10
```

<210> SEQ ID NO 213
<211> LENGTH: 10
<212> TYPE: PRT
<213> ORGANISM: Homo sapiens

<400> SEQUENCE: 213

```
Tyr Thr Phe Val Val Pro Glu Asp Thr Arg
1               5                   10
```

<210> SEQ ID NO 214
<211> LENGTH: 13
<212> TYPE: PRT
<213> ORGANISM: Homo sapiens

<400> SEQUENCE: 214

```
Leu Leu Glu Asn Ala Pro Ser Gly Thr Leu Val Ile Lys
1               5                   10
```

<210> SEQ ID NO 215
<211> LENGTH: 10
<212> TYPE: PRT
<213> ORGANISM: Homo sapiens

<400> SEQUENCE: 215

```
Ala Glu Gly Pro Gly Ser Gln Leu Gln Lys
1               5                   10
```

<210> SEQ ID NO 216
<211> LENGTH: 9
<212> TYPE: PRT
<213> ORGANISM: Homo sapiens

<400> SEQUENCE: 216

```
Ala Lys Pro Ala Leu Glu Asp Leu Arg
1               5
```

<210> SEQ ID NO 217
<211> LENGTH: 22
<212> TYPE: PRT
<213> ORGANISM: Homo sapiens

<400> SEQUENCE: 217

```
Asp Leu Gly Tyr Asp Tyr Ser Tyr Leu Gln Asp Ser Asp Pro Asp Ser
1               5                   10                  15
```

```
Phe Gln Asp Tyr Ile Lys
            20

<210> SEQ ID NO 218
<211> LENGTH: 10
<212> TYPE: PRT
<213> ORGANISM: Homo sapiens

<400> SEQUENCE: 218

Val Gln Ser Leu Val Leu Gly Ala Pro Arg
1               5                   10

<210> SEQ ID NO 219
<211> LENGTH: 12
<212> TYPE: PRT
<213> ORGANISM: Homo sapiens

<400> SEQUENCE: 219

Ile Tyr Ser Asn Ala Gly Glu Gln Ser Phe Asp Lys
1               5                   10

<210> SEQ ID NO 220
<211> LENGTH: 20
<212> TYPE: PRT
<213> ORGANISM: Homo sapiens

<400> SEQUENCE: 220

Leu Phe Gly Ala Ser Ser Pro Pro Gly Ala Val Pro Ser Gly Pro
1               5                   10                  15

Pro Leu Ser Arg
            20

<210> SEQ ID NO 221
<211> LENGTH: 11
<212> TYPE: PRT
<213> ORGANISM: Homo sapiens

<400> SEQUENCE: 221

Val Ile Val Ile Pro Asn Pro Val Asp Leu Arg
1               5                   10

<210> SEQ ID NO 222
<211> LENGTH: 8
<212> TYPE: PRT
<213> ORGANISM: Homo sapiens

<400> SEQUENCE: 222

Tyr Ile Asn Glu Gln Tyr Glu Lys
1               5

<210> SEQ ID NO 223
<211> LENGTH: 16
<212> TYPE: PRT
<213> ORGANISM: Homo sapiens

<400> SEQUENCE: 223

Ile Leu Asn Pro Leu Asp Ser Trp Val Ser Phe Leu Ser Ser Leu Arg
1               5                   10                  15

<210> SEQ ID NO 224
<211> LENGTH: 14
<212> TYPE: PRT
<213> ORGANISM: Homo sapiens

<400> SEQUENCE: 224
```

Gly Ser Pro Gln Ala Gly Val Asp Leu Ser Phe Ala Thr Arg
1               5                   10

<210> SEQ ID NO 225
<211> LENGTH: 14
<212> TYPE: PRT
<213> ORGANISM: Homo sapiens

<400> SEQUENCE: 225

Ser Leu Pro Val Asp Val Phe Ala Gly Val Ser Leu Ser Lys
1               5                   10

<210> SEQ ID NO 226
<211> LENGTH: 9
<212> TYPE: PRT
<213> ORGANISM: Homo sapiens

<400> SEQUENCE: 226

Ala Phe Leu Phe Asp Val Val Ser Lys
1               5

<210> SEQ ID NO 227
<211> LENGTH: 13
<212> TYPE: PRT
<213> ORGANISM: Homo sapiens

<400> SEQUENCE: 227

Leu Gln Glu Leu Asp Leu Ser Gln Asn Phe Leu Ala Lys
1               5                   10

<210> SEQ ID NO 228
<211> LENGTH: 22
<212> TYPE: PRT
<213> ORGANISM: Homo sapiens

<400> SEQUENCE: 228

Val Val His Gly Glu Asp Ala Val Pro Tyr Ser Trp Pro Trp Gln Val
1               5                   10                  15

Ser Leu Gln Tyr Glu Lys
            20

<210> SEQ ID NO 229
<211> LENGTH: 11
<212> TYPE: PRT
<213> ORGANISM: Homo sapiens

<400> SEQUENCE: 229

Trp Gly Gly Ser Ser Phe Gln Asp Ile Gln Arg
1               5                   10

<210> SEQ ID NO 230
<211> LENGTH: 10
<212> TYPE: PRT
<213> ORGANISM: Homo sapiens

<400> SEQUENCE: 230

Ala Leu Ile Glu Ser Asn Gln Thr Ala Arg
1               5                   10

<210> SEQ ID NO 231
<211> LENGTH: 9
<212> TYPE: PRT
<213> ORGANISM: Homo sapiens

<400> SEQUENCE: 231

Asp Ala Ala Val Ile Ser Trp Thr Lys
1               5

<210> SEQ ID NO 232
<211> LENGTH: 17
<212> TYPE: PRT
<213> ORGANISM: Homo sapiens

<400> SEQUENCE: 232

Asp Leu Lys Pro Glu Asn Leu Leu Tyr Leu Thr Pro Glu Glu Asn Ser
1               5                   10                  15

Lys

<210> SEQ ID NO 233
<211> LENGTH: 13
<212> TYPE: PRT
<213> ORGANISM: Homo sapiens

<400> SEQUENCE: 233

Ser Leu Asp Gly Ala Ala Ala Val Asp Ser Ala Asp Arg
1               5                   10

<210> SEQ ID NO 234
<211> LENGTH: 9
<212> TYPE: PRT
<213> ORGANISM: Homo sapiens

<400> SEQUENCE: 234

Trp Ala Asp Leu Ser Gly Ile Thr Lys
1               5

<210> SEQ ID NO 235
<211> LENGTH: 10
<212> TYPE: PRT
<213> ORGANISM: Homo sapiens

<400> SEQUENCE: 235

Trp Asp Leu Thr Phe Ser Pro Pro Gln Lys
1               5                   10

<210> SEQ ID NO 236
<211> LENGTH: 9
<212> TYPE: PRT
<213> ORGANISM: Homo sapiens

<400> SEQUENCE: 236

Leu Ser Leu Ala Tyr Leu Pro Val Lys
1               5

<210> SEQ ID NO 237
<211> LENGTH: 12
<212> TYPE: PRT
<213> ORGANISM: Homo sapiens

<400> SEQUENCE: 237

Phe Leu Val Glu Thr Phe Pro Ala Pro Glu Ser Arg
1               5                   10

<210> SEQ ID NO 238
<211> LENGTH: 12
<212> TYPE: PRT
<213> ORGANISM: Homo sapiens

<400> SEQUENCE: 238

Ala Leu Thr Pro Gly Leu Ser Trp Leu Leu Gln Arg
1               5                   10

<210> SEQ ID NO 239
<211> LENGTH: 12
<212> TYPE: PRT
<213> ORGANISM: Homo sapiens

<400> SEQUENCE: 239

Thr Gly Ala Glu Gly Ala Val Leu Asp Glu Ala Lys
1               5                   10

<210> SEQ ID NO 240
<211> LENGTH: 11
<212> TYPE: PRT
<213> ORGANISM: Homo sapiens

<400> SEQUENCE: 240

Ala Glu Gln Leu Val Glu Ile Leu Glu Ala Lys
1               5                   10

<210> SEQ ID NO 241
<211> LENGTH: 11
<212> TYPE: PRT
<213> ORGANISM: Homo sapiens

<400> SEQUENCE: 241

Asp Glu Ala Val Leu Ile Leu Ser Glu Ala Arg
1               5                   10

<210> SEQ ID NO 242
<211> LENGTH: 13
<212> TYPE: PRT
<213> ORGANISM: Homo sapiens

<400> SEQUENCE: 242

Ala His Val Ser Phe Lys Pro Thr Val Ala Gln Gln Arg
1               5                   10

<210> SEQ ID NO 243
<211> LENGTH: 9
<212> TYPE: PRT
<213> ORGANISM: Homo sapiens

<400> SEQUENCE: 243

Leu Gly Phe Gly Ser Phe Val Asp Lys
1               5

<210> SEQ ID NO 244
<211> LENGTH: 8
<212> TYPE: PRT
<213> ORGANISM: Homo sapiens

<400> SEQUENCE: 244

Ile Ala Phe Tyr Val Gly Leu Lys
1               5

<210> SEQ ID NO 245
<211> LENGTH: 7
<212> TYPE: PRT
<213> ORGANISM: Homo sapiens

<400> SEQUENCE: 245

Leu Tyr Trp Val Asp Ser Lys
1               5

<210> SEQ ID NO 246
<211> LENGTH: 13
<212> TYPE: PRT
<213> ORGANISM: Homo sapiens

<400> SEQUENCE: 246

Val Phe Leu Asp His Asn Ala Leu Pro Asp Thr Leu Lys
1               5                   10

<210> SEQ ID NO 247
<211> LENGTH: 16
<212> TYPE: PRT
<213> ORGANISM: Homo sapiens

<400> SEQUENCE: 247

Ala Thr His Pro Pro Ser Ser Ser Leu Pro Asn Pro Leu Leu Ser Arg
1               5                   10                  15

<210> SEQ ID NO 248
<211> LENGTH: 11
<212> TYPE: PRT
<213> ORGANISM: Homo sapiens

<400> SEQUENCE: 248

Gly Phe Ser Gly Pro Leu Pro Thr Val Gly Arg
1               5                   10

<210> SEQ ID NO 249
<211> LENGTH: 9
<212> TYPE: PRT
<213> ORGANISM: Homo sapiens

<400> SEQUENCE: 249

Trp Tyr Phe Asp Val Thr Glu Gly Lys
1               5

<210> SEQ ID NO 250
<211> LENGTH: 10
<212> TYPE: PRT
<213> ORGANISM: Homo sapiens

<400> SEQUENCE: 250

Tyr Gly Tyr Leu Pro Pro Thr Asp Pro Arg
1               5                   10

<210> SEQ ID NO 251
<211> LENGTH: 7
<212> TYPE: PRT
<213> ORGANISM: Homo sapiens

<400> SEQUENCE: 251

Leu Asp Asn Glu Phe Asp Arg
1               5

<210> SEQ ID NO 252
<211> LENGTH: 13
<212> TYPE: PRT
<213> ORGANISM: Homo sapiens

<400> SEQUENCE: 252

His Ile Gly His Ala Asn Leu Thr Phe Glu Gln Leu Arg
1               5                   10

<210> SEQ ID NO 253
<211> LENGTH: 19
<212> TYPE: PRT
<213> ORGANISM: Homo sapiens

<400> SEQUENCE: 253

Leu His Asp Ile Asn Ala Gln Leu Val Glu Asp Gln Gly Phe Leu Asp
1               5                   10                  15

Thr Leu Lys

<210> SEQ ID NO 254
<211> LENGTH: 10
<212> TYPE: PRT
<213> ORGANISM: Homo sapiens

<400> SEQUENCE: 254

Leu Asn Val Glu Asp Val Asp Ser Thr Lys
1               5                   10

<210> SEQ ID NO 255
<211> LENGTH: 8
<212> TYPE: PRT
<213> ORGANISM: Homo sapiens

<400> SEQUENCE: 255

Glu Ile Glu Val Leu Tyr Ile Arg
1               5

<210> SEQ ID NO 256
<211> LENGTH: 9
<212> TYPE: PRT
<213> ORGANISM: Homo sapiens

<400> SEQUENCE: 256

Leu Gln Ala Glu Ala Phe Gln Ala Arg
1               5

<210> SEQ ID NO 257
<211> LENGTH: 9
<212> TYPE: PRT
<213> ORGANISM: Homo sapiens

<400> SEQUENCE: 257

Val Leu Gln Phe Asp Pro Gly Thr Lys
1               5

<210> SEQ ID NO 258
<211> LENGTH: 14
<212> TYPE: PRT
<213> ORGANISM: Homo sapiens

<400> SEQUENCE: 258

Tyr Ile Tyr Gly Lys Pro Val Gln Gly Val Ala Tyr Val Arg
1               5                   10

<210> SEQ ID NO 259
<211> LENGTH: 9
<212> TYPE: PRT
<213> ORGANISM: Homo sapiens

<400> SEQUENCE: 259

Leu Leu Gln Thr Ser Asn Ile Thr Lys
1               5

<210> SEQ ID NO 260
<211> LENGTH: 19
<212> TYPE: PRT
<213> ORGANISM: Homo sapiens

<400> SEQUENCE: 260

Glu Leu Ser Ala Glu Arg Pro Leu Asn Glu Gln Ile Ala Glu Ala Glu
1               5                   10                  15

Glu Asp Lys

<210> SEQ ID NO 261
<211> LENGTH: 10
<212> TYPE: PRT
<213> ORGANISM: Homo sapiens

<400> SEQUENCE: 261

Ile Asn Glu Glu Asn Thr Ala Ile Ser Arg
1               5                   10

<210> SEQ ID NO 262
<211> LENGTH: 20
<212> TYPE: PRT
<213> ORGANISM: Homo sapiens

<400> SEQUENCE: 262

Ile Ser Glu Asp Ser Asn His Gly Ser Ala Pro Leu Ser Leu Ser Ser
1               5                   10                  15

Asp Pro Gly Lys
            20

<210> SEQ ID NO 263
<211> LENGTH: 8
<212> TYPE: PRT
<213> ORGANISM: Homo sapiens

<400> SEQUENCE: 263

Ile Thr Gln Val Thr Trp Gln Lys
1               5

<210> SEQ ID NO 264
<211> LENGTH: 10
<212> TYPE: PRT
<213> ORGANISM: Homo sapiens

<400> SEQUENCE: 264

Leu Leu Ser Thr Asp Pro Val Ala Ala Lys
1               5                   10

<210> SEQ ID NO 265
<211> LENGTH: 9
<212> TYPE: PRT
<213> ORGANISM: Homo sapiens

<400> SEQUENCE: 265

Ser Pro Glu Leu Gln Ala Glu Ala Lys
1               5

<210> SEQ ID NO 266
<211> LENGTH: 15
<212> TYPE: PRT
<213> ORGANISM: Homo sapiens

<400> SEQUENCE: 266

```
Thr Glu Thr Ile Ser Phe Gly Ser Val Ser Pro Gly Gly Val Lys
1               5                   10                  15

<210> SEQ ID NO 267
<211> LENGTH: 9
<212> TYPE: PRT
<213> ORGANISM: Homo sapiens

<400> SEQUENCE: 267

His Gly Glu Tyr Trp Leu Gly Asn Lys
1               5

<210> SEQ ID NO 268
<211> LENGTH: 17
<212> TYPE: PRT
<213> ORGANISM: Homo sapiens

<400> SEQUENCE: 268

Leu Ser Ile Asn Thr His Pro Ser Gln Lys Pro Leu Ser Ile Thr Val
1               5                   10                  15

Arg

<210> SEQ ID NO 269
<211> LENGTH: 14
<212> TYPE: PRT
<213> ORGANISM: Homo sapiens

<400> SEQUENCE: 269

Glu Gly Ala Phe Val Glu Leu Phe His Glu Ile Asp Asp Arg
1               5                   10

<210> SEQ ID NO 270
<211> LENGTH: 18
<212> TYPE: PRT
<213> ORGANISM: Homo sapiens

<400> SEQUENCE: 270

Ile Leu Asp Leu Leu Val His Ala Ile Ser Ile Asn Ser Ala Tyr Thr
1               5                   10                  15

Thr Lys

<210> SEQ ID NO 271
<211> LENGTH: 11
<212> TYPE: PRT
<213> ORGANISM: Homo sapiens

<400> SEQUENCE: 271

Leu Val Leu Gly Pro Glu Ala Ala Leu Ala Arg
1               5                   10

<210> SEQ ID NO 272
<211> LENGTH: 11
<212> TYPE: PRT
<213> ORGANISM: Homo sapiens

<400> SEQUENCE: 272

Leu Val Pro Phe Ala Thr Glu Leu His Glu Arg
1               5                   10

<210> SEQ ID NO 273
<211> LENGTH: 16
<212> TYPE: PRT
<213> ORGANISM: Homo sapiens
```

<400> SEQUENCE: 273

Ile Arg Pro Gly Glu Phe Glu Gln Phe Glu Ser Thr Ile Gly Phe Lys
1               5                   10                  15

<210> SEQ ID NO 274
<211> LENGTH: 14
<212> TYPE: PRT
<213> ORGANISM: Homo sapiens

<400> SEQUENCE: 274

Leu Leu Gly Phe Ala Thr Val Tyr Gly Thr Val Thr Leu Lys
1               5                   10

<210> SEQ ID NO 275
<211> LENGTH: 8
<212> TYPE: PRT
<213> ORGANISM: Homo sapiens

<400> SEQUENCE: 275

Thr Ala Ser Asp Phe Ile Thr Lys
1               5

<210> SEQ ID NO 276
<211> LENGTH: 9
<212> TYPE: PRT
<213> ORGANISM: Homo sapiens

<400> SEQUENCE: 276

Thr Gln Glu Ala Thr His Pro Val Lys
1               5

<210> SEQ ID NO 277
<211> LENGTH: 9
<212> TYPE: PRT
<213> ORGANISM: Homo sapiens

<400> SEQUENCE: 277

Ser Ala Pro Glu Asn Phe Asn Thr Arg
1               5

<210> SEQ ID NO 278
<211> LENGTH: 15
<212> TYPE: PRT
<213> ORGANISM: Homo sapiens

<400> SEQUENCE: 278

Gly Glu Ala Gly Ala Ala Gly Pro Ala Gly Pro Ala Gly Pro Arg
1               5                   10                  15

<210> SEQ ID NO 279
<211> LENGTH: 10
<212> TYPE: PRT
<213> ORGANISM: Homo sapiens

<400> SEQUENCE: 279

Thr Asp His Gly Ala Glu Ile Val Tyr Lys
1               5                   10

<210> SEQ ID NO 280
<211> LENGTH: 8
<212> TYPE: PRT
<213> ORGANISM: Homo sapiens

<400> SEQUENCE: 280

Trp Asn Leu Tyr Glu Val Val Arg
1               5

<210> SEQ ID NO 281
<211> LENGTH: 14
<212> TYPE: PRT
<213> ORGANISM: Homo sapiens

<400> SEQUENCE: 281

Phe Thr Gln Ser Tyr Asp Tyr Leu Thr Asp Glu Glu Glu Arg
1               5                   10

<210> SEQ ID NO 282
<211> LENGTH: 9
<212> TYPE: PRT
<213> ORGANISM: Homo sapiens

<400> SEQUENCE: 282

Tyr Leu Thr Val Ala Ala Ile Phe Arg
1               5

<210> SEQ ID NO 283
<211> LENGTH: 12
<212> TYPE: PRT
<213> ORGANISM: Homo sapiens

<400> SEQUENCE: 283

Gly Pro Asp Val Leu Thr Ala Thr Val Ser Gly Lys
1               5                   10

<210> SEQ ID NO 284
<211> LENGTH: 9
<212> TYPE: PRT
<213> ORGANISM: Homo sapiens

<400> SEQUENCE: 284

Gly His Ser Pro Phe Ala Asn Leu Lys
1               5

<210> SEQ ID NO 285
<211> LENGTH: 9
<212> TYPE: PRT
<213> ORGANISM: Homo sapiens

<400> SEQUENCE: 285

Ile Ala Ser Thr Ala Ser Ser Pro Arg
1               5

<210> SEQ ID NO 286
<211> LENGTH: 8
<212> TYPE: PRT
<213> ORGANISM: Homo sapiens

<400> SEQUENCE: 286

Asn Gly Asp Gln Asp Thr Leu Lys
1               5

<210> SEQ ID NO 287
<211> LENGTH: 18
<212> TYPE: PRT
<213> ORGANISM: Homo sapiens

<400> SEQUENCE: 287

Phe Ala His Tyr Val Val Thr Ser Gln Val Val Asn Thr Ala Asn Glu

```
                1               5                   10                  15
Ala Arg

<210> SEQ ID NO 288
<211> LENGTH: 8
<212> TYPE: PRT
<213> ORGANISM: Homo sapiens

<400> SEQUENCE: 288

Gln Leu Thr Glu Glu Ile Gln Arg
1               5

<210> SEQ ID NO 289
<211> LENGTH: 13
<212> TYPE: PRT
<213> ORGANISM: Homo sapiens

<400> SEQUENCE: 289

Gly Gly Asn Ile Gly Asp Gly Gly Gly Ala Ala Asp Arg
1               5                   10

<210> SEQ ID NO 290
<211> LENGTH: 15
<212> TYPE: PRT
<213> ORGANISM: Homo sapiens

<400> SEQUENCE: 290

Ala Lys Pro Gln Gly Gln Trp Ala Glu Asp Val Leu Gly Asn Lys
1               5                   10                  15

<210> SEQ ID NO 291
<211> LENGTH: 14
<212> TYPE: PRT
<213> ORGANISM: Homo sapiens

<400> SEQUENCE: 291

Val Ile Ser Asp Thr Glu Ala Asp Ile Gly Ser Asn Leu Arg
1               5                   10

<210> SEQ ID NO 292
<211> LENGTH: 10
<212> TYPE: PRT
<213> ORGANISM: Homo sapiens

<400> SEQUENCE: 292

Ala Glu Ala Ala Leu Thr Ala Ala Gln Lys
1               5                   10

<210> SEQ ID NO 293
<211> LENGTH: 9
<212> TYPE: PRT
<213> ORGANISM: Homo sapiens

<400> SEQUENCE: 293

Val Val Ile Asn Ile Ser Gly Leu Arg
1               5

<210> SEQ ID NO 294
<211> LENGTH: 9
<212> TYPE: PRT
<213> ORGANISM: Homo sapiens

<400> SEQUENCE: 294

Asp Asn Asn Pro Gln Val Asp Trp Lys
```

```
1               5

<210> SEQ ID NO 295
<211> LENGTH: 13
<212> TYPE: PRT
<213> ORGANISM: Homo sapiens

<400> SEQUENCE: 295

Gly Ser Phe Glu Phe Pro Val Gly Asp Ala Val Ser Lys
1               5                   10

<210> SEQ ID NO 296
<211> LENGTH: 7
<212> TYPE: PRT
<213> ORGANISM: Homo sapiens

<400> SEQUENCE: 296

Val Leu Asn Gln Glu Leu Arg
1               5

<210> SEQ ID NO 297
<211> LENGTH: 20
<212> TYPE: PRT
<213> ORGANISM: Homo sapiens

<400> SEQUENCE: 297

Gly Asp Asp Thr Gly Val Leu Leu Pro Thr Pro Gly Glu Ala Gln Asp
1               5                   10                  15

Ala Asp Leu Lys
            20

<210> SEQ ID NO 298
<211> LENGTH: 9
<212> TYPE: PRT
<213> ORGANISM: Homo sapiens

<400> SEQUENCE: 298

Thr Tyr Leu Pro Ala Val Asp Glu Lys
1               5

<210> SEQ ID NO 299
<211> LENGTH: 9
<212> TYPE: PRT
<213> ORGANISM: Homo sapiens

<400> SEQUENCE: 299

Val Asp Gly Leu Ser Asp Asp His Lys
1               5

<210> SEQ ID NO 300
<211> LENGTH: 13
<212> TYPE: PRT
<213> ORGANISM: Homo sapiens

<400> SEQUENCE: 300

Val Pro Glu Thr Ser Leu Ser Val Pro Ile Ile Ile Lys
1               5                   10

<210> SEQ ID NO 301
<211> LENGTH: 9
<212> TYPE: PRT
<213> ORGANISM: Homo sapiens

<400> SEQUENCE: 301
```

```
Asp Leu Val Gly Tyr Ser Ser Thr Arg
1               5

<210> SEQ ID NO 302
<211> LENGTH: 9
<212> TYPE: PRT
<213> ORGANISM: Homo sapiens

<400> SEQUENCE: 302

Phe Ala Tyr Leu Tyr Asp Ser Asp Arg
1               5

<210> SEQ ID NO 303
<211> LENGTH: 20
<212> TYPE: PRT
<213> ORGANISM: Homo sapiens

<400> SEQUENCE: 303

Gly Ile Gly Glu Thr Pro Ile Val Pro Leu Gly Ile Ser Tyr Ile Asp
1               5                   10                  15

Asp Phe Ala Lys
            20

<210> SEQ ID NO 304
<211> LENGTH: 17
<212> TYPE: PRT
<213> ORGANISM: Homo sapiens

<400> SEQUENCE: 304

Val Thr Asp Ala Asn Asp Asn Pro Pro Val Phe Ser Gln Asp Val Tyr
1               5                   10                  15

Arg

<210> SEQ ID NO 305
<211> LENGTH: 14
<212> TYPE: PRT
<213> ORGANISM: Homo sapiens

<400> SEQUENCE: 305

Phe Trp Trp Glu Asn Pro Gly Val Phe Thr Asn Glu Gln Lys
1               5                   10

<210> SEQ ID NO 306
<211> LENGTH: 10
<212> TYPE: PRT
<213> ORGANISM: Homo sapiens

<400> SEQUENCE: 306

Ala Gly Val Ala Tyr Thr Val Gln Val Arg
1               5                   10

<210> SEQ ID NO 307
<211> LENGTH: 9
<212> TYPE: PRT
<213> ORGANISM: Homo sapiens

<400> SEQUENCE: 307

Leu Glu Pro Tyr Ala Asp Gln Leu Arg
1               5

<210> SEQ ID NO 308
<211> LENGTH: 9
<212> TYPE: PRT
<213> ORGANISM: Homo sapiens
```

<400> SEQUENCE: 308

Leu Tyr Ile Glu Tyr Gly Ile Gln Arg
1               5

<210> SEQ ID NO 309
<211> LENGTH: 10
<212> TYPE: PRT
<213> ORGANISM: Homo sapiens

<400> SEQUENCE: 309

Ala Ile Ile Asn Leu Ala Val Tyr Gly Lys
1               5                   10

<210> SEQ ID NO 310
<211> LENGTH: 14
<212> TYPE: PRT
<213> ORGANISM: Homo sapiens

<400> SEQUENCE: 310

Val Asn His Ala Leu Asp Leu Tyr Asn Thr Glu Ile Leu Lys
1               5                   10

<210> SEQ ID NO 311
<211> LENGTH: 10
<212> TYPE: PRT
<213> ORGANISM: Homo sapiens

<400> SEQUENCE: 311

Glu Glu Thr Glu Ser Gly Ser Gly Pro Lys
1               5                   10

<210> SEQ ID NO 312
<211> LENGTH: 13
<212> TYPE: PRT
<213> ORGANISM: Homo sapiens

<400> SEQUENCE: 312

Ile Ala Asn Leu Leu Pro Ala Trp Tyr Tyr Asn Phe Arg
1               5                   10

<210> SEQ ID NO 313
<211> LENGTH: 7
<212> TYPE: PRT
<213> ORGANISM: Homo sapiens

<400> SEQUENCE: 313

Trp Glu Glu Glu Leu Ser Arg
1               5

<210> SEQ ID NO 314
<211> LENGTH: 7
<212> TYPE: PRT
<213> ORGANISM: Homo sapiens

<400> SEQUENCE: 314

Phe Ser Asp Tyr Tyr Ser Lys
1               5

<210> SEQ ID NO 315
<211> LENGTH: 13
<212> TYPE: PRT
<213> ORGANISM: Homo sapiens

<400> SEQUENCE: 315

```
Phe Glu Glu Phe Tyr Gly Leu Leu Gln His Val His Lys
1               5                   10

<210> SEQ ID NO 316
<211> LENGTH: 10
<212> TYPE: PRT
<213> ORGANISM: Homo sapiens

<400> SEQUENCE: 316

Leu Gly Leu Pro Gly Glu Val Phe Gly Arg
1               5                   10

<210> SEQ ID NO 317
<211> LENGTH: 18
<212> TYPE: PRT
<213> ORGANISM: Homo sapiens

<400> SEQUENCE: 317

Val Gly Ala Thr Asp His Gly Ser Pro Ala Leu Ser Ser Glu Ala Leu
1               5                   10                  15

Val Arg

<210> SEQ ID NO 318
<211> LENGTH: 14
<212> TYPE: PRT
<213> ORGANISM: Homo sapiens

<400> SEQUENCE: 318

Val Asp Leu Leu Gln Gly Ala Gly Asn Ser Ala Ala Gly Arg
1               5                   10

<210> SEQ ID NO 319
<211> LENGTH: 9
<212> TYPE: PRT
<213> ORGANISM: Homo sapiens

<400> SEQUENCE: 319

Asn Leu Tyr Ser Gly Asp Tyr Tyr Arg
1               5

<210> SEQ ID NO 320
<211> LENGTH: 9
<212> TYPE: PRT
<213> ORGANISM: Homo sapiens

<400> SEQUENCE: 320

Ile Pro Val Leu Gly Leu Thr Thr Arg
1               5

<210> SEQ ID NO 321
<211> LENGTH: 10
<212> TYPE: PRT
<213> ORGANISM: Homo sapiens

<400> SEQUENCE: 321

Ala Ser Tyr Pro Asp Ile Thr Gly Glu Lys
1               5                   10

<210> SEQ ID NO 322
<211> LENGTH: 17
<212> TYPE: PRT
<213> ORGANISM: Homo sapiens

<400> SEQUENCE: 322
```

Ser Leu Val Val Ser Trp Ser Pro Pro Ala Gly Asp Trp Glu Gln Tyr
1               5                   10                  15

Arg

<210> SEQ ID NO 323
<211> LENGTH: 10
<212> TYPE: PRT
<213> ORGANISM: Homo sapiens

<400> SEQUENCE: 323

Tyr Leu Glu Glu Ser Asn Phe Val His Arg
1               5                   10

<210> SEQ ID NO 324
<211> LENGTH: 10
<212> TYPE: PRT
<213> ORGANISM: Homo sapiens

<400> SEQUENCE: 324

Ser Leu Gly Ile Ser Ile Val Gly Gly Arg
1               5                   10

<210> SEQ ID NO 325
<211> LENGTH: 10
<212> TYPE: PRT
<213> ORGANISM: Homo sapiens

<400> SEQUENCE: 325

Trp Ala Glu Val Pro Pro Phe Leu Glu Arg
1               5                   10

<210> SEQ ID NO 326
<211> LENGTH: 9
<212> TYPE: PRT
<213> ORGANISM: Homo sapiens

<400> SEQUENCE: 326

Leu Ile Ala Thr Thr Ala His Glu Lys
1               5

<210> SEQ ID NO 327
<211> LENGTH: 15
<212> TYPE: PRT
<213> ORGANISM: Homo sapiens

<400> SEQUENCE: 327

Thr His Ser Trp Gln Asp Ala Pro Ala Ser Ala Gly Pro Thr Arg
1               5                   10                  15

<210> SEQ ID NO 328
<211> LENGTH: 8
<212> TYPE: PRT
<213> ORGANISM: Homo sapiens

<400> SEQUENCE: 328

Tyr Leu Asp Phe Ser Leu Phe Lys
1               5

<210> SEQ ID NO 329
<211> LENGTH: 12
<212> TYPE: PRT
<213> ORGANISM: Homo sapiens

<400> SEQUENCE: 329

Gln Phe Gly Ala Leu Leu Gln Pro Gly Val Asn Lys
1               5                   10

<210> SEQ ID NO 330
<211> LENGTH: 13
<212> TYPE: PRT
<213> ORGANISM: Homo sapiens

<400> SEQUENCE: 330

Leu Thr Leu Ser Asp Phe Leu Ile Lys Pro Ile Gln Arg
1               5                   10

<210> SEQ ID NO 331
<211> LENGTH: 14
<212> TYPE: PRT
<213> ORGANISM: Homo sapiens

<400> SEQUENCE: 331

Thr Val Pro Ser Asp Asn Ala Val Asn Pro Ala Ile Leu Lys
1               5                   10

<210> SEQ ID NO 332
<211> LENGTH: 13
<212> TYPE: PRT
<213> ORGANISM: Homo sapiens

<400> SEQUENCE: 332

Ala Glu Asn Gly Pro Gly Pro Gly Val Leu Val Leu Arg
1               5                   10

<210> SEQ ID NO 333
<211> LENGTH: 22
<212> TYPE: PRT
<213> ORGANISM: Homo sapiens

<400> SEQUENCE: 333

Glu Gly Pro Glu Gln Val Ile Pro Ile Asn Ser Gly Asp Leu Phe Val
1               5                   10                  15

His Pro Leu Trp Asn Arg
            20

<210> SEQ ID NO 334
<211> LENGTH: 12
<212> TYPE: PRT
<213> ORGANISM: Homo sapiens

<400> SEQUENCE: 334

Ile Leu Phe Leu Asn Pro Ile Pro Ser Asp Pro Lys
1               5                   10

<210> SEQ ID NO 335
<211> LENGTH: 11
<212> TYPE: PRT
<213> ORGANISM: Homo sapiens

<400> SEQUENCE: 335

Ser Pro Ala Leu Pro Pro Asp Pro Thr Ala Arg
1               5                   10

<210> SEQ ID NO 336
<211> LENGTH: 13
<212> TYPE: PRT
<213> ORGANISM: Homo sapiens -continued

```
<400> SEQUENCE: 336

Gly Gly Val Asp Leu Pro Ala Thr Pro Gly Gly Pro Arg
1               5                   10

<210> SEQ ID NO 337
<211> LENGTH: 9
<212> TYPE: PRT
<213> ORGANISM: Homo sapiens

<400> SEQUENCE: 337

Gln His Thr Val Thr Thr Thr Thr Lys
1               5

<210> SEQ ID NO 338
<211> LENGTH: 8
<212> TYPE: PRT
<213> ORGANISM: Homo sapiens

<400> SEQUENCE: 338

Val Ile Gln Thr Ala Phe Gln Arg
1               5

<210> SEQ ID NO 339
<211> LENGTH: 15
<212> TYPE: PRT
<213> ORGANISM: Homo sapiens

<400> SEQUENCE: 339

Val Thr Leu Ile Glu Thr Glu Pro Leu Ala Glu Tyr Val Ile Arg
1               5                   10                  15

<210> SEQ ID NO 340
<211> LENGTH: 14
<212> TYPE: PRT
<213> ORGANISM: Homo sapiens

<400> SEQUENCE: 340

Val Val His His Asp Pro Pro Leu Leu Phe Asp Leu Ser Arg
1               5                   10

<210> SEQ ID NO 341
<211> LENGTH: 22
<212> TYPE: PRT
<213> ORGANISM: Homo sapiens

<400> SEQUENCE: 341

Gly Leu Thr Ser Leu Ala Asp Thr Phe Glu His Val Ile Glu Glu Leu
1               5                   10                  15

Leu Asp Glu Asp Gln Lys
            20

<210> SEQ ID NO 342
<211> LENGTH: 10
<212> TYPE: PRT
<213> ORGANISM: Homo sapiens

<400> SEQUENCE: 342

Asn Asn Leu Leu Asn Glu Asp Leu Glu Lys
1               5                   10

<210> SEQ ID NO 343
<211> LENGTH: 14
<212> TYPE: PRT
<213> ORGANISM: Homo sapiens
```

<400> SEQUENCE: 343

Ser Thr Gly Thr Ile Ser Val Ile Ser Ser Gly Leu Asp Arg
1               5                   10

<210> SEQ ID NO 344
<211> LENGTH: 25
<212> TYPE: PRT
<213> ORGANISM: Homo sapiens

<400> SEQUENCE: 344

Thr Leu Ala Thr Ser Ser Leu Pro Leu Ser Pro Thr Leu Ala Ser Asn
1               5                   10                  15

Ser Gln Gly Ser Gln Gly Asp Gln Arg
            20                  25

<210> SEQ ID NO 345
<211> LENGTH: 8
<212> TYPE: PRT
<213> ORGANISM: Homo sapiens

<400> SEQUENCE: 345

Phe Gln Leu Thr Phe Pro Leu Arg
1               5

<210> SEQ ID NO 346
<211> LENGTH: 10
<212> TYPE: PRT
<213> ORGANISM: Homo sapiens

<400> SEQUENCE: 346

Gly Thr Gln Gly Ser Glu Leu Asp Pro Lys
1               5                   10

<210> SEQ ID NO 347
<211> LENGTH: 8
<212> TYPE: PRT
<213> ORGANISM: Homo sapiens

<400> SEQUENCE: 347

Ile Leu Val Ala Glu Gly Thr Arg
1               5

<210> SEQ ID NO 348
<211> LENGTH: 8
<212> TYPE: PRT
<213> ORGANISM: Homo sapiens

<400> SEQUENCE: 348

Tyr Tyr Leu Asn Asp Leu Asp Arg
1               5

<210> SEQ ID NO 349
<211> LENGTH: 12
<212> TYPE: PRT
<213> ORGANISM: Homo sapiens

<400> SEQUENCE: 349

Asp Glu Leu Ala Pro Ala Gly Thr Gly Val Ser Arg
1               5                   10

<210> SEQ ID NO 350
<211> LENGTH: 11
<212> TYPE: PRT

<213> ORGANISM: Homo sapiens

<400> SEQUENCE: 350

Asn Val Ser Ile Pro Ala Leu Asn Asp Ser Lys
1               5                   10

<210> SEQ ID NO 351
<211> LENGTH: 9
<212> TYPE: PRT
<213> ORGANISM: Homo sapiens

<400> SEQUENCE: 351

Thr Ser Glu Val Leu Asn Ala Ala Lys
1               5

<210> SEQ ID NO 352
<211> LENGTH: 10
<212> TYPE: PRT
<213> ORGANISM: Homo sapiens

<400> SEQUENCE: 352

Thr Thr Ile Asn Asn Glu Tyr Asn Tyr Arg
1               5                   10

<210> SEQ ID NO 353
<211> LENGTH: 11
<212> TYPE: PRT
<213> ORGANISM: Homo sapiens

<400> SEQUENCE: 353

Leu Ala Leu Leu Val Asp Thr Val Gly Pro Arg
1               5                   10

<210> SEQ ID NO 354
<211> LENGTH: 11
<212> TYPE: PRT
<213> ORGANISM: Homo sapiens

<400> SEQUENCE: 354

Tyr Gly Leu Val Thr Tyr Ala Thr Tyr Pro Lys
1               5                   10

<210> SEQ ID NO 355
<211> LENGTH: 15
<212> TYPE: PRT
<213> ORGANISM: Homo sapiens

<400> SEQUENCE: 355

Ala Asp Leu Gln Phe Ser Ser Ala Pro Ala Pro Asp Thr Leu Lys
1               5                   10                  15

<210> SEQ ID NO 356
<211> LENGTH: 9
<212> TYPE: PRT
<213> ORGANISM: Homo sapiens

<400> SEQUENCE: 356

Ala Arg Pro Asp Asp Gly Glu Leu Lys
1               5

<210> SEQ ID NO 357
<211> LENGTH: 19
<212> TYPE: PRT
<213> ORGANISM: Homo sapiens

```
<400> SEQUENCE: 357

Glu His Gly Val Pro Ile Leu Ile Ser Glu Ile His Pro Gly Gln Pro
1               5                   10                  15

Ala Asp Arg

<210> SEQ ID NO 358
<211> LENGTH: 8
<212> TYPE: PRT
<213> ORGANISM: Homo sapiens

<400> SEQUENCE: 358

His Leu Val Tyr Glu Ser Asp Lys
1               5

<210> SEQ ID NO 359
<211> LENGTH: 11
<212> TYPE: PRT
<213> ORGANISM: Homo sapiens

<400> SEQUENCE: 359

Ala Val Gly Tyr Leu Ile Thr Gly Tyr Gln Arg
1               5                   10

<210> SEQ ID NO 360
<211> LENGTH: 8
<212> TYPE: PRT
<213> ORGANISM: Homo sapiens

<400> SEQUENCE: 360

Leu Ala Gln Ala Tyr Leu Asp Lys
1               5

<210> SEQ ID NO 361
<211> LENGTH: 9
<212> TYPE: PRT
<213> ORGANISM: Homo sapiens

<400> SEQUENCE: 361

Asn Leu Ser Pro Gly Phe Asn Phe Arg
1               5

<210> SEQ ID NO 362
<211> LENGTH: 10
<212> TYPE: PRT
<213> ORGANISM: Homo sapiens

<400> SEQUENCE: 362

Ser Asp Leu Gly Ala Pro Leu His Asp Lys
1               5                   10

<210> SEQ ID NO 363
<211> LENGTH: 18
<212> TYPE: PRT
<213> ORGANISM: Homo sapiens

<400> SEQUENCE: 363

Gly Glu Gln Gly Pro Pro Gly Ile Pro Gly Pro Gln Gly Leu Pro Gly
1               5                   10                  15

Val Lys

<210> SEQ ID NO 364
<211> LENGTH: 22
<212> TYPE: PRT
```

```
<213> ORGANISM: Homo sapiens

<400> SEQUENCE: 364

Gln Glu Tyr Ser Glu Asn Asn Glu Asn Tyr Ile Glu Val Pro Leu Ile
1               5                   10                  15

Phe Asp Pro Val Thr Arg
            20

<210> SEQ ID NO 365
<211> LENGTH: 13
<212> TYPE: PRT
<213> ORGANISM: Homo sapiens

<400> SEQUENCE: 365

Ser Gly Glu Asn Pro Tyr Ala Ser Ile Asp Ile Ser Lys
1               5                   10

<210> SEQ ID NO 366
<211> LENGTH: 10
<212> TYPE: PRT
<213> ORGANISM: Homo sapiens

<400> SEQUENCE: 366

Ala Leu Ala His Leu Leu Glu Ala Glu Arg
1               5                   10

<210> SEQ ID NO 367
<211> LENGTH: 21
<212> TYPE: PRT
<213> ORGANISM: Homo sapiens

<400> SEQUENCE: 367

Thr Pro Ala Leu Ser Pro Gln Arg Pro Leu Thr Thr Gln Gln Pro Gln
1               5                   10                  15

Ser Gly Thr Leu Lys
            20

<210> SEQ ID NO 368
<211> LENGTH: 11
<212> TYPE: PRT
<213> ORGANISM: Homo sapiens

<400> SEQUENCE: 368

Ala Thr Trp Ser Gly Ala Val Leu Ala Gly Arg
1               5                   10

<210> SEQ ID NO 369
<211> LENGTH: 9
<212> TYPE: PRT
<213> ORGANISM: Homo sapiens

<400> SEQUENCE: 369

Ser Gly Leu Leu Glu Val Leu Val Arg
1               5

<210> SEQ ID NO 370
<211> LENGTH: 9
<212> TYPE: PRT
<213> ORGANISM: Homo sapiens

<400> SEQUENCE: 370

Thr Leu Gly Ser Gln Pro Val Leu Lys
1               5
```

```
<210> SEQ ID NO 371
<211> LENGTH: 10
<212> TYPE: PRT
<213> ORGANISM: Homo sapiens

<400> SEQUENCE: 371

Phe Val Leu Gly Pro Thr Pro Val Gln Lys
1               5                   10

<210> SEQ ID NO 372
<211> LENGTH: 22
<212> TYPE: PRT
<213> ORGANISM: Homo sapiens

<400> SEQUENCE: 372

Leu Glu Ala Gly Ile Asn Gln Leu Ser Phe Pro Leu Ser Ser Glu Pro
1               5                   10                  15

Ile Gln Gly Ser Tyr Arg
            20

<210> SEQ ID NO 373
<211> LENGTH: 8
<212> TYPE: PRT
<213> ORGANISM: Homo sapiens

<400> SEQUENCE: 373

Ile Tyr Asp Ser Thr Thr Phe Arg
1               5

<210> SEQ ID NO 374
<211> LENGTH: 8
<212> TYPE: PRT
<213> ORGANISM: Homo sapiens

<400> SEQUENCE: 374

Leu Tyr Tyr Gly Asp Asp Glu Lys
1               5

<210> SEQ ID NO 375
<211> LENGTH: 16
<212> TYPE: PRT
<213> ORGANISM: Homo sapiens

<400> SEQUENCE: 375

Leu Ala Lys Pro Leu Ser Ser Leu Thr Pro Leu Ile Ile Ala Ala Lys
1               5                   10                  15

<210> SEQ ID NO 376
<211> LENGTH: 12
<212> TYPE: PRT
<213> ORGANISM: Homo sapiens

<400> SEQUENCE: 376

Asp Pro Thr Phe Ile Pro Ala Pro Ile Gln Ala Lys
1               5                   10

<210> SEQ ID NO 377
<211> LENGTH: 9
<212> TYPE: PRT
<213> ORGANISM: Homo sapiens

<400> SEQUENCE: 377

Thr Val Ile Gly Pro Asp Gly His Lys
1               5
```

<210> SEQ ID NO 378
<211> LENGTH: 10
<212> TYPE: PRT
<213> ORGANISM: Homo sapiens

<400> SEQUENCE: 378

Val Ile Ser His Pro Asn Tyr Asp Ser Lys
1               5                   10

<210> SEQ ID NO 379
<211> LENGTH: 17
<212> TYPE: PRT
<213> ORGANISM: Homo sapiens

<400> SEQUENCE: 379

Ala Ala Pro Gly Pro Pro Pro Pro Pro Pro Pro Gly Gln Ala Pro
1               5                   10                  15

Arg

<210> SEQ ID NO 380
<211> LENGTH: 13
<212> TYPE: PRT
<213> ORGANISM: Homo sapiens

<400> SEQUENCE: 380

Glu Glu Ala Leu Glu Leu Ile Asn Gly Tyr Ile Gln Lys
1               5                   10

<210> SEQ ID NO 381
<211> LENGTH: 8
<212> TYPE: PRT
<213> ORGANISM: Homo sapiens

<400> SEQUENCE: 381

Ile Asp Leu Ala Asp Phe Glu Lys
1               5

<210> SEQ ID NO 382
<211> LENGTH: 9
<212> TYPE: PRT
<213> ORGANISM: Homo sapiens

<400> SEQUENCE: 382

Ala Val Gly Leu Ala Gly Thr Phe Arg
1               5

<210> SEQ ID NO 383
<211> LENGTH: 9
<212> TYPE: PRT
<213> ORGANISM: Homo sapiens

<400> SEQUENCE: 383

Ser Thr Leu Val Asn Thr Leu Phe Lys
1               5

<210> SEQ ID NO 384
<211> LENGTH: 9
<212> TYPE: PRT
<213> ORGANISM: Homo sapiens

<400> SEQUENCE: 384

Ser Glu Asp Ala Asp Ser Ser Val Lys
1               5

<210> SEQ ID NO 385
<211> LENGTH: 8
<212> TYPE: PRT
<213> ORGANISM: Homo sapiens

<400> SEQUENCE: 385

Thr Tyr Glu Thr Thr Leu Glu Lys
1               5

<210> SEQ ID NO 386
<211> LENGTH: 8
<212> TYPE: PRT
<213> ORGANISM: Homo sapiens

<400> SEQUENCE: 386

Tyr Phe Ile Asp Phe Val Ala Arg
1               5

<210> SEQ ID NO 387
<211> LENGTH: 9
<212> TYPE: PRT
<213> ORGANISM: Homo sapiens

<400> SEQUENCE: 387

Thr Glu Ala Asp Thr Ile Ser Gly Arg
1               5

<210> SEQ ID NO 388
<211> LENGTH: 7
<212> TYPE: PRT
<213> ORGANISM: Homo sapiens

<400> SEQUENCE: 388

Leu Ala Glu Tyr His Ala Lys
1               5

<210> SEQ ID NO 389
<211> LENGTH: 11
<212> TYPE: PRT
<213> ORGANISM: Homo sapiens

<400> SEQUENCE: 389

Asn Gly Glu Leu Leu Pro Glu Gly Phe Arg
1               5                   10

<210> SEQ ID NO 390
<211> LENGTH: 10
<212> TYPE: PRT
<213> ORGANISM: Homo sapiens

<400> SEQUENCE: 390

Ser Leu Val Ala Asp Gly Val Ala Glu Arg
1               5                   10

<210> SEQ ID NO 391
<211> LENGTH: 8
<212> TYPE: PRT
<213> ORGANISM: Homo sapiens

<400> SEQUENCE: 391

Thr Leu Leu Asp Leu Asn Asp Lys
1               5

```
<210> SEQ ID NO 392
<211> LENGTH: 11
<212> TYPE: PRT
<213> ORGANISM: Homo sapiens

<400> SEQUENCE: 392

Val Gly Gly Leu Glu Asp Gln Leu Ser Val Arg
1               5                   10

<210> SEQ ID NO 393
<211> LENGTH: 11
<212> TYPE: PRT
<213> ORGANISM: Homo sapiens

<400> SEQUENCE: 393

Gln Ile Gln Val Phe Glu Asp Glu Pro Ala Arg
1               5                   10

<210> SEQ ID NO 394
<211> LENGTH: 10
<212> TYPE: PRT
<213> ORGANISM: Homo sapiens

<400> SEQUENCE: 394

Val Ser Asp Ile Asn Asp Asn Glu Pro Lys
1               5                   10

<210> SEQ ID NO 395
<211> LENGTH: 15
<212> TYPE: PRT
<213> ORGANISM: Homo sapiens

<400> SEQUENCE: 395

Ile Gln Pro Ser Gly Gly Thr Asn Ile Asn Glu Ala Leu Leu Arg
1               5                   10                  15

<210> SEQ ID NO 396
<211> LENGTH: 7
<212> TYPE: PRT
<213> ORGANISM: Homo sapiens

<400> SEQUENCE: 396

Ile Thr Glu Gln Pro Leu Lys
1               5

<210> SEQ ID NO 397
<211> LENGTH: 18
<212> TYPE: PRT
<213> ORGANISM: Homo sapiens

<400> SEQUENCE: 397

Glu Asn Pro Ala Val Ile Asp Phe Glu Leu Ala Pro Ile Val Asp Leu
1               5                   10                  15

Val Arg

<210> SEQ ID NO 398
<211> LENGTH: 9
<212> TYPE: PRT
<213> ORGANISM: Homo sapiens

<400> SEQUENCE: 398

Leu Glu Asn Leu Val Tyr Tyr Asn Arg
1               5
```

<210> SEQ ID NO 399
<211> LENGTH: 8
<212> TYPE: PRT
<213> ORGANISM: Homo sapiens

<400> SEQUENCE: 399

Asn Ser Leu Phe Glu Tyr Gln Lys
1               5

<210> SEQ ID NO 400
<211> LENGTH: 9
<212> TYPE: PRT
<213> ORGANISM: Homo sapiens

<400> SEQUENCE: 400

Ser Phe Asn Pro Asn Ser Pro Gly Lys
1               5

<210> SEQ ID NO 401
<211> LENGTH: 11
<212> TYPE: PRT
<213> ORGANISM: Homo sapiens

<400> SEQUENCE: 401

Ala Pro Ile Ala Ala Pro Glu Pro Glu Leu Lys
1               5                   10

<210> SEQ ID NO 402
<211> LENGTH: 7
<212> TYPE: PRT
<213> ORGANISM: Homo sapiens

<400> SEQUENCE: 402

Phe Ala Phe Asn Leu Tyr Arg
1               5

<210> SEQ ID NO 403
<211> LENGTH: 8
<212> TYPE: PRT
<213> ORGANISM: Homo sapiens

<400> SEQUENCE: 403

Asn Val Tyr Asp Ser Ile Ser Lys
1               5

<210> SEQ ID NO 404
<211> LENGTH: 7
<212> TYPE: PRT
<213> ORGANISM: Homo sapiens

<400> SEQUENCE: 404

Phe Val Asn Thr Leu His Lys
1               5

<210> SEQ ID NO 405
<211> LENGTH: 16
<212> TYPE: PRT
<213> ORGANISM: Homo sapiens

<400> SEQUENCE: 405

Asn Ile Leu Val Gln Thr Pro Glu Ser Glu Ser Pro Gln Ser His Arg
1               5                   10                  15

<210> SEQ ID NO 406
<211> LENGTH: 9

```
<212> TYPE: PRT
<213> ORGANISM: Homo sapiens

<400> SEQUENCE: 406

Ser Leu Ala Pro Ala Glu Val Pro Lys
1               5

<210> SEQ ID NO 407
<211> LENGTH: 12
<212> TYPE: PRT
<213> ORGANISM: Homo sapiens

<400> SEQUENCE: 407

Val Gly Ser Ala Leu Phe Leu Ser His Asn Leu Lys
1               5                   10

<210> SEQ ID NO 408
<211> LENGTH: 8
<212> TYPE: PRT
<213> ORGANISM: Homo sapiens

<400> SEQUENCE: 408

Val Phe Tyr Gly Asn Ser Asp Arg
1               5

<210> SEQ ID NO 409
<211> LENGTH: 9
<212> TYPE: PRT
<213> ORGANISM: Homo sapiens

<400> SEQUENCE: 409

Ala Leu Gln Thr Val Phe Gly Glu Arg
1               5

<210> SEQ ID NO 410
<211> LENGTH: 27
<212> TYPE: PRT
<213> ORGANISM: Homo sapiens

<400> SEQUENCE: 410

Leu Gln Glu Thr Ser Asn Trp Leu Leu Ser Gln Gln Ala Asp Gly
1               5                   10                  15

Ser Phe Gln Asp Leu Ser Pro Val Ile His Arg
                20                  25

<210> SEQ ID NO 411
<211> LENGTH: 22
<212> TYPE: PRT
<213> ORGANISM: Homo sapiens

<400> SEQUENCE: 411

Asp Phe Glu Ser Asp Ile Ile Asp Ser Ser Ala Leu Asn Gly Gly Phe
1               5                   10                  15

Gln Pro Val Asn Ile Lys
            20

<210> SEQ ID NO 412
<211> LENGTH: 7
<212> TYPE: PRT
<213> ORGANISM: Homo sapiens

<400> SEQUENCE: 412

Ile Ala Ile Asp Leu Phe Lys
1               5
```

<210> SEQ ID NO 413
<211> LENGTH: 13
<212> TYPE: PRT
<213> ORGANISM: Homo sapiens

<400> SEQUENCE: 413

Glu Pro Glu Phe Leu Asn Ile Ser Ile Gln Asp Ser Arg
1               5                   10

<210> SEQ ID NO 414
<211> LENGTH: 7
<212> TYPE: PRT
<213> ORGANISM: Homo sapiens

<400> SEQUENCE: 414

Leu Gly Phe Leu Leu Gln Lys
1               5

<210> SEQ ID NO 415
<211> LENGTH: 12
<212> TYPE: PRT
<213> ORGANISM: Homo sapiens

<400> SEQUENCE: 415

Ser Ile Ala Asp Phe Val Ser Gly Ala Glu Ser Arg
1               5                   10

<210> SEQ ID NO 416
<211> LENGTH: 11
<212> TYPE: PRT
<213> ORGANISM: Homo sapiens

<400> SEQUENCE: 416

Asp Asp Leu Tyr Val Ser Asp Ala Phe His Lys
1               5                   10

<210> SEQ ID NO 417
<211> LENGTH: 15
<212> TYPE: PRT
<213> ORGANISM: Homo sapiens

<400> SEQUENCE: 417

Asn Trp Gly Leu Ser Phe Tyr Ala Asp Lys Pro Glu Thr Thr Lys
1               5                   10                  15

<210> SEQ ID NO 418
<211> LENGTH: 10
<212> TYPE: PRT
<213> ORGANISM: Homo sapiens

<400> SEQUENCE: 418

Asp Val Gln Pro Gly Ser Val Ala Asp Arg
1               5                   10

<210> SEQ ID NO 419
<211> LENGTH: 10
<212> TYPE: PRT
<213> ORGANISM: Homo sapiens

<400> SEQUENCE: 419

Gly Val Gly Val Val Asp Gln Ala Leu Arg
1               5                   10

```
<210> SEQ ID NO 420
<211> LENGTH: 8
<212> TYPE: PRT
<213> ORGANISM: Homo sapiens

<400> SEQUENCE: 420

Ile Thr Gly Pro Val Thr Val Lys
1               5

<210> SEQ ID NO 421
<211> LENGTH: 8
<212> TYPE: PRT
<213> ORGANISM: Homo sapiens

<400> SEQUENCE: 421

Leu Asn Glu Val Ile Val Asn Lys
1               5

<210> SEQ ID NO 422
<211> LENGTH: 10
<212> TYPE: PRT
<213> ORGANISM: Homo sapiens

<400> SEQUENCE: 422

Glu Ile Gln Asn Ala Val Asn Gly Val Lys
1               5                   10

<210> SEQ ID NO 423
<211> LENGTH: 7
<212> TYPE: PRT
<213> ORGANISM: Homo sapiens

<400> SEQUENCE: 423

Val Leu Glu Pro Thr Leu Lys
1               5

<210> SEQ ID NO 424
<211> LENGTH: 8
<212> TYPE: PRT
<213> ORGANISM: Homo sapiens

<400> SEQUENCE: 424

Val Pro Leu Asp Leu Ser Pro Arg
1               5

<210> SEQ ID NO 425
<211> LENGTH: 14
<212> TYPE: PRT
<213> ORGANISM: Homo sapiens

<400> SEQUENCE: 425

Val Thr Ala Pro Glu Ala Gln Ala Lys Pro Ser Ala Ala Arg
1               5                   10

<210> SEQ ID NO 426
<211> LENGTH: 11
<212> TYPE: PRT
<213> ORGANISM: Homo sapiens

<400> SEQUENCE: 426

Phe Val Tyr Leu Glu Leu Pro Ala Ala Ala Lys
1               5                   10

<210> SEQ ID NO 427
<211> LENGTH: 14
```

```
<212> TYPE: PRT
<213> ORGANISM: Homo sapiens

<400> SEQUENCE: 427

Thr Pro Ile Ile Trp Phe His Val Val Pro Ala Ala Asn Lys
1               5                   10

<210> SEQ ID NO 428
<211> LENGTH: 11
<212> TYPE: PRT
<213> ORGANISM: Homo sapiens

<400> SEQUENCE: 428

Tyr Ile Tyr Leu Gly Leu Pro Ala Ala Leu Arg
1               5                   10

<210> SEQ ID NO 429
<211> LENGTH: 14
<212> TYPE: PRT
<213> ORGANISM: Homo sapiens

<400> SEQUENCE: 429

Ala His Ser Asp Gly Gly Asp Gly Val Val Ser Gln Val Lys
1               5                   10

<210> SEQ ID NO 430
<211> LENGTH: 11
<212> TYPE: PRT
<213> ORGANISM: Homo sapiens

<400> SEQUENCE: 430

Glu Gly Pro Val His Gly Gly Glu Ala Ala Arg
1               5                   10

<210> SEQ ID NO 431
<211> LENGTH: 8
<212> TYPE: PRT
<213> ORGANISM: Homo sapiens

<400> SEQUENCE: 431

Thr Leu Tyr Ser Ser Ser Pro Arg
1               5

<210> SEQ ID NO 432
<211> LENGTH: 17
<212> TYPE: PRT
<213> ORGANISM: Homo sapiens

<400> SEQUENCE: 432

Asn Leu Gly Val Asp Leu Leu Pro Gly Tyr Gln Asp Pro Tyr Ser Gly
1               5                   10                  15

Arg

<210> SEQ ID NO 433
<211> LENGTH: 9
<212> TYPE: PRT
<213> ORGANISM: Homo sapiens

<400> SEQUENCE: 433

Val Gly Val Ile Ser Phe Ala Gln Lys
1               5

<210> SEQ ID NO 434
<211> LENGTH: 11
```

```
<212> TYPE: PRT
<213> ORGANISM: Homo sapiens

<400> SEQUENCE: 434

Val Ala Val Phe Gly Ala Gly Val Gly Lys
1               5                   10

<210> SEQ ID NO 435
<211> LENGTH: 10
<212> TYPE: PRT
<213> ORGANISM: Homo sapiens

<400> SEQUENCE: 435

Glu Asn Ala Thr Thr Asp Leu Leu Thr Lys
1               5                   10

<210> SEQ ID NO 436
<211> LENGTH: 14
<212> TYPE: PRT
<213> ORGANISM: Homo sapiens

<400> SEQUENCE: 436

Ala Ala Glu Trp Gln Leu Asp Gln Pro Ser Trp Ser Gly Arg
1               5                   10

<210> SEQ ID NO 437
<211> LENGTH: 9
<212> TYPE: PRT
<213> ORGANISM: Homo sapiens

<400> SEQUENCE: 437

Gly Pro Gly Gly Val Trp Ala Ala Lys
1               5

<210> SEQ ID NO 438
<211> LENGTH: 8
<212> TYPE: PRT
<213> ORGANISM: Homo sapiens

<400> SEQUENCE: 438

Val Leu Glu Gly Val Ile Asp Arg
1               5

<210> SEQ ID NO 439
<211> LENGTH: 8
<212> TYPE: PRT
<213> ORGANISM: Homo sapiens

<400> SEQUENCE: 439

Ile Ala Thr Leu Leu Leu Ala Arg
1               5

<210> SEQ ID NO 440
<211> LENGTH: 17
<212> TYPE: PRT
<213> ORGANISM: Homo sapiens

<400> SEQUENCE: 440

Gly Leu Asn Gly Gln Lys Pro Leu Gly Ala Ala Glu Pro Ile Thr Val
1               5                   10                  15

Lys

<210> SEQ ID NO 441
<211> LENGTH: 16
```

```
<212> TYPE: PRT
<213> ORGANISM: Homo sapiens

<400> SEQUENCE: 441

Leu Asp Leu Ile Thr Val Glu Ala Phe Lys Pro Ile Leu Ser Thr Arg
1               5                   10                  15

<210> SEQ ID NO 442
<211> LENGTH: 8
<212> TYPE: PRT
<213> ORGANISM: Homo sapiens

<400> SEQUENCE: 442

Tyr Glu Ile Val Val Glu Ala Arg
1               5

<210> SEQ ID NO 443
<211> LENGTH: 9
<212> TYPE: PRT
<213> ORGANISM: Homo sapiens

<400> SEQUENCE: 443

Ser Ile Pro Gln Val Ser Pro Val Arg
1               5

<210> SEQ ID NO 444
<211> LENGTH: 12
<212> TYPE: PRT
<213> ORGANISM: Homo sapiens

<400> SEQUENCE: 444

Ile Thr Gln Tyr Leu Asp Ala Gly Gly Ile Pro Arg
1               5                   10

<210> SEQ ID NO 445
<211> LENGTH: 24
<212> TYPE: PRT
<213> ORGANISM: Homo sapiens

<400> SEQUENCE: 445

Ala Leu Asp Tyr Glu Glu Arg Pro Glu Leu Ser Phe Ile Leu Thr Ala
1               5                   10                  15

Leu Asp Gly Gly Ser Pro Pro Arg
            20

<210> SEQ ID NO 446
<211> LENGTH: 13
<212> TYPE: PRT
<213> ORGANISM: Homo sapiens

<400> SEQUENCE: 446

Leu Thr Leu Thr Ala Val Asp Gly Gly Ser Pro Pro Arg
1               5                   10

<210> SEQ ID NO 447
<211> LENGTH: 13
<212> TYPE: PRT
<213> ORGANISM: Homo sapiens

<400> SEQUENCE: 447

Ser Leu Asp Tyr Glu Ala Leu Gln Ser Phe Glu Phe Arg
1               5                   10

<210> SEQ ID NO 448
```

```
<211> LENGTH: 10
<212> TYPE: PRT
<213> ORGANISM: Homo sapiens

<400> SEQUENCE: 448

Phe Gln Glu Leu Asn Val Gln Ala Pro Arg
1               5                   10

<210> SEQ ID NO 449
<211> LENGTH: 8
<212> TYPE: PRT
<213> ORGANISM: Homo sapiens

<400> SEQUENCE: 449

Gln Leu Ser His Gln Ser Pro Glu
1               5

<210> SEQ ID NO 450
<211> LENGTH: 13
<212> TYPE: PRT
<213> ORGANISM: Homo sapiens

<400> SEQUENCE: 450

Ile His Gly Phe Asp Leu Ala Ala Ile Asn Thr Gln Arg
1               5                   10

<210> SEQ ID NO 451
<211> LENGTH: 9
<212> TYPE: PRT
<213> ORGANISM: Homo sapiens

<400> SEQUENCE: 451

Asp Ile Ile Lys Pro Asp Pro Pro Lys
1               5

<210> SEQ ID NO 452
<211> LENGTH: 9
<212> TYPE: PRT
<213> ORGANISM: Homo sapiens

<400> SEQUENCE: 452

Leu Glu Asn Leu Glu Gln Tyr Ser Arg
1               5

<210> SEQ ID NO 453
<211> LENGTH: 9
<212> TYPE: PRT
<213> ORGANISM: Homo sapiens

<400> SEQUENCE: 453

Asp Leu Asp Ala Gly Ser Phe Gly Lys
1               5

<210> SEQ ID NO 454
<211> LENGTH: 8
<212> TYPE: PRT
<213> ORGANISM: Homo sapiens

<400> SEQUENCE: 454

Ala Glu Phe Ala Glu Val Ser Lys
1               5

<210> SEQ ID NO 455
<211> LENGTH: 8
<212> TYPE: PRT
```

<213> ORGANISM: Homo sapiens

<400> SEQUENCE: 455

Gly Leu Ser Leu Gln Ser Ser Arg
1               5

<210> SEQ ID NO 456
<211> LENGTH: 9
<212> TYPE: PRT
<213> ORGANISM: Homo sapiens

<400> SEQUENCE: 456

Thr Ile Ser Ala Ser Leu Gly Ser Arg
1               5

<210> SEQ ID NO 457
<211> LENGTH: 10
<212> TYPE: PRT
<213> ORGANISM: Homo sapiens

<400> SEQUENCE: 457

Val Leu Glu Val Thr Asn Ser Ser Leu Arg
1               5                   10

<210> SEQ ID NO 458
<211> LENGTH: 9
<212> TYPE: PRT
<213> ORGANISM: Homo sapiens

<400> SEQUENCE: 458

Asn Asp Gln Val Tyr Gln Pro Leu Arg
1               5

<210> SEQ ID NO 459
<211> LENGTH: 11
<212> TYPE: PRT
<213> ORGANISM: Homo sapiens

<400> SEQUENCE: 459

Thr Phe Asp Gln Leu Thr Pro Asp Glu Ser Lys
1               5                   10

<210> SEQ ID NO 460
<211> LENGTH: 8
<212> TYPE: PRT
<213> ORGANISM: Homo sapiens

<400> SEQUENCE: 460

Asp Pro Leu Gly Gln Thr Glu Lys
1               5

<210> SEQ ID NO 461
<211> LENGTH: 9
<212> TYPE: PRT
<213> ORGANISM: Homo sapiens

<400> SEQUENCE: 461

Val Ala Ala Thr Ala Leu Ser Gly Arg
1               5

<210> SEQ ID NO 462
<211> LENGTH: 7
<212> TYPE: PRT
<213> ORGANISM: Homo sapiens

```
<400> SEQUENCE: 462

Phe Ser Asp Thr Gln Pro Lys
1               5

<210> SEQ ID NO 463
<211> LENGTH: 9
<212> TYPE: PRT
<213> ORGANISM: Homo sapiens

<400> SEQUENCE: 463

Asn Thr Gly Val Ser Val Gly Gln Lys
1               5

<210> SEQ ID NO 464
<211> LENGTH: 9
<212> TYPE: PRT
<213> ORGANISM: Homo sapiens

<400> SEQUENCE: 464

Ala Glu Ala Gly Leu Ser Gly Leu Arg
1               5

<210> SEQ ID NO 465
<211> LENGTH: 13
<212> TYPE: PRT
<213> ORGANISM: Homo sapiens

<400> SEQUENCE: 465

Val Gly Asp Pro Gly Val Ala Gly Leu Pro Gly Glu Lys
1               5                   10

<210> SEQ ID NO 466
<211> LENGTH: 11
<212> TYPE: PRT
<213> ORGANISM: Homo sapiens

<400> SEQUENCE: 466

Ala Pro Ala Thr Ala Ser Ala Thr Leu Leu Glu
1               5                   10

<210> SEQ ID NO 467
<211> LENGTH: 8
<212> TYPE: PRT
<213> ORGANISM: Homo sapiens

<400> SEQUENCE: 467

Asp Phe Thr Gly Thr Val His Arg
1               5

<210> SEQ ID NO 468
<211> LENGTH: 11
<212> TYPE: PRT
<213> ORGANISM: Homo sapiens

<400> SEQUENCE: 468

Gly Pro Ala Gly Pro Ser Gly Pro Ala Gly Lys
1               5                   10

<210> SEQ ID NO 469
<211> LENGTH: 13
<212> TYPE: PRT
<213> ORGANISM: Homo sapiens

<400> SEQUENCE: 469
```

Trp Trp Asn Gln Tyr Glu Asn Leu Pro Trp Pro Asp Arg
1               5                   10

<210> SEQ ID NO 470
<211> LENGTH: 10
<212> TYPE: PRT
<213> ORGANISM: Homo sapiens

<400> SEQUENCE: 470

Thr Pro Ser Leu Pro Thr Pro Pro Thr Arg
1               5                   10

<210> SEQ ID NO 471
<211> LENGTH: 17
<212> TYPE: PRT
<213> ORGANISM: Homo sapiens

<400> SEQUENCE: 471

Ser Leu Ala Asp Pro Pro Ser Ser Ser Gln Ala Leu His Ser Pro Ala
1               5                   10                  15

Arg

<210> SEQ ID NO 472
<211> LENGTH: 9
<212> TYPE: PRT
<213> ORGANISM: Homo sapiens

<400> SEQUENCE: 472

Glu Gly Val Leu Tyr Val Gly Ser Lys
1               5

<210> SEQ ID NO 473
<211> LENGTH: 7
<212> TYPE: PRT
<213> ORGANISM: Homo sapiens

<400> SEQUENCE: 473

Phe Ser Val Val Tyr Ala Lys
1               5

<210> SEQ ID NO 474
<211> LENGTH: 10
<212> TYPE: PRT
<213> ORGANISM: Homo sapiens

<400> SEQUENCE: 474

Asn Asn Phe Leu Pro Pro Ile Ile Ala Arg
1               5                   10

<210> SEQ ID NO 475
<211> LENGTH: 8
<212> TYPE: PRT
<213> ORGANISM: Homo sapiens

<400> SEQUENCE: 475

Val Thr Thr His Pro Leu Ala Lys
1               5

<210> SEQ ID NO 476
<211> LENGTH: 7
<212> TYPE: PRT
<213> ORGANISM: Homo sapiens

<400> SEQUENCE: 476

Phe Thr Gln Asp Thr Phe Arg
1               5

<210> SEQ ID NO 477
<211> LENGTH: 9
<212> TYPE: PRT
<213> ORGANISM: Homo sapiens

<400> SEQUENCE: 477

Ile Ala Leu Glu Thr Ser Leu Ser Lys
1               5

<210> SEQ ID NO 478
<211> LENGTH: 9
<212> TYPE: PRT
<213> ORGANISM: Homo sapiens

<400> SEQUENCE: 478

Glu Gln Thr Leu Leu Gln Phe Gln Lys
1               5

<210> SEQ ID NO 479
<211> LENGTH: 15
<212> TYPE: PRT
<213> ORGANISM: Homo sapiens

<400> SEQUENCE: 479

Asn Asp Ser Ile Pro Gln Glu Asp Phe Thr Pro Glu Val Tyr Arg
1               5                   10                  15

<210> SEQ ID NO 480
<211> LENGTH: 14
<212> TYPE: PRT
<213> ORGANISM: Homo sapiens

<400> SEQUENCE: 480

Ala Ser Gly Phe Tyr Pro Trp Asn Ile Thr Leu Ser Trp Arg
1               5                   10

<210> SEQ ID NO 481
<211> LENGTH: 10
<212> TYPE: PRT
<213> ORGANISM: Homo sapiens

<400> SEQUENCE: 481

Phe Thr Ser Gln Pro Gly Tyr Ile Gly Arg
1               5                   10

<210> SEQ ID NO 482
<211> LENGTH: 7
<212> TYPE: PRT
<213> ORGANISM: Homo sapiens

<400> SEQUENCE: 482

Ala Gly Asp Glu Leu Thr Lys
1               5

<210> SEQ ID NO 483
<211> LENGTH: 10
<212> TYPE: PRT
<213> ORGANISM: Homo sapiens

<400> SEQUENCE: 483

Ala Asp Leu Ser Gly Ile Thr Gly Ala Arg
1               5                   10

<210> SEQ ID NO 484
<211> LENGTH: 10
<212> TYPE: PRT
<213> ORGANISM: Homo sapiens

<400> SEQUENCE: 484

Glu His Val Ala His Leu Leu Phe Leu Arg
1               5                   10

<210> SEQ ID NO 485
<211> LENGTH: 9
<212> TYPE: PRT
<213> ORGANISM: Homo sapiens

<400> SEQUENCE: 485

Val Gly Tyr Val Ser Gly Trp Gly Arg
1               5

<210> SEQ ID NO 486
<211> LENGTH: 22
<212> TYPE: PRT
<213> ORGANISM: Homo sapiens

<400> SEQUENCE: 486

Ser Leu Ala Leu Gly Thr Phe Ala His Thr Pro Ala Leu Ala Ser Leu
1               5                   10                  15

Gly Leu Ser Asn Asn Arg
            20

<210> SEQ ID NO 487
<211> LENGTH: 8
<212> TYPE: PRT
<213> ORGANISM: Homo sapiens

<400> SEQUENCE: 487

Leu Ser Ile Gln Ser Ser Pro Lys
1               5

<210> SEQ ID NO 488
<211> LENGTH: 11
<212> TYPE: PRT
<213> ORGANISM: Homo sapiens

<400> SEQUENCE: 488

Leu Gly Ala Ile Leu Thr Pro Asn Asp Gly Arg
1               5                   10

<210> SEQ ID NO 489
<211> LENGTH: 18
<212> TYPE: PRT
<213> ORGANISM: Homo sapiens

<400> SEQUENCE: 489

Val Ile Ala Ser Asn Ile Leu Gly Thr Gly Glu Pro Ser Gly Pro Ser
1               5                   10                  15

Ser Lys

<210> SEQ ID NO 490
<211> LENGTH: 12
<212> TYPE: PRT
<213> ORGANISM: Homo sapiens

<400> SEQUENCE: 490

```
Asp Leu Gly Phe Gly Val Gly Asp Leu Pro Thr Arg
1               5                   10
```

<210> SEQ ID NO 491
<211> LENGTH: 8
<212> TYPE: PRT
<213> ORGANISM: Homo sapiens

<400> SEQUENCE: 491

```
Thr Gly Ala Gln Glu Leu Leu Arg
1               5
```

<210> SEQ ID NO 492
<211> LENGTH: 7
<212> TYPE: PRT
<213> ORGANISM: Homo sapiens

<400> SEQUENCE: 492

```
Tyr Gly Asp Val Val Leu Arg
1               5
```

<210> SEQ ID NO 493
<211> LENGTH: 10
<212> TYPE: PRT
<213> ORGANISM: Homo sapiens

<400> SEQUENCE: 493

```
Asp Pro Asp Ala Ala Asn Ser Pro Ile Arg
1               5                   10
```

<210> SEQ ID NO 494
<211> LENGTH: 8
<212> TYPE: PRT
<213> ORGANISM: Homo sapiens

<400> SEQUENCE: 494

```
Ile Glu Asp Ile Pro Ala Asn Lys
1               5
```

<210> SEQ ID NO 495
<211> LENGTH: 19
<212> TYPE: PRT
<213> ORGANISM: Homo sapiens

<400> SEQUENCE: 495

```
Ser Ser Pro Val Val Ile Asp Ala Ser Thr Ala Ile Asp Ala Pro Ser
1               5                   10                  15

Asn Leu Arg
```

<210> SEQ ID NO 496
<211> LENGTH: 8
<212> TYPE: PRT
<213> ORGANISM: Homo sapiens

<400> SEQUENCE: 496

```
Asn Gly Ser Leu Phe Ala Phe Arg
1               5
```

<210> SEQ ID NO 497
<211> LENGTH: 13
<212> TYPE: PRT
<213> ORGANISM: Homo sapiens

<400> SEQUENCE: 497

```
Thr Val Val Leu Gln Thr Asp Pro Leu Pro Pro Ala Arg
1               5                   10

<210> SEQ ID NO 498
<211> LENGTH: 19
<212> TYPE: PRT
<213> ORGANISM: Homo sapiens

<400> SEQUENCE: 498

Val Arg Pro Ala Ser Thr Gly Gly Leu Ser Leu Leu Pro Pro Pro
1               5                   10                  15

Gly Gly Lys

<210> SEQ ID NO 499
<211> LENGTH: 15
<212> TYPE: PRT
<213> ORGANISM: Homo sapiens

<400> SEQUENCE: 499

Leu Ala Gly Leu Lys Pro Gly Thr Val Tyr Phe Val Gln Val Arg
1               5                   10                  15

<210> SEQ ID NO 500
<211> LENGTH: 12
<212> TYPE: PRT
<213> ORGANISM: Homo sapiens

<400> SEQUENCE: 500

Phe Glu Asp Gly Val Leu Asp Pro Asp Tyr Pro Arg
1               5                   10

<210> SEQ ID NO 501
<211> LENGTH: 12
<212> TYPE: PRT
<213> ORGANISM: Homo sapiens

<400> SEQUENCE: 501

Asp Gly Asn Gly Phe Val Ser Ala Ala Glu Leu Arg
1               5                   10

<210> SEQ ID NO 502
<211> LENGTH: 7
<212> TYPE: PRT
<213> ORGANISM: Homo sapiens

<400> SEQUENCE: 502

Val Leu Leu Glu Gln Glu Lys
1               5

<210> SEQ ID NO 503
<211> LENGTH: 30
<212> TYPE: PRT
<213> ORGANISM: Homo sapiens

<400> SEQUENCE: 503

Ser Val Leu Pro Gly Val Gly Asp Ala Ala Ala Ala Val Ala Ala
1               5                   10                  15

Thr Ala Val Pro Ala Val Ser Gln Ala Gln Leu Gly Thr Arg
            20                  25                  30

<210> SEQ ID NO 504
<211> LENGTH: 7
<212> TYPE: PRT
```

<213> ORGANISM: Homo sapiens

<400> SEQUENCE: 504

Leu Leu Glu Gln Val Asn Arg
1               5

<210> SEQ ID NO 505
<211> LENGTH: 14
<212> TYPE: PRT
<213> ORGANISM: Homo sapiens

<400> SEQUENCE: 505

Ala Pro Pro Pro His Leu Pro Leu Ser Pro Ala Leu Thr Arg
1               5                   10

<210> SEQ ID NO 506
<211> LENGTH: 13
<212> TYPE: PRT
<213> ORGANISM: Homo sapiens

<400> SEQUENCE: 506

Glu Thr Thr Ala Gly His Leu Ala Leu Leu Val Thr Lys
1               5                   10

<210> SEQ ID NO 507
<211> LENGTH: 12
<212> TYPE: PRT
<213> ORGANISM: Homo sapiens

<400> SEQUENCE: 507

Ile His Pro Glu Val Asp Pro Ser Val Ile Thr Lys
1               5                   10

<210> SEQ ID NO 508
<211> LENGTH: 13
<212> TYPE: PRT
<213> ORGANISM: Homo sapiens

<400> SEQUENCE: 508

Ile Ile Tyr Glu Asp Tyr Ile Ser Ile Leu Ser Pro Lys
1               5                   10

<210> SEQ ID NO 509
<211> LENGTH: 7
<212> TYPE: PRT
<213> ORGANISM: Homo sapiens

<400> SEQUENCE: 509

Ser Ile Leu Glu Asn Leu Arg
1               5

<210> SEQ ID NO 510
<211> LENGTH: 13
<212> TYPE: PRT
<213> ORGANISM: Homo sapiens

<400> SEQUENCE: 510

Phe Leu Gly Leu Gln Ser His Asp His His Pro Pro Arg
1               5                   10

<210> SEQ ID NO 511
<211> LENGTH: 10
<212> TYPE: PRT
<213> ORGANISM: Homo sapiens

```
<400> SEQUENCE: 511

Ala Asp Asp Ile Leu Ala Ser Pro Pro Arg
1               5                   10

<210> SEQ ID NO 512
<211> LENGTH: 8
<212> TYPE: PRT
<213> ORGANISM: Homo sapiens

<400> SEQUENCE: 512

Val Val Gly His Ser Ile Ala Arg
1               5

<210> SEQ ID NO 513
<211> LENGTH: 10
<212> TYPE: PRT
<213> ORGANISM: Homo sapiens

<400> SEQUENCE: 513

Asp Leu Tyr His Ile Leu Glu Asn His Lys
1               5                   10

<210> SEQ ID NO 514
<211> LENGTH: 7
<212> TYPE: PRT
<213> ORGANISM: Homo sapiens

<400> SEQUENCE: 514

Leu Ser Gly Ser Phe Leu Lys
1               5

<210> SEQ ID NO 515
<211> LENGTH: 8
<212> TYPE: PRT
<213> ORGANISM: Homo sapiens

<400> SEQUENCE: 515

Ile Ile His Thr Asp Val Phe Arg
1               5

<210> SEQ ID NO 516
<211> LENGTH: 12
<212> TYPE: PRT
<213> ORGANISM: Homo sapiens

<400> SEQUENCE: 516

Leu Pro Gln Leu Leu Gln Val His Gln Val Pro Arg
1               5                   10

<210> SEQ ID NO 517
<211> LENGTH: 13
<212> TYPE: PRT
<213> ORGANISM: Homo sapiens

<400> SEQUENCE: 517

Val Pro Gly Ala Tyr Phe Phe Ser Phe Thr Ala Gly Lys
1               5                   10

<210> SEQ ID NO 518
<211> LENGTH: 15
<212> TYPE: PRT
<213> ORGANISM: Homo sapiens

<400> SEQUENCE: 518
```

-continued

Ile Leu Val Leu Asp Val Asn Asp Asn Ala Pro Asp Phe Val Arg
1               5                   10                  15

<210> SEQ ID NO 519
<211> LENGTH: 8
<212> TYPE: PRT
<213> ORGANISM: Homo sapiens

<400> SEQUENCE: 519

Phe Leu Pro Ser Ile Ser Thr Lys
1               5

<210> SEQ ID NO 520
<211> LENGTH: 9
<212> TYPE: PRT
<213> ORGANISM: Homo sapiens

<400> SEQUENCE: 520

Ile Val Gln Leu Ile Gln Asp Thr Arg
1               5

<210> SEQ ID NO 521
<211> LENGTH: 10
<212> TYPE: PRT
<213> ORGANISM: Homo sapiens

<400> SEQUENCE: 521

Thr Leu Gly Leu Leu Gly Thr Glu Gly Arg
1               5                   10

<210> SEQ ID NO 522
<211> LENGTH: 7
<212> TYPE: PRT
<213> ORGANISM: Homo sapiens

<400> SEQUENCE: 522

Asp Asp Leu Asp Asn Ile Arg
1               5

<210> SEQ ID NO 523
<211> LENGTH: 8
<212> TYPE: PRT
<213> ORGANISM: Homo sapiens

<400> SEQUENCE: 523

Glu Asp Val Val Ser Val Val Lys
1               5

<210> SEQ ID NO 524
<211> LENGTH: 12
<212> TYPE: PRT
<213> ORGANISM: Homo sapiens

<400> SEQUENCE: 524

Trp Gly Ser Asn Glu Leu Pro Ala Glu Glu Gly Lys
1               5                   10

<210> SEQ ID NO 525
<211> LENGTH: 8
<212> TYPE: PRT
<213> ORGANISM: Homo sapiens

<400> SEQUENCE: 525

Glu Ser Gln Ala Tyr Tyr Gln Arg
1               5

<210> SEQ ID NO 526
<211> LENGTH: 16
<212> TYPE: PRT
<213> ORGANISM: Homo sapiens

<400> SEQUENCE: 526

Ser Pro Ser Asp Gln Leu Pro Pro Gln Gln Pro Leu Glu Ala Glu Lys
1               5                   10                  15

<210> SEQ ID NO 527
<211> LENGTH: 10
<212> TYPE: PRT
<213> ORGANISM: Homo sapiens

<400> SEQUENCE: 527

Thr Gly Ala Val Ser Gly His Ser Leu Lys
1               5                   10

<210> SEQ ID NO 528
<211> LENGTH: 9
<212> TYPE: PRT
<213> ORGANISM: Homo sapiens

<400> SEQUENCE: 528

Ala Val Ala Leu Leu Pro Glu Leu Arg
1               5

<210> SEQ ID NO 529
<211> LENGTH: 13
<212> TYPE: PRT
<213> ORGANISM: Homo sapiens

<400> SEQUENCE: 529

Gly Phe Gln Gln Leu Leu Gln Glu Leu Asn Gln Pro Arg
1               5                   10

<210> SEQ ID NO 530
<211> LENGTH: 18
<212> TYPE: PRT
<213> ORGANISM: Homo sapiens

<400> SEQUENCE: 530

Asp Pro Ala Gly Glu Pro Ala Val Gly Glu Glu Val Pro Ala Pro Ala
1               5                   10                  15

Asp Arg

<210> SEQ ID NO 531
<211> LENGTH: 7
<212> TYPE: PRT
<213> ORGANISM: Homo sapiens

<400> SEQUENCE: 531

Trp Gly Pro Pro Gln Glu Arg
1               5

<210> SEQ ID NO 532
<211> LENGTH: 8
<212> TYPE: PRT
<213> ORGANISM: Homo sapiens

<400> SEQUENCE: 532

Ser Pro Pro Pro Pro Ser Ala Arg
1               5

<210> SEQ ID NO 533
<211> LENGTH: 7
<212> TYPE: PRT
<213> ORGANISM: Homo sapiens

<400> SEQUENCE: 533

Asn Thr Glu Ile Ser Phe Lys
1               5

<210> SEQ ID NO 534
<211> LENGTH: 15
<212> TYPE: PRT
<213> ORGANISM: Homo sapiens

<400> SEQUENCE: 534

Ile His Leu Ile Ser Thr Gln Ser Ala Ile Pro Tyr Ala Leu Arg
1               5                   10                  15

<210> SEQ ID NO 535
<211> LENGTH: 14
<212> TYPE: PRT
<213> ORGANISM: Homo sapiens

<400> SEQUENCE: 535

Leu Glu Gly Ile Ser Glu Phe Leu Leu Pro Leu Tyr Val Lys
1               5                   10

<210> SEQ ID NO 536
<211> LENGTH: 17
<212> TYPE: PRT
<213> ORGANISM: Homo sapiens

<400> SEQUENCE: 536

Leu Ser Pro Ser Tyr His Trp Leu Glu Ser Asn Val Asp Ala Glu Glu
1               5                   10                  15

Arg

<210> SEQ ID NO 537
<211> LENGTH: 7
<212> TYPE: PRT
<213> ORGANISM: Homo sapiens

<400> SEQUENCE: 537

Asn Trp Gln Glu Ser Gln Lys
1               5

<210> SEQ ID NO 538
<211> LENGTH: 10
<212> TYPE: PRT
<213> ORGANISM: Homo sapiens

<400> SEQUENCE: 538

Gly Gln Val Phe Ala Thr Ser Ala Ile Arg
1               5                   10

<210> SEQ ID NO 539
<211> LENGTH: 23
<212> TYPE: PRT
<213> ORGANISM: Homo sapiens

<400> SEQUENCE: 539

Ala Ser Ser Ser Trp Gln Ser Val Asn Glu Ser Gly Asp Gln Val His
1               5                   10                  15

Trp Ser Pro Gly Gln Ala Arg
            20

<210> SEQ ID NO 540
<211> LENGTH: 11
<212> TYPE: PRT
<213> ORGANISM: Homo sapiens

<400> SEQUENCE: 540

Asn Glu Asp Ile Ile Asp Pro Val Glu Asp Arg
1               5                   10

<210> SEQ ID NO 541
<211> LENGTH: 7
<212> TYPE: PRT
<213> ORGANISM: Homo sapiens

<400> SEQUENCE: 541

Phe Ala Phe Pro Gly His Arg
1               5

<210> SEQ ID NO 542
<211> LENGTH: 6
<212> TYPE: PRT
<213> ORGANISM: Homo sapiens

<400> SEQUENCE: 542

Phe Thr Asp His Leu Lys
1               5

<210> SEQ ID NO 543
<211> LENGTH: 6
<212> TYPE: PRT
<213> ORGANISM: Homo sapiens

<400> SEQUENCE: 543

Trp Gly Phe Ser Phe Arg
1               5

<210> SEQ ID NO 544
<211> LENGTH: 14
<212> TYPE: PRT
<213> ORGANISM: Homo sapiens

<400> SEQUENCE: 544

Ile Val Pro Pro Thr Ser Leu Asp Val Pro Leu Val Gly Lys
1               5                   10

<210> SEQ ID NO 545
<211> LENGTH: 10
<212> TYPE: PRT
<213> ORGANISM: Homo sapiens

<400> SEQUENCE: 545

Glu Thr Gly Trp His Ser Ser Gly Gln Arg
1               5                   10

<210> SEQ ID NO 546
<211> LENGTH: 18
<212> TYPE: PRT
<213> ORGANISM: Homo sapiens

<400> SEQUENCE: 546

Gly Phe Ser Leu Ala Asp Ile Pro Tyr Gln Glu Ile Ala Gly Glu His

Leu Arg

<210> SEQ ID NO 547
<211> LENGTH: 8
<212> TYPE: PRT
<213> ORGANISM: Homo sapiens

<400> SEQUENCE: 547

Glu Ala Phe Ser Leu Phe Asp Lys
1               5

<210> SEQ ID NO 548
<211> LENGTH: 12
<212> TYPE: PRT
<213> ORGANISM: Homo sapiens

<400> SEQUENCE: 548

Tyr Ser Ser Ser Glu Val Asn His Leu Ser Pro Arg
1               5                   10

<210> SEQ ID NO 549
<211> LENGTH: 6
<212> TYPE: PRT
<213> ORGANISM: Homo sapiens

<400> SEQUENCE: 549

Ile Gln Ala Ser Phe Arg
1               5

<210> SEQ ID NO 550
<211> LENGTH: 10
<212> TYPE: PRT
<213> ORGANISM: Homo sapiens

<400> SEQUENCE: 550

Ile Gln Gly Thr Leu Gln Pro His Ala Arg
1               5                   10

<210> SEQ ID NO 551
<211> LENGTH: 8
<212> TYPE: PRT
<213> ORGANISM: Homo sapiens

<400> SEQUENCE: 551

Asn Gly Phe Tyr Pro Ala Thr Arg
1               5

<210> SEQ ID NO 552
<211> LENGTH: 14
<212> TYPE: PRT
<213> ORGANISM: Homo sapiens

<400> SEQUENCE: 552

His Phe Pro Thr Ile Ser Ala Asp Tyr Ser Gln Asp Glu Lys
1               5                   10

<210> SEQ ID NO 553
<211> LENGTH: 8
<212> TYPE: PRT
<213> ORGANISM: Homo sapiens

<400> SEQUENCE: 553

Asn Ala Thr Ser Ile Ser Ala Lys

<210> SEQ ID NO 554
<211> LENGTH: 10
<212> TYPE: PRT
<213> ORGANISM: Homo sapiens

<400> SEQUENCE: 554

His His Ser Ala Gly Asp Val Ala Glu Arg
1               5                   10

<210> SEQ ID NO 555
<211> LENGTH: 11
<212> TYPE: PRT
<213> ORGANISM: Homo sapiens

<400> SEQUENCE: 555

Gly Asp Asp Asn Ala Val Thr Gly Val Thr Lys
1               5                   10

<210> SEQ ID NO 556
<211> LENGTH: 8
<212> TYPE: PRT
<213> ORGANISM: Homo sapiens

<400> SEQUENCE: 556

Asn His Gln Leu Ile Val Thr Arg
1               5

<210> SEQ ID NO 557
<211> LENGTH: 18
<212> TYPE: PRT
<213> ORGANISM: Homo sapiens

<400> SEQUENCE: 557

Asn Leu Glu Thr Leu Asp Leu Ser His Asn Gln Leu Thr Thr Val Pro
1               5                   10                  15

Glu Arg

<210> SEQ ID NO 558
<211> LENGTH: 12
<212> TYPE: PRT
<213> ORGANISM: Homo sapiens

<400> SEQUENCE: 558

Thr His Gly Thr Leu Glu Ser Val Asn Gly Pro Lys
1               5                   10

<210> SEQ ID NO 559
<211> LENGTH: 17
<212> TYPE: PRT
<213> ORGANISM: Homo sapiens

<400> SEQUENCE: 559

Leu Ala Ser Ile Phe Ser Gly Thr Gly Ala Asp Pro Val Val Ser Ala
1               5                   10                  15

Lys

<210> SEQ ID NO 560
<211> LENGTH: 6
<212> TYPE: PRT
<213> ORGANISM: Homo sapiens

<400> SEQUENCE: 560

Leu Leu Gln Ala Leu Arg
1               5

<210> SEQ ID NO 561
<211> LENGTH: 8
<212> TYPE: PRT
<213> ORGANISM: Homo sapiens

<400> SEQUENCE: 561

Leu Ser Leu Val Gly Ile Ala Lys
1               5

<210> SEQ ID NO 562
<211> LENGTH: 7
<212> TYPE: PRT
<213> ORGANISM: Homo sapiens

<400> SEQUENCE: 562

Ser Leu Leu Gln Pro Asn Lys
1               5

<210> SEQ ID NO 563
<211> LENGTH: 14
<212> TYPE: PRT
<213> ORGANISM: Homo sapiens

<400> SEQUENCE: 563

Leu Glu Ile Gln Leu Leu Glu Asn Ser Leu Ser Thr Tyr Lys
1               5                   10

<210> SEQ ID NO 564
<211> LENGTH: 10
<212> TYPE: PRT
<213> ORGANISM: Homo sapiens

<400> SEQUENCE: 564

Glu Pro Glu Asp Pro Ala Pro Ala Leu Lys
1               5                   10

<210> SEQ ID NO 565
<211> LENGTH: 13
<212> TYPE: PRT
<213> ORGANISM: Homo sapiens

<400> SEQUENCE: 565

Asp Ala Pro His Val Glu Pro Asp Phe Ser Ser Gln Lys
1               5                   10

<210> SEQ ID NO 566
<211> LENGTH: 11
<212> TYPE: PRT
<213> ORGANISM: Homo sapiens

<400> SEQUENCE: 566

Ala Val Val Ala Phe His Thr Gly Asn Phe Arg
1               5                   10

<210> SEQ ID NO 567
<211> LENGTH: 20
<212> TYPE: PRT
<213> ORGANISM: Homo sapiens

<400> SEQUENCE: 567

Ile Leu Asp Thr Phe Leu Gly Leu Pro Gln Tyr His Gly Leu Gln Val

```
                1               5                  10                  15

Ala Val Ser Lys
            20

<210> SEQ ID NO 568
<211> LENGTH: 8
<212> TYPE: PRT
<213> ORGANISM: Homo sapiens

<400> SEQUENCE: 568

Asp Gly Leu Ile Leu Thr Ser Arg
1               5

<210> SEQ ID NO 569
<211> LENGTH: 13
<212> TYPE: PRT
<213> ORGANISM: Homo sapiens

<400> SEQUENCE: 569

Leu Asn Gln Tyr Asp Leu Leu Gly Gln Ser Ile Gly Lys
1               5                  10

<210> SEQ ID NO 570
<211> LENGTH: 9
<212> TYPE: PRT
<213> ORGANISM: Homo sapiens

<400> SEQUENCE: 570

Glu Gly Val Val Ala Ala Ala Glu Lys
1               5

<210> SEQ ID NO 571
<211> LENGTH: 9
<212> TYPE: PRT
<213> ORGANISM: Homo sapiens

<400> SEQUENCE: 571

Leu Gly Pro Leu Val Glu Gln Gly Arg
1               5

<210> SEQ ID NO 572
<211> LENGTH: 8
<212> TYPE: PRT
<213> ORGANISM: Homo sapiens

<400> SEQUENCE: 572

Ser Gly Ser Gly Leu Val Gly Arg
1               5

<210> SEQ ID NO 573
<211> LENGTH: 9
<212> TYPE: PRT
<213> ORGANISM: Homo sapiens

<400> SEQUENCE: 573

Glu Asp Gly Ile Leu Val Leu Ser Arg
1               5

<210> SEQ ID NO 574
<211> LENGTH: 15
<212> TYPE: PRT
<213> ORGANISM: Homo sapiens

<400> SEQUENCE: 574
```

Ser Glu Pro Trp Thr Leu Ala Leu Glu Asn Val Val Gly Ala Lys
1               5                   10                  15

<210> SEQ ID NO 575
<211> LENGTH: 10
<212> TYPE: PRT
<213> ORGANISM: Homo sapiens

<400> SEQUENCE: 575

Asp Gly Thr Gly Leu Val Pro Ser Glu Arg
1               5                   10

<210> SEQ ID NO 576
<211> LENGTH: 6
<212> TYPE: PRT
<213> ORGANISM: Homo sapiens

<400> SEQUENCE: 576

Trp Ser Ile Asp Pro Arg
1               5

<210> SEQ ID NO 577
<211> LENGTH: 15
<212> TYPE: PRT
<213> ORGANISM: Homo sapiens

<400> SEQUENCE: 577

Ala Asp Glu Ala Glu Ala Pro Phe Ala Gly Gln Asn Trp Leu Lys
1               5                   10                  15

<210> SEQ ID NO 578
<211> LENGTH: 7
<212> TYPE: PRT
<213> ORGANISM: Homo sapiens

<400> SEQUENCE: 578

Ala His Ala Gln Leu Val Arg
1               5

<210> SEQ ID NO 579
<211> LENGTH: 12
<212> TYPE: PRT
<213> ORGANISM: Homo sapiens

<400> SEQUENCE: 579

Gly Asp Val Ile Tyr Ile Gly Gly Leu Pro Asp Lys
1               5                   10

<210> SEQ ID NO 580
<211> LENGTH: 8
<212> TYPE: PRT
<213> ORGANISM: Homo sapiens

<400> SEQUENCE: 580

Tyr Ala Ser Pro Gly Ala Pro Arg
1               5

<210> SEQ ID NO 581
<211> LENGTH: 9
<212> TYPE: PRT
<213> ORGANISM: Homo sapiens

<400> SEQUENCE: 581

Glu Gly Ala Gly Ala Leu Phe Phe Arg
1               5

<210> SEQ ID NO 582
<211> LENGTH: 15
<212> TYPE: PRT
<213> ORGANISM: Homo sapiens

<400> SEQUENCE: 582

Leu Thr Ile Gly Glu Gly Gln Gln His His Leu Gly Gly Ala Lys
1               5                   10                  15

<210> SEQ ID NO 583
<211> LENGTH: 11
<212> TYPE: PRT
<213> ORGANISM: Homo sapiens

<400> SEQUENCE: 583

Tyr Glu Asn Tyr Thr Ser Ser Phe Phe Ile Arg
1               5                   10

<210> SEQ ID NO 584
<211> LENGTH: 7
<212> TYPE: PRT
<213> ORGANISM: Homo sapiens

<400> SEQUENCE: 584

Asn Asp Phe Thr Trp Phe Lys
1               5

<210> SEQ ID NO 585
<211> LENGTH: 9
<212> TYPE: PRT
<213> ORGANISM: Homo sapiens

<400> SEQUENCE: 585

Glu Ala Gln Leu Glu Ala Glu Val Lys
1               5

<210> SEQ ID NO 586
<211> LENGTH: 8
<212> TYPE: PRT
<213> ORGANISM: Homo sapiens

<400> SEQUENCE: 586

Phe Val Gly Glu Gly Gly Val Arg
1               5

<210> SEQ ID NO 587
<211> LENGTH: 7
<212> TYPE: PRT
<213> ORGANISM: Homo sapiens

<400> SEQUENCE: 587

Asp Leu Glu Val Val Ala Arg
1               5

<210> SEQ ID NO 588
<211> LENGTH: 8
<212> TYPE: PRT
<213> ORGANISM: Homo sapiens

<400> SEQUENCE: 588

Val Thr Leu Ala Ala Asn Gly Lys
1               5

```
<210> SEQ ID NO 589
<211> LENGTH: 20
<212> TYPE: PRT
<213> ORGANISM: Homo sapiens

<400> SEQUENCE: 589

Ala Ala Glu Asp Ser Ala Arg Pro Glu Leu Pro Asp Ser Ala Val Gly
1               5                   10                  15

Pro Gly Ser Arg
            20

<210> SEQ ID NO 590
<211> LENGTH: 17
<212> TYPE: PRT
<213> ORGANISM: Homo sapiens

<400> SEQUENCE: 590

Asp Tyr Thr Gly Glu Asp Val Thr Pro Gln Asn Phe Leu Ala Val Leu
1               5                   10                  15

Arg

<210> SEQ ID NO 591
<211> LENGTH: 8
<212> TYPE: PRT
<213> ORGANISM: Homo sapiens

<400> SEQUENCE: 591

Asp Phe Val Gln Pro Pro Thr Lys
1               5

<210> SEQ ID NO 592
<211> LENGTH: 7
<212> TYPE: PRT
<213> ORGANISM: Homo sapiens

<400> SEQUENCE: 592

His Phe Gly Ser Phe Gln Lys
1               5

<210> SEQ ID NO 593
<211> LENGTH: 13
<212> TYPE: PRT
<213> ORGANISM: Homo sapiens

<400> SEQUENCE: 593

Leu Pro Ser Glu Phe Ser Gln Phe Pro His Gly Gln Lys
1               5                   10

<210> SEQ ID NO 594
<211> LENGTH: 12
<212> TYPE: PRT
<213> ORGANISM: Homo sapiens

<400> SEQUENCE: 594

His Tyr Gln His Val Ala Ala Val Asp Pro Glu Lys
1               5                   10

<210> SEQ ID NO 595
<211> LENGTH: 8
<212> TYPE: PRT
<213> ORGANISM: Homo sapiens

<400> SEQUENCE: 595

Glu Leu Asn Val Asn Ile Tyr Arg
```

```
1               5

<210> SEQ ID NO 596
<211> LENGTH: 11
<212> TYPE: PRT
<213> ORGANISM: Homo sapiens

<400> SEQUENCE: 596

Leu Gln His Thr Val Gly His Phe Asp Gln Arg
1               5                   10

<210> SEQ ID NO 597
<211> LENGTH: 7
<212> TYPE: PRT
<213> ORGANISM: Homo sapiens

<400> SEQUENCE: 597

Glu Leu Gly Thr Val Met Arg
1               5

<210> SEQ ID NO 598
<211> LENGTH: 15
<212> TYPE: PRT
<213> ORGANISM: Homo sapiens

<400> SEQUENCE: 598

Leu Leu Gly Glu Gly Phe Ser Asp Leu Phe Leu Thr Asp Gly Arg
1               5                   10                  15

<210> SEQ ID NO 599
<211> LENGTH: 7
<212> TYPE: PRT
<213> ORGANISM: Homo sapiens

<400> SEQUENCE: 599

Asn Gly Ala Glu Gln Gly Arg
1               5

<210> SEQ ID NO 600
<211> LENGTH: 10
<212> TYPE: PRT
<213> ORGANISM: Homo sapiens

<400> SEQUENCE: 600

Ile His Trp Glu Ser Ala Ser Leu Leu Arg
1               5                   10

<210> SEQ ID NO 601
<211> LENGTH: 9
<212> TYPE: PRT
<213> ORGANISM: Homo sapiens

<400> SEQUENCE: 601

Val Ala Glu Gln Val Gly Ile Asp Arg
1               5

<210> SEQ ID NO 602
<211> LENGTH: 11
<212> TYPE: PRT
<213> ORGANISM: Homo sapiens

<400> SEQUENCE: 602

Glu Phe Asp Glu Leu Asn Pro Ser Ala Gln Arg
1               5                   10
```

<210> SEQ ID NO 603
<211> LENGTH: 7
<212> TYPE: PRT
<213> ORGANISM: Homo sapiens

<400> SEQUENCE: 603

Phe Ala Glu His Val Phe Arg
1               5

<210> SEQ ID NO 604
<211> LENGTH: 10
<212> TYPE: PRT
<213> ORGANISM: Homo sapiens

<400> SEQUENCE: 604

Tyr Leu Ser Ser Leu Asn Phe Val His Arg
1               5                   10

<210> SEQ ID NO 605
<211> LENGTH: 11
<212> TYPE: PRT
<213> ORGANISM: Homo sapiens

<400> SEQUENCE: 605

Leu Pro Asn Asp Asp Leu Gln Gly Ile Gln Lys
1               5                   10

<210> SEQ ID NO 606
<211> LENGTH: 9
<212> TYPE: PRT
<213> ORGANISM: Homo sapiens

<400> SEQUENCE: 606

Glu Gly Val Leu Tyr Val Gly Ser Lys
1               5

<210> SEQ ID NO 607
<211> LENGTH: 15
<212> TYPE: PRT
<213> ORGANISM: Homo sapiens

<400> SEQUENCE: 607

Leu Asp Ala Phe Ser Ser Ala Asp Leu Glu Ser Ala Tyr Gly Arg
1               5                   10                  15

<210> SEQ ID NO 608
<211> LENGTH: 14
<212> TYPE: PRT
<213> ORGANISM: Homo sapiens

<400> SEQUENCE: 608

Tyr Gly Pro Gln Phe Thr Leu Gln His Val Pro Asp Tyr Arg
1               5                   10

<210> SEQ ID NO 609
<211> LENGTH: 16
<212> TYPE: PRT
<213> ORGANISM: Homo sapiens

<400> SEQUENCE: 609

Ala Leu Asn His Leu Pro Leu Glu Tyr Asn Ser Ala Leu Tyr Ser Arg
1               5                   10                  15

<210> SEQ ID NO 610

```
<211> LENGTH: 18
<212> TYPE: PRT
<213> ORGANISM: Homo sapiens

<400> SEQUENCE: 610

Tyr Ser Gln Ala Val Pro Ala Val Thr Glu Gly Pro Ile Pro Glu Val
1               5                   10                  15

Leu Lys

<210> SEQ ID NO 611
<211> LENGTH: 6
<212> TYPE: PRT
<213> ORGANISM: Homo sapiens

<400> SEQUENCE: 611

Ala Glu Glu Trp Gly Arg
1               5

<210> SEQ ID NO 612
<211> LENGTH: 8
<212> TYPE: PRT
<213> ORGANISM: Homo sapiens

<400> SEQUENCE: 612

Glu Tyr Ile Ile Ser Ser Leu Lys
1               5

<210> SEQ ID NO 613
<211> LENGTH: 8
<212> TYPE: PRT
<213> ORGANISM: Homo sapiens

<400> SEQUENCE: 613

Asn Leu Leu Ile Ala Thr Asp Lys
1               5

<210> SEQ ID NO 614
<211> LENGTH: 8
<212> TYPE: PRT
<213> ORGANISM: Homo sapiens

<400> SEQUENCE: 614

Gln Ala Leu Gly Gly Ala Thr Lys
1               5

<210> SEQ ID NO 615
<211> LENGTH: 12
<212> TYPE: PRT
<213> ORGANISM: Homo sapiens

<400> SEQUENCE: 615

His Ser Gln Pro Trp Gln Val Leu Val Ala Ser Arg
1               5                   10

<210> SEQ ID NO 616
<211> LENGTH: 11
<212> TYPE: PRT
<213> ORGANISM: Homo sapiens

<400> SEQUENCE: 616

Thr Val Gly Ser Asp Thr Phe Tyr Ser Phe Lys
1               5                   10

<210> SEQ ID NO 617
```

```
<211> LENGTH: 8
<212> TYPE: PRT
<213> ORGANISM: Homo sapiens

<400> SEQUENCE: 617

Tyr Asp Leu Gly Gln Val Ile Lys
1               5

<210> SEQ ID NO 618
<211> LENGTH: 9
<212> TYPE: PRT
<213> ORGANISM: Homo sapiens

<400> SEQUENCE: 618

Glu Leu Leu Glu Asp Pro Val Gly Arg
1               5

<210> SEQ ID NO 619
<211> LENGTH: 12
<212> TYPE: PRT
<213> ORGANISM: Homo sapiens

<400> SEQUENCE: 619

Leu Gly Ser Ser Ser Glu Ile Glu Val Pro Ala Lys
1               5                   10

<210> SEQ ID NO 620
<211> LENGTH: 21
<212> TYPE: PRT
<213> ORGANISM: Homo sapiens

<400> SEQUENCE: 620

Asp Pro Thr Leu Leu Pro Pro Glu Thr Gly Gly Ala Gly Gly Glu Ala
1               5                   10                  15

Pro Ser Lys Pro Lys
            20

<210> SEQ ID NO 621
<211> LENGTH: 12
<212> TYPE: PRT
<213> ORGANISM: Homo sapiens

<400> SEQUENCE: 621

His Asn Ala Glu Ile Ala Ala Phe His Leu Asp Arg
1               5                   10

<210> SEQ ID NO 622
<211> LENGTH: 7
<212> TYPE: PRT
<213> ORGANISM: Homo sapiens

<400> SEQUENCE: 622

Thr Ala Val Asp His Ile Arg
1               5

<210> SEQ ID NO 623
<211> LENGTH: 7
<212> TYPE: PRT
<213> ORGANISM: Homo sapiens

<400> SEQUENCE: 623

Ala Leu Gly Leu Gly His Arg
1               5
```

```
<210> SEQ ID NO 624
<211> LENGTH: 9
<212> TYPE: PRT
<213> ORGANISM: Homo sapiens

<400> SEQUENCE: 624

Asp Pro Val Leu Ser Thr Ile Ser Lys
1               5

<210> SEQ ID NO 625
<211> LENGTH: 7
<212> TYPE: PRT
<213> ORGANISM: Homo sapiens

<400> SEQUENCE: 625

Ser Asn Ser Thr Leu Ser Lys
1               5

<210> SEQ ID NO 626
<211> LENGTH: 10
<212> TYPE: PRT
<213> ORGANISM: Homo sapiens

<400> SEQUENCE: 626

Ala Asn Arg Pro Phe Leu Val Phe Ile Arg
1               5                   10

<210> SEQ ID NO 627
<211> LENGTH: 14
<212> TYPE: PRT
<213> ORGANISM: Homo sapiens

<400> SEQUENCE: 627

His Ser Val Pro Leu Pro Thr Glu Leu Ser Ser Glu Ala Lys
1               5                   10

<210> SEQ ID NO 628
<211> LENGTH: 13
<212> TYPE: PRT
<213> ORGANISM: Homo sapiens

<400> SEQUENCE: 628

Gln Ile Pro Leu Gln Asp Val Ala Phe Pro Asp Phe Arg
1               5                   10

<210> SEQ ID NO 629
<211> LENGTH: 22
<212> TYPE: PRT
<213> ORGANISM: Homo sapiens

<400> SEQUENCE: 629

Ser Phe Glu Gly Leu Gly Gln Leu Glu Val Leu Thr Leu Asp His Asn
1               5                   10                  15

Gln Leu Gln Glu Val Lys
            20

<210> SEQ ID NO 630
<211> LENGTH: 7
<212> TYPE: PRT
<213> ORGANISM: Homo sapiens

<400> SEQUENCE: 630

Asn Leu Thr Asp Leu Gly Lys
1               5
```

```
<210> SEQ ID NO 631
<211> LENGTH: 9
<212> TYPE: PRT
<213> ORGANISM: Homo sapiens

<400> SEQUENCE: 631

Asp Asn Gly Val Thr Pro Gly Glu Lys
1               5

<210> SEQ ID NO 632
<211> LENGTH: 8
<212> TYPE: PRT
<213> ORGANISM: Homo sapiens

<400> SEQUENCE: 632

Phe Asp Ile Leu Val Asp Gly Lys
1               5

<210> SEQ ID NO 633
<211> LENGTH: 9
<212> TYPE: PRT
<213> ORGANISM: Homo sapiens

<400> SEQUENCE: 633

His Ser His Glu Ser Gln Asp Leu Arg
1               5

<210> SEQ ID NO 634
<211> LENGTH: 7
<212> TYPE: PRT
<213> ORGANISM: Homo sapiens

<400> SEQUENCE: 634

Leu Leu Ile Ala Ala Gln Lys
1               5

<210> SEQ ID NO 635
<211> LENGTH: 6
<212> TYPE: PRT
<213> ORGANISM: Homo sapiens

<400> SEQUENCE: 635

Val Pro Glu Leu Ile Arg
1               5

<210> SEQ ID NO 636
<211> LENGTH: 12
<212> TYPE: PRT
<213> ORGANISM: Homo sapiens

<400> SEQUENCE: 636

Asp Pro Gln Ile Leu Leu Glu Pro Glu Gly Val Lys
1               5                   10

<210> SEQ ID NO 637
<211> LENGTH: 8
<212> TYPE: PRT
<213> ORGANISM: Homo sapiens

<400> SEQUENCE: 637

Asn Gly Gln Gly Glu Pro Ala Arg
1               5

<210> SEQ ID NO 638
```

```
<211> LENGTH: 10
<212> TYPE: PRT
<213> ORGANISM: Homo sapiens

<400> SEQUENCE: 638

Leu Ser Ser Ala Ile Ile Ala Ala Pro Arg
1               5                   10

<210> SEQ ID NO 639
<211> LENGTH: 15
<212> TYPE: PRT
<213> ORGANISM: Homo sapiens

<400> SEQUENCE: 639

Glu Ala Ile Leu Ala Leu Asp Ile Gln Asp Pro Gly Val Pro Arg
1               5                   10                  15

<210> SEQ ID NO 640
<211> LENGTH: 13
<212> TYPE: PRT
<213> ORGANISM: Homo sapiens

<400> SEQUENCE: 640

Glu His Leu Ser Gln Ala Thr Gly Ile Leu Thr Glu Arg
1               5                   10

<210> SEQ ID NO 641
<211> LENGTH: 6
<212> TYPE: PRT
<213> ORGANISM: Homo sapiens

<400> SEQUENCE: 641

Ser Asp Glu Leu Val Arg
1               5

<210> SEQ ID NO 642
<211> LENGTH: 15
<212> TYPE: PRT
<213> ORGANISM: Homo sapiens

<400> SEQUENCE: 642

Ser Pro Ala Ala Gln Tyr Val Asp Leu Leu Asn Pro Glu Arg
1               5                   10                  15

<210> SEQ ID NO 643
<211> LENGTH: 13
<212> TYPE: PRT
<213> ORGANISM: Homo sapiens

<400> SEQUENCE: 643

Asn Leu Tyr Ile Asn Asn Glu Leu Gln Asp Phe Thr Lys
1               5                   10

<210> SEQ ID NO 644
<211> LENGTH: 10
<212> TYPE: PRT
<213> ORGANISM: Homo sapiens

<400> SEQUENCE: 644

Tyr Asn Phe Thr Pro Asp Pro Asp Phe Lys
1               5                   10

<210> SEQ ID NO 645
<211> LENGTH: 9
<212> TYPE: PRT
```

-continued

<213> ORGANISM: Homo sapiens

<400> SEQUENCE: 645

Val Gly Ala Val Gly Gly Asp Val Arg
1               5

<210> SEQ ID NO 646
<211> LENGTH: 9
<212> TYPE: PRT
<213> ORGANISM: Homo sapiens

<400> SEQUENCE: 646

Asp Gly Glu Tyr Val Val Glu Val Arg
1               5

<210> SEQ ID NO 647
<211> LENGTH: 19
<212> TYPE: PRT
<213> ORGANISM: Homo sapiens

<400> SEQUENCE: 647

Phe Leu Gly Pro Leu Asp Glu Asp Phe Tyr Ala Glu Asp Phe Tyr Leu
1               5                   10                  15

Leu Glu Lys

<210> SEQ ID NO 648
<211> LENGTH: 6
<212> TYPE: PRT
<213> ORGANISM: Homo sapiens

<400> SEQUENCE: 648

Tyr Leu Leu Ile Thr Arg
1               5

<210> SEQ ID NO 649
<211> LENGTH: 11
<212> TYPE: PRT
<213> ORGANISM: Homo sapiens

<400> SEQUENCE: 649

Asp Ala Asn Leu Tyr Val Ser Gly Leu Pro Lys
1               5                   10

<210> SEQ ID NO 650
<211> LENGTH: 16
<212> TYPE: PRT
<213> ORGANISM: Homo sapiens

<400> SEQUENCE: 650

Gly Asp Ile Thr Leu Val Pro Thr Ile Asn Gly Thr Leu Pro Ile Arg
1               5                   10                  15

<210> SEQ ID NO 651
<211> LENGTH: 13
<212> TYPE: PRT
<213> ORGANISM: Homo sapiens

<400> SEQUENCE: 651

Leu Asn Gly Glu His Leu Tyr Phe Thr Leu Asn Pro Arg
1               5                   10

<210> SEQ ID NO 652
<211> LENGTH: 13
<212> TYPE: PRT

```
<213> ORGANISM: Homo sapiens

<400> SEQUENCE: 652

Ala Gln Ala Gln Val Glu Glu Ala Glu Glu Leu Phe Arg
1               5                   10

<210> SEQ ID NO 653
<211> LENGTH: 18
<212> TYPE: PRT
<213> ORGANISM: Homo sapiens

<400> SEQUENCE: 653

Ile Gly Gln Leu Gln Gly Glu Ile Ile Pro Thr Ser Phe Tyr His Gln
1               5                   10                  15

Gly Arg

<210> SEQ ID NO 654
<211> LENGTH: 16
<212> TYPE: PRT
<213> ORGANISM: Homo sapiens

<400> SEQUENCE: 654

Leu Asp Leu Thr Gly Ser Ser Gly His Ser Leu Gln Pro Gln Pro Arg
1               5                   10                  15

<210> SEQ ID NO 655
<211> LENGTH: 6
<212> TYPE: PRT
<213> ORGANISM: Homo sapiens

<400> SEQUENCE: 655

Leu Phe Ile Val His Lys
1               5

<210> SEQ ID NO 656
<211> LENGTH: 10
<212> TYPE: PRT
<213> ORGANISM: Homo sapiens

<400> SEQUENCE: 656

Leu Asn Pro Gly Ile Tyr Pro Gln Gln Val
1               5                   10

<210> SEQ ID NO 657
<211> LENGTH: 9
<212> TYPE: PRT
<213> ORGANISM: Homo sapiens

<400> SEQUENCE: 657

Asn Asp His Gln Glu Asp Phe Trp Lys
1               5

<210> SEQ ID NO 658
<211> LENGTH: 6
<212> TYPE: PRT
<213> ORGANISM: Homo sapiens

<400> SEQUENCE: 658

Phe Leu Gly Thr Trp Lys
1               5

<210> SEQ ID NO 659
<211> LENGTH: 6
<212> TYPE: PRT
```

```
<213> ORGANISM: Homo sapiens

<400> SEQUENCE: 659

Phe Glu Thr Gln Leu Lys
1               5

<210> SEQ ID NO 660
<211> LENGTH: 13
<212> TYPE: PRT
<213> ORGANISM: Homo sapiens

<400> SEQUENCE: 660

Leu Thr Ala Thr Ser Thr Asp Gln Leu Glu Ala Leu Arg
1               5                   10

<210> SEQ ID NO 661
<211> LENGTH: 11
<212> TYPE: PRT
<213> ORGANISM: Homo sapiens

<400> SEQUENCE: 661

Ile Glu Gln Asp Gly Ile Lys Pro Glu Asp Lys
1               5                   10

<210> SEQ ID NO 662
<211> LENGTH: 6
<212> TYPE: PRT
<213> ORGANISM: Homo sapiens

<400> SEQUENCE: 662

Ala His Tyr Asp Leu Arg
1               5

<210> SEQ ID NO 663
<211> LENGTH: 12
<212> TYPE: PRT
<213> ORGANISM: Homo sapiens

<400> SEQUENCE: 663

Gly Phe Pro Ala Leu Ser Ser Glu Ala Leu Val Arg
1               5                   10

<210> SEQ ID NO 664
<211> LENGTH: 19
<212> TYPE: PRT
<213> ORGANISM: Homo sapiens

<400> SEQUENCE: 664

Glu Gly Ala Asp Ile Pro Trp Asp Ile Pro Val Ala Thr Asn Thr Pro
1               5                   10                  15

Ser Gly Lys

<210> SEQ ID NO 665
<211> LENGTH: 12
<212> TYPE: PRT
<213> ORGANISM: Homo sapiens

<400> SEQUENCE: 665

Leu Gln Glu Ile Tyr Gln Glu Leu Thr Glu Leu Lys
1               5                   10

<210> SEQ ID NO 666
<211> LENGTH: 15
<212> TYPE: PRT
```

<213> ORGANISM: Homo sapiens

<400> SEQUENCE: 666

Leu Leu Asp Val Val Thr Leu Glu Leu Gly Pro Gly Gly Pro Arg
1               5                   10                  15

<210> SEQ ID NO 667
<211> LENGTH: 9
<212> TYPE: PRT
<213> ORGANISM: Homo sapiens

<400> SEQUENCE: 667

Glu Tyr Ser Ser Leu Pro Leu Pro Arg
1               5

<210> SEQ ID NO 668
<211> LENGTH: 9
<212> TYPE: PRT
<213> ORGANISM: Homo sapiens

<400> SEQUENCE: 668

Gln Glu Glu Thr Leu Asp Tyr Gly Lys
1               5

<210> SEQ ID NO 669
<211> LENGTH: 8
<212> TYPE: PRT
<213> ORGANISM: Homo sapiens

<400> SEQUENCE: 669

Ala Val Arg Pro Gly Tyr Pro Lys
1               5

<210> SEQ ID NO 670
<211> LENGTH: 7
<212> TYPE: PRT
<213> ORGANISM: Homo sapiens

<400> SEQUENCE: 670

Glu Asp Glu Gly Tyr Ile Lys
1               5

<210> SEQ ID NO 671
<211> LENGTH: 7
<212> TYPE: PRT
<213> ORGANISM: Homo sapiens

<400> SEQUENCE: 671

Glu Leu Tyr Gly Leu Tyr Lys
1               5

<210> SEQ ID NO 672
<211> LENGTH: 5
<212> TYPE: PRT
<213> ORGANISM: Homo sapiens

<400> SEQUENCE: 672

Asn Phe Phe Trp Lys
1               5

<210> SEQ ID NO 673
<211> LENGTH: 14
<212> TYPE: PRT
<213> ORGANISM: Homo sapiens

<400> SEQUENCE: 673

Val His Gly Leu Ala Leu Gly His Glu Ala His Leu Gln Arg
1               5                   10

<210> SEQ ID NO 674
<211> LENGTH: 10
<212> TYPE: PRT
<213> ORGANISM: Homo sapiens

<400> SEQUENCE: 674

Asp Ile Tyr Ser Ser Phe Gly Phe Pro Arg
1               5                   10

<210> SEQ ID NO 675
<211> LENGTH: 17
<212> TYPE: PRT
<213> ORGANISM: Homo sapiens

<400> SEQUENCE: 675

Glu Tyr Phe Thr Val Asn Pro Glu Ser Gly Asp Leu Leu Val Ser Asp
1               5                   10                  15

Arg

<210> SEQ ID NO 676
<211> LENGTH: 10
<212> TYPE: PRT
<213> ORGANISM: Homo sapiens

<400> SEQUENCE: 676

Ala Ile Lys Pro Tyr Gln Thr Leu Ile Lys
1               5                   10

<210> SEQ ID NO 677
<211> LENGTH: 10
<212> TYPE: PRT
<213> ORGANISM: Homo sapiens

<400> SEQUENCE: 677

Asp Leu Gly Leu Gly Val Gly Glu Leu Arg
1               5                   10

<210> SEQ ID NO 678
<211> LENGTH: 8
<212> TYPE: PRT
<213> ORGANISM: Homo sapiens

<400> SEQUENCE: 678

Tyr Glu Glu Glu Val Leu Ser Arg
1               5

<210> SEQ ID NO 679
<211> LENGTH: 10
<212> TYPE: PRT
<213> ORGANISM: Homo sapiens

<400> SEQUENCE: 679

His Ala Thr Leu Ser Leu Ser Ile Pro Arg
1               5                   10

<210> SEQ ID NO 680
<211> LENGTH: 22
<212> TYPE: PRT
<213> ORGANISM: Homo sapiens

```
<400> SEQUENCE: 680

His Leu Tyr Val Leu Glu Phe Ser Asp His Pro Gly Ile His Glu Pro
1               5                   10                  15

Leu Glu Pro Glu Val Lys
            20

<210> SEQ ID NO 681
<211> LENGTH: 15
<212> TYPE: PRT
<213> ORGANISM: Homo sapiens

<400> SEQUENCE: 681

Phe Asn Phe Gln Gln Thr Asn Glu Asp Glu Leu Ser Phe Ser Lys
1               5                   10                  15

<210> SEQ ID NO 682
<211> LENGTH: 10
<212> TYPE: PRT
<213> ORGANISM: Homo sapiens

<400> SEQUENCE: 682

Asp Asp Gly Asn Ser Val Phe Pro Ala Lys
1               5                   10

<210> SEQ ID NO 683
<211> LENGTH: 15
<212> TYPE: PRT
<213> ORGANISM: Homo sapiens

<400> SEQUENCE: 683

Ser Gly Asp Glu Ala Pro Gly Leu Phe Phe Val Asp Ala Glu Arg
1               5                   10                  15

<210> SEQ ID NO 684
<211> LENGTH: 11
<212> TYPE: PRT
<213> ORGANISM: Homo sapiens

<400> SEQUENCE: 684

Ala Leu His Pro Glu Glu Asp Pro Glu Gly Arg
1               5                   10

<210> SEQ ID NO 685
<211> LENGTH: 17
<212> TYPE: PRT
<213> ORGANISM: Homo sapiens

<400> SEQUENCE: 685

Ile Asp Asp Ile Pro Gly Leu Ser Asp Thr Ser Pro Asp Leu Ser Ser
1               5                   10                  15

Arg

<210> SEQ ID NO 686
<211> LENGTH: 20
<212> TYPE: PRT
<213> ORGANISM: Homo sapiens

<400> SEQUENCE: 686

Asp Gln Leu Val Ile Pro Asp Gly Gln Glu Glu Gln Glu Ala Ala
1               5                   10                  15

Gly Glu Gly Arg
            20
```

```
<210> SEQ ID NO 687
<211> LENGTH: 12
<212> TYPE: PRT
<213> ORGANISM: Homo sapiens

<400> SEQUENCE: 687

Trp Val Asp Gly Thr Asp Tyr Glu Thr Gly Phe Lys
1               5                   10

<210> SEQ ID NO 688
<211> LENGTH: 13
<212> TYPE: PRT
<213> ORGANISM: Homo sapiens

<400> SEQUENCE: 688

Glu Arg Pro Glu Asp Arg Pro Thr Phe Asp Tyr Leu Arg
1               5                   10

<210> SEQ ID NO 689
<211> LENGTH: 13
<212> TYPE: PRT
<213> ORGANISM: Homo sapiens

<400> SEQUENCE: 689

Asp Asp Ser Glu Pro Ser Gly Glu Glu Thr Val Glu Arg
1               5                   10

<210> SEQ ID NO 690
<211> LENGTH: 22
<212> TYPE: PRT
<213> ORGANISM: Homo sapiens

<400> SEQUENCE: 690

Ala Gln Pro Val Gln Val Ala Glu Gly Ser Glu Pro Asp Gly Phe Trp
1               5                   10                  15

Glu Ala Leu Gly Gly Lys
            20

<210> SEQ ID NO 691
<211> LENGTH: 14
<212> TYPE: PRT
<213> ORGANISM: Homo sapiens

<400> SEQUENCE: 691

Glu Ala Leu Glu Pro Ser Gly Glu Asn Val Ile Gln Asn Lys
1               5                   10

<210> SEQ ID NO 692
<211> LENGTH: 10
<212> TYPE: PRT
<213> ORGANISM: Homo sapiens

<400> SEQUENCE: 692

Asp Gly Pro Asn Ser Leu Thr Pro Pro Lys
1               5                   10

<210> SEQ ID NO 693
<211> LENGTH: 10
<212> TYPE: PRT
<213> ORGANISM: Homo sapiens

<400> SEQUENCE: 693

Asn Pro Leu Ser Glu Leu Pro Val Val Lys
1               5                   10
```

<210> SEQ ID NO 694
<211> LENGTH: 15
<212> TYPE: PRT
<213> ORGANISM: Homo sapiens

<400> SEQUENCE: 694

Glu Val Phe Glu Asn Asp Pro Glu Thr Asp Tyr Phe Tyr Pro Arg
1               5                   10                  15

<210> SEQ ID NO 695
<211> LENGTH: 16
<212> TYPE: PRT
<213> ORGANISM: Homo sapiens

<400> SEQUENCE: 695

Gly Thr Tyr Ile Pro Val Pro Ile Val Ser Glu Leu Gln Ser Gly Lys
1               5                   10                  15

<210> SEQ ID NO 696
<211> LENGTH: 16
<212> TYPE: PRT
<213> ORGANISM: Homo sapiens

<400> SEQUENCE: 696

Val Ala Ala Tyr Phe Gly Leu Asp His Asn Val Asp Gln Thr Gly Lys
1               5                   10                  15

<210> SEQ ID NO 697
<211> LENGTH: 13
<212> TYPE: PRT
<213> ORGANISM: Homo sapiens

<400> SEQUENCE: 697

Ser Val Tyr Arg Pro Leu Asn Pro Leu Ala Pro Ser Arg
1               5                   10

<210> SEQ ID NO 698
<211> LENGTH: 13
<212> TYPE: PRT
<213> ORGANISM: Homo sapiens

<400> SEQUENCE: 698

Ser Val Glu Ile Thr Thr Asp Asn Ile Leu Glu Gly Arg
1               5                   10

<210> SEQ ID NO 699
<211> LENGTH: 15
<212> TYPE: PRT
<213> ORGANISM: Homo sapiens

<400> SEQUENCE: 699

Leu Gln Leu Leu Phe Pro Ser Glu Thr His Ser Pro Leu Ala Lys
1               5                   10                  15

<210> SEQ ID NO 700
<211> LENGTH: 14
<212> TYPE: PRT
<213> ORGANISM: Homo sapiens

<400> SEQUENCE: 700

Leu Gln Ala Leu Pro Ser Tyr Gly Leu Glu Ser Ile Gln Arg
1               5                   10

```
<210> SEQ ID NO 701
<211> LENGTH: 10
<212> TYPE: PRT
<213> ORGANISM: Homo sapiens

<400> SEQUENCE: 701

Leu Ser Pro Gln Gln Asp Ala Gly Gly Val
1               5                   10

<210> SEQ ID NO 702
<211> LENGTH: 6
<212> TYPE: PRT
<213> ORGANISM: Homo sapiens

<400> SEQUENCE: 702

Leu Val Asn His Ile Arg
1               5

<210> SEQ ID NO 703
<211> LENGTH: 10
<212> TYPE: PRT
<213> ORGANISM: Homo sapiens

<400> SEQUENCE: 703

Ser Pro Ala Phe Thr Asp Leu His Leu Arg
1               5                   10

<210> SEQ ID NO 704
<211> LENGTH: 17
<212> TYPE: PRT
<213> ORGANISM: Homo sapiens

<400> SEQUENCE: 704

Gly Asp Pro Gly Pro Pro Gly Ala Glu Gly Pro Pro Gly Leu Pro Gly
1               5                   10                  15

Lys

<210> SEQ ID NO 705
<211> LENGTH: 12
<212> TYPE: PRT
<213> ORGANISM: Homo sapiens

<400> SEQUENCE: 705

Ile Asn Val Tyr Tyr Asn Glu Ala Thr Gly Asn Lys
1               5                   10

<210> SEQ ID NO 706
<211> LENGTH: 20
<212> TYPE: PRT
<213> ORGANISM: Homo sapiens

<400> SEQUENCE: 706

Leu Asn Gly Leu Ala Ser Ser Ala Gly Val Tyr Phe Gly Pro Ala Ala
1               5                   10                  15

Ala Val Ala Arg
            20

<210> SEQ ID NO 707
<211> LENGTH: 9
<212> TYPE: PRT
<213> ORGANISM: Homo sapiens

<400> SEQUENCE: 707

Tyr Leu Leu Leu Ala Gly Ala Pro Arg
```

```
1               5

<210> SEQ ID NO 708
<211> LENGTH: 9
<212> TYPE: PRT
<213> ORGANISM: Homo sapiens

<400> SEQUENCE: 708

Leu Ser Gly Leu Ala Leu Asp His Lys
1               5

<210> SEQ ID NO 709
<211> LENGTH: 20
<212> TYPE: PRT
<213> ORGANISM: Homo sapiens

<400> SEQUENCE: 709

Leu Gly Asn Leu Pro Thr Gly Ser Phe Ser Ser Ser Pro Ser Ser
1               5                   10                  15

Ser Ser Ser Arg
            20

<210> SEQ ID NO 710
<211> LENGTH: 12
<212> TYPE: PRT
<213> ORGANISM: Homo sapiens

<400> SEQUENCE: 710

Thr Pro Val Val Ile Asp Tyr Thr Pro Tyr Leu Lys
1               5                   10

<210> SEQ ID NO 711
<211> LENGTH: 13
<212> TYPE: PRT
<213> ORGANISM: Homo sapiens

<400> SEQUENCE: 711

Asn Tyr Leu Asn Tyr Gly Glu Glu Gly Ala Pro Gly Lys
1               5                   10

<210> SEQ ID NO 712
<211> LENGTH: 8
<212> TYPE: PRT
<213> ORGANISM: Homo sapiens

<400> SEQUENCE: 712

Ser Leu Glu Ser Gln Leu Glu Lys
1               5

<210> SEQ ID NO 713
<211> LENGTH: 16
<212> TYPE: PRT
<213> ORGANISM: Homo sapiens

<400> SEQUENCE: 713

Gly Glu Ala Gly Ala Pro Gly Glu Glu Asp Ile Gln Gly Pro Thr Lys
1               5                   10                  15

<210> SEQ ID NO 714
<211> LENGTH: 15
<212> TYPE: PRT
<213> ORGANISM: Homo sapiens

<400> SEQUENCE: 714
```

```
Phe Ser Ile Ser Gly Ser Tyr Val Leu Asp Gln Ile Leu Pro Arg
1               5                   10                  15
```

<210> SEQ ID NO 715
<211> LENGTH: 23
<212> TYPE: PRT
<213> ORGANISM: Homo sapiens

<400> SEQUENCE: 715

```
Phe Leu Asp Pro Ser Phe Val Pro Ile Thr Asn Ser Leu Thr Gln Glu
1               5                   10                  15

Leu Gln Glu Lys Pro Ser Lys
            20
```

<210> SEQ ID NO 716
<211> LENGTH: 14
<212> TYPE: PRT
<213> ORGANISM: Homo sapiens

<400> SEQUENCE: 716

```
Ile Ala Gln Trp Gln Ser Phe Gln Leu Glu Gly Gly Leu Lys
1               5                   10
```

<210> SEQ ID NO 717
<211> LENGTH: 14
<212> TYPE: PRT
<213> ORGANISM: Homo sapiens

<400> SEQUENCE: 717

```
Asn Gly Ser Asp Val Pro Val Glu Asn Leu Tyr Pro Ser Lys
1               5                   10
```

<210> SEQ ID NO 718
<211> LENGTH: 8
<212> TYPE: PRT
<213> ORGANISM: Homo sapiens

<400> SEQUENCE: 718

```
Ile Arg Pro Phe Phe Pro Gln Gln
1               5
```

<210> SEQ ID NO 719
<211> LENGTH: 18
<212> TYPE: PRT
<213> ORGANISM: Homo sapiens

<400> SEQUENCE: 719

```
Val Asp Glu Val Pro Gly Leu Ser Gly Gln Ser Asp Asp Val Pro Ala
1               5                   10                  15

Gly Lys
```

<210> SEQ ID NO 720
<211> LENGTH: 8
<212> TYPE: PRT
<213> ORGANISM: Homo sapiens

<400> SEQUENCE: 720

```
Ser Glu Leu Leu Leu Ser Glu Lys
1               5
```

<210> SEQ ID NO 721
<211> LENGTH: 10
<212> TYPE: PRT
<213> ORGANISM: Homo sapiens

<400> SEQUENCE: 721

Leu Tyr Thr Asn Gly Pro Leu Pro Asp Lys
1               5                   10

<210> SEQ ID NO 722
<211> LENGTH: 13
<212> TYPE: PRT
<213> ORGANISM: Homo sapiens

<400> SEQUENCE: 722

Asp Leu Gly Ala Ser Thr Gln Glu Ser Gln Phe Leu Lys
1               5                   10

<210> SEQ ID NO 723
<211> LENGTH: 14
<212> TYPE: PRT
<213> ORGANISM: Homo sapiens

<400> SEQUENCE: 723

Phe Leu Ser Leu Gly Pro Phe Ser Asp Thr Thr Thr Val Lys
1               5                   10

<210> SEQ ID NO 724
<211> LENGTH: 14
<212> TYPE: PRT
<213> ORGANISM: Homo sapiens

<400> SEQUENCE: 724

Asn Val Glu Thr Thr Val Asp Glu Asp Val Leu Pro Gly Lys
1               5                   10

<210> SEQ ID NO 725
<211> LENGTH: 17
<212> TYPE: PRT
<213> ORGANISM: Homo sapiens

<400> SEQUENCE: 725

Asn Ala Ile Gln Ala Phe Gly Asn Gly Thr Asp Val Asn Val Ser Pro
1               5                   10                  15

Lys

<210> SEQ ID NO 726
<211> LENGTH: 14
<212> TYPE: PRT
<213> ORGANISM: Homo sapiens

<400> SEQUENCE: 726

Asn Ala Ala Ala Phe Gln Glu Thr Leu Glu Thr Leu Ile Lys
1               5                   10

<210> SEQ ID NO 727
<211> LENGTH: 10
<212> TYPE: PRT
<213> ORGANISM: Homo sapiens

<400> SEQUENCE: 727

Ser Pro His Glu Gly Tyr Glu Val Leu Lys
1               5                   10

<210> SEQ ID NO 728
<211> LENGTH: 9
<212> TYPE: PRT
<213> ORGANISM: Homo sapiens

<400> SEQUENCE: 728

Asp Ile Ser Glu Val Val Thr Pro Arg
1               5

<210> SEQ ID NO 729
<211> LENGTH: 18
<212> TYPE: PRT
<213> ORGANISM: Homo sapiens

<400> SEQUENCE: 729

Ala Trp Gly Ala Ala Pro Ser Ala Pro His Trp Asn Glu Thr Ala
1               5                   10                  15

Glu Lys

<210> SEQ ID NO 730
<211> LENGTH: 9
<212> TYPE: PRT
<213> ORGANISM: Homo sapiens

<400> SEQUENCE: 730

Tyr Glu Leu Ala Gly Leu Pro Gly Lys
1               5

<210> SEQ ID NO 731
<211> LENGTH: 9
<212> TYPE: PRT
<213> ORGANISM: Homo sapiens

<400> SEQUENCE: 731

Ile Trp Ser Val Leu Glu Ser Pro Arg
1               5

<210> SEQ ID NO 732
<211> LENGTH: 9
<212> TYPE: PRT
<213> ORGANISM: Homo sapiens

<400> SEQUENCE: 732

Tyr Glu Pro Pro Leu Gly Asp Ile Lys
1               5

<210> SEQ ID NO 733
<211> LENGTH: 16
<212> TYPE: PRT
<213> ORGANISM: Homo sapiens

<400> SEQUENCE: 733

Ile Arg Pro Gly Glu Gln Glu Gln Tyr Glu Ser Thr Ile Gly Phe Lys
1               5                   10                  15

<210> SEQ ID NO 734
<211> LENGTH: 9
<212> TYPE: PRT
<213> ORGANISM: Homo sapiens

<400> SEQUENCE: 734

His Thr Asn Glu Pro Val Ile Glu Lys
1               5

<210> SEQ ID NO 735
<211> LENGTH: 7
<212> TYPE: PRT
<213> ORGANISM: Homo sapiens

<400> SEQUENCE: 735

Asn Pro Ile Glu His Ser Arg
1               5

<210> SEQ ID NO 736
<211> LENGTH: 15
<212> TYPE: PRT
<213> ORGANISM: Homo sapiens

<400> SEQUENCE: 736

Asn Trp Gly Leu Ser Val Tyr Ala Asp Lys Pro Glu Thr Thr Lys
1               5                   10                  15

<210> SEQ ID NO 737
<211> LENGTH: 8
<212> TYPE: PRT
<213> ORGANISM: Homo sapiens

<400> SEQUENCE: 737

Thr Glu Asp Thr Ile Phe Leu Arg
1               5

<210> SEQ ID NO 738
<211> LENGTH: 7
<212> TYPE: PRT
<213> ORGANISM: Homo sapiens

<400> SEQUENCE: 738

Glu Asn Gly Thr Val Ser Arg
1               5

<210> SEQ ID NO 739
<211> LENGTH: 6
<212> TYPE: PRT
<213> ORGANISM: Homo sapiens

<400> SEQUENCE: 739

Asn Glu Glu Tyr Asn Lys
1               5

<210> SEQ ID NO 740
<211> LENGTH: 8
<212> TYPE: PRT
<213> ORGANISM: Homo sapiens

<400> SEQUENCE: 740

Thr Glu Asp Thr Ile Phe Leu Arg
1               5

<210> SEQ ID NO 741
<211> LENGTH: 16
<212> TYPE: PRT
<213> ORGANISM: Homo sapiens

<400> SEQUENCE: 741

Asn Gly Val Ala Gln Glu Pro Val His Leu Asp Ser Pro Ala Ile Lys
1               5                   10                  15

<210> SEQ ID NO 742
<211> LENGTH: 19
<212> TYPE: PRT
<213> ORGANISM: Homo sapiens

<400> SEQUENCE: 742

Val Asp Leu Ser Phe Ser Pro Ser Gln Ser Leu Pro Ala Ser His Ala
1               5                   10                  15

His Leu Arg

<210> SEQ ID NO 743
<211> LENGTH: 12
<212> TYPE: PRT
<213> ORGANISM: Homo sapiens

<400> SEQUENCE: 743

Val Glu Ser Leu Glu Gln Glu Ala Ala Asn Glu Arg
1               5                   10

<210> SEQ ID NO 744
<211> LENGTH: 16
<212> TYPE: PRT
<213> ORGANISM: Homo sapiens

<400> SEQUENCE: 744

Tyr Leu Glu Thr Pro Gly Asp Glu Asn Glu His Ala His Phe Gln Lys
1               5                   10                  15

<210> SEQ ID NO 745
<211> LENGTH: 6
<212> TYPE: PRT
<213> ORGANISM: Homo sapiens

<400> SEQUENCE: 745

Asp Ser Leu Glu Phe Arg
1               5

<210> SEQ ID NO 746
<211> LENGTH: 10
<212> TYPE: PRT
<213> ORGANISM: Homo sapiens

<400> SEQUENCE: 746

Asn Leu Ala Val Ser Gln Val Val His Lys
1               5                   10

<210> SEQ ID NO 747
<211> LENGTH: 14
<212> TYPE: PRT
<213> ORGANISM: Homo sapiens

<400> SEQUENCE: 747

Ile Leu Asp Gly Gly Gly Gln Asn Asp Ile Leu Glu Ile Lys
1               5                   10

<210> SEQ ID NO 748
<211> LENGTH: 13
<212> TYPE: PRT
<213> ORGANISM: Homo sapiens

<400> SEQUENCE: 748

Leu Glu Pro Ile Ala Thr Glu Val Trp Leu Ile Asn Lys
1               5                   10

<210> SEQ ID NO 749
<211> LENGTH: 16
<212> TYPE: PRT
<213> ORGANISM: Homo sapiens

<400> SEQUENCE: 749

Tyr Pro Thr Pro Gly Glu Ala Pro Gly Val Val Gly Asn Phe Asn Lys
1               5                   10                  15

<210> SEQ ID NO 750
<211> LENGTH: 15
<212> TYPE: PRT
<213> ORGANISM: Homo sapiens

<400> SEQUENCE: 750

Gly Asp Tyr Glu Val Asn Gly Val Asp Gly Tyr Asp Tyr Ser Arg
1               5                   10                  15

<210> SEQ ID NO 751
<211> LENGTH: 11
<212> TYPE: PRT
<213> ORGANISM: Homo sapiens

<400> SEQUENCE: 751

Ile Ser Phe Asn Phe Phe Val Thr Ala Pro Lys
1               5                   10

<210> SEQ ID NO 752
<211> LENGTH: 26
<212> TYPE: PRT
<213> ORGANISM: Homo sapiens

<400> SEQUENCE: 752

Ala Pro Gly Asp Pro Leu Ser Ser Pro Ser Pro Thr Ala Leu Pro Gln
1               5                   10                  15

Gly Gly Ser His Thr Glu Thr Glu Asp Arg
            20                  25

<210> SEQ ID NO 753
<211> LENGTH: 15
<212> TYPE: PRT
<213> ORGANISM: Homo sapiens

<400> SEQUENCE: 753

Trp Ala Arg Pro Val Pro Asn Thr Ser Asp Val Val Ile Val Arg
1               5                   10                  15

<210> SEQ ID NO 754
<211> LENGTH: 13
<212> TYPE: PRT
<213> ORGANISM: Homo sapiens

<400> SEQUENCE: 754

Trp Asn Pro Thr Asp Phe Gly Asn Ile Thr Ser Leu Arg
1               5                   10

<210> SEQ ID NO 755
<211> LENGTH: 18
<212> TYPE: PRT
<213> ORGANISM: Homo sapiens

<400> SEQUENCE: 755

Asp Asp Ala Ala Pro Glu Ala Asp Gly Gln Ala Ala Gly Ala Leu Ala
1               5                   10                  15

Ser Arg

<210> SEQ ID NO 756
<211> LENGTH: 15
<212> TYPE: PRT

<213> ORGANISM: Homo sapiens

<400> SEQUENCE: 756

Leu Leu Pro Pro Leu Leu Leu Leu Gly Thr Gly Leu Leu Arg
1               5                   10                  15

<210> SEQ ID NO 757
<211> LENGTH: 13
<212> TYPE: PRT
<213> ORGANISM: Homo sapiens

<400> SEQUENCE: 757

Trp Asp Pro Ala Asp Tyr Glu Asn Val Thr Ser Ile Arg
1               5                   10

<210> SEQ ID NO 758
<211> LENGTH: 20
<212> TYPE: PRT
<213> ORGANISM: Homo sapiens

<400> SEQUENCE: 758

Val Pro Ser Asp Ser Val Trp Thr Pro Asp Ile Val Leu Phe Asp Asn
1               5                   10                  15

Ala Asp Gly Arg
            20

<210> SEQ ID NO 759
<211> LENGTH: 14
<212> TYPE: PRT
<213> ORGANISM: Homo sapiens

<400> SEQUENCE: 759

Tyr Asn Gly Thr Val Thr Trp Thr Pro Pro Ala Asn Tyr Lys
1               5                   10

<210> SEQ ID NO 760
<211> LENGTH: 11
<212> TYPE: PRT
<213> ORGANISM: Homo sapiens

<400> SEQUENCE: 760

Glu Val Val Ser Ser Ile Ser Tyr Ile Ala Arg
1               5                   10

<210> SEQ ID NO 761
<211> LENGTH: 9
<212> TYPE: PRT
<213> ORGANISM: Homo sapiens

<400> SEQUENCE: 761

Leu Ile Gln Pro Pro Gly Asp Pro Arg
1               5

<210> SEQ ID NO 762
<211> LENGTH: 11
<212> TYPE: PRT
<213> ORGANISM: Homo sapiens

<400> SEQUENCE: 762

Val Tyr Leu Asp Leu Glu Trp Thr Asp Tyr Arg
1               5                   10

<210> SEQ ID NO 763
<211> LENGTH: 22

```
<212> TYPE: PRT
<213> ORGANISM: Homo sapiens

<400> SEQUENCE: 763

Ala Ser Val Gln Gly Leu Ala Gly Ala Phe Gly Ala Glu Pro Ala Pro
1               5                   10                  15

Val Ala Gly Pro Gly Arg
            20

<210> SEQ ID NO 764
<211> LENGTH: 13
<212> TYPE: PRT
<213> ORGANISM: Homo sapiens

<400> SEQUENCE: 764

Ser Glu Asp Asp Asp Gln Ser Val Ser Glu Asp Trp Lys
1               5                   10

<210> SEQ ID NO 765
<211> LENGTH: 8
<212> TYPE: PRT
<213> ORGANISM: Homo sapiens

<400> SEQUENCE: 765

Thr Glu Ile Asp Leu Val Leu Lys
1               5

<210> SEQ ID NO 766
<211> LENGTH: 19
<212> TYPE: PRT
<213> ORGANISM: Homo sapiens

<400> SEQUENCE: 766

Ala Asp Glu Val Val Ser Ala Ser Val Gly Ser Gly Asp Leu Trp Ile
1               5                   10                  15

Pro Val Lys

<210> SEQ ID NO 767
<211> LENGTH: 10
<212> TYPE: PRT
<213> ORGANISM: Homo sapiens

<400> SEQUENCE: 767

Leu Ile Glu Ile Ala Asn His Val Asp Lys
1               5                   10

<210> SEQ ID NO 768
<211> LENGTH: 13
<212> TYPE: PRT
<213> ORGANISM: Homo sapiens

<400> SEQUENCE: 768

Gly Pro Ala Gly Ser Val Pro Ala Ser Ala Pro Ala Arg
1               5                   10

<210> SEQ ID NO 769
<211> LENGTH: 11
<212> TYPE: PRT
<213> ORGANISM: Homo sapiens

<400> SEQUENCE: 769

Ser Val Val Asn Leu Val Asp Ser Ile Tyr Lys
1               5                   10
```

<210> SEQ ID NO 770
<211> LENGTH: 12
<212> TYPE: PRT
<213> ORGANISM: Homo sapiens

<400> SEQUENCE: 770

Val Val Leu Val Ala Val Glu Thr Trp Thr Glu Lys
1               5                   10

<210> SEQ ID NO 771
<211> LENGTH: 7
<212> TYPE: PRT
<213> ORGANISM: Homo sapiens

<400> SEQUENCE: 771

His Phe Gln Asn Leu Gly Lys
1               5

<210> SEQ ID NO 772
<211> LENGTH: 16
<212> TYPE: PRT
<213> ORGANISM: Homo sapiens

<400> SEQUENCE: 772

Ile Ala Pro Gln Leu Ser Thr Glu Glu Leu Val Ser Leu Gly Glu Lys
1               5                   10                  15

<210> SEQ ID NO 773
<211> LENGTH: 9
<212> TYPE: PRT
<213> ORGANISM: Homo sapiens

<400> SEQUENCE: 773

Leu Pro Asn Asn Val Leu Gln Glu Lys
1               5

<210> SEQ ID NO 774
<211> LENGTH: 12
<212> TYPE: PRT
<213> ORGANISM: Homo sapiens

<400> SEQUENCE: 774

Asp Val Ile Ala Ile Asn Gln Asp Pro Leu Gly Lys
1               5                   10

<210> SEQ ID NO 775
<211> LENGTH: 7
<212> TYPE: PRT
<213> ORGANISM: Homo sapiens

<400> SEQUENCE: 775

Leu Gln Ala Asp Pro Gln Arg
1               5

<210> SEQ ID NO 776
<211> LENGTH: 11
<212> TYPE: PRT
<213> ORGANISM: Homo sapiens

<400> SEQUENCE: 776

Ser Tyr Thr Ile Ala Val Ala Ser Leu Gly Lys
1               5                   10

<210> SEQ ID NO 777

```
<211> LENGTH: 16
<212> TYPE: PRT
<213> ORGANISM: Homo sapiens

<400> SEQUENCE: 777

Ala Ile Ser Ala Phe Gly Pro Ser Ala Ser Ile Asn Gly Leu Val Lys
1               5                   10                  15

<210> SEQ ID NO 778
<211> LENGTH: 8
<212> TYPE: PRT
<213> ORGANISM: Homo sapiens

<400> SEQUENCE: 778

Asp Asp Asn Pro Asn Leu Pro Arg
1               5

<210> SEQ ID NO 779
<211> LENGTH: 8
<212> TYPE: PRT
<213> ORGANISM: Homo sapiens

<400> SEQUENCE: 779

Asp Leu Gly Glu Glu Asn Phe Lys
1               5

<210> SEQ ID NO 780
<211> LENGTH: 9
<212> TYPE: PRT
<213> ORGANISM: Homo sapiens

<400> SEQUENCE: 780

Ser Leu His Thr Leu Phe Gly Asp Lys
1               5

<210> SEQ ID NO 781
<211> LENGTH: 12
<212> TYPE: PRT
<213> ORGANISM: Homo sapiens

<400> SEQUENCE: 781

Asp Phe Ala Leu Gln Asn Pro Ser Ala Val Pro Arg
1               5                   10

<210> SEQ ID NO 782
<211> LENGTH: 11
<212> TYPE: PRT
<213> ORGANISM: Homo sapiens

<400> SEQUENCE: 782

Thr Phe Thr Pro Gln Pro Pro Gly Leu Glu Arg
1               5                   10

<210> SEQ ID NO 783
<211> LENGTH: 16
<212> TYPE: PRT
<213> ORGANISM: Homo sapiens

<400> SEQUENCE: 783

Val Ala Gly Leu Leu Glu Asp Thr Phe Pro Gly Leu Leu Gly Leu Arg
1               5                   10                  15

<210> SEQ ID NO 784
<211> LENGTH: 23
<212> TYPE: PRT
```

<213> ORGANISM: Homo sapiens

<400> SEQUENCE: 784

Ala Ala Ala Asp Ser Thr Ser His Ser Tyr Phe Val Asn Pro Leu Phe
1               5                   10                  15

Ala Gly Ala Glu Ala Glu Ala
            20

<210> SEQ ID NO 785
<211> LENGTH: 11
<212> TYPE: PRT
<213> ORGANISM: Homo sapiens

<400> SEQUENCE: 785

Asp Glu Asp Leu Ala Val Phe Leu Ala Ser Arg
1               5                   10

<210> SEQ ID NO 786
<211> LENGTH: 11
<212> TYPE: PRT
<213> ORGANISM: Homo sapiens

<400> SEQUENCE: 786

Val Gly Leu Gly Pro Gly Ala Ser Pro Val Arg
1               5                   10

<210> SEQ ID NO 787
<211> LENGTH: 13
<212> TYPE: PRT
<213> ORGANISM: Homo sapiens

<400> SEQUENCE: 787

Ala Glu Phe Gly Pro Pro Gly Pro Gly Ala Gly Ser Arg
1               5                   10

<210> SEQ ID NO 788
<211> LENGTH: 16
<212> TYPE: PRT
<213> ORGANISM: Homo sapiens

<400> SEQUENCE: 788

Glu Glu Tyr Asn Gly Val Ile Glu Glu Phe Leu Ala Thr Gly Glu Lys
1               5                   10                  15

<210> SEQ ID NO 789
<211> LENGTH: 18
<212> TYPE: PRT
<213> ORGANISM: Homo sapiens

<400> SEQUENCE: 789

Ile Glu Pro Gly Val Asp Pro Asp Asp Thr Tyr Asn Glu Thr Pro Tyr
1               5                   10                  15

Glu Lys

<210> SEQ ID NO 790
<211> LENGTH: 11
<212> TYPE: PRT
<213> ORGANISM: Homo sapiens

<400> SEQUENCE: 790

Gln Leu Leu Gln Gln Thr Asn Glu Ile Leu Lys
1               5                   10

```
<210> SEQ ID NO 791
<211> LENGTH: 14
<212> TYPE: PRT
<213> ORGANISM: Homo sapiens

<400> SEQUENCE: 791

Gln Ser Ser Leu Ile Leu His Gly Ala Asp Phe Ser Thr Lys
1               5                   10

<210> SEQ ID NO 792
<211> LENGTH: 10
<212> TYPE: PRT
<213> ORGANISM: Homo sapiens

<400> SEQUENCE: 792

Gln Thr Tyr Ile Ile Gln Glu Leu Glu Lys
1               5                   10

<210> SEQ ID NO 793
<211> LENGTH: 12
<212> TYPE: PRT
<213> ORGANISM: Homo sapiens

<400> SEQUENCE: 793

Ala Leu Gln Asp Gln Leu Val Leu Val Ala Ala Lys
1               5                   10

<210> SEQ ID NO 794
<211> LENGTH: 13
<212> TYPE: PRT
<213> ORGANISM: Homo sapiens

<400> SEQUENCE: 794

Ser Leu Asp Phe Thr Glu Leu Asp Val Ala Ala Glu Lys
1               5                   10

<210> SEQ ID NO 795
<211> LENGTH: 12
<212> TYPE: PRT
<213> ORGANISM: Homo sapiens

<400> SEQUENCE: 795

Ser Phe Ile Ala Tyr Leu Ile Pro Asp Val Pro Lys
1               5                   10

<210> SEQ ID NO 796
<211> LENGTH: 12
<212> TYPE: PRT
<213> ORGANISM: Homo sapiens

<400> SEQUENCE: 796

Thr Glu Ser Glu Trp Glu Asn Ser Phe Ala Leu Lys
1               5                   10

<210> SEQ ID NO 797
<211> LENGTH: 13
<212> TYPE: PRT
<213> ORGANISM: Homo sapiens

<400> SEQUENCE: 797

Phe Ala Thr Thr Phe Tyr Gln His Leu Ala Asp Ser Lys
1               5                   10

<210> SEQ ID NO 798
<211> LENGTH: 11
```

```
<212> TYPE: PRT
<213> ORGANISM: Homo sapiens

<400> SEQUENCE: 798

Thr Ser Asp Gln Ile His Phe Phe Ala Lys
1               5                   10

<210> SEQ ID NO 799
<211> LENGTH: 17
<212> TYPE: PRT
<213> ORGANISM: Homo sapiens

<400> SEQUENCE: 799

Ala Pro Glu Val Ser Gln His Val Tyr Gln Ala Tyr Glu Thr Ile Leu
1               5                   10                  15

Lys

<210> SEQ ID NO 800
<211> LENGTH: 13
<212> TYPE: PRT
<213> ORGANISM: Homo sapiens

<400> SEQUENCE: 800

Asp Ile Pro Asn Glu Asn Glu Ala Gln Phe Gln Ile Arg
1               5                   10

<210> SEQ ID NO 801
<211> LENGTH: 10
<212> TYPE: PRT
<213> ORGANISM: Homo sapiens

<400> SEQUENCE: 801

Gly Leu Glu Ile Ser Gly Thr Phe Thr Arg
1               5                   10

<210> SEQ ID NO 802
<211> LENGTH: 11
<212> TYPE: PRT
<213> ORGANISM: Homo sapiens

<400> SEQUENCE: 802

Asp Thr Ser Gly Glu Ala Ala Val Ala Ala Lys
1               5                   10

<210> SEQ ID NO 803
<211> LENGTH: 13
<212> TYPE: PRT
<213> ORGANISM: Homo sapiens

<400> SEQUENCE: 803

Phe Gln Pro Pro Thr Leu Gly Pro Glu Pro Ala Ala Arg
1               5                   10

<210> SEQ ID NO 804
<211> LENGTH: 14
<212> TYPE: PRT
<213> ORGANISM: Homo sapiens

<400> SEQUENCE: 804

Val Ala Ser Ala Leu Ser Ser Gly Ser Glu Ser Ser Asp Arg
1               5                   10

<210> SEQ ID NO 805
<211> LENGTH: 13
```

```
<212> TYPE: PRT
<213> ORGANISM: Homo sapiens

<400> SEQUENCE: 805

Phe Gln Val His Thr His Leu Gln Val Ile Glu Glu Arg
1               5                   10

<210> SEQ ID NO 806
<211> LENGTH: 12
<212> TYPE: PRT
<213> ORGANISM: Homo sapiens

<400> SEQUENCE: 806

Gly Ser Thr Glu Gln Asp Ala Ala Ser Pro Glu Lys
1               5                   10

<210> SEQ ID NO 807
<211> LENGTH: 22
<212> TYPE: PRT
<213> ORGANISM: Homo sapiens

<400> SEQUENCE: 807

Gln Ala Leu Asn Glu His Phe Gln Ser Ile Leu Gln Thr Leu Glu Glu
1               5                   10                  15

Gln Val Ser Gly Glu Arg
            20

<210> SEQ ID NO 808
<211> LENGTH: 8
<212> TYPE: PRT
<213> ORGANISM: Homo sapiens

<400> SEQUENCE: 808

Ala Glu Leu Gln Glu Gly Ala Arg
1               5

<210> SEQ ID NO 809
<211> LENGTH: 11
<212> TYPE: PRT
<213> ORGANISM: Homo sapiens

<400> SEQUENCE: 809

Ala Thr Glu His Leu Ser Thr Leu Ser Glu Lys
1               5                   10

<210> SEQ ID NO 810
<211> LENGTH: 7
<212> TYPE: PRT
<213> ORGANISM: Homo sapiens

<400> SEQUENCE: 810

Leu His Glu Leu Gln Glu Lys
1               5

<210> SEQ ID NO 811
<211> LENGTH: 9
<212> TYPE: PRT
<213> ORGANISM: Homo sapiens

<400> SEQUENCE: 811

Ile Asp Gln Asn Val Glu Glu Leu Lys
1               5

<210> SEQ ID NO 812
```

```
<211> LENGTH: 17
<212> TYPE: PRT
<213> ORGANISM: Homo sapiens

<400> SEQUENCE: 812

Leu Gly Pro His Ala Gly Asp Val Glu Gly His Leu Ser Phe Leu Glu
1               5                   10                  15

Lys

<210> SEQ ID NO 813
<211> LENGTH: 9
<212> TYPE: PRT
<213> ORGANISM: Homo sapiens

<400> SEQUENCE: 813

Val Asn Ser Phe Phe Ser Thr Phe Lys
1               5

<210> SEQ ID NO 814
<211> LENGTH: 16
<212> TYPE: PRT
<213> ORGANISM: Homo sapiens

<400> SEQUENCE: 814

Ala Thr Phe Gln Thr Pro Asp Phe Ile Val Pro Leu Thr Asp Leu Arg
1               5                   10                  15

<210> SEQ ID NO 815
<211> LENGTH: 18
<212> TYPE: PRT
<213> ORGANISM: Homo sapiens

<400> SEQUENCE: 815

Phe Ser Val Pro Ala Gly Ile Val Ile Pro Ser Phe Gln Ala Leu Thr
1               5                   10                  15

Ala Arg

<210> SEQ ID NO 816
<211> LENGTH: 10
<212> TYPE: PRT
<213> ORGANISM: Homo sapiens

<400> SEQUENCE: 816

Ile Tyr Ser Leu Trp Glu His Ser Thr Lys
1               5                   10

<210> SEQ ID NO 817
<211> LENGTH: 11
<212> TYPE: PRT
<213> ORGANISM: Homo sapiens

<400> SEQUENCE: 817

Glu Ser Leu Ser Ser Tyr Trp Glu Ser Ala Lys
1               5                   10

<210> SEQ ID NO 818
<211> LENGTH: 22
<212> TYPE: PRT
<213> ORGANISM: Homo sapiens

<400> SEQUENCE: 818

Ala Asp Gly Thr Val Asn Gln Ile Glu Gly Glu Ala Thr Pro Val Asn
1               5                   10                  15
```

-continued

Leu Thr Glu Pro Ala Lys
            20

<210> SEQ ID NO 819
<211> LENGTH: 13
<212> TYPE: PRT
<213> ORGANISM: Homo sapiens

<400> SEQUENCE: 819

Asn Pro Asn Leu Pro Pro Glu Thr Val Asp Ser Leu Lys
1               5                   10

<210> SEQ ID NO 820
<211> LENGTH: 6
<212> TYPE: PRT
<213> ORGANISM: Homo sapiens

<400> SEQUENCE: 820

Trp Tyr Glu Ile Glu Lys
1               5

<210> SEQ ID NO 821
<211> LENGTH: 15
<212> TYPE: PRT
<213> ORGANISM: Homo sapiens

<400> SEQUENCE: 821

Ala Ala Thr Val Gly Ser Leu Ala Gly Gln Pro Leu Gln Glu Arg
1               5                   10                  15

<210> SEQ ID NO 822
<211> LENGTH: 15
<212> TYPE: PRT
<213> ORGANISM: Homo sapiens

<400> SEQUENCE: 822

Ser Glu Leu Glu Glu Gln Leu Thr Pro Val Ala Glu Glu Thr Arg
1               5                   10                  15

<210> SEQ ID NO 823
<211> LENGTH: 23
<212> TYPE: PRT
<213> ORGANISM: Homo sapiens

<400> SEQUENCE: 823

Trp Val Gln Thr Leu Ser Glu Gln Val Gln Glu Glu Leu Leu Ser Ser
1               5                   10                  15

Gln Val Thr Gln Glu Leu Arg
            20

<210> SEQ ID NO 824
<211> LENGTH: 11
<212> TYPE: PRT
<213> ORGANISM: Homo sapiens

<400> SEQUENCE: 824

Glu Glu Ala Asp Ala Leu Tyr Glu Ala Leu Lys
1               5                   10

<210> SEQ ID NO 825
<211> LENGTH: 11
<212> TYPE: PRT
<213> ORGANISM: Homo sapiens

<400> SEQUENCE: 825

```
Tyr Val Pro Ile Asn Val Val Glu Thr Leu Arg
1               5                   10

<210> SEQ ID NO 826
<211> LENGTH: 7
<212> TYPE: PRT
<213> ORGANISM: Homo sapiens

<400> SEQUENCE: 826

Asp Ala Tyr Val Tyr Leu Lys
1               5

<210> SEQ ID NO 827
<211> LENGTH: 8
<212> TYPE: PRT
<213> ORGANISM: Homo sapiens

<400> SEQUENCE: 827

Glu Glu Ser Leu Pro Lys Pro Lys
1               5

<210> SEQ ID NO 828
<211> LENGTH: 8
<212> TYPE: PRT
<213> ORGANISM: Homo sapiens

<400> SEQUENCE: 828

Gly Asp Val Ile His Val Thr Arg
1               5

<210> SEQ ID NO 829
<211> LENGTH: 9
<212> TYPE: PRT
<213> ORGANISM: Homo sapiens

<400> SEQUENCE: 829

Gly Phe Asp Thr Thr Ala Ile Asn Lys
1               5

<210> SEQ ID NO 830
<211> LENGTH: 17
<212> TYPE: PRT
<213> ORGANISM: Homo sapiens

<400> SEQUENCE: 830

Ala Gly Ser Glu Ser Ser Ser Ala Gly Ser Ser Gly Ser Leu Ser
1               5                   10                  15

Arg

<210> SEQ ID NO 831
<211> LENGTH: 12
<212> TYPE: PRT
<213> ORGANISM: Homo sapiens

<400> SEQUENCE: 831

Ala Trp Ser Ser Thr Asp Ser Asp Ser Ser Asn Arg
1               5                   10

<210> SEQ ID NO 832
<211> LENGTH: 9
<212> TYPE: PRT
<213> ORGANISM: Homo sapiens

<400> SEQUENCE: 832
```

Gln Ser Ser Ser Glu Asn Glu Leu Lys
1               5

<210> SEQ ID NO 833
<211> LENGTH: 16
<212> TYPE: PRT
<213> ORGANISM: Homo sapiens

<400> SEQUENCE: 833

Ala Gln Leu Asp Ala Ala Val Thr Phe Gly Pro Ser Gln Val Ala Arg
1               5                   10                  15

<210> SEQ ID NO 834
<211> LENGTH: 20
<212> TYPE: PRT
<213> ORGANISM: Homo sapiens

<400> SEQUENCE: 834

Trp His Leu Gly Val Gly Pro Glu Gly Ala Phe Leu Pro Pro His Gln
1               5                   10                  15

Gly Phe His Arg
            20

<210> SEQ ID NO 835
<211> LENGTH: 11
<212> TYPE: PRT
<213> ORGANISM: Homo sapiens

<400> SEQUENCE: 835

Thr Leu Ser Pro Val Pro Leu Gln Leu Asp Arg
1               5                   10

<210> SEQ ID NO 836
<211> LENGTH: 20
<212> TYPE: PRT
<213> ORGANISM: Homo sapiens

<400> SEQUENCE: 836

Val Leu Gln Trp Thr Gly Ala Ser Gly Gly Leu Pro Thr Asn Glu Thr
1               5                   10                  15

Thr Phe Ala Lys
            20

<210> SEQ ID NO 837
<211> LENGTH: 10
<212> TYPE: PRT
<213> ORGANISM: Homo sapiens

<400> SEQUENCE: 837

Val Gln Gln Ala Val Trp Glu His Gln Arg
1               5                   10

<210> SEQ ID NO 838
<211> LENGTH: 18
<212> TYPE: PRT
<213> ORGANISM: Homo sapiens

<400> SEQUENCE: 838

Glu Gly Pro Pro Pro Val Leu Ala Ser Pro Ala Gly His Leu Pro Gly
1               5                   10                  15

Gly Arg

```
<210> SEQ ID NO 839
<211> LENGTH: 7
<212> TYPE: PRT
<213> ORGANISM: Homo sapiens

<400> SEQUENCE: 839

Ser Gln Leu Val Pro Val Arg
1               5

<210> SEQ ID NO 840
<211> LENGTH: 8
<212> TYPE: PRT
<213> ORGANISM: Homo sapiens

<400> SEQUENCE: 840

Ala Ser Gln Glu Pro Pro Leu Leu
1               5

<210> SEQ ID NO 841
<211> LENGTH: 15
<212> TYPE: PRT
<213> ORGANISM: Homo sapiens

<400> SEQUENCE: 841

Glu Thr Phe Ser Asn Phe Thr Ala Ser Thr Glu Ala Gln Val Lys
1               5                   10                  15

<210> SEQ ID NO 842
<211> LENGTH: 16
<212> TYPE: PRT
<213> ORGANISM: Homo sapiens

<400> SEQUENCE: 842

Leu Glu Asp Ala His Leu Val Val Val Thr Ser Trp Glu Glu Gln Lys
1               5                   10                  15

<210> SEQ ID NO 843
<211> LENGTH: 15
<212> TYPE: PRT
<213> ORGANISM: Homo sapiens

<400> SEQUENCE: 843

Val Asp Asn Ser Ser Leu Thr Gly Glu Ser Glu Pro Gln Pro Arg
1               5                   10                  15

<210> SEQ ID NO 844
<211> LENGTH: 15
<212> TYPE: PRT
<213> ORGANISM: Homo sapiens

<400> SEQUENCE: 844

Asp Ile Val Pro Gly Asp Ile Val Glu Ile Ala Val Gly Asp Lys
1               5                   10                  15

<210> SEQ ID NO 845
<211> LENGTH: 10
<212> TYPE: PRT
<213> ORGANISM: Homo sapiens

<400> SEQUENCE: 845

Glu Trp Gly Ser Gly Ser Asp Thr Leu Arg
1               5                   10

<210> SEQ ID NO 846
<211> LENGTH: 17
```

```
<212> TYPE: PRT
<213> ORGANISM: Homo sapiens

<400> SEQUENCE: 846

Glu Ala Ser Asp Ile Ile Leu Thr Asp Asp Asn Phe Thr Ser Ile Val
1               5                   10                  15

Lys

<210> SEQ ID NO 847
<211> LENGTH: 7
<212> TYPE: PRT
<213> ORGANISM: Homo sapiens

<400> SEQUENCE: 847

Leu Ala Val Gln Ile Gly Lys
1               5

<210> SEQ ID NO 848
<211> LENGTH: 14
<212> TYPE: PRT
<213> ORGANISM: Homo sapiens

<400> SEQUENCE: 848

Ala Ser Phe Gly Ser Gly Pro Ala Val Glu Trp Ile Pro Lys
1               5                   10

<210> SEQ ID NO 849
<211> LENGTH: 11
<212> TYPE: PRT
<213> ORGANISM: Homo sapiens

<400> SEQUENCE: 849

Gly Ile Gly Tyr Phe Phe Val Leu Gln Pro Lys
1               5                   10

<210> SEQ ID NO 850
<211> LENGTH: 23
<212> TYPE: PRT
<213> ORGANISM: Homo sapiens

<400> SEQUENCE: 850

Thr Asp Asn Val Ala Thr Ser Ser Pro Glu Thr Thr Glu Ile Ser Ala
1               5                   10                  15

Val Ala Asp Ala Asn Gly Lys
            20

<210> SEQ ID NO 851
<211> LENGTH: 14
<212> TYPE: PRT
<213> ORGANISM: Homo sapiens

<400> SEQUENCE: 851

Thr Gly Asp Gln Ala Ala Asp Ser Ser Leu Gly Ser Val Lys
1               5                   10

<210> SEQ ID NO 852
<211> LENGTH: 8
<212> TYPE: PRT
<213> ORGANISM: Homo sapiens

<400> SEQUENCE: 852

Asp Ala Asp Leu Tyr Thr Ser Arg
1               5
```

```
<210> SEQ ID NO 853
<211> LENGTH: 11
<212> TYPE: PRT
<213> ORGANISM: Homo sapiens

<400> SEQUENCE: 853

Gly Gln Gly Gly Leu Ala Tyr Pro Gly Val Arg
1               5                   10

<210> SEQ ID NO 854
<211> LENGTH: 7
<212> TYPE: PRT
<213> ORGANISM: Homo sapiens

<400> SEQUENCE: 854

Gln Tyr Phe Tyr Glu Thr Lys
1               5

<210> SEQ ID NO 855
<211> LENGTH: 15
<212> TYPE: PRT
<213> ORGANISM: Homo sapiens

<400> SEQUENCE: 855

Glu Pro Leu Glu Gln Ser Pro Thr Asn Ile His Thr Thr Leu Lys
1               5                   10                  15

<210> SEQ ID NO 856
<211> LENGTH: 24
<212> TYPE: PRT
<213> ORGANISM: Homo sapiens

<400> SEQUENCE: 856

Val Ala Glu Gln Leu Ile Asn Pro Phe Gly Glu Asp Asp Asp Asp Phe
1               5                   10                  15

Glu Thr Asn Trp Ile Val Asp Arg
            20

<210> SEQ ID NO 857
<211> LENGTH: 12
<212> TYPE: PRT
<213> ORGANISM: Homo sapiens

<400> SEQUENCE: 857

Gly Pro Gln Gly Gln Asp Leu Ser Thr Asp Ser Arg
1               5                   10

<210> SEQ ID NO 858
<211> LENGTH: 13
<212> TYPE: PRT
<213> ORGANISM: Homo sapiens

<400> SEQUENCE: 858

Leu Pro Gly Ala Tyr Phe Phe Ser Phe Thr Leu Gly Lys
1               5                   10

<210> SEQ ID NO 859
<211> LENGTH: 17
<212> TYPE: PRT
<213> ORGANISM: Homo sapiens

<400> SEQUENCE: 859

Val Tyr Val Asn Ile Gly Gly Asp Phe Asp Val Ala Thr Gly Gln Phe
1               5                   10                  15
```

Arg

<210> SEQ ID NO 860
<211> LENGTH: 17
<212> TYPE: PRT
<213> ORGANISM: Homo sapiens

<400> SEQUENCE: 860

Gly Ser Asp Gly Ser Thr Ser Ser Asp Thr Thr Ser Asn Ser Phe Val
1               5                   10                  15

Arg

<210> SEQ ID NO 861
<211> LENGTH: 12
<212> TYPE: PRT
<213> ORGANISM: Homo sapiens

<400> SEQUENCE: 861

Ser Ser Leu Ala Glu Val Gln Ser Glu Ile Glu Arg
1               5                   10

<210> SEQ ID NO 862
<211> LENGTH: 11
<212> TYPE: PRT
<213> ORGANISM: Homo sapiens

<400> SEQUENCE: 862

Thr Ser Leu Ala Pro Ile Ile Val Tyr Val Lys
1               5                   10

<210> SEQ ID NO 863
<211> LENGTH: 12
<212> TYPE: PRT
<213> ORGANISM: Homo sapiens

<400> SEQUENCE: 863

Phe Phe Thr Ile Asn Pro Glu Asp Gly Phe Ile Lys
1               5                   10

<210> SEQ ID NO 864
<211> LENGTH: 14
<212> TYPE: PRT
<213> ORGANISM: Homo sapiens

<400> SEQUENCE: 864

Val Thr Ile Thr Leu Thr Asp Val Asn Asp Asn Pro Pro Lys
1               5                   10

<210> SEQ ID NO 865
<211> LENGTH: 13
<212> TYPE: PRT
<213> ORGANISM: Homo sapiens

<400> SEQUENCE: 865

Glu Leu Gln Asp Glu Tyr Trp Val Ile Ile Gln Ala Lys
1               5                   10

<210> SEQ ID NO 866
<211> LENGTH: 15
<212> TYPE: PRT
<213> ORGANISM: Homo sapiens

<400> SEQUENCE: 866

```
Leu Leu Gly Ala Gly Ala Gly Ser Thr Phe Ile Ile Asp Glu Arg
1               5                   10                  15

<210> SEQ ID NO 867
<211> LENGTH: 11
<212> TYPE: PRT
<213> ORGANISM: Homo sapiens

<400> SEQUENCE: 867

Asp Glu Ser Ser Ser Gly Gly Asp Val Phe Lys
1               5                   10

<210> SEQ ID NO 868
<211> LENGTH: 18
<212> TYPE: PRT
<213> ORGANISM: Homo sapiens

<400> SEQUENCE: 868

His Ser Leu Pro Gln Gly Pro Pro Ser Pro Glu Pro Asp Phe Ser Val
1               5                   10                  15

Phe Arg

<210> SEQ ID NO 869
<211> LENGTH: 9
<212> TYPE: PRT
<213> ORGANISM: Homo sapiens

<400> SEQUENCE: 869

Gln Asp Gly Ala Leu Gly Ala Gly Arg
1               5

<210> SEQ ID NO 870
<211> LENGTH: 15
<212> TYPE: PRT
<213> ORGANISM: Homo sapiens

<400> SEQUENCE: 870

Leu Thr Val Thr Asp Leu Asp Ala Pro Asn Ser Pro Ala Trp Arg
1               5                   10                  15

<210> SEQ ID NO 871
<211> LENGTH: 16
<212> TYPE: PRT
<213> ORGANISM: Homo sapiens

<400> SEQUENCE: 871

Tyr Glu Ala His Val Pro Glu Asn Ala Val Gly His Glu Val Gln Arg
1               5                   10                  15

<210> SEQ ID NO 872
<211> LENGTH: 13
<212> TYPE: PRT
<213> ORGANISM: Homo sapiens

<400> SEQUENCE: 872

Val Asp Ala Glu Thr Gly Asp Val Phe Ala Ile Glu Arg
1               5                   10

<210> SEQ ID NO 873
<211> LENGTH: 19
<212> TYPE: PRT
<213> ORGANISM: Homo sapiens

<400> SEQUENCE: 873
```

```
Val Gly Thr Ser Val Gly Ser Leu Phe Val Glu Asp Pro Asp Glu Pro
1               5                   10                  15

Gln Asn Arg

<210> SEQ ID NO 874
<211> LENGTH: 10
<212> TYPE: PRT
<213> ORGANISM: Homo sapiens

<400> SEQUENCE: 874

Asp Gln Tyr Leu Leu Val Ile Gln Ala Lys
1               5                   10

<210> SEQ ID NO 875
<211> LENGTH: 11
<212> TYPE: PRT
<213> ORGANISM: Homo sapiens

<400> SEQUENCE: 875

Ile Val Asp Gly Asp Gly Leu Gly Ile Phe Lys
1               5                   10

<210> SEQ ID NO 876
<211> LENGTH: 15
<212> TYPE: PRT
<213> ORGANISM: Homo sapiens

<400> SEQUENCE: 876

Tyr Phe Asn Ile Asp Ala Asn Ser Gly Val Ile Thr Thr Ala Lys
1               5                   10                  15

<210> SEQ ID NO 877
<211> LENGTH: 17
<212> TYPE: PRT
<213> ORGANISM: Homo sapiens

<400> SEQUENCE: 877

Ala Ala Asp Thr Asp Gly Asp Gly Gln Val Asn Tyr Glu Glu Phe Val
1               5                   10                  15

Arg

<210> SEQ ID NO 878
<211> LENGTH: 9
<212> TYPE: PRT
<213> ORGANISM: Homo sapiens

<400> SEQUENCE: 878

Asp Thr Asp Asn Glu Glu Glu Ile Arg
1               5

<210> SEQ ID NO 879
<211> LENGTH: 12
<212> TYPE: PRT
<213> ORGANISM: Homo sapiens

<400> SEQUENCE: 879

Ser Leu Gly Gln Asn Pro Thr Glu Ala Glu Leu Arg
1               5                   10

<210> SEQ ID NO 880
<211> LENGTH: 13
<212> TYPE: PRT
<213> ORGANISM: Homo sapiens
```

```
<400> SEQUENCE: 880

Gly Glu Glu Ala Ala Gly Tyr Ala Gln Glu Ser Gln Arg
1               5                   10

<210> SEQ ID NO 881
<211> LENGTH: 10
<212> TYPE: PRT
<213> ORGANISM: Homo sapiens

<400> SEQUENCE: 881

Ile Val Ile Ser Asp Phe His Leu Ala Lys
1               5                   10

<210> SEQ ID NO 882
<211> LENGTH: 11
<212> TYPE: PRT
<213> ORGANISM: Homo sapiens

<400> SEQUENCE: 882

Asp Ile Leu Glu Gln Ser Leu Asp Glu Ala Arg
1               5                   10

<210> SEQ ID NO 883
<211> LENGTH: 11
<212> TYPE: PRT
<213> ORGANISM: Homo sapiens

<400> SEQUENCE: 883

Gln Leu Gln Ala Glu Pro Pro Gly Val Leu Lys
1               5                   10

<210> SEQ ID NO 884
<211> LENGTH: 10
<212> TYPE: PRT
<213> ORGANISM: Homo sapiens

<400> SEQUENCE: 884

Val Ser Thr Leu Pro Ala Ile Thr Leu Lys
1               5                   10

<210> SEQ ID NO 885
<211> LENGTH: 7
<212> TYPE: PRT
<213> ORGANISM: Homo sapiens

<400> SEQUENCE: 885

Tyr Tyr Thr Val Phe Asp Arg
1               5

<210> SEQ ID NO 886
<211> LENGTH: 8
<212> TYPE: PRT
<213> ORGANISM: Homo sapiens

<400> SEQUENCE: 886

Glu Ala Asn Ala Thr Glu Trp Lys
1               5

<210> SEQ ID NO 887
<211> LENGTH: 7
<212> TYPE: PRT
<213> ORGANISM: Homo sapiens

<400> SEQUENCE: 887
```

Glu Asn Glu Phe Asp Pro Lys
1               5

<210> SEQ ID NO 888
<211> LENGTH: 14
<212> TYPE: PRT
<213> ORGANISM: Homo sapiens

<400> SEQUENCE: 888

Ile Tyr Gly Ala Asp Ser Ser Ala Asp Ser Gly Thr Ile Lys
1               5                   10

<210> SEQ ID NO 889
<211> LENGTH: 12
<212> TYPE: PRT
<213> ORGANISM: Homo sapiens

<400> SEQUENCE: 889

Asp Ala Val Ala Glu Val Ala Glu Gly Asn Gly Lys
1               5                   10

<210> SEQ ID NO 890
<211> LENGTH: 16
<212> TYPE: PRT
<213> ORGANISM: Homo sapiens

<400> SEQUENCE: 890

Gly Asn Phe Pro Ala Thr Ala Trp Gly Gly Thr Gly Thr Val Ser Arg
1               5                   10                  15

<210> SEQ ID NO 891
<211> LENGTH: 14
<212> TYPE: PRT
<213> ORGANISM: Homo sapiens

<400> SEQUENCE: 891

Asn Phe Pro Asp Leu Asn Thr Tyr Ile Tyr Tyr Asn Glu Lys
1               5                   10

<210> SEQ ID NO 892
<211> LENGTH: 10
<212> TYPE: PRT
<213> ORGANISM: Homo sapiens

<400> SEQUENCE: 892

Asn Asn Ala Asn Gly Val Asp Leu Asn Arg
1               5                   10

<210> SEQ ID NO 893
<211> LENGTH: 15
<212> TYPE: PRT
<213> ORGANISM: Homo sapiens

<400> SEQUENCE: 893

Tyr Gly Gly Pro Asn His His Leu Pro Leu Pro Asp Asn Trp Lys
1               5                   10                  15

<210> SEQ ID NO 894
<211> LENGTH: 14
<212> TYPE: PRT
<213> ORGANISM: Homo sapiens

<400> SEQUENCE: 894

Asp Asp Ala Gln Tyr Ser His Leu Gly Gly Asn Trp Ala Arg
1               5                   10

<210> SEQ ID NO 895
<211> LENGTH: 9
<212> TYPE: PRT
<213> ORGANISM: Homo sapiens

<400> SEQUENCE: 895

Glu Ser Thr Val Gln Val His Tyr Arg
1               5

<210> SEQ ID NO 896
<211> LENGTH: 9
<212> TYPE: PRT
<213> ORGANISM: Homo sapiens

<400> SEQUENCE: 896

Ile Pro Ile Glu Glu Leu Glu Asp Arg
1               5

<210> SEQ ID NO 897
<211> LENGTH: 9
<212> TYPE: PRT
<213> ORGANISM: Homo sapiens

<400> SEQUENCE: 897

Ala Val Thr Ser Pro Ala Val Gly Arg
1               5

<210> SEQ ID NO 898
<211> LENGTH: 9
<212> TYPE: PRT
<213> ORGANISM: Homo sapiens

<400> SEQUENCE: 898

Ser Glu Gln Pro Thr Ala Ser Trp Arg
1               5

<210> SEQ ID NO 899
<211> LENGTH: 13
<212> TYPE: PRT
<213> ORGANISM: Homo sapiens

<400> SEQUENCE: 899

Tyr Leu Gln Val Ser Gln Gln Leu Gln Gln Thr Asn Arg
1               5                   10

<210> SEQ ID NO 900
<211> LENGTH: 7
<212> TYPE: PRT
<213> ORGANISM: Homo sapiens

<400> SEQUENCE: 900

Leu Pro Val Val Asp Tyr Lys
1               5

<210> SEQ ID NO 901
<211> LENGTH: 23
<212> TYPE: PRT
<213> ORGANISM: Homo sapiens

<400> SEQUENCE: 901

Ser Ala Gln Leu Gly Asp Ala Val Gln Leu Ala Ser Leu Pro Pro Ala
1               5                   10                  15

Gly Asp Ile Leu Pro Asn Lys

<210> SEQ ID NO 902
<211> LENGTH: 15
<212> TYPE: PRT
<213> ORGANISM: Homo sapiens

<400> SEQUENCE: 902

Val Ser Ala Phe Ile Asp Trp Ile Glu Glu Thr Ile Ala Ser His
1               5                   10                  15

<210> SEQ ID NO 903
<211> LENGTH: 22
<212> TYPE: PRT
<213> ORGANISM: Homo sapiens

<400> SEQUENCE: 903

Val Val Asn Gly Glu Asp Ala Val Pro Tyr Ser Trp Pro Trp Gln Val
1               5                   10                  15

Ser Leu Gln Tyr Glu Lys
            20

<210> SEQ ID NO 904
<211> LENGTH: 10
<212> TYPE: PRT
<213> ORGANISM: Homo sapiens

<400> SEQUENCE: 904

Ile Tyr His Ser His Ile Asp Ala Pro Lys
1               5                   10

<210> SEQ ID NO 905
<211> LENGTH: 16
<212> TYPE: PRT
<213> ORGANISM: Homo sapiens

<400> SEQUENCE: 905

Asn Asn Glu Gly Thr Tyr Tyr Ser Pro Asn Tyr Asn Pro Gln Ser Arg
1               5                   10                  15

<210> SEQ ID NO 906
<211> LENGTH: 15
<212> TYPE: PRT
<213> ORGANISM: Homo sapiens

<400> SEQUENCE: 906

Gly Val Ser Leu Phe Asp Ile Ile Asn Pro Glu Ile Ile Thr Arg
1               5                   10                  15

<210> SEQ ID NO 907
<211> LENGTH: 15
<212> TYPE: PRT
<213> ORGANISM: Homo sapiens

<400> SEQUENCE: 907

Ile Thr Lys Pro Ala Leu Leu Val Leu Asn His Glu Thr Ala Lys
1               5                   10                  15

<210> SEQ ID NO 908
<211> LENGTH: 24
<212> TYPE: PRT
<213> ORGANISM: Homo sapiens

<400> SEQUENCE: 908

Tyr Gly Leu His Asn Ile Gln Ile Ser His Leu Ser Ile Ala Ser Ser
1               5                   10                  15

Gln Val Glu Leu Val Glu Ala Lys
            20

<210> SEQ ID NO 909
<211> LENGTH: 9
<212> TYPE: PRT
<213> ORGANISM: Homo sapiens

<400> SEQUENCE: 909

Glu Tyr Phe Gly Ile Val Ser Val Arg
1               5

<210> SEQ ID NO 910
<211> LENGTH: 10
<212> TYPE: PRT
<213> ORGANISM: Homo sapiens

<400> SEQUENCE: 910

Asp Ala Gln Tyr Ala Pro Gly Tyr Asp Lys
1               5                   10

<210> SEQ ID NO 911
<211> LENGTH: 14
<212> TYPE: PRT
<213> ORGANISM: Homo sapiens

<400> SEQUENCE: 911

Asp Phe His Ile Asn Leu Phe Gln Val Leu Pro Trp Leu Lys
1               5                   10

<210> SEQ ID NO 912
<211> LENGTH: 14
<212> TYPE: PRT
<213> ORGANISM: Homo sapiens

<400> SEQUENCE: 912

Val Ser Glu Ala Asp Ser Ser Asn Ala Asp Trp Val Thr Lys
1               5                   10

<210> SEQ ID NO 913
<211> LENGTH: 12
<212> TYPE: PRT
<213> ORGANISM: Homo sapiens

<400> SEQUENCE: 913

Ser Ser Asn Leu Ile Ile Leu Glu Glu His Leu Lys
1               5                   10

<210> SEQ ID NO 914
<211> LENGTH: 11
<212> TYPE: PRT
<213> ORGANISM: Homo sapiens

<400> SEQUENCE: 914

Ser Ser Gln Glu Ser Tyr Ala His Gly Thr Lys
1               5                   10

<210> SEQ ID NO 915
<211> LENGTH: 19
<212> TYPE: PRT
<213> ORGANISM: Homo sapiens

<400> SEQUENCE: 915

Ala Gly Ala Phe Asp Asp Leu Thr Glu Leu Thr Tyr Leu Tyr Leu Asp
1               5                   10                  15

His Asn Lys

<210> SEQ ID NO 916
<211> LENGTH: 13
<212> TYPE: PRT
<213> ORGANISM: Homo sapiens

<400> SEQUENCE: 916

Phe Ser Asp Gly Ala Phe Leu Gly Val Thr Thr Leu Lys
1               5                   10

<210> SEQ ID NO 917
<211> LENGTH: 20
<212> TYPE: PRT
<213> ORGANISM: Homo sapiens

<400> SEQUENCE: 917

Ala Glu Asn Thr Asp Ala Val Leu Pro Ala Ala Ser Ala Ala Val Val
1               5                   10                  15

Thr Thr Gly Lys
            20

<210> SEQ ID NO 918
<211> LENGTH: 15
<212> TYPE: PRT
<213> ORGANISM: Homo sapiens

<400> SEQUENCE: 918

Asp Phe Gln Thr Ala Glu Val Ala Tyr Tyr Ser Pro Thr Thr Arg
1               5                   10                  15

<210> SEQ ID NO 919
<211> LENGTH: 14
<212> TYPE: PRT
<213> ORGANISM: Homo sapiens

<400> SEQUENCE: 919

Ser Gln Glu Ser Ser Ala Val Leu Asn Gly Glu Val Asn Lys
1               5                   10

<210> SEQ ID NO 920
<211> LENGTH: 12
<212> TYPE: PRT
<213> ORGANISM: Homo sapiens

<400> SEQUENCE: 920

Gln Gln Gln Ile Tyr Gln Glu Leu Thr Asp Leu Lys
1               5                   10

<210> SEQ ID NO 921
<211> LENGTH: 14
<212> TYPE: PRT
<213> ORGANISM: Homo sapiens

<400> SEQUENCE: 921

Thr Ala Glu Glu Gln Asn Phe Leu Gln Leu Gln Thr Ser Arg
1               5                   10

<210> SEQ ID NO 922
<211> LENGTH: 17
<212> TYPE: PRT

-continued

```
<213> ORGANISM: Homo sapiens

<400> SEQUENCE: 922

Val Gln Gln Leu Gly Leu Leu Glu Glu Asp Pro Thr Thr Ser Gly Ile
1               5                   10                  15

Arg

<210> SEQ ID NO 923
<211> LENGTH: 9
<212> TYPE: PRT
<213> ORGANISM: Homo sapiens

<400> SEQUENCE: 923

Ile Asp Ser Leu Leu Glu Asn Asp Arg
1               5

<210> SEQ ID NO 924
<211> LENGTH: 23
<212> TYPE: PRT
<213> ORGANISM: Homo sapiens

<400> SEQUENCE: 924

Val Thr Thr Val Ala Ser His Thr Ser Asp Ser Asp Val Pro Ser Gly
1               5                   10                  15

Val Thr Glu Val Val Val Lys
            20

<210> SEQ ID NO 925
<211> LENGTH: 9
<212> TYPE: PRT
<213> ORGANISM: Homo sapiens

<400> SEQUENCE: 925

His Ser Ile Glu Val Pro Ile Pro Arg
1               5

<210> SEQ ID NO 926
<211> LENGTH: 14
<212> TYPE: PRT
<213> ORGANISM: Homo sapiens

<400> SEQUENCE: 926

Thr Thr Lys Pro Tyr Pro Ala Asp Ile Val Val Gln Phe Lys
1               5                   10

<210> SEQ ID NO 927
<211> LENGTH: 17
<212> TYPE: PRT
<213> ORGANISM: Homo sapiens

<400> SEQUENCE: 927

Thr Thr Gly Pro Gly Gly Asp Gly Ile Pro Ala Glu Val His Ile Val
1               5                   10                  15

Arg

<210> SEQ ID NO 928
<211> LENGTH: 9
<212> TYPE: PRT
<213> ORGANISM: Homo sapiens

<400> SEQUENCE: 928

Asp Tyr Glu Val Asp Ala Thr Leu Lys
1               5
```

-continued

<210> SEQ ID NO 929
<211> LENGTH: 9
<212> TYPE: PRT
<213> ORGANISM: Homo sapiens

<400> SEQUENCE: 929

Gly Pro Ser Gly Pro Gln Gly Ile Arg
1               5

<210> SEQ ID NO 930
<211> LENGTH: 10
<212> TYPE: PRT
<213> ORGANISM: Homo sapiens

<400> SEQUENCE: 930

His Ala Ile Ile Leu Leu Thr Asp Gly Lys
1               5                   10

<210> SEQ ID NO 931
<211> LENGTH: 6
<212> TYPE: PRT
<213> ORGANISM: Homo sapiens

<400> SEQUENCE: 931

Leu Asp Val Asp Trp Arg
1               5

<210> SEQ ID NO 932
<211> LENGTH: 10
<212> TYPE: PRT
<213> ORGANISM: Homo sapiens

<400> SEQUENCE: 932

Thr Pro Trp His Val Thr Ile Lys Pro Lys
1               5                   10

<210> SEQ ID NO 933
<211> LENGTH: 24
<212> TYPE: PRT
<213> ORGANISM: Homo sapiens

<400> SEQUENCE: 933

Asp Tyr Ala Gly Val Phe Ser Asp Ala Gly Leu Thr Phe Thr Ser Ser
1               5                   10                  15

Ser Gly Gln Gln Thr Ala Gln Arg
            20

<210> SEQ ID NO 934
<211> LENGTH: 16
<212> TYPE: PRT
<213> ORGANISM: Homo sapiens

<400> SEQUENCE: 934

Ser Asn Leu Asp Glu Asp Ile Ile Ala Glu Glu Asn Ile Val Ser Arg
1               5                   10                  15

<210> SEQ ID NO 935
<211> LENGTH: 22
<212> TYPE: PRT
<213> ORGANISM: Homo sapiens

<400> SEQUENCE: 935

Val Pro Val Ala Val Gln Gly Glu Asp Thr Val Gln Ser Leu Thr Gln

```
1               5                   10                  15
Gly Asp Gly Val Ala Lys
            20

<210> SEQ ID NO 936
<211> LENGTH: 26
<212> TYPE: PRT
<213> ORGANISM: Homo sapiens

<400> SEQUENCE: 936

Leu Leu Leu Phe Ser Pro Ser Val Val His Leu Gly Val Pro Leu Ser
1               5                   10                  15

Val Gly Val Gln Leu Gln Asp Val Pro Arg
            20                  25

<210> SEQ ID NO 937
<211> LENGTH: 15
<212> TYPE: PRT
<213> ORGANISM: Homo sapiens

<400> SEQUENCE: 937

Val Leu Ser Leu Ala Gln Glu Gln Val Gly Gly Ser Pro Glu Lys
1               5                   10                  15

<210> SEQ ID NO 938
<211> LENGTH: 18
<212> TYPE: PRT
<213> ORGANISM: Homo sapiens

<400> SEQUENCE: 938

Ala Gly Pro Val Gly Pro Pro Gly Leu Gly Phe Pro Gly Pro Pro Gly
1               5                   10                  15

Glu Arg

<210> SEQ ID NO 939
<211> LENGTH: 20
<212> TYPE: PRT
<213> ORGANISM: Homo sapiens

<400> SEQUENCE: 939

Asp Ile Pro Asp Pro Gly Pro Pro Gly Asp Gln Gly Pro Pro Gly Pro
1               5                   10                  15

Asp Gly Pro Arg
            20

<210> SEQ ID NO 940
<211> LENGTH: 15
<212> TYPE: PRT
<213> ORGANISM: Homo sapiens

<400> SEQUENCE: 940

Leu Trp Thr Gly Tyr Ser Leu Leu Tyr Leu Glu Gly Gln Glu Lys
1               5                   10                  15

<210> SEQ ID NO 941
<211> LENGTH: 15
<212> TYPE: PRT
<213> ORGANISM: Homo sapiens

<400> SEQUENCE: 941

Val Leu Ser Leu Ala Gln Glu Gln Val Gly Gly Ser Pro Glu Lys
1               5                   10                  15
```

<210> SEQ ID NO 942
<211> LENGTH: 23
<212> TYPE: PRT
<213> ORGANISM: Homo sapiens

<400> SEQUENCE: 942

Tyr Val Ser His Phe Glu Thr Glu Gly Pro His Val Leu Leu Tyr Phe
1               5                   10                  15

Asp Ser Val Pro Thr Ser Arg
            20

<210> SEQ ID NO 943
<211> LENGTH: 10
<212> TYPE: PRT
<213> ORGANISM: Homo sapiens

<400> SEQUENCE: 943

Asp Leu His Leu Ser Asp Val Phe Leu Lys
1               5                   10

<210> SEQ ID NO 944
<211> LENGTH: 11
<212> TYPE: PRT
<213> ORGANISM: Homo sapiens

<400> SEQUENCE: 944

Ser Glu Tyr Gly Ala Ala Leu Ala Trp Glu Lys
1               5                   10

<210> SEQ ID NO 945
<211> LENGTH: 20
<212> TYPE: PRT
<213> ORGANISM: Homo sapiens

<400> SEQUENCE: 945

Val Pro Ala Asn Leu Glu Asn Val Gly Phe Glu Val Gln Thr Ala Glu
1               5                   10                  15

Asp Asp Leu Lys
            20

<210> SEQ ID NO 946
<211> LENGTH: 14
<212> TYPE: PRT
<213> ORGANISM: Homo sapiens

<400> SEQUENCE: 946

Gly Gly Ser Ser Gly Trp Ser Gly Gly Leu Ala Gln Asn Arg
1               5                   10

<210> SEQ ID NO 947
<211> LENGTH: 25
<212> TYPE: PRT
<213> ORGANISM: Homo sapiens

<400> SEQUENCE: 947

Tyr His Phe Glu Ala Leu Ala Asp Thr Gly Ile Ser Ser Glu Phe Tyr
1               5                   10                  15

Asp Asn Ala Asn Asp Leu Leu Ser Lys
            20                  25

<210> SEQ ID NO 948
<211> LENGTH: 13
<212> TYPE: PRT

<213> ORGANISM: Homo sapiens

<400> SEQUENCE: 948

Asp Ala Thr Asp Gln His Ile Val Asp Val Ala Leu Lys
1               5                   10

<210> SEQ ID NO 949
<211> LENGTH: 18
<212> TYPE: PRT
<213> ORGANISM: Homo sapiens

<400> SEQUENCE: 949

Gly Val Pro Gly Ile Val Gly Ala Val Gly Gln Ile Gly Asn Thr Gly
1               5                   10                  15

Pro Lys

<210> SEQ ID NO 950
<211> LENGTH: 17
<212> TYPE: PRT
<213> ORGANISM: Homo sapiens

<400> SEQUENCE: 950

Thr Glu Ala Pro Ser Ala Thr Gly Gln Ala Ser Ser Leu Leu Gly Gly
1               5                   10                  15

Arg

<210> SEQ ID NO 951
<211> LENGTH: 12
<212> TYPE: PRT
<213> ORGANISM: Homo sapiens

<400> SEQUENCE: 951

Leu Leu Glu Glu Glu Thr Leu Ile Asp Gly Val Arg
1               5                   10

<210> SEQ ID NO 952
<211> LENGTH: 10
<212> TYPE: PRT
<213> ORGANISM: Homo sapiens

<400> SEQUENCE: 952

Leu Tyr Pro Pro Ala Trp Gly Thr Phe Arg
1               5                   10

<210> SEQ ID NO 953
<211> LENGTH: 18
<212> TYPE: PRT
<213> ORGANISM: Homo sapiens

<400> SEQUENCE: 953

Val Leu Asn Ala Ser Thr Leu Ala Leu Ala Leu Ala Asn Leu Asn Gly
1               5                   10                  15

Ser Arg

<210> SEQ ID NO 954
<211> LENGTH: 11
<212> TYPE: PRT
<213> ORGANISM: Homo sapiens

<400> SEQUENCE: 954

Gln Glu Thr Glu Leu Asn Gly Gly Phe Phe Lys
1               5                   10

<210> SEQ ID NO 955
<211> LENGTH: 9
<212> TYPE: PRT
<213> ORGANISM: Homo sapiens

<400> SEQUENCE: 955

Asp Pro Pro Glu Pro Gly Ser Pro Arg
1               5

<210> SEQ ID NO 956
<211> LENGTH: 12
<212> TYPE: PRT
<213> ORGANISM: Homo sapiens

<400> SEQUENCE: 956

Thr Phe Tyr Glu Thr Pro Leu Gln Leu Leu Glu Lys
1               5                   10

<210> SEQ ID NO 957
<211> LENGTH: 10
<212> TYPE: PRT
<213> ORGANISM: Homo sapiens

<400> SEQUENCE: 957

Asp Tyr Thr Asn Leu Pro Ser Ser Ser Arg
1               5                   10

<210> SEQ ID NO 958
<211> LENGTH: 13
<212> TYPE: PRT
<213> ORGANISM: Homo sapiens

<400> SEQUENCE: 958

Leu Ala Ile Pro Gln Gln Ser Asp Phe His Asn Asn Arg
1               5                   10

<210> SEQ ID NO 959
<211> LENGTH: 11
<212> TYPE: PRT
<213> ORGANISM: Homo sapiens

<400> SEQUENCE: 959

Asn Val Leu Leu Thr Asn Gly His Val Ala Lys
1               5                   10

<210> SEQ ID NO 960
<211> LENGTH: 10
<212> TYPE: PRT
<213> ORGANISM: Homo sapiens

<400> SEQUENCE: 960

Leu Leu Gln Ser Ala Thr Glu Ala Gln Arg
1               5                   10

<210> SEQ ID NO 961
<211> LENGTH: 12
<212> TYPE: PRT
<213> ORGANISM: Homo sapiens

<400> SEQUENCE: 961

Glu Leu Leu Leu Asn Thr Ser Glu Val Thr Val Arg
1               5                   10

<210> SEQ ID NO 962

```
<211> LENGTH: 28
<212> TYPE: PRT
<213> ORGANISM: Homo sapiens

<400> SEQUENCE: 962

Ala Gly Lys Pro Gly Leu Pro Ala Pro Asp Glu Leu Val Tyr Gln Val
1               5                   10                  15

Pro Gln Ser Thr Gln Glu Val Ser Gly Ala Gly Arg
            20                  25

<210> SEQ ID NO 963
<211> LENGTH: 19
<212> TYPE: PRT
<213> ORGANISM: Homo sapiens

<400> SEQUENCE: 963

Ala Thr Gly Asn Gln Pro Pro Pro Leu Val Gly Thr Tyr Asn Thr Leu
1               5                   10                  15

Leu Ser Arg

<210> SEQ ID NO 964
<211> LENGTH: 15
<212> TYPE: PRT
<213> ORGANISM: Homo sapiens

<400> SEQUENCE: 964

Gln Val Leu Asp Gly Asn Ser Asn Pro Tyr Asp Ile Phe Leu Lys
1               5                   10                  15

<210> SEQ ID NO 965
<211> LENGTH: 15
<212> TYPE: PRT
<213> ORGANISM: Homo sapiens

<400> SEQUENCE: 965

Ser Ser Ser Pro Ser Glu Gln Gly Ser Asn Ser Thr Tyr Asp Arg
1               5                   10                  15

<210> SEQ ID NO 966
<211> LENGTH: 12
<212> TYPE: PRT
<213> ORGANISM: Homo sapiens

<400> SEQUENCE: 966

Glu Val Gln Ser Ser Glu Ala Glu Ala Leu Ala Arg
1               5                   10

<210> SEQ ID NO 967
<211> LENGTH: 6
<212> TYPE: PRT
<213> ORGANISM: Homo sapiens

<400> SEQUENCE: 967

Leu Asn His Asn Val Lys
1               5

<210> SEQ ID NO 968
<211> LENGTH: 13
<212> TYPE: PRT
<213> ORGANISM: Homo sapiens

<400> SEQUENCE: 968

Ala Val Leu Glu Gln Glu Glu Thr Ala Ala Ala Ser Arg
1               5                   10
```

<210> SEQ ID NO 969
<211> LENGTH: 10
<212> TYPE: PRT
<213> ORGANISM: Homo sapiens

<400> SEQUENCE: 969

Glu Val Pro Val Val His Thr Glu Thr Lys
1               5                   10

<210> SEQ ID NO 970
<211> LENGTH: 21
<212> TYPE: PRT
<213> ORGANISM: Homo sapiens

<400> SEQUENCE: 970

Thr Glu Ser Ser Gly Ile Glu Thr Glu Pro Thr Val His His Leu Pro
1               5                   10                  15

Leu Ser Thr Glu Lys
            20

<210> SEQ ID NO 971
<211> LENGTH: 11
<212> TYPE: PRT
<213> ORGANISM: Homo sapiens

<400> SEQUENCE: 971

Ser Glu Leu Asp Thr Ile Asp Ser Gln His Arg
1               5                   10

<210> SEQ ID NO 972
<211> LENGTH: 10
<212> TYPE: PRT
<213> ORGANISM: Homo sapiens

<400> SEQUENCE: 972

Ala Asn Asp His Gly Tyr Asp Asn Phe Arg
1               5                   10

<210> SEQ ID NO 973
<211> LENGTH: 7
<212> TYPE: PRT
<213> ORGANISM: Homo sapiens

<400> SEQUENCE: 973

Leu Val Pro Phe Ile Gln Lys
1               5

<210> SEQ ID NO 974
<211> LENGTH: 9
<212> TYPE: PRT
<213> ORGANISM: Homo sapiens

<400> SEQUENCE: 974

Ala Ile Asn Thr Leu Asn Gly Leu Lys
1               5

<210> SEQ ID NO 975
<211> LENGTH: 11
<212> TYPE: PRT
<213> ORGANISM: Homo sapiens

<400> SEQUENCE: 975

Ile Leu Val Asp Gln Val Thr Gly Val Ser Arg

-continued

```
1               5                   10
```

<210> SEQ ID NO 976
<211> LENGTH: 21
<212> TYPE: PRT
<213> ORGANISM: Homo sapiens

<400> SEQUENCE: 976

```
Ile Thr Gly Gln Ser Leu Gly Tyr Gly Phe Val Asn Tyr Ser Asp Pro
1               5                   10                  15

Asn Asp Ala Asp Lys
            20
```

<210> SEQ ID NO 977
<211> LENGTH: 31
<212> TYPE: PRT
<213> ORGANISM: Homo sapiens

<400> SEQUENCE: 977

```
Ala Pro Gly Leu Ser Ser Gln His Pro Lys Pro Asp Thr Thr Val Ser
1               5                   10                  15

Gly Asp Thr Glu Thr Gly Gln Ser Pro Gly Val Phe Asn Thr Lys
            20                  25                  30
```

<210> SEQ ID NO 978
<211> LENGTH: 11
<212> TYPE: PRT
<213> ORGANISM: Homo sapiens

<400> SEQUENCE: 978

```
Gly Ala Ile Asn Gly Glu Val Gly Asp Leu Lys
1               5                   10
```

<210> SEQ ID NO 979
<211> LENGTH: 17
<212> TYPE: PRT
<213> ORGANISM: Homo sapiens

<400> SEQUENCE: 979

```
Thr Val Leu Asp Leu Gln Ser Ser Leu Ala Gly Val Ser Glu Asn Leu
1               5                   10                  15

Lys
```

<210> SEQ ID NO 980
<211> LENGTH: 11
<212> TYPE: PRT
<213> ORGANISM: Homo sapiens

<400> SEQUENCE: 980

```
Tyr Ser Leu Tyr Thr Thr Gly Trp Arg Pro Arg
1               5                   10
```

<210> SEQ ID NO 981
<211> LENGTH: 13
<212> TYPE: PRT
<213> ORGANISM: Homo sapiens

<400> SEQUENCE: 981

```
Phe Ser Gln Ile Val Ser Val Leu Asp Ala Leu Ile Arg
1               5                   10
```

<210> SEQ ID NO 982
<211> LENGTH: 19

```
<212> TYPE: PRT
<213> ORGANISM: Homo sapiens

<400> SEQUENCE: 982

Gly Gly Ser Gly Gly Gly Gly Leu Thr Val Gly Asp Trp Leu Asp
1               5                   10                  15

Ser Ile Arg

<210> SEQ ID NO 983
<211> LENGTH: 16
<212> TYPE: PRT
<213> ORGANISM: Homo sapiens

<400> SEQUENCE: 983

Val Leu Glu Asp Asp Pro Asp Ala Ala Tyr Thr Thr Thr Gly Gly Lys
1               5                   10                  15

<210> SEQ ID NO 984
<211> LENGTH: 10
<212> TYPE: PRT
<213> ORGANISM: Homo sapiens

<400> SEQUENCE: 984

Ala Asp Ala Glu Tyr Tyr Ala Ala His Lys
1               5                   10

<210> SEQ ID NO 985
<211> LENGTH: 11
<212> TYPE: PRT
<213> ORGANISM: Homo sapiens

<400> SEQUENCE: 985

Ile Glu Glu Gly His Leu Ala Val Tyr Tyr Arg
1               5                   10

<210> SEQ ID NO 986
<211> LENGTH: 12
<212> TYPE: PRT
<213> ORGANISM: Homo sapiens

<400> SEQUENCE: 986

Ser Val Gln Thr Thr Leu Gln Thr Asp Glu Val Lys
1               5                   10

<210> SEQ ID NO 987
<211> LENGTH: 7
<212> TYPE: PRT
<213> ORGANISM: Homo sapiens

<400> SEQUENCE: 987

Glu Gly His Gln Trp Glu Lys
1               5

<210> SEQ ID NO 988
<211> LENGTH: 16
<212> TYPE: PRT
<213> ORGANISM: Homo sapiens

<400> SEQUENCE: 988

Ile Ser Glu Glu Leu Thr Asp Val Asp Ser Pro Leu Pro His Tyr Arg
1               5                   10                  15

<210> SEQ ID NO 989
<211> LENGTH: 11
```

```
<212> TYPE: PRT
<213> ORGANISM: Homo sapiens

<400> SEQUENCE: 989

Val Glu Pro Ser Leu Glu Gly Ala Leu Thr Lys
1               5                   10

<210> SEQ ID NO 990
<211> LENGTH: 17
<212> TYPE: PRT
<213> ORGANISM: Homo sapiens

<400> SEQUENCE: 990

Ser Ile Val Asp Leu Tyr Thr Gly Asn Ala Glu Glu Asp Ala Asp Thr
1               5                   10                  15
Lys

<210> SEQ ID NO 991
<211> LENGTH: 16
<212> TYPE: PRT
<213> ORGANISM: Homo sapiens

<400> SEQUENCE: 991

Ala Ala Gly Pro Gly Gly Gly Ser Leu Ala Ser Ser Ser Val Ala Lys
1               5                   10                  15

<210> SEQ ID NO 992
<211> LENGTH: 11
<212> TYPE: PRT
<213> ORGANISM: Homo sapiens

<400> SEQUENCE: 992

Glu Pro Glu Glu Pro Ser Gln Asp Ala Pro Arg
1               5                   10

<210> SEQ ID NO 993
<211> LENGTH: 13
<212> TYPE: PRT
<213> ORGANISM: Homo sapiens

<400> SEQUENCE: 993

Thr Val Pro Leu Val Asp Ser Glu Gly Gly Ser Gly Arg
1               5                   10

<210> SEQ ID NO 994
<211> LENGTH: 9
<212> TYPE: PRT
<213> ORGANISM: Homo sapiens

<400> SEQUENCE: 994

Phe Gln Glu Gly Gln Glu Glu Glu Arg
1               5

<210> SEQ ID NO 995
<211> LENGTH: 16
<212> TYPE: PRT
<213> ORGANISM: Homo sapiens

<400> SEQUENCE: 995

Asp Glu Glu Thr Pro Val Asp Phe Phe Tyr Phe Ile Asp Phe Gln Arg
1               5                   10                  15

<210> SEQ ID NO 996
<211> LENGTH: 18
```

```
<212> TYPE: PRT
<213> ORGANISM: Homo sapiens

<400> SEQUENCE: 996

Asp Ser Ala Ala Ala Ala Ser Asp Pro Gly Thr Ile Val His Asn Phe
1               5                   10                  15

Ser Arg

<210> SEQ ID NO 997
<211> LENGTH: 17
<212> TYPE: PRT
<213> ORGANISM: Homo sapiens

<400> SEQUENCE: 997

Gln Gly Thr Trp Gly Gly Asp Trp Pro Glu Ala Leu Ala Ile Ser Gln
1               5                   10                  15

Arg

<210> SEQ ID NO 998
<211> LENGTH: 10
<212> TYPE: PRT
<213> ORGANISM: Homo sapiens

<400> SEQUENCE: 998

His Thr Leu Asn Gln Ile Asp Glu Val Lys
1               5                   10

<210> SEQ ID NO 999
<211> LENGTH: 10
<212> TYPE: PRT
<213> ORGANISM: Homo sapiens

<400> SEQUENCE: 999

Gln Thr Phe Gly Ser Ser Gly Thr Asp Lys
1               5                   10

<210> SEQ ID NO 1000
<211> LENGTH: 8
<212> TYPE: PRT
<213> ORGANISM: Homo sapiens

<400> SEQUENCE: 1000

Thr Glu Asn Leu Ala Pro Val Lys
1               5

<210> SEQ ID NO 1001
<211> LENGTH: 10
<212> TYPE: PRT
<213> ORGANISM: Homo sapiens

<400> SEQUENCE: 1001

Tyr Gly Pro Asp Gly Leu Pro Tyr Leu Lys
1               5                   10

<210> SEQ ID NO 1002
<211> LENGTH: 20
<212> TYPE: PRT
<213> ORGANISM: Homo sapiens

<400> SEQUENCE: 1002

Tyr Gln Ile Ser Gln Pro Glu Val Tyr Val Ala Ala Pro Gly Glu Ser
1               5                   10                  15

Leu Glu Val Arg
```

```
            20

<210> SEQ ID NO 1003
<211> LENGTH: 22
<212> TYPE: PRT
<213> ORGANISM: Homo sapiens

<400> SEQUENCE: 1003

Leu Ser Ser Gly Glu Gly Pro Thr Leu Ala Asn Val Ser Glu Leu Glu
1               5                   10                  15

Leu Pro Ala Asp Pro Lys
            20

<210> SEQ ID NO 1004
<211> LENGTH: 8
<212> TYPE: PRT
<213> ORGANISM: Homo sapiens

<400> SEQUENCE: 1004

Gln Leu Val Glu Asp Leu Asp Arg
1               5

<210> SEQ ID NO 1005
<211> LENGTH: 9
<212> TYPE: PRT
<213> ORGANISM: Homo sapiens

<400> SEQUENCE: 1005

Thr Ala Gly Ala Asn Thr Thr Asp Lys
1               5

<210> SEQ ID NO 1006
<211> LENGTH: 12
<212> TYPE: PRT
<213> ORGANISM: Homo sapiens

<400> SEQUENCE: 1006

Asp Tyr Glu Asn Gly Phe Gly Asn Phe Val Gln Lys
1               5                   10

<210> SEQ ID NO 1007
<211> LENGTH: 14
<212> TYPE: PRT
<213> ORGANISM: Homo sapiens

<400> SEQUENCE: 1007

Asn Leu His Phe Leu Thr Thr Gln Glu Asp Tyr Thr Leu Lys
1               5                   10

<210> SEQ ID NO 1008
<211> LENGTH: 16
<212> TYPE: PRT
<213> ORGANISM: Homo sapiens

<400> SEQUENCE: 1008

Gly Gly Ser Thr Ser Tyr Gly Thr Gly Ser Glu Thr Glu Ser Pro Arg
1               5                   10                  15

<210> SEQ ID NO 1009
<211> LENGTH: 13
<212> TYPE: PRT
<213> ORGANISM: Homo sapiens

<400> SEQUENCE: 1009
```

```
Gly Leu Ile Asp Glu Val Asn Gln Asp Phe Thr Asn Arg
1               5                   10
```

<210> SEQ ID NO 1010
<211> LENGTH: 9
<212> TYPE: PRT
<213> ORGANISM: Homo sapiens

<400> SEQUENCE: 1010

```
Val Gln His Ile Gln Leu Leu Gln Lys
1               5
```

<210> SEQ ID NO 1011
<211> LENGTH: 6
<212> TYPE: PRT
<213> ORGANISM: Homo sapiens

<400> SEQUENCE: 1011

```
Ile Ser Gln Leu Thr Arg
1               5
```

<210> SEQ ID NO 1012
<211> LENGTH: 15
<212> TYPE: PRT
<213> ORGANISM: Homo sapiens

<400> SEQUENCE: 1012

```
Ser Gln Gly Val Asn Asp Asn Glu Glu Gly Phe Phe Ser Ala Arg
1               5                   10                  15
```

<210> SEQ ID NO 1013
<211> LENGTH: 7
<212> TYPE: PRT
<213> ORGANISM: Homo sapiens

<400> SEQUENCE: 1013

```
Tyr Gln Ile Ser Val Asn Lys
1               5
```

<210> SEQ ID NO 1014
<211> LENGTH: 11
<212> TYPE: PRT
<213> ORGANISM: Homo sapiens

<400> SEQUENCE: 1014

```
Asp Thr Val Gln Ile His Asp Ile Thr Gly Lys
1               5                   10
```

<210> SEQ ID NO 1015
<211> LENGTH: 27
<212> TYPE: PRT
<213> ORGANISM: Homo sapiens

<400> SEQUENCE: 1015

```
Leu Thr Tyr Ala Tyr Phe Ala Gly Gly Asp Ala Gly Asp Ala Phe Asp
1               5                   10                  15

Gly Phe Asp Phe Gly Asp Asp Pro Ser Asp Lys
            20                  25
```

<210> SEQ ID NO 1016
<211> LENGTH: 7
<212> TYPE: PRT
<213> ORGANISM: Homo sapiens

<400> SEQUENCE: 1016

Val Gly Pro Glu Ala Asp Lys
1               5

<210> SEQ ID NO 1017
<211> LENGTH: 18
<212> TYPE: PRT
<213> ORGANISM: Homo sapiens

<400> SEQUENCE: 1017

His Thr Ser Val Gln Thr Thr Ser Ser Gly Ser Gly Pro Phe Thr Asp
1               5                   10                  15

Val Arg

<210> SEQ ID NO 1018
<211> LENGTH: 15
<212> TYPE: PRT
<213> ORGANISM: Homo sapiens

<400> SEQUENCE: 1018

Val Pro Gly Thr Ser Thr Ser Ala Thr Leu Thr Gly Leu Thr Arg
1               5                   10                  15

<210> SEQ ID NO 1019
<211> LENGTH: 28
<212> TYPE: PRT
<213> ORGANISM: Homo sapiens

<400> SEQUENCE: 1019

Val Val Thr Pro Leu Ser Pro Pro Thr Asn Leu His Leu Glu Ala Asn
1               5                   10                  15

Pro Asp Thr Gly Val Leu Thr Val Ser Trp Glu Arg
                20                  25

<210> SEQ ID NO 1020
<211> LENGTH: 18
<212> TYPE: PRT
<213> ORGANISM: Homo sapiens

<400> SEQUENCE: 1020

Thr Pro Thr Thr Pro Gly Phe Ala Ala Gln Asn Leu Pro Asn Gly Tyr
1               5                   10                  15

Pro Arg

<210> SEQ ID NO 1021
<211> LENGTH: 10
<212> TYPE: PRT
<213> ORGANISM: Homo sapiens

<400> SEQUENCE: 1021

Val Ser Asn Ala Glu Ser Ser Thr Pro Lys
1               5                   10

<210> SEQ ID NO 1022
<211> LENGTH: 14
<212> TYPE: PRT
<213> ORGANISM: Homo sapiens

<400> SEQUENCE: 1022

Tyr Pro Ser Phe Gly Asp Ala Ser Ser His Pro Ser Ser Arg
1               5                   10

<210> SEQ ID NO 1023

```
<211> LENGTH: 17
<212> TYPE: PRT
<213> ORGANISM: Homo sapiens

<400> SEQUENCE: 1023

Ser Ser Gly Gln Pro Gly Pro Pro Pro Pro Pro Pro Pro Pro Pro Ala
1               5                   10                  15

Arg

<210> SEQ ID NO 1024
<211> LENGTH: 15
<212> TYPE: PRT
<213> ORGANISM: Homo sapiens

<400> SEQUENCE: 1024

Thr Ser Thr Ser Val Thr Ser Val Asn Gln Ala Ser Thr Ser Arg
1               5                   10                  15

<210> SEQ ID NO 1025
<211> LENGTH: 25
<212> TYPE: PRT
<213> ORGANISM: Homo sapiens

<400> SEQUENCE: 1025

Ala Ala Val Gly Leu Val Trp Leu Leu Ala Ala Leu Phe Ser Ala Pro
1               5                   10                  15

Tyr Leu Ser Tyr Tyr Gly Thr Val Arg
            20                  25

<210> SEQ ID NO 1026
<211> LENGTH: 12
<212> TYPE: PRT
<213> ORGANISM: Homo sapiens

<400> SEQUENCE: 1026

Asp Gly Glu Ala Thr Leu Glu Val Asp Gly Thr Arg
1               5                   10

<210> SEQ ID NO 1027
<211> LENGTH: 13
<212> TYPE: PRT
<213> ORGANISM: Homo sapiens

<400> SEQUENCE: 1027

Gly Gln Ser Glu Val Ser Ala Ala Gln Leu Gln Glu Arg
1               5                   10

<210> SEQ ID NO 1028
<211> LENGTH: 17
<212> TYPE: PRT
<213> ORGANISM: Homo sapiens

<400> SEQUENCE: 1028

Ser Trp Asn Trp Leu Asn Gly Glu Asp Thr Thr Ile Gln Glu Thr Val
1               5                   10                  15

Lys

<210> SEQ ID NO 1029
<211> LENGTH: 12
<212> TYPE: PRT
<213> ORGANISM: Homo sapiens

<400> SEQUENCE: 1029
```

Leu Val Leu Ala Asn Ile Gln Glu Asp Glu Ala Lys
1               5                   10

<210> SEQ ID NO 1030
<211> LENGTH: 8
<212> TYPE: PRT
<213> ORGANISM: Homo sapiens

<400> SEQUENCE: 1030

Asn Asn Ile Thr Ile Phe Thr Arg
1               5

<210> SEQ ID NO 1031
<211> LENGTH: 14
<212> TYPE: PRT
<213> ORGANISM: Homo sapiens

<400> SEQUENCE: 1031

Ile Thr Ile Pro Asp Leu Thr Asp Val Asn Ala Ile Asp Arg
1               5                   10

<210> SEQ ID NO 1032
<211> LENGTH: 8
<212> TYPE: PRT
<213> ORGANISM: Homo sapiens

<400> SEQUENCE: 1032

Glu Pro Gly Leu Gln Ile Trp Arg
1               5

<210> SEQ ID NO 1033
<211> LENGTH: 24
<212> TYPE: PRT
<213> ORGANISM: Homo sapiens

<400> SEQUENCE: 1033

Phe Asp Leu Val Pro Val Pro Thr Asn Leu Tyr Gly Asp Phe Phe Thr
1               5                   10                  15

Gly Asp Ala Tyr Val Ile Leu Lys
            20

<210> SEQ ID NO 1034
<211> LENGTH: 18
<212> TYPE: PRT
<213> ORGANISM: Homo sapiens

<400> SEQUENCE: 1034

Thr Pro Ser Ala Ala Tyr Leu Trp Val Gly Thr Gly Ala Ser Glu Ala
1               5                   10                  15

Glu Lys

<210> SEQ ID NO 1035
<211> LENGTH: 11
<212> TYPE: PRT
<213> ORGANISM: Homo sapiens

<400> SEQUENCE: 1035

Gly Pro Ser Phe Gln Ala Thr Gln Ala Pro Arg
1               5                   10

<210> SEQ ID NO 1036
<211> LENGTH: 8
<212> TYPE: PRT
<213> ORGANISM: Homo sapiens

```
<400> SEQUENCE: 1036

Val Pro Ser Glu Tyr Thr Tyr Arg
1               5

<210> SEQ ID NO 1037
<211> LENGTH: 15
<212> TYPE: PRT
<213> ORGANISM: Homo sapiens

<400> SEQUENCE: 1037

Val Ala Asp Pro Ala Tyr Leu Pro Thr Gln Gln Asp Val Leu Arg
1               5                   10                  15

<210> SEQ ID NO 1038
<211> LENGTH: 19
<212> TYPE: PRT
<213> ORGANISM: Homo sapiens

<400> SEQUENCE: 1038

Val Pro Thr Thr Gly Ile Ile Glu Tyr Pro Phe Asp Leu Gln Ser Val
1               5                   10                  15

Ile Phe Arg

<210> SEQ ID NO 1039
<211> LENGTH: 13
<212> TYPE: PRT
<213> ORGANISM: Homo sapiens

<400> SEQUENCE: 1039

Val Ser Ala Phe Glu Asn Pro Tyr Val Asp Ala Ile Lys
1               5                   10

<210> SEQ ID NO 1040
<211> LENGTH: 15
<212> TYPE: PRT
<213> ORGANISM: Homo sapiens

<400> SEQUENCE: 1040

Glu Glu Thr Asn Glu Ile Gln Val Val Asn Glu Glu Pro Gln Arg
1               5                   10                  15

<210> SEQ ID NO 1041
<211> LENGTH: 14
<212> TYPE: PRT
<213> ORGANISM: Homo sapiens

<400> SEQUENCE: 1041

Ile Gln Ser Ser His Asn Phe Gln Leu Glu Ser Val Asn Lys
1               5                   10

<210> SEQ ID NO 1042
<211> LENGTH: 10
<212> TYPE: PRT
<213> ORGANISM: Homo sapiens

<400> SEQUENCE: 1042

Leu Gln Gln Asp Val Leu Gln Phe Gln Lys
1               5                   10

<210> SEQ ID NO 1043
<211> LENGTH: 14
<212> TYPE: PRT
<213> ORGANISM: Homo sapiens
```

<400> SEQUENCE: 1043

Glu Asp His Glu Gly Leu Gly Ile Ser Ile Thr Gly Gly Lys
1               5                   10

<210> SEQ ID NO 1044
<211> LENGTH: 10
<212> TYPE: PRT
<213> ORGANISM: Homo sapiens

<400> SEQUENCE: 1044

Ser Glu Leu Thr Glu Thr Gln Ala Glu Lys
1               5                   10

<210> SEQ ID NO 1045
<211> LENGTH: 9
<212> TYPE: PRT
<213> ORGANISM: Homo sapiens

<400> SEQUENCE: 1045

Val Gln Gln Ile Gln Leu Leu Gly Arg
1               5

<210> SEQ ID NO 1046
<211> LENGTH: 15
<212> TYPE: PRT
<213> ORGANISM: Homo sapiens

<400> SEQUENCE: 1046

Gln Leu Leu Ala Tyr Thr Val Glu Ala Ala Asn Phe Ser Asp Lys
1               5                   10                  15

<210> SEQ ID NO 1047
<211> LENGTH: 18
<212> TYPE: PRT
<213> ORGANISM: Homo sapiens

<400> SEQUENCE: 1047

Ser Asn Gly Gln Glu Gly Pro Leu Leu Gly Thr Asp Ser Thr Gly Asn
1               5                   10                  15

Val Arg

<210> SEQ ID NO 1048
<211> LENGTH: 12
<212> TYPE: PRT
<213> ORGANISM: Homo sapiens

<400> SEQUENCE: 1048

Ala Ser Ala Ser Asp Ser Ser Ala Pro Trp Ser Arg
1               5                   10

<210> SEQ ID NO 1049
<211> LENGTH: 16
<212> TYPE: PRT
<213> ORGANISM: Homo sapiens

<400> SEQUENCE: 1049

Gly Ser Tyr Asn Ser Ser Asn Asn Phe Gln Gln Pro Leu Thr Ser Arg
1               5                   10                  15

<210> SEQ ID NO 1050
<211> LENGTH: 14
<212> TYPE: PRT
<213> ORGANISM: Homo sapiens

<400> SEQUENCE: 1050

Ser Val Ala Leu Pro Ala Ser Ser Ala Leu Ser Ala Asn Lys
1               5                   10

<210> SEQ ID NO 1051
<211> LENGTH: 8
<212> TYPE: PRT
<213> ORGANISM: Homo sapiens

<400> SEQUENCE: 1051

Asp Pro Ser Thr Val Glu Asp Lys
1               5

<210> SEQ ID NO 1052
<211> LENGTH: 16
<212> TYPE: PRT
<213> ORGANISM: Homo sapiens

<400> SEQUENCE: 1052

Asp Ser Thr Ile His Val Glu Glu Asn Gly Gln Ser Ser Glu Ser Arg
1               5                   10                  15

<210> SEQ ID NO 1053
<211> LENGTH: 10
<212> TYPE: PRT
<213> ORGANISM: Homo sapiens

<400> SEQUENCE: 1053

Ser Glu Val Pro Ala Ile Asp Leu Ala Arg
1               5                   10

<210> SEQ ID NO 1054
<211> LENGTH: 9
<212> TYPE: PRT
<213> ORGANISM: Homo sapiens

<400> SEQUENCE: 1054

Ala Gln Ser Gly Asn Pro Glu Val Lys
1               5

<210> SEQ ID NO 1055
<211> LENGTH: 23
<212> TYPE: PRT
<213> ORGANISM: Homo sapiens

<400> SEQUENCE: 1055

Thr Phe Leu Gln Ala Leu Asn Leu Gly Ile Glu Val Ile Asn Thr Thr
1               5                   10                  15

Asp Tyr Leu His Phe Ser Lys
            20

<210> SEQ ID NO 1056
<211> LENGTH: 20
<212> TYPE: PRT
<213> ORGANISM: Homo sapiens

<400> SEQUENCE: 1056

Phe Arg Pro Tyr Asn Pro Glu Glu Arg Pro Thr Thr Ala Ala Gly Thr
1               5                   10                  15

Ser Leu Asp Arg
            20

```
<210> SEQ ID NO 1057
<211> LENGTH: 15
<212> TYPE: PRT
<213> ORGANISM: Homo sapiens

<400> SEQUENCE: 1057

Leu Glu Phe Glu Asn Leu Val Glu Glu Thr Ser His Phe Val Arg
1               5                   10                  15

<210> SEQ ID NO 1058
<211> LENGTH: 10
<212> TYPE: PRT
<213> ORGANISM: Homo sapiens

<400> SEQUENCE: 1058

Thr Phe Val Gln Gly Leu Thr Val Gly Arg
1               5                   10

<210> SEQ ID NO 1059
<211> LENGTH: 12
<212> TYPE: PRT
<213> ORGANISM: Homo sapiens

<400> SEQUENCE: 1059

Gln Val Gln Val Glu Gly Leu Ser Gly Asn Ile Lys
1               5                   10

<210> SEQ ID NO 1060
<211> LENGTH: 9
<212> TYPE: PRT
<213> ORGANISM: Homo sapiens

<400> SEQUENCE: 1060

Glu Ala Val Gly Gly Ile Thr Ile Lys
1               5

<210> SEQ ID NO 1061
<211> LENGTH: 10
<212> TYPE: PRT
<213> ORGANISM: Homo sapiens

<400> SEQUENCE: 1061

Ser Ala Phe Thr Thr Ser Thr Val Val Arg
1               5                   10

<210> SEQ ID NO 1062
<211> LENGTH: 10
<212> TYPE: PRT
<213> ORGANISM: Homo sapiens

<400> SEQUENCE: 1062

Gly Ser Glu Ile Val Ala Gly Leu Glu Lys
1               5                   10

<210> SEQ ID NO 1063
<211> LENGTH: 10
<212> TYPE: PRT
<213> ORGANISM: Homo sapiens

<400> SEQUENCE: 1063

Leu Pro Ala His Thr Val Gly Asp Val Lys
1               5                   10

<210> SEQ ID NO 1064
<211> LENGTH: 7
```

```
<212> TYPE: PRT
<213> ORGANISM: Homo sapiens

<400> SEQUENCE: 1064

Trp Pro Thr Thr Leu Ser Arg
1               5

<210> SEQ ID NO 1065
<211> LENGTH: 9
<212> TYPE: PRT
<213> ORGANISM: Homo sapiens

<400> SEQUENCE: 1065

Val Leu Val Phe Glu Asp Asp Val Arg
1               5

<210> SEQ ID NO 1066
<211> LENGTH: 8
<212> TYPE: PRT
<213> ORGANISM: Homo sapiens

<400> SEQUENCE: 1066

Leu Ala Val Glu Ala Leu Val Arg
1               5

<210> SEQ ID NO 1067
<211> LENGTH: 17
<212> TYPE: PRT
<213> ORGANISM: Homo sapiens

<400> SEQUENCE: 1067

Ser Val Ala Leu Thr Ile Ser Ala Tyr Gln Glu Asp Pro Ala Tyr Leu
1               5                   10                  15

Arg

<210> SEQ ID NO 1068
<211> LENGTH: 16
<212> TYPE: PRT
<213> ORGANISM: Homo sapiens

<400> SEQUENCE: 1068

Ile Phe Asp Glu Glu Asn Ile Leu Asn Glu Leu Asn Asp Pro Leu Arg
1               5                   10                  15

<210> SEQ ID NO 1069
<211> LENGTH: 16
<212> TYPE: PRT
<213> ORGANISM: Homo sapiens

<400> SEQUENCE: 1069

Thr Gly Thr Val Asn Glu Asp Ser Ser Glu Ile Ile Leu Asp Pro Lys
1               5                   10                  15

<210> SEQ ID NO 1070
<211> LENGTH: 28
<212> TYPE: PRT
<213> ORGANISM: Homo sapiens

<400> SEQUENCE: 1070

Gly Ala Ala Ser Gly Pro Ala Pro Gly Pro Gly Pro Ala Glu Glu Ala
1               5                   10                  15

Gly Ser Glu Glu Ala Gly Pro Ala Gly Glu Pro Arg
                20                  25
```

<210> SEQ ID NO 1071
<211> LENGTH: 22
<212> TYPE: PRT
<213> ORGANISM: Homo sapiens

<400> SEQUENCE: 1071

Thr Trp Phe Val Val Asp Phe Val Ser Ser Ile Pro Val Asp Tyr Ile
1               5                   10                  15

Phe Leu Ile Val Glu Lys
            20

<210> SEQ ID NO 1072
<211> LENGTH: 6
<212> TYPE: PRT
<213> ORGANISM: Homo sapiens

<400> SEQUENCE: 1072

Gly Glu Phe Val Trp Lys
1               5

<210> SEQ ID NO 1073
<211> LENGTH: 20
<212> TYPE: PRT
<213> ORGANISM: Homo sapiens

<400> SEQUENCE: 1073

Glu Tyr Tyr Phe Ala Glu Ala Gln Ile Ala Asp Phe Ser Asp Pro Ala
1               5                   10                  15

Phe Ile Ser Lys
            20

<210> SEQ ID NO 1074
<211> LENGTH: 9
<212> TYPE: PRT
<213> ORGANISM: Homo sapiens

<400> SEQUENCE: 1074

Thr Leu Glu Ala Gln Leu Thr Pro Arg
1               5

<210> SEQ ID NO 1075
<211> LENGTH: 11
<212> TYPE: PRT
<213> ORGANISM: Homo sapiens

<400> SEQUENCE: 1075

Glu Phe Ile Ile Ala Leu Ser Val Thr Ser Arg
1               5                   10

<210> SEQ ID NO 1076
<211> LENGTH: 15
<212> TYPE: PRT
<213> ORGANISM: Homo sapiens

<400> SEQUENCE: 1076

Glu Asn Thr Glu Phe Ser Glu Leu Glu Leu Gln Glu Trp Tyr Lys
1               5                   10                  15

<210> SEQ ID NO 1077
<211> LENGTH: 13
<212> TYPE: PRT
<213> ORGANISM: Homo sapiens

<400> SEQUENCE: 1077

```
Thr Phe Asp Thr Asn Ser Asp Gly Thr Ile Asp Phe Arg
1               5                   10

<210> SEQ ID NO 1078
<211> LENGTH: 7
<212> TYPE: PRT
<213> ORGANISM: Homo sapiens

<400> SEQUENCE: 1078

Asp Tyr Ala Glu Val Gly Arg
1               5

<210> SEQ ID NO 1079
<211> LENGTH: 10
<212> TYPE: PRT
<213> ORGANISM: Homo sapiens

<400> SEQUENCE: 1079

Val Thr Ser Ile Gln Asp Trp Val Gln Lys
1               5                   10

<210> SEQ ID NO 1080
<211> LENGTH: 16
<212> TYPE: PRT
<213> ORGANISM: Homo sapiens

<400> SEQUENCE: 1080

Val Val Leu His Pro Asn Tyr Ser Gln Val Asp Ile Gly Leu Ile Lys
1               5                   10                  15

<210> SEQ ID NO 1081
<211> LENGTH: 14
<212> TYPE: PRT
<213> ORGANISM: Homo sapiens

<400> SEQUENCE: 1081

Asp Ser Pro Val Leu Ile Asp Phe Phe Glu Asp Thr Glu Arg
1               5                   10

<210> SEQ ID NO 1082
<211> LENGTH: 14
<212> TYPE: PRT
<213> ORGANISM: Homo sapiens

<400> SEQUENCE: 1082

Gly Gly Glu Gly Thr Gly Tyr Phe Val Asp Phe Ser Val Arg
1               5                   10

<210> SEQ ID NO 1083
<211> LENGTH: 12
<212> TYPE: PRT
<213> ORGANISM: Homo sapiens

<400> SEQUENCE: 1083

Ala Ile Ser Asp Tyr Thr Gln Val Leu Glu Gly Lys
1               5                   10

<210> SEQ ID NO 1084
<211> LENGTH: 13
<212> TYPE: PRT
<213> ORGANISM: Homo sapiens

<400> SEQUENCE: 1084

Ser Pro Ala Tyr Phe Ile Thr Glu Glu Val Pro Glu Arg
```

```
1               5               10

<210> SEQ ID NO 1085
<211> LENGTH: 23
<212> TYPE: PRT
<213> ORGANISM: Homo sapiens

<400> SEQUENCE: 1085

Thr Glu Leu Pro Glu Gly Ala Pro Glu Leu Ala Leu Asp Thr Glu Leu
1               5                   10                  15

Ser Leu Glu Asp Gly Asp Arg
            20

<210> SEQ ID NO 1086
<211> LENGTH: 10
<212> TYPE: PRT
<213> ORGANISM: Homo sapiens

<400> SEQUENCE: 1086

Leu Leu Asp Ser Leu Pro Ser Asp Thr Arg
1               5                   10

<210> SEQ ID NO 1087
<211> LENGTH: 11
<212> TYPE: PRT
<213> ORGANISM: Homo sapiens

<400> SEQUENCE: 1087

Thr Asn Leu Glu Ser Ile Leu Ser Tyr Pro Lys
1               5                   10

<210> SEQ ID NO 1088
<211> LENGTH: 10
<212> TYPE: PRT
<213> ORGANISM: Homo sapiens

<400> SEQUENCE: 1088

Thr Phe Val Leu Pro Val Thr Pro Pro Arg
1               5                   10

<210> SEQ ID NO 1089
<211> LENGTH: 12
<212> TYPE: PRT
<213> ORGANISM: Homo sapiens

<400> SEQUENCE: 1089

His Ser His Ala Leu Val Ser Leu Ser Phe Leu Lys
1               5                   10

<210> SEQ ID NO 1090
<211> LENGTH: 18
<212> TYPE: PRT
<213> ORGANISM: Homo sapiens

<400> SEQUENCE: 1090

Val Ala Gly Leu Glu Ser Leu Gly Asp Leu Phe Pro Asn Leu Thr Val
1               5                   10                  15

Ile Arg

<210> SEQ ID NO 1091
<211> LENGTH: 9
<212> TYPE: PRT
<213> ORGANISM: Homo sapiens
```

```
<400> SEQUENCE: 1091

Tyr Gly Ser Gln Val Glu Asp Gln Arg
1               5

<210> SEQ ID NO 1092
<211> LENGTH: 8
<212> TYPE: PRT
<213> ORGANISM: Homo sapiens

<400> SEQUENCE: 1092

Asn Leu Gln Leu Lys Pro Leu Lys
1               5

<210> SEQ ID NO 1093
<211> LENGTH: 7
<212> TYPE: PRT
<213> ORGANISM: Homo sapiens

<400> SEQUENCE: 1093

Thr Leu Thr Ile Gln Val Lys
1               5

<210> SEQ ID NO 1094
<211> LENGTH: 9
<212> TYPE: PRT
<213> ORGANISM: Homo sapiens

<400> SEQUENCE: 1094

Asp Leu Glu Glu Pro Ile Asn Phe Arg
1               5

<210> SEQ ID NO 1095
<211> LENGTH: 18
<212> TYPE: PRT
<213> ORGANISM: Homo sapiens

<400> SEQUENCE: 1095

Asp Ser Leu Pro Gly Gly Ile Val Thr Asp Glu Thr Leu Ser Phe Ile
1               5                   10                  15

Gln Lys

<210> SEQ ID NO 1096
<211> LENGTH: 10
<212> TYPE: PRT
<213> ORGANISM: Homo sapiens

<400> SEQUENCE: 1096

Val Ala Phe Pro Leu Glu Val Val Gln Lys
1               5                   10

<210> SEQ ID NO 1097
<211> LENGTH: 7
<212> TYPE: PRT
<213> ORGANISM: Homo sapiens

<400> SEQUENCE: 1097

Asp Ser Leu Leu Leu Asp Lys
1               5

<210> SEQ ID NO 1098
<211> LENGTH: 9
<212> TYPE: PRT
<213> ORGANISM: Homo sapiens
```

<400> SEQUENCE: 1098

Leu Glu Gly Glu Pro Val Ala Leu Arg
1               5

<210> SEQ ID NO 1099
<211> LENGTH: 10
<212> TYPE: PRT
<213> ORGANISM: Homo sapiens

<400> SEQUENCE: 1099

Ser His Gln Asn Ala Ser Ala Ile Ile Lys
1               5                   10

<210> SEQ ID NO 1100
<211> LENGTH: 8
<212> TYPE: PRT
<213> ORGANISM: Homo sapiens

<400> SEQUENCE: 1100

Ala Glu Val Trp Leu Phe Leu Lys
1               5

<210> SEQ ID NO 1101
<211> LENGTH: 10
<212> TYPE: PRT
<213> ORGANISM: Homo sapiens

<400> SEQUENCE: 1101

Glu Gly Ser Asp Leu Ser Val Val Glu Arg
1               5                   10

<210> SEQ ID NO 1102
<211> LENGTH: 18
<212> TYPE: PRT
<213> ORGANISM: Homo sapiens

<400> SEQUENCE: 1102

His Pro Gln Gly Ser Leu Asp Thr Gly Glu Glu Ala Glu Glu Val Gly
1               5                   10                  15

Leu Lys

<210> SEQ ID NO 1103
<211> LENGTH: 11
<212> TYPE: PRT
<213> ORGANISM: Homo sapiens

<400> SEQUENCE: 1103

Phe Ser Ile Glu Gly Ser Tyr Gln Leu Glu Lys
1               5                   10

<210> SEQ ID NO 1104
<211> LENGTH: 13
<212> TYPE: PRT
<213> ORGANISM: Homo sapiens

<400> SEQUENCE: 1104

Thr Leu Tyr Leu Ala Asp Thr Phe Pro Thr Asn Phe Arg
1               5                   10

<210> SEQ ID NO 1105
<211> LENGTH: 10
<212> TYPE: PRT
<213> ORGANISM: Homo sapiens

```
<400> SEQUENCE: 1105

Ala Ala Phe Val Ser Glu Gln Gln Gln Lys
1               5                   10

<210> SEQ ID NO 1106
<211> LENGTH: 17
<212> TYPE: PRT
<213> ORGANISM: Homo sapiens

<400> SEQUENCE: 1106

Glu Ala Gly Asn Pro Gly Ser Leu Phe Gly Tyr Ser Val Ala Leu His
1               5                   10                  15

Arg

<210> SEQ ID NO 1107
<211> LENGTH: 9
<212> TYPE: PRT
<213> ORGANISM: Homo sapiens

<400> SEQUENCE: 1107

Val Tyr Ile Tyr His Ser Ser Ser Lys
1               5

<210> SEQ ID NO 1108
<211> LENGTH: 13
<212> TYPE: PRT
<213> ORGANISM: Homo sapiens

<400> SEQUENCE: 1108

Ser Leu Pro Ile Ser Leu Val Phe Leu Val Pro Val Arg
1               5                   10

<210> SEQ ID NO 1109
<211> LENGTH: 12
<212> TYPE: PRT
<213> ORGANISM: Homo sapiens

<400> SEQUENCE: 1109

Ser Leu Val Lys Pro Ile Thr Gln Leu Leu Gly Arg
1               5                   10

<210> SEQ ID NO 1110
<211> LENGTH: 10
<212> TYPE: PRT
<213> ORGANISM: Homo sapiens

<400> SEQUENCE: 1110

Ala Leu Asn Glu Ile Thr Glu Ser Gly Arg
1               5                   10

<210> SEQ ID NO 1111
<211> LENGTH: 15
<212> TYPE: PRT
<213> ORGANISM: Homo sapiens

<400> SEQUENCE: 1111

Leu Ala Glu Asn Asn Ile Gln Pro Ile Phe Ala Val Thr Ser Arg
1               5                   10                  15

<210> SEQ ID NO 1112
<211> LENGTH: 11
<212> TYPE: PRT
<213> ORGANISM: Homo sapiens
```

```
<400> SEQUENCE: 1112

Ser Gln Trp Asn Asn Asp Asn Pro Leu Phe Lys
1               5                   10

<210> SEQ ID NO 1113
<211> LENGTH: 16
<212> TYPE: PRT
<213> ORGANISM: Homo sapiens

<400> SEQUENCE: 1113

Gly Phe Ser Leu Asp Glu Ala Thr Asn Leu Asn Gly Gly Leu Leu Arg
1               5                   10                  15

<210> SEQ ID NO 1114
<211> LENGTH: 11
<212> TYPE: PRT
<213> ORGANISM: Homo sapiens

<400> SEQUENCE: 1114

Val Gln Phe Glu Leu His Tyr Gln Glu Val Lys
1               5                   10

<210> SEQ ID NO 1115
<211> LENGTH: 10
<212> TYPE: PRT
<213> ORGANISM: Homo sapiens

<400> SEQUENCE: 1115

Glu Val Ser Phe Asp Val Glu Leu Pro Lys
1               5                   10

<210> SEQ ID NO 1116
<211> LENGTH: 20
<212> TYPE: PRT
<213> ORGANISM: Homo sapiens

<400> SEQUENCE: 1116

Val Ser Asp Ile Arg Pro Gly Ser Asp Pro Thr Lys Pro Asp Ala Thr
1               5                   10                  15

Leu Val Val Lys
            20

<210> SEQ ID NO 1117
<211> LENGTH: 17
<212> TYPE: PRT
<213> ORGANISM: Homo sapiens

<400> SEQUENCE: 1117

Asn Pro Leu Val Trp Val His Ala Ser Pro Glu His Val Val Val Thr
1               5                   10                  15

Arg

<210> SEQ ID NO 1118
<211> LENGTH: 16
<212> TYPE: PRT
<213> ORGANISM: Homo sapiens

<400> SEQUENCE: 1118

Ser Pro Glu Gln Gln Glu Thr Val Leu Asp Gly Asn Leu Ile Ile Arg
1               5                   10                  15

<210> SEQ ID NO 1119
<211> LENGTH: 9
```

<212> TYPE: PRT
<213> ORGANISM: Homo sapiens

<400> SEQUENCE: 1119

Gly Gly Leu Leu Val Asp Asp Phe Arg
1               5

<210> SEQ ID NO 1120
<211> LENGTH: 17
<212> TYPE: PRT
<213> ORGANISM: Homo sapiens

<400> SEQUENCE: 1120

Ser Leu Pro Val Ala Leu Glu Ser Asp Glu Glu Asn Gly Asp Glu Leu
1               5                   10                  15

Lys

<210> SEQ ID NO 1121
<211> LENGTH: 12
<212> TYPE: PRT
<213> ORGANISM: Homo sapiens

<400> SEQUENCE: 1121

Ser Ser Trp Gly Glu Glu Gln Ala Gly Gly Ser Arg
1               5                   10

<210> SEQ ID NO 1122
<211> LENGTH: 11
<212> TYPE: PRT
<213> ORGANISM: Homo sapiens

<400> SEQUENCE: 1122

Ile Ala Pro Ala Asn Ala Asp Phe Ala Phe Arg
1               5                   10

<210> SEQ ID NO 1123
<211> LENGTH: 12
<212> TYPE: PRT
<213> ORGANISM: Homo sapiens

<400> SEQUENCE: 1123

Gly Ser Ser Tyr Asn Pro Pro Leu Pro Pro Leu Lys
1               5                   10

<210> SEQ ID NO 1124
<211> LENGTH: 13
<212> TYPE: PRT
<213> ORGANISM: Homo sapiens

<400> SEQUENCE: 1124

Leu Gln Gly Phe Glu Gly Thr Leu Thr Ala Gln Gly Lys
1               5                   10

<210> SEQ ID NO 1125
<211> LENGTH: 15
<212> TYPE: PRT
<213> ORGANISM: Homo sapiens

<400> SEQUENCE: 1125

Ala Leu Ser His Pro Trp Ile Asp Gly Asn Thr Ala Leu His Arg
1               5                   10                  15

<210> SEQ ID NO 1126
<211> LENGTH: 19

```
<212> TYPE: PRT
<213> ORGANISM: Homo sapiens

<400> SEQUENCE: 1126

Glu Gly Tyr Tyr Glu Phe Glu Ser Pro Phe Trp Asp Asp Ile Ser Glu
1               5                   10                  15

Ser Ala Lys

<210> SEQ ID NO 1127
<211> LENGTH: 16
<212> TYPE: PRT
<213> ORGANISM: Homo sapiens

<400> SEQUENCE: 1127

Glu Ser Ser Glu Ser Thr Asn Thr Thr Ile Glu Asp Glu Asp Thr Lys
1               5                   10                  15

<210> SEQ ID NO 1128
<211> LENGTH: 13
<212> TYPE: PRT
<213> ORGANISM: Homo sapiens

<400> SEQUENCE: 1128

Phe Thr Glu Glu Tyr Gln Leu Phe Glu Glu Leu Gly Lys
1               5                   10

<210> SEQ ID NO 1129
<211> LENGTH: 7
<212> TYPE: PRT
<213> ORGANISM: Homo sapiens

<400> SEQUENCE: 1129

Glu Asp Glu Gly Phe Ile Lys
1               5

<210> SEQ ID NO 1130
<211> LENGTH: 11
<212> TYPE: PRT
<213> ORGANISM: Homo sapiens

<400> SEQUENCE: 1130

Gly Glu Gln Ala Thr Ser Leu Ala Ile Leu Arg
1               5                   10

<210> SEQ ID NO 1131
<211> LENGTH: 13
<212> TYPE: PRT
<213> ORGANISM: Homo sapiens

<400> SEQUENCE: 1131

Glu Glu Glu Arg Pro Leu Pro Glu Asn Glu Phe Gln Arg
1               5                   10

<210> SEQ ID NO 1132
<211> LENGTH: 9
<212> TYPE: PRT
<213> ORGANISM: Homo sapiens

<400> SEQUENCE: 1132

Val Val Ile Asn Ile Ser Gly Leu Arg
1               5

<210> SEQ ID NO 1133
<211> LENGTH: 22
```

```
<212> TYPE: PRT
<213> ORGANISM: Homo sapiens

<400> SEQUENCE: 1133

Asp Tyr Pro Ala Ser Thr Ser Gln Asp Ser Phe Glu Ala Ala Gly Asn
1               5                   10                  15

Ser Thr Ser Gly Ser Arg
            20

<210> SEQ ID NO 1134
<211> LENGTH: 7
<212> TYPE: PRT
<213> ORGANISM: Homo sapiens

<400> SEQUENCE: 1134

Glu Asp Glu Gly Phe Leu Arg
1               5

<210> SEQ ID NO 1135
<211> LENGTH: 11
<212> TYPE: PRT
<213> ORGANISM: Homo sapiens

<400> SEQUENCE: 1135

Glu Thr Asp His Glu Glu Pro Ala Val Leu Lys
1               5                   10

<210> SEQ ID NO 1136
<211> LENGTH: 16
<212> TYPE: PRT
<213> ORGANISM: Homo sapiens

<400> SEQUENCE: 1136

Gln Val Trp Leu Ile Phe Glu Tyr Pro Glu Ser Ser Gly Ser Ala Arg
1               5                   10                  15

<210> SEQ ID NO 1137
<211> LENGTH: 9
<212> TYPE: PRT
<213> ORGANISM: Homo sapiens

<400> SEQUENCE: 1137

Val His Ile Asn Ile Ser Gly Leu Arg
1               5

<210> SEQ ID NO 1138
<211> LENGTH: 14
<212> TYPE: PRT
<213> ORGANISM: Homo sapiens

<400> SEQUENCE: 1138

Gln Ile Pro Ala Ala Ala Ser Leu Ile Gln Thr Ala Trp Arg
1               5                   10

<210> SEQ ID NO 1139
<211> LENGTH: 25
<212> TYPE: PRT
<213> ORGANISM: Homo sapiens

<400> SEQUENCE: 1139

Val Glu Phe Gly Ser Tyr Ala Asp Ala Leu Trp Trp Gly Val Val Thr
1               5                   10                  15

Val Thr Thr Ile Gly Tyr Gly Asp Lys
            20                  25
```

```
<210> SEQ ID NO 1140
<211> LENGTH: 7
<212> TYPE: PRT
<213> ORGANISM: Homo sapiens

<400> SEQUENCE: 1140

Ala Phe Gly Phe Thr Leu Arg
1               5

<210> SEQ ID NO 1141
<211> LENGTH: 15
<212> TYPE: PRT
<213> ORGANISM: Homo sapiens

<400> SEQUENCE: 1141

Glu Asn Gln Leu Leu Ala Gln Glu Ala Glu Phe Phe Gln Leu Lys
1               5                   10                  15

<210> SEQ ID NO 1142
<211> LENGTH: 13
<212> TYPE: PRT
<213> ORGANISM: Homo sapiens

<400> SEQUENCE: 1142

Gly Ser Ile Val His Ser Asp Ala Leu His Phe Ile Lys
1               5                   10

<210> SEQ ID NO 1143
<211> LENGTH: 18
<212> TYPE: PRT
<213> ORGANISM: Homo sapiens

<400> SEQUENCE: 1143

Leu Asp Gly Phe Pro Glu Glu Phe Ser Ile Ser Ser Asn Ile Ile Gln
1               5                   10                  15

Phe Lys

<210> SEQ ID NO 1144
<211> LENGTH: 13
<212> TYPE: PRT
<213> ORGANISM: Homo sapiens

<400> SEQUENCE: 1144

Ile Ser Phe Leu Glu Asn Asn Leu Glu Gln Leu Thr Lys
1               5                   10

<210> SEQ ID NO 1145
<211> LENGTH: 13
<212> TYPE: PRT
<213> ORGANISM: Homo sapiens

<400> SEQUENCE: 1145

Leu Gln Ala Gln Glu Thr Val His Glu Val Ala Leu Lys
1               5                   10

<210> SEQ ID NO 1146
<211> LENGTH: 17
<212> TYPE: PRT
<213> ORGANISM: Homo sapiens

<400> SEQUENCE: 1146

Ser Leu Ser Ala Leu Gly Asn Val Ile Ser Ala Leu Ala Glu Gly Thr
1               5                   10                  15
```

Lys

<210> SEQ ID NO 1147
<211> LENGTH: 10
<212> TYPE: PRT
<213> ORGANISM: Homo sapiens

<400> SEQUENCE: 1147

Gly Pro Glu Glu Glu Thr Gly Ser Arg
1               5                   10

<210> SEQ ID NO 1148
<211> LENGTH: 11
<212> TYPE: PRT
<213> ORGANISM: Homo sapiens

<400> SEQUENCE: 1148

Ile Pro Gly Ser Ser Asp Gly Ser Ser Arg
1               5                   10

<210> SEQ ID NO 1149
<211> LENGTH: 7
<212> TYPE: PRT
<213> ORGANISM: Homo sapiens

<400> SEQUENCE: 1149

Ser Val Ile Leu Leu Gly Arg
1               5

<210> SEQ ID NO 1150
<211> LENGTH: 9
<212> TYPE: PRT
<213> ORGANISM: Homo sapiens

<400> SEQUENCE: 1150

Glu Ile Ile Ile His Gln Asn Tyr Lys
1               5

<210> SEQ ID NO 1151
<211> LENGTH: 14
<212> TYPE: PRT
<213> ORGANISM: Homo sapiens

<400> SEQUENCE: 1151

Ile Ala Tyr Gly Thr Gln Gly Ser Ser Gly Tyr Ser Leu Arg
1               5                   10

<210> SEQ ID NO 1152
<211> LENGTH: 12
<212> TYPE: PRT
<213> ORGANISM: Homo sapiens

<400> SEQUENCE: 1152

Val Ser Glu Gly Asn His Asp Ile Ala Leu Ile Lys
1               5                   10

<210> SEQ ID NO 1153
<211> LENGTH: 19
<212> TYPE: PRT
<213> ORGANISM: Homo sapiens

<400> SEQUENCE: 1153

Asp Ile Pro Thr Asn Ser Pro Glu Leu Glu Glu Thr Leu Thr His Thr
1               5                   10                  15

Ile Thr Lys

<210> SEQ ID NO 1154
<211> LENGTH: 18
<212> TYPE: PRT
<213> ORGANISM: Homo sapiens

<400> SEQUENCE: 1154

Leu Asp Asp Asp Leu Glu His Gln Gly Gly His Val Leu Asp His Gly
1               5                   10                  15

His Lys

<210> SEQ ID NO 1155
<211> LENGTH: 12
<212> TYPE: PRT
<213> ORGANISM: Homo sapiens

<400> SEQUENCE: 1155

Glu Glu Ser Glu Gln Ile Val Leu Ile Gly Ser Lys
1               5                   10

<210> SEQ ID NO 1156
<211> LENGTH: 12
<212> TYPE: PRT
<213> ORGANISM: Homo sapiens

<400> SEQUENCE: 1156

Glu Leu Asn Gly Thr Tyr Ala Ile Ala Gly Gly Arg
1               5                   10

<210> SEQ ID NO 1157
<211> LENGTH: 11
<212> TYPE: PRT
<213> ORGANISM: Homo sapiens

<400> SEQUENCE: 1157

Asn Val Leu Leu Val Thr Gln His Tyr Ala Lys
1               5                   10

<210> SEQ ID NO 1158
<211> LENGTH: 12
<212> TYPE: PRT
<213> ORGANISM: Homo sapiens

<400> SEQUENCE: 1158

Asp Thr Glu Gln Thr Leu Tyr Gln Val Gln Glu Arg
1               5                   10

<210> SEQ ID NO 1159
<211> LENGTH: 23
<212> TYPE: PRT
<213> ORGANISM: Homo sapiens

<400> SEQUENCE: 1159

Val Leu Glu Leu Ser Ile Pro Ala Ser Ala Glu Gln Ile Gln His Leu
1               5                   10                  15

Ala Gly Ala Ile Ala Glu Arg
            20

<210> SEQ ID NO 1160
<211> LENGTH: 9
<212> TYPE: PRT
<213> ORGANISM: Homo sapiens

<400> SEQUENCE: 1160

Val Gln Asp Ile Phe Thr Ala Gly Lys
1               5

<210> SEQ ID NO 1161
<211> LENGTH: 14
<212> TYPE: PRT
<213> ORGANISM: Homo sapiens

<400> SEQUENCE: 1161

Glu Ser Glu Ser Thr Ala Gly Ser Phe Ser Leu Ser Val Arg
1               5                   10

<210> SEQ ID NO 1162
<211> LENGTH: 10
<212> TYPE: PRT
<213> ORGANISM: Homo sapiens

<400> SEQUENCE: 1162

Ile Leu Glu Gln Ser Gly Glu Trp Trp Lys
1               5                   10

<210> SEQ ID NO 1163
<211> LENGTH: 16
<212> TYPE: PRT
<213> ORGANISM: Homo sapiens

<400> SEQUENCE: 1163

Glu Ile His Val Leu Asp Thr Asp Tyr Glu Gly Tyr Ala Ile Leu Arg
1               5                   10                  15

<210> SEQ ID NO 1164
<211> LENGTH: 11
<212> TYPE: PRT
<213> ORGANISM: Homo sapiens

<400> SEQUENCE: 1164

Asp Thr Asp Val Glu Tyr Leu Glu Ile Val Arg
1               5                   10

<210> SEQ ID NO 1165
<211> LENGTH: 11
<212> TYPE: PRT
<213> ORGANISM: Homo sapiens

<400> SEQUENCE: 1165

Gly Leu Asp Ser Leu Thr Asn Val Asp Leu Arg
1               5                   10

<210> SEQ ID NO 1166
<211> LENGTH: 14
<212> TYPE: PRT
<213> ORGANISM: Homo sapiens

<400> SEQUENCE: 1166

Phe Ile Ser Thr Tyr Ser Trp Ala Asp Ala Glu Glu Glu Lys
1               5                   10

<210> SEQ ID NO 1167
<211> LENGTH: 26
<212> TYPE: PRT
<213> ORGANISM: Homo sapiens

<400> SEQUENCE: 1167

```
Ser Ala Ser Pro Thr Ile Glu Ala Gln Gly Thr Ser Pro Ala His Asp
1               5                   10                  15

Asn Ile Ala Phe Gln Asp Ser Thr Ser Lys
            20                  25

<210> SEQ ID NO 1168
<211> LENGTH: 8
<212> TYPE: PRT
<213> ORGANISM: Homo sapiens

<400> SEQUENCE: 1168

Ala Ile Ala Val Asp Pro Leu Arg
1               5

<210> SEQ ID NO 1169
<211> LENGTH: 10
<212> TYPE: PRT
<213> ORGANISM: Homo sapiens

<400> SEQUENCE: 1169

Glu Leu Phe Val Leu Pro Gly Glu Pro Arg
1               5                   10

<210> SEQ ID NO 1170
<211> LENGTH: 15
<212> TYPE: PRT
<213> ORGANISM: Homo sapiens

<400> SEQUENCE: 1170

Ser Ile Phe Gly Asp Leu Thr Asn Leu Thr Glu Leu Gln Leu Arg
1               5                   10                  15

<210> SEQ ID NO 1171
<211> LENGTH: 8
<212> TYPE: PRT
<213> ORGANISM: Homo sapiens

<400> SEQUENCE: 1171

Thr Leu Leu Leu Leu Asn Asn Lys
1               5

<210> SEQ ID NO 1172
<211> LENGTH: 11
<212> TYPE: PRT
<213> ORGANISM: Homo sapiens

<400> SEQUENCE: 1172

Ile Glu Ile Ser Gln Ile Asp Ser Leu Glu Arg
1               5                   10

<210> SEQ ID NO 1173
<211> LENGTH: 11
<212> TYPE: PRT
<213> ORGANISM: Homo sapiens

<400> SEQUENCE: 1173

Leu Leu Leu Leu Leu Gln Pro Pro Leu Pro Arg
1               5                   10

<210> SEQ ID NO 1174
<211> LENGTH: 12
<212> TYPE: PRT
<213> ORGANISM: Homo sapiens
```

```
<400> SEQUENCE: 1174

Tyr Ile Glu Pro Gly Ala Phe Ile Asn Leu Pro Arg
1               5                   10

<210> SEQ ID NO 1175
<211> LENGTH: 24
<212> TYPE: PRT
<213> ORGANISM: Homo sapiens

<400> SEQUENCE: 1175

Ala Leu Gly Thr His Val Ile His Ser Thr His Thr Leu Pro Leu Thr
1               5                   10                  15

Val Thr Ser Gln Gln Gly Val Lys
            20

<210> SEQ ID NO 1176
<211> LENGTH: 23
<212> TYPE: PRT
<213> ORGANISM: Homo sapiens

<400> SEQUENCE: 1176

Thr Gln Thr Ile His Ser Thr Tyr Ser His Gln Gln Val Ile Pro His
1               5                   10                  15

Val Tyr Pro Val Ala Ala Lys
            20

<210> SEQ ID NO 1177
<211> LENGTH: 15
<212> TYPE: PRT
<213> ORGANISM: Homo sapiens

<400> SEQUENCE: 1177

Glu Ser His Gly Gly Ser Val Leu Gln Asp Gly Trp Asp His Arg
1               5                   10                  15

<210> SEQ ID NO 1178
<211> LENGTH: 23
<212> TYPE: PRT
<213> ORGANISM: Homo sapiens

<400> SEQUENCE: 1178

Ser Gly Ile Glu Ala Ile Ala Thr Pro Ser Asp Ile Asp Asn Asp Phe
1               5                   10                  15

Val Asn Asp Ile Ile Ala Arg
            20

<210> SEQ ID NO 1179
<211> LENGTH: 17
<212> TYPE: PRT
<213> ORGANISM: Homo sapiens

<400> SEQUENCE: 1179

Ala Gly Asp His Thr Thr Gly Leu Gly Tyr Tyr Leu Leu Ala Asn Thr
1               5                   10                  15

Lys

<210> SEQ ID NO 1180
<211> LENGTH: 11
<212> TYPE: PRT
<213> ORGANISM: Homo sapiens

<400> SEQUENCE: 1180
```

Asp Val Ala Gly Leu Tyr Glu Glu Ile Trp Lys
1               5                   10

<210> SEQ ID NO 1181
<211> LENGTH: 9
<212> TYPE: PRT
<213> ORGANISM: Homo sapiens

<400> SEQUENCE: 1181

Ser Asp Ile Ala Ile Asp Asp Val Lys
1               5

<210> SEQ ID NO 1182
<211> LENGTH: 15
<212> TYPE: PRT
<213> ORGANISM: Homo sapiens

<400> SEQUENCE: 1182

Thr Thr Thr Ala Ala Ala Val Ala Ser Thr Gly Pro Ser Ser Arg
1               5                   10                  15

<210> SEQ ID NO 1183
<211> LENGTH: 17
<212> TYPE: PRT
<213> ORGANISM: Homo sapiens

<400> SEQUENCE: 1183

Val Gly Ser Leu Asp Asn Val Gly His Leu Pro Ala Gly Gly Ala Val
1               5                   10                  15

Lys

<210> SEQ ID NO 1184
<211> LENGTH: 11
<212> TYPE: PRT
<213> ORGANISM: Homo sapiens

<400> SEQUENCE: 1184

Trp Pro Thr Glu Thr Asp Val Ser Ser Ala Lys
1               5                   10

<210> SEQ ID NO 1185
<211> LENGTH: 11
<212> TYPE: PRT
<213> ORGANISM: Homo sapiens

<400> SEQUENCE: 1185

Asp Gly Phe Phe Tyr Phe Phe His Gly Thr Arg
1               5                   10

<210> SEQ ID NO 1186
<211> LENGTH: 10
<212> TYPE: PRT
<213> ORGANISM: Homo sapiens

<400> SEQUENCE: 1186

Ile Glu Asn Tyr Thr Pro Asp Leu Pro Arg
1               5                   10

<210> SEQ ID NO 1187
<211> LENGTH: 10
<212> TYPE: PRT
<213> ORGANISM: Homo sapiens

<400> SEQUENCE: 1187

```
Leu Thr Phe Asp Ala Ile Thr Thr Ile Arg
1               5                   10

<210> SEQ ID NO 1188
<211> LENGTH: 14
<212> TYPE: PRT
<213> ORGANISM: Homo sapiens

<400> SEQUENCE: 1188

Glu Gly His Ser Pro Pro Asp Asp Val Asp Ile Val Ile Lys
1               5                   10

<210> SEQ ID NO 1189
<211> LENGTH: 13
<212> TYPE: PRT
<213> ORGANISM: Homo sapiens

<400> SEQUENCE: 1189

Gly Ile Pro Glu Ser Pro Gln Gly Ala Phe Val His Lys
1               5                   10

<210> SEQ ID NO 1190
<211> LENGTH: 21
<212> TYPE: PRT
<213> ORGANISM: Homo sapiens

<400> SEQUENCE: 1190

Gly Leu Pro Pro Ser Ile Asp Ala Val Tyr Glu Asn Ser Asp Gly Asn
1               5                   10                  15

Phe Val Phe Phe Lys
            20

<210> SEQ ID NO 1191
<211> LENGTH: 13
<212> TYPE: PRT
<213> ORGANISM: Homo sapiens

<400> SEQUENCE: 1191

Ala Glu Asp Leu Ser Leu Gly Val Glu Trp Leu Ser Arg
1               5                   10

<210> SEQ ID NO 1192
<211> LENGTH: 24
<212> TYPE: PRT
<213> ORGANISM: Homo sapiens

<400> SEQUENCE: 1192

Gly Thr Leu Ala His Ala Phe Ala Pro Gly Glu Gly Leu Gly Gly Asp
1               5                   10                  15

Thr His Phe Asp Asn Ala Glu Lys
            20

<210> SEQ ID NO 1193
<211> LENGTH: 11
<212> TYPE: PRT
<213> ORGANISM: Homo sapiens

<400> SEQUENCE: 1193

Ala Ala Ala Ala Ala Ala Gly Ala Gly Asn Arg
1               5                   10

<210> SEQ ID NO 1194
<211> LENGTH: 13
<212> TYPE: PRT
```

```
<213> ORGANISM: Homo sapiens

<400> SEQUENCE: 1194

Gly Ile Pro Gln Ala Pro Gln Gly Ala Phe Ile Ser Lys
1               5                   10

<210> SEQ ID NO 1195
<211> LENGTH: 11
<212> TYPE: PRT
<213> ORGANISM: Homo sapiens

<400> SEQUENCE: 1195

Leu Pro Gln Asp Asp Leu Gln Gly Ile Gln Lys
1               5                   10

<210> SEQ ID NO 1196
<211> LENGTH: 9
<212> TYPE: PRT
<213> ORGANISM: Homo sapiens

<400> SEQUENCE: 1196

Ala Val Ile Asp Asp Ala Phe Ala Arg
1               5

<210> SEQ ID NO 1197
<211> LENGTH: 9
<212> TYPE: PRT
<213> ORGANISM: Homo sapiens

<400> SEQUENCE: 1197

Phe Gln Thr Phe Glu Gly Asp Leu Lys
1               5

<210> SEQ ID NO 1198
<211> LENGTH: 15
<212> TYPE: PRT
<213> ORGANISM: Homo sapiens

<400> SEQUENCE: 1198

Leu Gly Leu Gly Ala Asp Val Ala Gln Val Thr Gly Ala Leu Arg
1               5                   10                  15

<210> SEQ ID NO 1199
<211> LENGTH: 7
<212> TYPE: PRT
<213> ORGANISM: Homo sapiens

<400> SEQUENCE: 1199

Ala Val Thr Val Phe Phe Lys
1               5

<210> SEQ ID NO 1200
<211> LENGTH: 8
<212> TYPE: PRT
<213> ORGANISM: Homo sapiens

<400> SEQUENCE: 1200

His Ser Glu Asp Val Asn Val Lys
1               5

<210> SEQ ID NO 1201
<211> LENGTH: 11
<212> TYPE: PRT
<213> ORGANISM: Homo sapiens
```

```
<400> SEQUENCE: 1201

Val Ser Asn Ala Gln Ser Val Thr Ser Glu Arg
1               5                   10

<210> SEQ ID NO 1202
<211> LENGTH: 12
<212> TYPE: PRT
<213> ORGANISM: Homo sapiens

<400> SEQUENCE: 1202

Asn Ala Thr Gln Glu Ala Val Ala Ala Leu Leu Lys
1               5                   10

<210> SEQ ID NO 1203
<211> LENGTH: 13
<212> TYPE: PRT
<213> ORGANISM: Homo sapiens

<400> SEQUENCE: 1203

Ser Leu Thr Glu His Gly Val Ala Ala Thr Asp Gly Arg
1               5                   10

<210> SEQ ID NO 1204
<211> LENGTH: 11
<212> TYPE: PRT
<213> ORGANISM: Homo sapiens

<400> SEQUENCE: 1204

Asp Ala Ser Ala Val Ser Leu Ser Glu Ser Lys
1               5                   10

<210> SEQ ID NO 1205
<211> LENGTH: 18
<212> TYPE: PRT
<213> ORGANISM: Homo sapiens

<400> SEQUENCE: 1205

Asp Leu Glu Leu Ala Val Pro Gly Thr Tyr Asp Pro Asn Gln Pro Ile
1               5                   10                  15

Ile Arg

<210> SEQ ID NO 1206
<211> LENGTH: 16
<212> TYPE: PRT
<213> ORGANISM: Homo sapiens

<400> SEQUENCE: 1206

Gly Pro Thr Pro Ala Ile Leu Glu Ser Leu Ile Ser Ile Asn Asn Lys
1               5                   10                  15

<210> SEQ ID NO 1207
<211> LENGTH: 6
<212> TYPE: PRT
<213> ORGANISM: Homo sapiens

<400> SEQUENCE: 1207

Thr Glu Ser Thr Phe Lys
1               5

<210> SEQ ID NO 1208
<211> LENGTH: 31
<212> TYPE: PRT
<213> ORGANISM: Homo sapiens
```

<400> SEQUENCE: 1208

Ala His His Pro Thr Ser Gln His Gly Asp Leu Glu Thr Pro Ser Ser
1               5                   10                  15

Gly Asp Glu Gly Glu Ile Leu Ser Ala Glu Gly Pro Pro Val Arg
                20                  25                  30

<210> SEQ ID NO 1209
<211> LENGTH: 21
<212> TYPE: PRT
<213> ORGANISM: Homo sapiens

<400> SEQUENCE: 1209

Gly Ile Glu Asp Glu Gln Asp Leu Val Pro Leu Glu Val Thr Gly Val
1               5                   10                  15

Val Phe His Tyr Arg
            20

<210> SEQ ID NO 1210
<211> LENGTH: 8
<212> TYPE: PRT
<213> ORGANISM: Homo sapiens

<400> SEQUENCE: 1210

Tyr Asn Val His Ala Thr Val Arg
1               5

<210> SEQ ID NO 1211
<211> LENGTH: 8
<212> TYPE: PRT
<213> ORGANISM: Homo sapiens

<400> SEQUENCE: 1211

Val Ala Gln Gly Tyr His Gln Arg
1               5

<210> SEQ ID NO 1212
<211> LENGTH: 7
<212> TYPE: PRT
<213> ORGANISM: Homo sapiens

<400> SEQUENCE: 1212

Glu Glu Glu Glu Glu Asp Arg
1               5

<210> SEQ ID NO 1213
<211> LENGTH: 14
<212> TYPE: PRT
<213> ORGANISM: Homo sapiens

<400> SEQUENCE: 1213

Leu Pro Thr Asp Ser His Phe Pro Tyr Asp Leu His Leu Arg
1               5                   10

<210> SEQ ID NO 1214
<211> LENGTH: 28
<212> TYPE: PRT
<213> ORGANISM: Homo sapiens

<400> SEQUENCE: 1214

Ser Pro Tyr Ser Thr Phe Tyr Pro Pro Tyr His Ser Pro Glu Leu Thr
1               5                   10                  15

Thr Pro Pro Gly His Gly Thr Leu Asp Asn Ser Lys
                20                  25

<210> SEQ ID NO 1215
<211> LENGTH: 15
<212> TYPE: PRT
<213> ORGANISM: Homo sapiens

<400> SEQUENCE: 1215

Gly Asp Ala Phe Asp Phe Asn Val Ala Leu Gln Asp His Phe Lys
1               5                   10                  15

<210> SEQ ID NO 1216
<211> LENGTH: 27
<212> TYPE: PRT
<213> ORGANISM: Homo sapiens

<400> SEQUENCE: 1216

Thr Ser Gly Glu Leu Phe Ala Gln Ala Pro Val Asp Gln Phe Pro Gly
1               5                   10                  15

Thr Ala Val Glu Ser Val Thr Asp Ser Ser Arg
            20                  25

<210> SEQ ID NO 1217
<211> LENGTH: 20
<212> TYPE: PRT
<213> ORGANISM: Homo sapiens

<400> SEQUENCE: 1217

Gly Thr Gly Ala Thr Ala Asp Phe Ala Asp Val Ala Asp Asp Phe Glu
1               5                   10                  15

Asn Tyr His Lys
            20

<210> SEQ ID NO 1218
<211> LENGTH: 15
<212> TYPE: PRT
<213> ORGANISM: Homo sapiens

<400> SEQUENCE: 1218

His Ala Glu Gly Gly Ile Phe Thr Ser Pro Asn Tyr Pro Ser Lys
1               5                   10                  15

<210> SEQ ID NO 1219
<211> LENGTH: 9
<212> TYPE: PRT
<213> ORGANISM: Homo sapiens

<400> SEQUENCE: 1219

Gln Leu Gly Leu Ser Gly Ile Ala Lys
1               5

<210> SEQ ID NO 1220
<211> LENGTH: 10
<212> TYPE: PRT
<213> ORGANISM: Homo sapiens

<400> SEQUENCE: 1220

Ser Pro Pro Ala Ser Trp Ala Gln Leu Arg
1               5                   10

<210> SEQ ID NO 1221
<211> LENGTH: 10
<212> TYPE: PRT
<213> ORGANISM: Homo sapiens -continued

<400> SEQUENCE: 1221

Ala Ser Thr Asp Asn Ser Pro Ser Ser Lys
1               5                   10

<210> SEQ ID NO 1222
<211> LENGTH: 28
<212> TYPE: PRT
<213> ORGANISM: Homo sapiens

<400> SEQUENCE: 1222

Ala Thr Ala Gln Pro Pro Thr Glu Thr Gly Glu Ser Ser Gln Ala Glu
1               5                   10                  15

Glu Asn Ile Glu Ala Val Asp Glu Thr Lys Pro Lys
            20                  25

<210> SEQ ID NO 1223
<211> LENGTH: 24
<212> TYPE: PRT
<213> ORGANISM: Homo sapiens

<400> SEQUENCE: 1223

Gln Ala Asp Val Pro Ala Ala Val Thr Ala Ala Ala Thr Thr Pro
1               5                   10                  15

Ala Ala Glu Asp Ala Ala Ala Lys
            20

<210> SEQ ID NO 1224
<211> LENGTH: 8
<212> TYPE: PRT
<213> ORGANISM: Homo sapiens

<400> SEQUENCE: 1224

Ala Leu Tyr Glu Gln Glu Ile Arg
1               5

<210> SEQ ID NO 1225
<211> LENGTH: 15
<212> TYPE: PRT
<213> ORGANISM: Homo sapiens

<400> SEQUENCE: 1225

Glu Glu Glu Glu Gly Gly Glu Gly Glu Gly Glu Glu Thr Lys
1               5                   10                  15

<210> SEQ ID NO 1226
<211> LENGTH: 10
<212> TYPE: PRT
<213> ORGANISM: Homo sapiens

<400> SEQUENCE: 1226

Phe Thr Val Leu Thr Glu Ser Ala Ala Lys
1               5                   10

<210> SEQ ID NO 1227
<211> LENGTH: 15
<212> TYPE: PRT
<213> ORGANISM: Homo sapiens

<400> SEQUENCE: 1227

Thr Ser Leu Phe Pro Tyr Ala Leu Gln Gly Pro Ala Gly Phe Lys
1               5                   10                  15

<210> SEQ ID NO 1228

```
<211> LENGTH: 14
<212> TYPE: PRT
<213> ORGANISM: Homo sapiens

<400> SEQUENCE: 1228

Asp Leu Ser Phe Thr Glu Glu Gly Tyr Gln Val His Pro Arg
1               5                   10

<210> SEQ ID NO 1229
<211> LENGTH: 10
<212> TYPE: PRT
<213> ORGANISM: Homo sapiens

<400> SEQUENCE: 1229

Gly Pro Ala Pro Ser Ala Ala Ala Glu Lys
1               5                   10

<210> SEQ ID NO 1230
<211> LENGTH: 14
<212> TYPE: PRT
<213> ORGANISM: Homo sapiens

<400> SEQUENCE: 1230

His Ser Leu Pro Ser Gln Ala Val Asn Asp Ser Tyr Leu Arg
1               5                   10

<210> SEQ ID NO 1231
<211> LENGTH: 12
<212> TYPE: PRT
<213> ORGANISM: Homo sapiens

<400> SEQUENCE: 1231

Phe Ser Tyr Asp Leu Tyr Leu Val Thr Asn Gly Lys
1               5                   10

<210> SEQ ID NO 1232
<211> LENGTH: 12
<212> TYPE: PRT
<213> ORGANISM: Homo sapiens

<400> SEQUENCE: 1232

Tyr Ser Ala Ser Leu Gln Pro Val Val Asp Ser Arg
1               5                   10

<210> SEQ ID NO 1233
<211> LENGTH: 8
<212> TYPE: PRT
<213> ORGANISM: Homo sapiens

<400> SEQUENCE: 1233

Ile Thr Gly Ile Asn Asp Pro Arg
1               5

<210> SEQ ID NO 1234
<211> LENGTH: 16
<212> TYPE: PRT
<213> ORGANISM: Homo sapiens

<400> SEQUENCE: 1234

Val Ile Ile Leu Ser Ala Ser Glu Asp Asp Ala Ala Thr Val Tyr Arg
1               5                   10                  15

<210> SEQ ID NO 1235
<211> LENGTH: 15
<212> TYPE: PRT
```

<213> ORGANISM: Homo sapiens

<400> SEQUENCE: 1235

Glu Gly Trp Gln Val Tyr Ser Ser Ala Gln Asp Pro Asp Gly Arg
1               5                   10                  15

<210> SEQ ID NO 1236
<211> LENGTH: 13
<212> TYPE: PRT
<213> ORGANISM: Homo sapiens

<400> SEQUENCE: 1236

Leu Ser Thr Pro Asp Thr Leu Thr Gln Ile Ser Pro Lys
1               5                   10

<210> SEQ ID NO 1237
<211> LENGTH: 13
<212> TYPE: PRT
<213> ORGANISM: Homo sapiens

<400> SEQUENCE: 1237

Ser Ser Ile Leu Gly Gly Gln Phe Ala Ile Trp Glu Lys
1               5                   10

<210> SEQ ID NO 1238
<211> LENGTH: 8
<212> TYPE: PRT
<213> ORGANISM: Homo sapiens

<400> SEQUENCE: 1238

Thr Glu Leu Ser Pro Thr Ala Arg
1               5

<210> SEQ ID NO 1239
<211> LENGTH: 22
<212> TYPE: PRT
<213> ORGANISM: Homo sapiens

<400> SEQUENCE: 1239

Ala Leu Ser Gly Asn Val Ile Ala Trp Ala Glu Ser His Ile Glu Ile
1               5                   10                  15

Tyr Gly Gly Ala Thr Lys
            20

<210> SEQ ID NO 1240
<211> LENGTH: 11
<212> TYPE: PRT
<213> ORGANISM: Homo sapiens

<400> SEQUENCE: 1240

Ile Glu Thr Ala Leu Thr Ser Leu His Gln Arg
1               5                   10

<210> SEQ ID NO 1241
<211> LENGTH: 18
<212> TYPE: PRT
<213> ORGANISM: Homo sapiens

<400> SEQUENCE: 1241

Thr Pro Ala Ala Glu Thr Leu Ser Gln Leu Gly Gln Thr Leu Gln Ser
1               5                   10                  15

Leu Lys

```
<210> SEQ ID NO 1242
<211> LENGTH: 12
<212> TYPE: PRT
<213> ORGANISM: Homo sapiens

<400> SEQUENCE: 1242

Glu Thr Asn Pro Tyr Phe Asn Ser Leu Glu Gln Lys
1               5                   10

<210> SEQ ID NO 1243
<211> LENGTH: 11
<212> TYPE: PRT
<213> ORGANISM: Homo sapiens

<400> SEQUENCE: 1243

Ile Leu Leu Glu Thr Val Gln Glu Gln Ile Arg
1               5                   10

<210> SEQ ID NO 1244
<211> LENGTH: 16
<212> TYPE: PRT
<213> ORGANISM: Homo sapiens

<400> SEQUENCE: 1244

Leu Gly Gly Ile Val Gly Pro Ala Tyr Gln Gln Leu Glu Glu Ser Arg
1               5                   10                  15

<210> SEQ ID NO 1245
<211> LENGTH: 20
<212> TYPE: PRT
<213> ORGANISM: Homo sapiens

<400> SEQUENCE: 1245

Gly Asn Pro Lys Pro Ala Leu Gln Trp Phe Tyr Asn Gly Ala Ile Leu
1               5                   10                  15

Asn Glu Ser Lys
            20

<210> SEQ ID NO 1246
<211> LENGTH: 8
<212> TYPE: PRT
<213> ORGANISM: Homo sapiens

<400> SEQUENCE: 1246

Gly Ile Asp Leu Thr Gln Val Lys
1               5

<210> SEQ ID NO 1247
<211> LENGTH: 14
<212> TYPE: PRT
<213> ORGANISM: Homo sapiens

<400> SEQUENCE: 1247

Ile Asn Glu Gly Asp Leu Ile Ala Glu Val Glu Thr Asp Lys
1               5                   10

<210> SEQ ID NO 1248
<211> LENGTH: 9
<212> TYPE: PRT
<213> ORGANISM: Homo sapiens

<400> SEQUENCE: 1248

Ile Ser Val Asn Asp Phe Ile Ile Lys
1               5
```

```
<210> SEQ ID NO 1249
<211> LENGTH: 14
<212> TYPE: PRT
<213> ORGANISM: Homo sapiens

<400> SEQUENCE: 1249

Gln Leu Tyr Ala Trp Asp Asp Gly Tyr Gln Ile Val Tyr Lys
1               5                   10

<210> SEQ ID NO 1250
<211> LENGTH: 8
<212> TYPE: PRT
<213> ORGANISM: Homo sapiens

<400> SEQUENCE: 1250

Val Thr Gly Gly Pro Gly Thr Lys
1               5

<210> SEQ ID NO 1251
<211> LENGTH: 11
<212> TYPE: PRT
<213> ORGANISM: Homo sapiens

<400> SEQUENCE: 1251

Ile Thr Val Asn Tyr Pro Pro Tyr Ile Ser Lys
1               5                   10

<210> SEQ ID NO 1252
<211> LENGTH: 25
<212> TYPE: PRT
<213> ORGANISM: Homo sapiens

<400> SEQUENCE: 1252

Leu Gly Asn Thr Asn Ala Ser Ile Thr Leu Tyr Gly Pro Gly Ala Val
1               5                   10                  15

Ile Asp Gly Val Asn Ser Ala Ser Arg
            20                  25

<210> SEQ ID NO 1253
<211> LENGTH: 10
<212> TYPE: PRT
<213> ORGANISM: Homo sapiens

<400> SEQUENCE: 1253

Ser Thr Ile Leu Tyr Ala Gly Asn Asp Lys
1               5                   10

<210> SEQ ID NO 1254
<211> LENGTH: 11
<212> TYPE: PRT
<213> ORGANISM: Homo sapiens

<400> SEQUENCE: 1254

Phe Pro Glu Ile Leu Leu Gln Ala Ala Ser Lys
1               5                   10

<210> SEQ ID NO 1255
<211> LENGTH: 10
<212> TYPE: PRT
<213> ORGANISM: Homo sapiens

<400> SEQUENCE: 1255

Glu Ala Glu Asn Phe Thr Leu Phe Ile Lys
1               5                   10
```

<210> SEQ ID NO 1256
<211> LENGTH: 15
<212> TYPE: PRT
<213> ORGANISM: Homo sapiens

<400> SEQUENCE: 1256

Gly Tyr Gln Thr Ser Ser Gly Leu Ile Ser Ser Val Ser Val Lys
1               5                   10                  15

<210> SEQ ID NO 1257
<211> LENGTH: 19
<212> TYPE: PRT
<213> ORGANISM: Homo sapiens

<400> SEQUENCE: 1257

Val Ala Ala Ala Ala Gly Ser Gly Pro Ser Pro Pro Gly Ser Pro Gly
1               5                   10                  15

His Asp Arg

<210> SEQ ID NO 1258
<211> LENGTH: 16
<212> TYPE: PRT
<213> ORGANISM: Homo sapiens

<400> SEQUENCE: 1258

Ala Leu Tyr Asp Tyr Asp Gly Gln Glu Gln Asp Glu Leu Ser Phe Lys
1               5                   10                  15

<210> SEQ ID NO 1259
<211> LENGTH: 9
<212> TYPE: PRT
<213> ORGANISM: Homo sapiens

<400> SEQUENCE: 1259

Gly Pro Gln Tyr Gly Ser Leu Glu Arg
1               5

<210> SEQ ID NO 1260
<211> LENGTH: 17
<212> TYPE: PRT
<213> ORGANISM: Homo sapiens

<400> SEQUENCE: 1260

Leu Asp Ser Gly Gln Leu Gly Leu Tyr Pro Ala Asn Tyr Val Glu Ala
1               5                   10                  15

Ile

<210> SEQ ID NO 1261
<211> LENGTH: 18
<212> TYPE: PRT
<213> ORGANISM: Homo sapiens

<400> SEQUENCE: 1261

Ala Leu Tyr Leu Ile Ala Thr Asn Gly Thr Pro Glu Leu Gln Asn Pro
1               5                   10                  15

Glu Arg

<210> SEQ ID NO 1262
<211> LENGTH: 9
<212> TYPE: PRT
<213> ORGANISM: Homo sapiens

```
<400> SEQUENCE: 1262

Glu Leu Leu Gln His Pro Phe Leu Lys
1               5

<210> SEQ ID NO 1263
<211> LENGTH: 24
<212> TYPE: PRT
<213> ORGANISM: Homo sapiens

<400> SEQUENCE: 1263

Ile Gly Gln Gly Ala Ser Gly Thr Val Tyr Thr Ala Leu Asp Ile Ala
1               5                   10                  15

Thr Gly Gln Glu Val Ala Ile Lys
            20

<210> SEQ ID NO 1264
<211> LENGTH: 11
<212> TYPE: PRT
<213> ORGANISM: Homo sapiens

<400> SEQUENCE: 1264

Leu Leu Ala Leu Ala Gly Gly Pro Gly Phe Arg
1               5                   10

<210> SEQ ID NO 1265
<211> LENGTH: 18
<212> TYPE: PRT
<213> ORGANISM: Homo sapiens

<400> SEQUENCE: 1265

Thr Gly Ala Phe Ala Tyr Pro Phe Leu Phe Asp Asn Leu Pro Leu Phe
1               5                   10                  15

Tyr Arg

<210> SEQ ID NO 1266
<211> LENGTH: 12
<212> TYPE: PRT
<213> ORGANISM: Homo sapiens

<400> SEQUENCE: 1266

Tyr Gly Thr Glu Lys Pro Leu Gly Phe Tyr Ile Arg
1               5                   10

<210> SEQ ID NO 1267
<211> LENGTH: 14
<212> TYPE: PRT
<213> ORGANISM: Homo sapiens

<400> SEQUENCE: 1267

Ala Glu Asp Glu Asp Ile Val Leu Thr Pro Asp Gly Thr Arg
1               5                   10

<210> SEQ ID NO 1268
<211> LENGTH: 19
<212> TYPE: PRT
<213> ORGANISM: Homo sapiens

<400> SEQUENCE: 1268

Ser Pro Gly Ser Pro Gly Pro Glu Leu Pro Ile Glu Thr Ala Leu
1               5                   10                  15

Asp Asp Arg
```

```
<210> SEQ ID NO 1269
<211> LENGTH: 16
<212> TYPE: PRT
<213> ORGANISM: Homo sapiens

<400> SEQUENCE: 1269

Val Asn Asp Gln Leu Ile Ala Val Asn Gly Glu Ser Leu Leu Gly Lys
1               5                   10                  15

<210> SEQ ID NO 1270
<211> LENGTH: 7
<212> TYPE: PRT
<213> ORGANISM: Homo sapiens

<400> SEQUENCE: 1270

Glu Val Ala Ala Gln Val Lys
1               5

<210> SEQ ID NO 1271
<211> LENGTH: 9
<212> TYPE: PRT
<213> ORGANISM: Homo sapiens

<400> SEQUENCE: 1271

Val Thr Val Ala Gly Leu Ala Gly Lys
1               5

<210> SEQ ID NO 1272
<211> LENGTH: 14
<212> TYPE: PRT
<213> ORGANISM: Homo sapiens

<400> SEQUENCE: 1272

Gly Asp Ser Glu Ala Gly Asp Ser Asp Tyr Asp Leu Gly Arg
1               5                   10

<210> SEQ ID NO 1273
<211> LENGTH: 11
<212> TYPE: PRT
<213> ORGANISM: Homo sapiens

<400> SEQUENCE: 1273

Leu Ser Glu Asp Val Ala Asp Val Leu Leu Lys
1               5                   10

<210> SEQ ID NO 1274
<211> LENGTH: 16
<212> TYPE: PRT
<213> ORGANISM: Homo sapiens

<400> SEQUENCE: 1274

Ser Leu Ile Pro Ile Glu Ile Ser Glu Ser Ala Ala Val Gly Thr Arg
1               5                   10                  15

<210> SEQ ID NO 1275
<211> LENGTH: 17
<212> TYPE: PRT
<213> ORGANISM: Homo sapiens

<400> SEQUENCE: 1275

Glu Asp Ala Pro Leu Ser Thr Val Ile Ala Leu Ile Ser Val Ser Asp
1               5                   10                  15

Arg
```

```
<210> SEQ ID NO 1276
<211> LENGTH: 13
<212> TYPE: PRT
<213> ORGANISM: Homo sapiens

<400> SEQUENCE: 1276

Glu Ser Val Ser Val Tyr Glu Leu Val Val Thr Ala Arg
1               5                   10

<210> SEQ ID NO 1277
<211> LENGTH: 18
<212> TYPE: PRT
<213> ORGANISM: Homo sapiens

<400> SEQUENCE: 1277

Phe Pro Leu Glu Gly Ala Ser Asp Leu Asp Ile Gly Ala Asn Ala Gln
1               5                   10                  15

Leu Arg

<210> SEQ ID NO 1278
<211> LENGTH: 24
<212> TYPE: PRT
<213> ORGANISM: Homo sapiens

<400> SEQUENCE: 1278

Ala Val Asp Ala Asp Ser Gly Tyr Asn Ala Trp Leu Ser Tyr Glu Leu
1               5                   10                  15

Gln Ser Ala Ala Val Gly Ala Arg
            20

<210> SEQ ID NO 1279
<211> LENGTH: 20
<212> TYPE: PRT
<213> ORGANISM: Homo sapiens

<400> SEQUENCE: 1279

Phe Pro Leu Glu Gly Ala Ser Asp Ala Asp Val Gly Glu Asn Ala Leu
1               5                   10                  15

Leu Thr Tyr Lys
            20

<210> SEQ ID NO 1280
<211> LENGTH: 13
<212> TYPE: PRT
<213> ORGANISM: Homo sapiens

<400> SEQUENCE: 1280

Leu Thr Leu Ile Ala Leu Asp Gly Gly Ser Pro Pro Arg
1               5                   10

<210> SEQ ID NO 1281
<211> LENGTH: 25
<212> TYPE: PRT
<213> ORGANISM: Homo sapiens

<400> SEQUENCE: 1281

Val Ser Tyr Ala Leu Phe Gln Val Asp Asp Val Asn Gln Pro Phe Glu
1               5                   10                  15

Ile Asn Ala Ile Thr Gly Glu Ile Arg
            20                  25

<210> SEQ ID NO 1282
<211> LENGTH: 20
```

```
<212> TYPE: PRT
<213> ORGANISM: Homo sapiens

<400> SEQUENCE: 1282

Glu Glu Ile Pro Glu Phe Ser Leu Thr Leu Thr Ala Leu Asp Gly Gly
1               5                   10                  15

Ser Pro Pro Arg
            20

<210> SEQ ID NO 1283
<211> LENGTH: 17
<212> TYPE: PRT
<213> ORGANISM: Homo sapiens

<400> SEQUENCE: 1283

Glu Asn Asn Ser Pro Ala Leu Pro Ile Gly Ser Val Ser Ala Thr Asp
1               5                   10                  15

Arg

<210> SEQ ID NO 1284
<211> LENGTH: 14
<212> TYPE: PRT
<213> ORGANISM: Homo sapiens

<400> SEQUENCE: 1284

Glu Val Glu Glu Asn Arg Pro Phe Gln Asn Asn Leu Gly Phe
1               5                   10

<210> SEQ ID NO 1285
<211> LENGTH: 17
<212> TYPE: PRT
<213> ORGANISM: Homo sapiens

<400> SEQUENCE: 1285

Glu Asn Asn Ser Pro Ala Leu His Ile Gly Ser Ile Ser Ala Thr Asp
1               5                   10                  15

Arg

<210> SEQ ID NO 1286
<211> LENGTH: 13
<212> TYPE: PRT
<213> ORGANISM: Homo sapiens

<400> SEQUENCE: 1286

Asn Pro Thr Gln Phe Leu Gln Ile Glu Leu Gln Val Arg
1               5                   10

<210> SEQ ID NO 1287
<211> LENGTH: 12
<212> TYPE: PRT
<213> ORGANISM: Homo sapiens

<400> SEQUENCE: 1287

Thr Leu Gly Leu Glu Val Ser Glu Leu Ser Ser Arg
1               5                   10

<210> SEQ ID NO 1288
<211> LENGTH: 16
<212> TYPE: PRT
<213> ORGANISM: Homo sapiens

<400> SEQUENCE: 1288

Asp Ser Gly Thr Asn Ala Gln Val Thr Tyr Ser Leu Leu Pro Pro Arg
```

-continued

```
                1               5                  10                 15
```

<210> SEQ ID NO 1289
<211> LENGTH: 17
<212> TYPE: PRT
<213> ORGANISM: Homo sapiens

<400> SEQUENCE: 1289

```
Glu Asp Val Pro Pro Gly Phe Phe Val Leu Gln Val Thr Ala Thr Asp
1               5                   10                  15

Arg
```

<210> SEQ ID NO 1290
<211> LENGTH: 14
<212> TYPE: PRT
<213> ORGANISM: Homo sapiens

<400> SEQUENCE: 1290

```
Asp Gln Gly Ser Pro Thr Leu Ser Ala Asn Val Ser Leu Arg
1               5                   10
```

<210> SEQ ID NO 1291
<211> LENGTH: 15
<212> TYPE: PRT
<213> ORGANISM: Homo sapiens

<400> SEQUENCE: 1291

```
Val Asn Val Ala Glu Asn Leu Pro Ala Gly Ser Ser Val Leu Lys
1               5                   10                  15
```

<210> SEQ ID NO 1292
<211> LENGTH: 12
<212> TYPE: PRT
<213> ORGANISM: Homo sapiens

<400> SEQUENCE: 1292

```
Gly Glu Ala Ala Gly Ala Val Gln Glu Leu Ala Arg
1               5                   10
```

<210> SEQ ID NO 1293
<211> LENGTH: 21
<212> TYPE: PRT
<213> ORGANISM: Homo sapiens

<400> SEQUENCE: 1293

```
Asn Ser Asp Pro Ala Leu Gly Leu Asp Asp Pro Asp Ala Pro Ala
1               5                   10                  15

Ala Gln Leu Ala Arg
            20
```

<210> SEQ ID NO 1294
<211> LENGTH: 7
<212> TYPE: PRT
<213> ORGANISM: Homo sapiens

<400> SEQUENCE: 1294

```
Val Leu Ala Gln Leu Leu Arg
1               5
```

<210> SEQ ID NO 1295
<211> LENGTH: 7
<212> TYPE: PRT
<213> ORGANISM: Homo sapiens

```
<400> SEQUENCE: 1295

Asp Leu Glu Thr Phe Ser Lys
1               5

<210> SEQ ID NO 1296
<211> LENGTH: 15
<212> TYPE: PRT
<213> ORGANISM: Homo sapiens

<400> SEQUENCE: 1296

Glu Leu Ala Glu Glu Phe Gly Val Thr Glu Tyr Pro Thr Leu Lys
1               5                   10                  15

<210> SEQ ID NO 1297
<211> LENGTH: 7
<212> TYPE: PRT
<213> ORGANISM: Homo sapiens

<400> SEQUENCE: 1297

Gly Leu Ser Asp Gly Phe Arg
1               5

<210> SEQ ID NO 1298
<211> LENGTH: 12
<212> TYPE: PRT
<213> ORGANISM: Homo sapiens

<400> SEQUENCE: 1298

Ser Val Gly Glu Gly Pro Tyr Ser Glu Leu Ala Lys
1               5                   10

<210> SEQ ID NO 1299
<211> LENGTH: 12
<212> TYPE: PRT
<213> ORGANISM: Homo sapiens

<400> SEQUENCE: 1299

Asp Thr Asp Thr Gly Ala Leu Leu Phe Ile Gly Lys
1               5                   10

<210> SEQ ID NO 1300
<211> LENGTH: 11
<212> TYPE: PRT
<213> ORGANISM: Homo sapiens

<400> SEQUENCE: 1300

Glu Leu Leu Asp Thr Val Thr Ala Pro Gln Lys
1               5                   10

<210> SEQ ID NO 1301
<211> LENGTH: 10
<212> TYPE: PRT
<213> ORGANISM: Homo sapiens

<400> SEQUENCE: 1301

Thr Val Gln Ala Val Leu Thr Val Pro Lys
1               5                   10

<210> SEQ ID NO 1302
<211> LENGTH: 7
<212> TYPE: PRT
<213> ORGANISM: Homo sapiens

<400> SEQUENCE: 1302
```

```
Gly Val Val Phe Leu Tyr Arg
1               5
```

<210> SEQ ID NO 1303
<211> LENGTH: 9
<212> TYPE: PRT
<213> ORGANISM: Homo sapiens

<400> SEQUENCE: 1303

```
Tyr Pro Ile Val Thr Pro Ser Gln Arg
1               5
```

<210> SEQ ID NO 1304
<211> LENGTH: 18
<212> TYPE: PRT
<213> ORGANISM: Homo sapiens

<400> SEQUENCE: 1304

```
Thr Tyr Pro Asp Thr Asp Ser Phe Asn Thr Val Ala Glu Ile Thr Gly
1               5                   10                  15

Ser Lys
```

<210> SEQ ID NO 1305
<211> LENGTH: 9
<212> TYPE: PRT
<213> ORGANISM: Homo sapiens

<400> SEQUENCE: 1305

```
Val Gly Ala Leu Ala Ser Leu Ile Arg
1               5
```

<210> SEQ ID NO 1306
<211> LENGTH: 20
<212> TYPE: PRT
<213> ORGANISM: Homo sapiens

<400> SEQUENCE: 1306

```
Ala Thr Thr Leu Ser Asn Ala Val Ser Ser Leu Ala Ser Thr Gly Leu
1               5                   10                  15

Ser Leu Thr Lys
            20
```

<210> SEQ ID NO 1307
<211> LENGTH: 25
<212> TYPE: PRT
<213> ORGANISM: Homo sapiens

<400> SEQUENCE: 1307

```
Leu Val Ser Asp Asp Leu Asp Ser Ser Leu Ala Asn Leu Val Gly Asn
1               5                   10                  15

Leu Gly Ile Gly Asn Gly Thr Thr Lys
            20                  25
```

<210> SEQ ID NO 1308
<211> LENGTH: 33
<212> TYPE: PRT
<213> ORGANISM: Homo sapiens

<400> SEQUENCE: 1308

```
Ser Thr Asn Val Ile Val Asp Ser Gly Gly Phe Asp Glu Leu Gly Gly
1               5                   10                  15

Leu Leu Lys Pro Thr Val Ala Ser Gln Asn Gln Asn Leu Pro Val Ala
            20                  25                  30
```

Lys

<210> SEQ ID NO 1309
<211> LENGTH: 8
<212> TYPE: PRT
<213> ORGANISM: Homo sapiens

<400> SEQUENCE: 1309

Gly Asp Leu Gly Ala Phe Ser Arg
1               5

<210> SEQ ID NO 1310
<211> LENGTH: 14
<212> TYPE: PRT
<213> ORGANISM: Homo sapiens

<400> SEQUENCE: 1310

Val Trp Gln Ala Asn Gln Ala Leu Gln Glu Tyr Gln Gln Lys
1               5                   10

<210> SEQ ID NO 1311
<211> LENGTH: 17
<212> TYPE: PRT
<213> ORGANISM: Homo sapiens

<400> SEQUENCE: 1311

Trp Pro Trp Ala Ser Gly Pro Val Leu Thr Leu Leu Pro Glu Thr Leu
1               5                   10                  15

Lys

<210> SEQ ID NO 1312
<211> LENGTH: 19
<212> TYPE: PRT
<213> ORGANISM: Homo sapiens

<400> SEQUENCE: 1312

Asp Tyr Val Pro Asp Thr Tyr Ala Asp Val Ile Glu Ala Leu Ser Asn
1               5                   10                  15

Pro Ile Arg

<210> SEQ ID NO 1313
<211> LENGTH: 10
<212> TYPE: PRT
<213> ORGANISM: Homo sapiens

<400> SEQUENCE: 1313

Ser Pro Val Glu Phe Val Glu Tyr Asn Lys
1               5                   10

<210> SEQ ID NO 1314
<211> LENGTH: 24
<212> TYPE: PRT
<213> ORGANISM: Homo sapiens

<400> SEQUENCE: 1314

Gly Ile Glu Thr Gly Ser Glu Asp Leu Glu Ile Leu Pro Asn Gly Leu
1               5                   10                  15

Ala Phe Ile Ser Ser Gly Leu Lys
            20

<210> SEQ ID NO 1315
<211> LENGTH: 16

```
<212> TYPE: PRT
<213> ORGANISM: Homo sapiens

<400> SEQUENCE: 1315

Ile Phe Phe Tyr Asp Ser Glu Asn Pro Pro Ala Ser Glu Val Leu Arg
1               5                   10                  15

<210> SEQ ID NO 1316
<211> LENGTH: 11
<212> TYPE: PRT
<213> ORGANISM: Homo sapiens

<400> SEQUENCE: 1316

Tyr Val Tyr Ile Ala Glu Leu Leu Ala His Lys
1               5                   10

<210> SEQ ID NO 1317
<211> LENGTH: 10
<212> TYPE: PRT
<213> ORGANISM: Homo sapiens

<400> SEQUENCE: 1317

Gly Glu Asn Phe Thr Glu Thr Asp Val Lys
1               5                   10

<210> SEQ ID NO 1318
<211> LENGTH: 11
<212> TYPE: PRT
<213> ORGANISM: Homo sapiens

<400> SEQUENCE: 1318

Tyr Pro Gly Gln Gly Ser Pro Gly Gly Asn Arg
1               5                   10

<210> SEQ ID NO 1319
<211> LENGTH: 6
<212> TYPE: PRT
<213> ORGANISM: Homo sapiens

<400> SEQUENCE: 1319

His Val Thr Asp Tyr Lys
1               5

<210> SEQ ID NO 1320
<211> LENGTH: 10
<212> TYPE: PRT
<213> ORGANISM: Homo sapiens

<400> SEQUENCE: 1320

Thr Ser Leu Glu Val Ser Leu Leu Glu Lys
1               5                   10

<210> SEQ ID NO 1321
<211> LENGTH: 8
<212> TYPE: PRT
<213> ORGANISM: Homo sapiens

<400> SEQUENCE: 1321

Glu Tyr Leu Leu Ser Ala Ser Arg
1               5

<210> SEQ ID NO 1322
<211> LENGTH: 9
<212> TYPE: PRT
<213> ORGANISM: Homo sapiens
```

<400> SEQUENCE: 1322

Gln Glu Gly Val Val Asp Ile Leu Lys
1               5

<210> SEQ ID NO 1323
<211> LENGTH: 10
<212> TYPE: PRT
<213> ORGANISM: Homo sapiens

<400> SEQUENCE: 1323

Thr Val Pro Ala Ala Val Thr Asp Leu Arg
1               5                   10

<210> SEQ ID NO 1324
<211> LENGTH: 16
<212> TYPE: PRT
<213> ORGANISM: Homo sapiens

<400> SEQUENCE: 1324

Thr Val Pro Ser Ser Val Ser Gly Val Thr Val Asn Asn Ser Gly Arg
1               5                   10                  15

<210> SEQ ID NO 1325
<211> LENGTH: 14
<212> TYPE: PRT
<213> ORGANISM: Homo sapiens

<400> SEQUENCE: 1325

Ser Thr Leu Val Glu Tyr Ser Gly Val Ser His Glu Pro Lys
1               5                   10

<210> SEQ ID NO 1326
<211> LENGTH: 18
<212> TYPE: PRT
<213> ORGANISM: Homo sapiens

<400> SEQUENCE: 1326

Glu Glu Tyr Glu Ala Leu Pro Glu Gly Gln Thr Ala Ser Trp Asp Thr
1               5                   10                  15

Ala Lys

<210> SEQ ID NO 1327
<211> LENGTH: 16
<212> TYPE: PRT
<213> ORGANISM: Homo sapiens

<400> SEQUENCE: 1327

Ser Asp Gly Gly Ser Gly Val Ser Asn Tyr Ala Glu Leu Ile Val Lys
1               5                   10                  15

<210> SEQ ID NO 1328
<211> LENGTH: 18
<212> TYPE: PRT
<213> ORGANISM: Homo sapiens

<400> SEQUENCE: 1328

Gly Ser Phe Ala Leu Ser Phe Pro Val Glu Ser Asp Val Ala Pro Ile
1               5                   10                  15

Ala Arg

<210> SEQ ID NO 1329
<211> LENGTH: 23

<212> TYPE: PRT
<213> ORGANISM: Homo sapiens

<400> SEQUENCE: 1329

Gln Gln Asn Ala Gln Gly Gly Phe Ser Ser Thr Gln Asp Thr Val Val
1               5                   10                  15

Ala Leu His Ala Leu Ser Arg
            20

<210> SEQ ID NO 1330
<211> LENGTH: 10
<212> TYPE: PRT
<213> ORGANISM: Homo sapiens

<400> SEQUENCE: 1330

Gln Thr Leu Ser Trp Thr Val Thr Pro Lys
1               5                   10

<210> SEQ ID NO 1331
<211> LENGTH: 15
<212> TYPE: PRT
<213> ORGANISM: Homo sapiens

<400> SEQUENCE: 1331

Ile Asp Asn Asp Gly Asp Gly Phe Val Thr Thr Glu Glu Leu Lys
1               5                   10                  15

<210> SEQ ID NO 1332
<211> LENGTH: 7
<212> TYPE: PRT
<213> ORGANISM: Homo sapiens

<400> SEQUENCE: 1332

Ile Ser Trp Glu Glu Tyr Lys
1               5

<210> SEQ ID NO 1333
<211> LENGTH: 7
<212> TYPE: PRT
<213> ORGANISM: Homo sapiens

<400> SEQUENCE: 1333

Phe Leu Gln Phe Thr Leu Arg
1               5

<210> SEQ ID NO 1334
<211> LENGTH: 14
<212> TYPE: PRT
<213> ORGANISM: Homo sapiens

<400> SEQUENCE: 1334

Phe Ser Tyr Ser Asp Pro Ser Ile Ile Val Leu Tyr Ala Lys
1               5                   10

<210> SEQ ID NO 1335
<211> LENGTH: 19
<212> TYPE: PRT
<213> ORGANISM: Homo sapiens

<400> SEQUENCE: 1335

Val Pro Ser Leu Val Ser Val Val Ile Asn Pro Glu Leu Gln Thr Pro
1               5                   10                  15

Ala Thr Lys

<210> SEQ ID NO 1336
<211> LENGTH: 8
<212> TYPE: PRT
<213> ORGANISM: Homo sapiens

<400> SEQUENCE: 1336

Gln Glu Val Ala Asn Pro Val Lys
1               5

<210> SEQ ID NO 1337
<211> LENGTH: 7
<212> TYPE: PRT
<213> ORGANISM: Homo sapiens

<400> SEQUENCE: 1337

Thr Thr Glu Gln Glu Glu Lys
1               5

<210> SEQ ID NO 1338
<211> LENGTH: 22
<212> TYPE: PRT
<213> ORGANISM: Homo sapiens

<400> SEQUENCE: 1338

Leu Leu Val Thr Val Ile Pro His Ala Val Thr Gly Ser Asp Val Val
1               5                   10                  15

Gln Trp Leu Ala Gln Lys
            20

<210> SEQ ID NO 1339
<211> LENGTH: 9
<212> TYPE: PRT
<213> ORGANISM: Homo sapiens

<400> SEQUENCE: 1339

Asp Leu Leu Gln Ser Leu Ser Glu Lys
1               5

<210> SEQ ID NO 1340
<211> LENGTH: 15
<212> TYPE: PRT
<213> ORGANISM: Homo sapiens

<400> SEQUENCE: 1340

Ser Phe Pro Pro Ala Gln Leu Pro Asp Ser Pro Ala Ala Pro Lys
1               5                   10                  15

<210> SEQ ID NO 1341
<211> LENGTH: 12
<212> TYPE: PRT
<213> ORGANISM: Homo sapiens

<400> SEQUENCE: 1341

Ala Asn Asp Asp Leu Ala Asp Ala Gly Leu Glu Lys
1               5                   10

<210> SEQ ID NO 1342
<211> LENGTH: 23
<212> TYPE: PRT
<213> ORGANISM: Homo sapiens

<400> SEQUENCE: 1342

Leu Ile Pro Gln Leu Pro Thr Leu Glu Asn Leu Leu Asn Ile Phe Ile
1               5                   10                  15

Ser Asn Ser Gly Ile Glu Lys
            20

<210> SEQ ID NO 1343
<211> LENGTH: 10
<212> TYPE: PRT
<213> ORGANISM: Homo sapiens

<400> SEQUENCE: 1343

Leu Asn Asn Thr Thr Val Leu Tyr Leu Lys
1               5                   10

<210> SEQ ID NO 1344
<211> LENGTH: 27
<212> TYPE: PRT
<213> ORGANISM: Homo sapiens

<400> SEQUENCE: 1344

Tyr Thr Ala Glu Pro Ile Asp Asp Ser Ser Glu Glu Phe Val Asn Phe
1               5                   10                  15

Ala Ala Ile Leu Glu Gln Ile Leu Ser His Arg
            20                  25

<210> SEQ ID NO 1345
<211> LENGTH: 13
<212> TYPE: PRT
<213> ORGANISM: Homo sapiens

<400> SEQUENCE: 1345

Glu Ser Ser Pro Phe Ile Asn Ser Thr Asp Thr Glu Lys
1               5                   10

<210> SEQ ID NO 1346
<211> LENGTH: 20
<212> TYPE: PRT
<213> ORGANISM: Homo sapiens

<400> SEQUENCE: 1346

Val Asp Gln Asp Gln Asn Val Val His Pro Gln Leu Leu Ser Leu Thr
1               5                   10                  15

Ser Gln Leu Lys
            20

<210> SEQ ID NO 1347
<211> LENGTH: 8
<212> TYPE: PRT
<213> ORGANISM: Homo sapiens

<400> SEQUENCE: 1347

Leu Asp Glu Asp Leu His Val Lys
1               5

<210> SEQ ID NO 1348
<211> LENGTH: 9
<212> TYPE: PRT
<213> ORGANISM: Homo sapiens

<400> SEQUENCE: 1348

Leu Leu Thr Phe Ala Ser Gln Leu Lys
1               5

<210> SEQ ID NO 1349
<211> LENGTH: 18

```
<212> TYPE: PRT
<213> ORGANISM: Homo sapiens

<400> SEQUENCE: 1349

Leu Thr Ser Ile Gly Ser Asp Glu Asp Glu Thr Glu Thr Tyr Gln
1               5                   10                  15

Glu Lys

<210> SEQ ID NO 1350
<211> LENGTH: 17
<212> TYPE: PRT
<213> ORGANISM: Homo sapiens

<400> SEQUENCE: 1350

Ile Tyr Asn Lys Pro Pro Glu Gly Asn Ile Val Ala Gln Val Phe
1               5                   10                  15

Lys

<210> SEQ ID NO 1351
<211> LENGTH: 17
<212> TYPE: PRT
<213> ORGANISM: Homo sapiens

<400> SEQUENCE: 1351

Val Thr Val Val Gly Asn Glu Asn Ser Leu Leu Ile Glu Ser Ile
1               5                   10                  15

Lys

<210> SEQ ID NO 1352
<211> LENGTH: 13
<212> TYPE: PRT
<213> ORGANISM: Homo sapiens

<400> SEQUENCE: 1352

Ala Ser Glu Glu Glu Pro Glu Tyr Gly Glu Glu Ile Lys
1               5                   10

<210> SEQ ID NO 1353
<211> LENGTH: 12
<212> TYPE: PRT
<213> ORGANISM: Homo sapiens

<400> SEQUENCE: 1353

Ser Ser Gln Gly Gly Ser Leu Pro Ser Glu Glu Lys
1               5                   10

<210> SEQ ID NO 1354
<211> LENGTH: 11
<212> TYPE: PRT
<213> ORGANISM: Homo sapiens

<400> SEQUENCE: 1354

Trp Gln Gln Gln Gly Asp Leu Gln Asp Thr Lys
1               5                   10

<210> SEQ ID NO 1355
<211> LENGTH: 22
<212> TYPE: PRT
<213> ORGANISM: Homo sapiens

<400> SEQUENCE: 1355

Glu Ala Asn Asn Tyr Glu Glu Asp Pro Asn Lys Pro Thr Ser Trp Thr
1               5                   10                  15
```

Glu Asn Gln Ala Gly Lys
            20

<210> SEQ ID NO 1356
<211> LENGTH: 20
<212> TYPE: PRT
<213> ORGANISM: Homo sapiens

<400> SEQUENCE: 1356

Asp Phe Ser Gly Ala Gly Gly Ile Gly Val Phe Ser Glu Ser Ser Ser
1               5                   10                  15

Val Ala Ser Lys
            20

<210> SEQ ID NO 1357
<211> LENGTH: 15
<212> TYPE: PRT
<213> ORGANISM: Homo sapiens

<400> SEQUENCE: 1357

Asp Gly Asn Gly Thr Thr Ser Gly Ile Gly Ser Ser Val Glu Lys
1               5                   10                  15

<210> SEQ ID NO 1358
<211> LENGTH: 14
<212> TYPE: PRT
<213> ORGANISM: Homo sapiens

<400> SEQUENCE: 1358

Thr Val Ser Ile Phe Asn Trp Asp Glu Tyr Ile Glu Asp Lys
1               5                   10

<210> SEQ ID NO 1359
<211> LENGTH: 17
<212> TYPE: PRT
<213> ORGANISM: Homo sapiens

<400> SEQUENCE: 1359

Ala Glu Gln Asn Asp Phe Ile Pro Leu Leu Ser Thr Val Thr Gly Ala
1               5                   10                  15

Arg

<210> SEQ ID NO 1360
<211> LENGTH: 11
<212> TYPE: PRT
<213> ORGANISM: Homo sapiens

<400> SEQUENCE: 1360

Ile Thr Glu Gln Thr Leu Phe Asp Leu Tyr Lys
1               5                   10

<210> SEQ ID NO 1361
<211> LENGTH: 12
<212> TYPE: PRT
<213> ORGANISM: Homo sapiens

<400> SEQUENCE: 1361

Tyr Ser Ser Phe Thr Thr Leu Val Ala Gly Ser Arg
1               5                   10

<210> SEQ ID NO 1362
<211> LENGTH: 11
<212> TYPE: PRT

<213> ORGANISM: Homo sapiens

<400> SEQUENCE: 1362

Ala Gly Pro Gly Ala Ala Gly Ala Gly Gly Arg
1               5                   10

<210> SEQ ID NO 1363
<211> LENGTH: 19
<212> TYPE: PRT
<213> ORGANISM: Homo sapiens

<400> SEQUENCE: 1363

Gly Gly Ala Gly Gly Pro Ala Ala Pro Ala Pro Pro Gln Leu Ser Pro
1               5                   10                  15

Val Gln Ala

<210> SEQ ID NO 1364
<211> LENGTH: 23
<212> TYPE: PRT
<213> ORGANISM: Homo sapiens

<400> SEQUENCE: 1364

Gly Tyr Leu Ser Asp Tyr Val Gly Pro Ser Val Tyr Asp Gly Asp
1               5                   10                  15

Ala Glu Ala Ala Leu Leu Lys
            20

<210> SEQ ID NO 1365
<211> LENGTH: 25
<212> TYPE: PRT
<213> ORGANISM: Homo sapiens

<400> SEQUENCE: 1365

Ala Val Val Ser Gly Asp Ser Ser Ala His Leu Val Glu Glu Ile Gln
1               5                   10                  15

Leu Phe Pro Asp Pro Glu Pro Val Arg
            20                  25

<210> SEQ ID NO 1366
<211> LENGTH: 22
<212> TYPE: PRT
<213> ORGANISM: Homo sapiens

<400> SEQUENCE: 1366

Gly Leu Gln Asp Phe Asp Thr Leu Leu Leu Ser Gly Asp Gly Asn Thr
1               5                   10                  15

Leu Tyr Val Gly Ala Arg
            20

<210> SEQ ID NO 1367
<211> LENGTH: 12
<212> TYPE: PRT
<213> ORGANISM: Homo sapiens

<400> SEQUENCE: 1367

Gly Ile Ser Ser Gln Tyr Ser Asn Thr Glu Glu Arg
1               5                   10

<210> SEQ ID NO 1368
<211> LENGTH: 8
<212> TYPE: PRT
<213> ORGANISM: Homo sapiens

```
<400> SEQUENCE: 1368

Asp Asp Phe Leu Ile Tyr Asp Arg
1               5

<210> SEQ ID NO 1369
<211> LENGTH: 25
<212> TYPE: PRT
<213> ORGANISM: Homo sapiens

<400> SEQUENCE: 1369

Val Ser Glu His Ile Pro Val Tyr Gln Gln Glu Asn Gln Thr Asp
1               5                   10                  15

Val Trp Thr Leu Leu Asn Gly Ser Lys
            20                  25

<210> SEQ ID NO 1370
<211> LENGTH: 12
<212> TYPE: PRT
<213> ORGANISM: Homo sapiens

<400> SEQUENCE: 1370

Ala Ile Gly His Val Ile Glu Glu Gly Gly Val Lys
1               5                   10

<210> SEQ ID NO 1371
<211> LENGTH: 12
<212> TYPE: PRT
<213> ORGANISM: Homo sapiens

<400> SEQUENCE: 1371

Glu Val Thr His Asn Ile His Tyr Glu Thr Tyr Arg
1               5                   10

<210> SEQ ID NO 1372
<211> LENGTH: 10
<212> TYPE: PRT
<213> ORGANISM: Homo sapiens

<400> SEQUENCE: 1372

Val Val Asn Ile Ile Pro Val Ile Ala Lys
1               5                   10

<210> SEQ ID NO 1373
<211> LENGTH: 14
<212> TYPE: PRT
<213> ORGANISM: Homo sapiens

<400> SEQUENCE: 1373

Glu Gln Tyr Ile Leu Ala Thr Gln Gln Asn Asn Leu Pro Arg
1               5                   10

<210> SEQ ID NO 1374
<211> LENGTH: 12
<212> TYPE: PRT
<213> ORGANISM: Homo sapiens

<400> SEQUENCE: 1374

Gly Val Gln Val Ser Ala Ala Ala Gly Asp Phe Lys
1               5                   10

<210> SEQ ID NO 1375
<211> LENGTH: 16
<212> TYPE: PRT
<213> ORGANISM: Homo sapiens
```

<400> SEQUENCE: 1375

Val Leu Phe Ser Ala Asp Glu Asp Glu Ile Thr Ile Gly Ala Glu Lys
1               5                   10                  15

<210> SEQ ID NO 1376
<211> LENGTH: 22
<212> TYPE: PRT
<213> ORGANISM: Homo sapiens

<400> SEQUENCE: 1376

Ala Ser Leu Ala Ala Ser His Ser Asn Leu Leu Gly Pro Gly Gly
1               5                   10                  15

Pro Pro Thr Pro Leu Arg
            20

<210> SEQ ID NO 1377
<211> LENGTH: 12
<212> TYPE: PRT
<213> ORGANISM: Homo sapiens

<400> SEQUENCE: 1377

Thr Gly Pro Ala Gly Gly Ala Gly Ala Ala Ala Arg
1               5                   10

<210> SEQ ID NO 1378
<211> LENGTH: 34
<212> TYPE: PRT
<213> ORGANISM: Homo sapiens

<400> SEQUENCE: 1378

Trp Ala Thr Thr Pro Pro Leu Ala Gly Gly Ala Gly Gly Ala Gly
1               5                   10                  15

Gly Ala Gly Gly Gly Pro Gly Pro Gly Gln Ala Gly Trp Leu Glu Gly
            20                  25                  30

Gly Arg

<210> SEQ ID NO 1379
<211> LENGTH: 10
<212> TYPE: PRT
<213> ORGANISM: Homo sapiens

<400> SEQUENCE: 1379

Thr Leu Val Asp Phe Phe Val Glu His Arg
1               5                   10

<210> SEQ ID NO 1380
<211> LENGTH: 16
<212> TYPE: PRT
<213> ORGANISM: Homo sapiens

<400> SEQUENCE: 1380

Trp Gln Glu Ser His Gln Leu Pro Ala Glu Phe Gln Leu Leu Tyr Arg
1               5                   10                  15

<210> SEQ ID NO 1381
<211> LENGTH: 11
<212> TYPE: PRT
<213> ORGANISM: Homo sapiens

<400> SEQUENCE: 1381

Tyr Tyr Asn Asn Leu Leu Thr Ile Gln Asp Arg
1               5                   10

<210> SEQ ID NO 1382
<211> LENGTH: 23
<212> TYPE: PRT
<213> ORGANISM: Homo sapiens

<400> SEQUENCE: 1382

Ala Gln Asn Pro Leu Gly Ser Gln His Ile Ser Leu Ser Leu
1               5                   10                  15

Gln Asn Glu Tyr Thr Gly Lys
            20

<210> SEQ ID NO 1383
<211> LENGTH: 23
<212> TYPE: PRT
<213> ORGANISM: Homo sapiens

<400> SEQUENCE: 1383

Ala Arg Pro Gln Tyr Pro Gln Glu Gln Glu Ala Ile Gly Tyr Glu Tyr
1               5                   10                  15

Ser Glu Ile Asn Ile Pro Lys
            20

<210> SEQ ID NO 1384
<211> LENGTH: 17
<212> TYPE: PRT
<213> ORGANISM: Homo sapiens

<400> SEQUENCE: 1384

Tyr Asp Gln Leu Ser Val Asn Val Thr Ala Ser Gln Asp Leu Leu Ser
1               5                   10                  15

Arg

<210> SEQ ID NO 1385
<211> LENGTH: 6
<212> TYPE: PRT
<213> ORGANISM: Homo sapiens

<400> SEQUENCE: 1385

His Glu Ser Ile Leu Arg
1               5

<210> SEQ ID NO 1386
<211> LENGTH: 21
<212> TYPE: PRT
<213> ORGANISM: Homo sapiens

<400> SEQUENCE: 1386

Ser Pro Leu Asp Leu Tyr Ser Ser His Phe Leu Leu Pro Asn Phe Ala
1               5                   10                  15

Asp Ser His His Arg
            20

<210> SEQ ID NO 1387
<211> LENGTH: 20
<212> TYPE: PRT
<213> ORGANISM: Homo sapiens

<400> SEQUENCE: 1387

Phe Thr Ala Pro Thr Ser Gln Phe Tyr His Leu Phe Leu His Gly Asn
1               5                   10                  15

Ser Leu Thr Arg

```
           20

<210> SEQ ID NO 1388
<211> LENGTH: 19
<212> TYPE: PRT
<213> ORGANISM: Homo sapiens

<400> SEQUENCE: 1388

Thr Asn Gly Gln Glu Asp His Ala Thr Pro Gly Ser Ala Pro Asn Gly
1               5                   10                  15

Gly Thr Lys

<210> SEQ ID NO 1389
<211> LENGTH: 14
<212> TYPE: PRT
<213> ORGANISM: Homo sapiens

<400> SEQUENCE: 1389

Asp Thr Tyr Leu Gln Phe Thr Asp Leu Gln Asn Trp Pro Arg
1               5                   10

<210> SEQ ID NO 1390
<211> LENGTH: 7
<212> TYPE: PRT
<213> ORGANISM: Homo sapiens

<400> SEQUENCE: 1390

Ile Asp Glu Ala Asn Gln Arg
1               5

<210> SEQ ID NO 1391
<211> LENGTH: 22
<212> TYPE: PRT
<213> ORGANISM: Homo sapiens

<400> SEQUENCE: 1391

Gly Ala Gly Ala Gly His Pro Gly Ala Gly Gly Ala Gln Pro Pro Asp
1               5                   10                  15

Ser Pro Ala Gly Val Arg
            20

<210> SEQ ID NO 1392
<211> LENGTH: 8
<212> TYPE: PRT
<213> ORGANISM: Homo sapiens

<400> SEQUENCE: 1392

His Leu Gly Trp Leu Ala Glu Lys
1               5

<210> SEQ ID NO 1393
<211> LENGTH: 11
<212> TYPE: PRT
<213> ORGANISM: Homo sapiens

<400> SEQUENCE: 1393

Gln Glu Leu Gly Gly Leu Gly Ile Ser Ile Lys
1               5                   10

<210> SEQ ID NO 1394
<211> LENGTH: 11
<212> TYPE: PRT
<213> ORGANISM: Homo sapiens
```

```
<400> SEQUENCE: 1394

Glu Gly Leu Glu Thr Asn Ala Asp Ile Ile Lys
1               5                   10

<210> SEQ ID NO 1395
<211> LENGTH: 10
<212> TYPE: PRT
<213> ORGANISM: Homo sapiens

<400> SEQUENCE: 1395

Asn Val Thr Gly Phe Phe Gln Ser Leu Lys
1               5                   10

<210> SEQ ID NO 1396
<211> LENGTH: 17
<212> TYPE: PRT
<213> ORGANISM: Homo sapiens

<400> SEQUENCE: 1396

Thr Leu Gly Gly Ile Leu Ala Pro Ile Tyr Phe Gly Ala Leu Ile Asp
1               5                   10                  15

Lys

<210> SEQ ID NO 1397
<211> LENGTH: 14
<212> TYPE: PRT
<213> ORGANISM: Homo sapiens

<400> SEQUENCE: 1397

Asp Glu Leu Asn Ala Asp His Pro Phe Ile Tyr Ile Ile Arg
1               5                   10

<210> SEQ ID NO 1398
<211> LENGTH: 21
<212> TYPE: PRT
<213> ORGANISM: Homo sapiens

<400> SEQUENCE: 1398

Asp Leu Thr Asp Gly His Phe Glu Asn Ile Leu Ala Asp Asn Ser Val
1               5                   10                  15

Asn Asp Gln Thr Lys
            20

<210> SEQ ID NO 1399
<211> LENGTH: 12
<212> TYPE: PRT
<213> ORGANISM: Homo sapiens

<400> SEQUENCE: 1399

Ile Leu Val Val Asn Ala Ala Tyr Phe Val Gly Lys
1               5                   10

<210> SEQ ID NO 1400
<211> LENGTH: 13
<212> TYPE: PRT
<213> ORGANISM: Homo sapiens

<400> SEQUENCE: 1400

Phe Pro Leu Ile Glu Gln Thr Tyr Tyr Pro Asn His Lys
1               5                   10

<210> SEQ ID NO 1401
<211> LENGTH: 10
```

```
<212> TYPE: PRT
<213> ORGANISM: Homo sapiens

<400> SEQUENCE: 1401

Ser Phe Arg Pro Asp Phe Val Leu Ile Arg
1               5                   10

<210> SEQ ID NO 1402
<211> LENGTH: 30
<212> TYPE: PRT
<213> ORGANISM: Homo sapiens

<400> SEQUENCE: 1402

Val Glu Asn His Tyr Asp Phe Gln Asp Ile Ala Ser Val Val Ala Leu
1               5                   10                  15

Thr Gln Thr Tyr Ala Thr Ala Glu Pro Phe Ile Asp Ser Lys
            20                  25                  30

<210> SEQ ID NO 1403
<211> LENGTH: 12
<212> TYPE: PRT
<213> ORGANISM: Homo sapiens

<400> SEQUENCE: 1403

Gly Gly Glu Gly Gly Glu Leu Gln Val Trp Ile Lys
1               5                   10

<210> SEQ ID NO 1404
<211> LENGTH: 13
<212> TYPE: PRT
<213> ORGANISM: Homo sapiens

<400> SEQUENCE: 1404

Glu Gly Val Val His Gly Val Ala Thr Val Ala Glu Lys
1               5                   10

<210> SEQ ID NO 1405
<211> LENGTH: 20
<212> TYPE: PRT
<213> ORGANISM: Homo sapiens

<400> SEQUENCE: 1405

Glu Gln Val Thr Asn Val Gly Gly Ala Val Val Thr Gly Val Thr Ala
1               5                   10                  15

Val Ala Gln Lys
            20

<210> SEQ ID NO 1406
<211> LENGTH: 9
<212> TYPE: PRT
<213> ORGANISM: Homo sapiens

<400> SEQUENCE: 1406

Gln Gly Val Ala Glu Ala Ala Gly Lys
1               5

<210> SEQ ID NO 1407
<211> LENGTH: 9
<212> TYPE: PRT
<213> ORGANISM: Homo sapiens

<400> SEQUENCE: 1407

Glu Gly Val Val Ala Ala Ala Glu Lys
1               5
```

<210> SEQ ID NO 1408
<211> LENGTH: 13
<212> TYPE: PRT
<213> ORGANISM: Homo sapiens

<400> SEQUENCE: 1408

Glu Gly Val Val Gln Gly Val Ala Ser Val Ala Glu Lys
1               5                   10

<210> SEQ ID NO 1409
<211> LENGTH: 9
<212> TYPE: PRT
<213> ORGANISM: Homo sapiens

<400> SEQUENCE: 1409

Gln Gly Val Thr Glu Ala Ala Glu Lys
1               5

<210> SEQ ID NO 1410
<211> LENGTH: 12
<212> TYPE: PRT
<213> ORGANISM: Homo sapiens

<400> SEQUENCE: 1410

Glu Leu Val Gly Leu Ala Glu His Ala Ala Thr Arg
1               5                   10

<210> SEQ ID NO 1411
<211> LENGTH: 15
<212> TYPE: PRT
<213> ORGANISM: Homo sapiens

<400> SEQUENCE: 1411

Phe Phe Ser Ala Asn Glu Gly Leu Asp Asp Tyr Leu Glu Ala Arg
1               5                   10                  15

<210> SEQ ID NO 1412
<211> LENGTH: 12
<212> TYPE: PRT
<213> ORGANISM: Homo sapiens

<400> SEQUENCE: 1412

Gly Ile Ser Val His Ile Ser Asn Ala Glu Pro Lys
1               5                   10

<210> SEQ ID NO 1413
<211> LENGTH: 24
<212> TYPE: PRT
<213> ORGANISM: Homo sapiens

<400> SEQUENCE: 1413

Leu Val Glu Gly Ile Leu His Ala Pro Asp Ala Gly Trp Gly Asn Leu
1               5                   10                  15

Val Tyr Val Val Asn Tyr Pro Lys
            20

<210> SEQ ID NO 1414
<211> LENGTH: 7
<212> TYPE: PRT
<213> ORGANISM: Homo sapiens

<400> SEQUENCE: 1414

Thr Thr Glu Gln Asp Leu Lys

<210> SEQ ID NO 1415
<211> LENGTH: 23
<212> TYPE: PRT
<213> ORGANISM: Homo sapiens

<400> SEQUENCE: 1415

Glu Ser Pro Leu Gln Thr Pro Thr Glu Asp Gly Ser Glu Glu Pro Gly
1               5                   10                  15

Ser Glu Thr Ser Asp Ala Lys
            20

<210> SEQ ID NO 1416
<211> LENGTH: 15
<212> TYPE: PRT
<213> ORGANISM: Homo sapiens

<400> SEQUENCE: 1416

Ser Gly Tyr Ser Ser Pro Gly Ser Pro Gly Thr Pro Gly Ser Arg
1               5                   10                  15

<210> SEQ ID NO 1417
<211> LENGTH: 10
<212> TYPE: PRT
<213> ORGANISM: Homo sapiens

<400> SEQUENCE: 1417

Thr Pro Pro Ser Ser Gly Glu Pro Pro Lys
1               5                   10

<210> SEQ ID NO 1418
<211> LENGTH: 14
<212> TYPE: PRT
<213> ORGANISM: Homo sapiens

<400> SEQUENCE: 1418

Asn Ser Ser Tyr Phe Val Glu Trp Ile Pro Asn Asn Val Lys
1               5                   10

<210> SEQ ID NO 1419
<211> LENGTH: 26
<212> TYPE: PRT
<213> ORGANISM: Homo sapiens

<400> SEQUENCE: 1419

Ser Gly Pro Phe Gly Gln Ile Phe Arg Pro Asp Asn Phe Val Phe Gly
1               5                   10                  15

Gln Ser Gly Ala Gly Asn Asn Trp Ala Lys
            20                  25

<210> SEQ ID NO 1420
<211> LENGTH: 9
<212> TYPE: PRT
<213> ORGANISM: Homo sapiens

<400> SEQUENCE: 1420

Asp Val Asp Leu Glu Phe Leu Ala Lys
1               5

<210> SEQ ID NO 1421
<211> LENGTH: 18
<212> TYPE: PRT
<213> ORGANISM: Homo sapiens

<400> SEQUENCE: 1421

Leu Pro Ala Val Ala Gln Ala Val Ala Gln Leu Ala Gly Gln Leu Leu
1               5                   10                  15

Ile Arg

<210> SEQ ID NO 1422
<211> LENGTH: 14
<212> TYPE: PRT
<213> ORGANISM: Homo sapiens

<400> SEQUENCE: 1422

Thr Ser Pro Leu Leu Thr Ser Leu Ile Glu Ser Val Leu Lys
1               5                   10

<210> SEQ ID NO 1423
<211> LENGTH: 12
<212> TYPE: PRT
<213> ORGANISM: Homo sapiens

<400> SEQUENCE: 1423

Thr Ser Phe Pro Glu Asn Val Leu Asn Asn Leu Lys
1               5                   10

<210> SEQ ID NO 1424
<211> LENGTH: 11
<212> TYPE: PRT
<213> ORGANISM: Homo sapiens

<400> SEQUENCE: 1424

Ala Gly Asp Pro Val Ile Leu Tyr Val Asn Lys
1               5                   10

<210> SEQ ID NO 1425
<211> LENGTH: 9
<212> TYPE: PRT
<213> ORGANISM: Homo sapiens

<400> SEQUENCE: 1425

Ile Ile Phe Ala Asn Val Ser Val Arg
1               5

<210> SEQ ID NO 1426
<211> LENGTH: 11
<212> TYPE: PRT
<213> ORGANISM: Homo sapiens

<400> SEQUENCE: 1426

His Tyr Thr Gln Phe Trp Asn Tyr Leu Glu Arg
1               5                   10

<210> SEQ ID NO 1427
<211> LENGTH: 7
<212> TYPE: PRT
<213> ORGANISM: Homo sapiens

<400> SEQUENCE: 1427

Glu Asp Trp Gly Phe Gln Lys
1               5

<210> SEQ ID NO 1428
<211> LENGTH: 5
<212> TYPE: PRT
<213> ORGANISM: Homo sapiens

```
<400> SEQUENCE: 1428

Gln Gln Glu Phe Arg
1               5

<210> SEQ ID NO 1429
<211> LENGTH: 22
<212> TYPE: PRT
<213> ORGANISM: Homo sapiens

<400> SEQUENCE: 1429

Ser Gln Leu Asp Gln Glu Ser Gly Ala Val Ile His Pro Ala Thr Gln
1               5                   10                  15

Thr Ser Leu Gln Val Arg
            20

<210> SEQ ID NO 1430
<211> LENGTH: 17
<212> TYPE: PRT
<213> ORGANISM: Homo sapiens

<400> SEQUENCE: 1430

Phe Thr Pro Asn Trp Leu Ser Val Leu Val Asp Asn Leu Pro Gly Thr
1               5                   10                  15

Lys

<210> SEQ ID NO 1431
<211> LENGTH: 8
<212> TYPE: PRT
<213> ORGANISM: Homo sapiens

<400> SEQUENCE: 1431

Val Asn Ala Glu Ser Val Glu Arg
1               5

<210> SEQ ID NO 1432
<211> LENGTH: 10
<212> TYPE: PRT
<213> ORGANISM: Homo sapiens

<400> SEQUENCE: 1432

Trp Thr Thr Gln Glu Thr Phe Pro Pro Lys
1               5                   10

<210> SEQ ID NO 1433
<211> LENGTH: 16
<212> TYPE: PRT
<213> ORGANISM: Homo sapiens

<400> SEQUENCE: 1433

Ala Ala Gly Ser Gly Val Ser Asp Tyr Asp Tyr Leu Asp Leu Asp Lys
1               5                   10                  15

<210> SEQ ID NO 1434
<211> LENGTH: 13
<212> TYPE: PRT
<213> ORGANISM: Homo sapiens

<400> SEQUENCE: 1434

Ser Gln Leu Ser Gln Ala Leu Asn Gly Leu Ser Asp Arg
1               5                   10

<210> SEQ ID NO 1435
```

```
<211> LENGTH: 9
<212> TYPE: PRT
<213> ORGANISM: Homo sapiens

<400> SEQUENCE: 1435

Gln Ile Leu Glu Gln Thr Pro Val Lys
1               5

<210> SEQ ID NO 1436
<211> LENGTH: 12
<212> TYPE: PRT
<213> ORGANISM: Homo sapiens

<400> SEQUENCE: 1436

Gln Pro Ser Gly Ala Glu Ser Gly Thr Leu Ala Arg
1               5                   10

<210> SEQ ID NO 1437
<211> LENGTH: 16
<212> TYPE: PRT
<213> ORGANISM: Homo sapiens

<400> SEQUENCE: 1437

Asp Ile Asp Phe Ala His Glu Ala Pro Ala Phe Leu Pro Trp His Arg
1               5                   10                  15

<210> SEQ ID NO 1438
<211> LENGTH: 11
<212> TYPE: PRT
<213> ORGANISM: Homo sapiens

<400> SEQUENCE: 1438

Glu Asp Tyr His Ser Leu Tyr Gln Ser His Leu
1               5                   10

<210> SEQ ID NO 1439
<211> LENGTH: 10
<212> TYPE: PRT
<213> ORGANISM: Homo sapiens

<400> SEQUENCE: 1439

Glu Ser Trp Pro Ser Val Phe Tyr Asn Arg
1               5                   10

<210> SEQ ID NO 1440
<211> LENGTH: 9
<212> TYPE: PRT
<213> ORGANISM: Homo sapiens

<400> SEQUENCE: 1440

Ala Asn Pro Gly Ala Trp Ile Leu Arg
1               5

<210> SEQ ID NO 1441
<211> LENGTH: 11
<212> TYPE: PRT
<213> ORGANISM: Homo sapiens

<400> SEQUENCE: 1441

Ile Ile Phe Val Asp Ala Asp Gln Ile Val Arg
1               5                   10

<210> SEQ ID NO 1442
<211> LENGTH: 14
<212> TYPE: PRT
```

<213> ORGANISM: Homo sapiens

<400> SEQUENCE: 1442

Ile Leu Phe Leu Asp Val Leu Phe Pro Leu Ala Val Asp Lys
1               5                   10

<210> SEQ ID NO 1443
<211> LENGTH: 13
<212> TYPE: PRT
<213> ORGANISM: Homo sapiens

<400> SEQUENCE: 1443

His Glu Thr Val Val Ser Leu Ala Ala Glu Gly Gln Tyr
1               5                   10

<210> SEQ ID NO 1444
<211> LENGTH: 10
<212> TYPE: PRT
<213> ORGANISM: Homo sapiens

<400> SEQUENCE: 1444

Val Asp Glu Thr Ser Gly Leu Ile Val Arg
1               5                   10

<210> SEQ ID NO 1445
<211> LENGTH: 20
<212> TYPE: PRT
<213> ORGANISM: Homo sapiens

<400> SEQUENCE: 1445

Val Tyr Asn Thr Ser Gly Ala Val Thr Pro Gln Asp Asp Leu Ser Glu
1               5                   10                  15

Phe Thr Ser Lys
            20

<210> SEQ ID NO 1446
<211> LENGTH: 14
<212> TYPE: PRT
<213> ORGANISM: Homo sapiens

<400> SEQUENCE: 1446

Ile Glu Gly Thr Thr Ala Ala Ser Ser Tyr Val Phe Val Arg
1               5                   10

<210> SEQ ID NO 1447
<211> LENGTH: 11
<212> TYPE: PRT
<213> ORGANISM: Homo sapiens

<400> SEQUENCE: 1447

Asn Ile Leu Leu Ser Glu Ser Asp Val Val Lys
1               5                   10

<210> SEQ ID NO 1448
<211> LENGTH: 7
<212> TYPE: PRT
<213> ORGANISM: Homo sapiens

<400> SEQUENCE: 1448

Glu Phe Ser His Leu Gly Lys
1               5

<210> SEQ ID NO 1449
<211> LENGTH: 8

```
<212> TYPE: PRT
<213> ORGANISM: Homo sapiens

<400> SEQUENCE: 1449

Glu Leu Pro Glu His Thr Val Lys
1               5

<210> SEQ ID NO 1450
<211> LENGTH: 14
<212> TYPE: PRT
<213> ORGANISM: Homo sapiens

<400> SEQUENCE: 1450

Asp Ser Trp Glu Asp Ile Phe Glu Leu Leu Phe Trp Gly Arg
1               5                   10

<210> SEQ ID NO 1451
<211> LENGTH: 15
<212> TYPE: PRT
<213> ORGANISM: Homo sapiens

<400> SEQUENCE: 1451

Asp Val Trp Gly Ile Glu Gly Pro Ile Asp Ala Ala Phe Thr Arg
1               5                   10                  15

<210> SEQ ID NO 1452
<211> LENGTH: 17
<212> TYPE: PRT
<213> ORGANISM: Homo sapiens

<400> SEQUENCE: 1452

Ala Ala Glu Gly Leu Gly Ala Gly Val Glu Glu Gly Asp Asp Gly
1               5                   10                  15

Lys

<210> SEQ ID NO 1453
<211> LENGTH: 14
<212> TYPE: PRT
<213> ORGANISM: Homo sapiens

<400> SEQUENCE: 1453

Glu Pro Pro Glu Gly Thr Trp Thr Glu Gly Ala Pro Val Lys
1               5                   10

<210> SEQ ID NO 1454
<211> LENGTH: 11
<212> TYPE: PRT
<213> ORGANISM: Homo sapiens

<400> SEQUENCE: 1454

Ala Leu Gln Leu Ser Ser His Gly Gly Leu Arg
1               5                   10

<210> SEQ ID NO 1455
<211> LENGTH: 13
<212> TYPE: PRT
<213> ORGANISM: Homo sapiens

<400> SEQUENCE: 1455

Gln Phe Val Asp Ala Leu Glu Thr Gly Gln Asp Ala Arg
1               5                   10

<210> SEQ ID NO 1456
<211> LENGTH: 13
```

```
<212> TYPE: PRT
<213> ORGANISM: Homo sapiens

<400> SEQUENCE: 1456

Phe Gln Asp Ser Ser Gln Trp Leu Gln Ile Asp Leu Lys
1               5                   10

<210> SEQ ID NO 1457
<211> LENGTH: 9
<212> TYPE: PRT
<213> ORGANISM: Homo sapiens

<400> SEQUENCE: 1457

Leu Ile Pro Leu Gly Trp His Val Arg
1               5

<210> SEQ ID NO 1458
<211> LENGTH: 11
<212> TYPE: PRT
<213> ORGANISM: Homo sapiens

<400> SEQUENCE: 1458

Ala Gln Gly Pro Gly Ala Ser Pro Trp Gly Arg
1               5                   10

<210> SEQ ID NO 1459
<211> LENGTH: 14
<212> TYPE: PRT
<213> ORGANISM: Homo sapiens

<400> SEQUENCE: 1459

Gly Pro Glu Ser Pro Ser Asp Leu Gln Gly Trp Gly Ala Arg
1               5                   10

<210> SEQ ID NO 1460
<211> LENGTH: 6
<212> TYPE: PRT
<213> ORGANISM: Homo sapiens

<400> SEQUENCE: 1460

Leu Val Asn His Ile Arg
1               5
```